United States Patent

Sugimoto et al.

[11] Patent Number: 5,910,506
[45] Date of Patent: Jun. 8, 1999

[54] IMIDAZOLE DERIVATIVES AS ANTI-HIV AGENTS

[75] Inventors: Hirohiko Sugimoto, Osaka; Tamio Fujiwara, Hyogo, both of Japan

[73] Assignee: Shionogi & Co., Ltd., Osaka, Japan

[21] Appl. No.: 08/809,624

[22] PCT Filed: Sep. 25, 1995

[86] PCT No.: PCT/JP95/01936

§ 371 Date: May 30, 1997

§ 102(e) Date: May 30, 1997

[87] PCT Pub. No.: WO96/10019

PCT Pub. Date: May 4, 1996

[30] Foreign Application Priority Data

Sep. 26, 1994 [JP] Japan ..................................... 6-257490
Mar. 15, 1995 [JP] Japan ..................................... 7-84690
Aug. 12, 1995 [JP] Japan ..................................... 7-227205

[51] Int. Cl.[6] ....................... A01N 43/50; C07D 233/40; C07D 233/28
[52] U.S. Cl. ....................... 514/397; 514/398; 548/311.1; 548/316.4
[58] Field of Search ..................... 548/311.1, 316.4; 514/397, 398

[56] References Cited

U.S. PATENT DOCUMENTS

| 5,326,780 | 7/1994 | Sugimoto et al. | 514/398 |
| 5,412,101 | 5/1995 | Caille et al. | 548/253 |
| 5,599,830 | 2/1997 | Caille et al. | 514/398 |
| 5,684,028 | 11/1997 | Caille et al. | 514/381 |

FOREIGN PATENT DOCUMENTS

| 465368 | 1/1992 | European Pat. Off. . |
| 552 060 | 7/1993 | European Pat. Off. . |
| 47-7791 | 3/1972 | Japan . |
| 63-150266 | 6/1988 | Japan . |
| 2-83373 | 3/1990 | Japan . |

OTHER PUBLICATIONS

Masaichiro Masui et al.; "Reactions of N–(1–cyanoalkyl)alkylideneamine N–oxides with dipolarophles and nucleophiles", Part I; *Journal of the Chemical Society*, Perkin Transactions 1, 1972, pp. 1955–1960, pp. 1957 and 1959, compound lIId.

Masaichiro Masui et al.; "Convenient syntheses of 2,4(5)–dialkylimidazoles and 1–methyl–2,4–dialkyl–imidazoles", *Journal of the Chemical Society*, Perkins Transactions 1, 1972, pp. 1960–1963.

*Primary Examiner*—Richard L. Raymond
*Assistant Examiner*—Tamthom T. Ngo
*Attorney, Agent, or Firm*—Wenderoth, Lind & Ponack, L.L.P.

[57] ABSTRACT

An imidazole derivative represented by general formula (I) or a salt thereof, having the effect of specifically inhibiting the growth of HIV as a pathogenic virus and being reduced in toxicity. In said formula $R^1$ represents hydrogen, $C_1$–$C_{20}$ alkyl, $C_2$–$C_7$ alkenyl, $C_4$–$C_{12}$ cycloalkylalkyl, etc.; $R^2$ represents $C_1$–$C_6$ alkyl, $C_1$–$C_6$ acyl, hydroxyiminomethyl, hydrazonomethyl or —($CH_2$)n—$R^4$ ($R^4$ being halogeno, alkoxy, hydroxy, etc.; and n being an integer of 1 to 3); $R^3$ represents substituted or unsubstituted $C_1$–$C_6$ alkyl; X and Y represent each independently hydrogen, $C_1$–$C_3$ alkyl, halogeno, or nitro; and Z represents S, SO, $SO_2$ or $CH_2$.

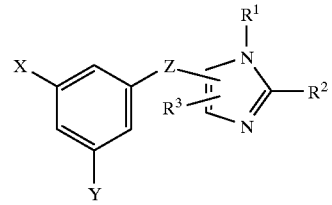

(I)

4 Claims, No Drawings

IMIDAZOLE DERIVATIVES AS ANTI-HIV AGENTS

This is a 371 application of PCT/JP 95/01936 filed on Sep. 25, 1995.

TECHNICAL FIELD

The present invention relates to a novel imidazole derivative and a medicinal composition comprising it as an active ingredient.

BACKGROUND OF THE INVENTION

AIDS (acquired immune deficiency syndrome) is a serious social problem spread over the world as a refractory viral disease caused by HIV and the research and development of anti-HIV drugs have been undertaken on a worldwide scale. To this day, nucleic acid derivatives such as azidodeoxythymidine (AZT), dideoxyinosine (DDI), dideoxycytidine (DDC), dideoxydidehydrothymidine (D4T), and 3'-thiacytidine (3TC) have been developed as major target and put to use clinically, but severe adverse reactions and decreace of the efficacy due to occurrence of resistant strains have produced new problems and, therefore, the development of new therapeutic drugs has been eagerly awaited.

The pathologic picture of AIDS has not been fully elucidated yet, and recently it has been found that even in asymptomatic patients whose clinical stage is considered to be at a latent period, virologically the virus is actively proliferated in the lymph node. Therefore, development of an improved anti-HIV drug is an important social need today.

Meanwhile, explorations into various imidazole derivatives have been undertaken with the view of utilizing them as medicines.

U.S. Pat. No. 3,968,228 describes imidazole derivatives effective for the therapy of coccidiosis in animals as well as a variety of imidazole derivatives as intermediates for their synthesis. In the imidazole derivatives disclosed, however, the substituent attached directly to the inidazole ring via a —S—, —SO—, or —SO$_2$— moiety is limited to alkyl groups.

U.S. Pat. No. 4,592,774 discloses imidazole derivatives which are of use as herbicides. However, all the disclosed imidazole derivatives necessarily have an opionally substituted phenylmethyl in the 2-position of the imidazole ring.

Japanese Kokai Hei-2-83373 discloses a series of imidazole derivatives of value as agrochemicals, medicines, perfumes, or polymer materials. These imidazole derivatives are substituted by hydrogen, cyano, carbamoyl, thiocarbamoyl, or a group of the formula COOR$^2$ (those represented by substituent Y in the publication) in the 4- and/or 5-position(s).

Japanese Kokai Hei-5-252270 describes imidazole derivatives having anti-HIV activity In the disclose,, imidazole derivative, however, the substituent in the 1-position of the imidazole ring is limited to groups of the formula —(CH$_2$)n—O—R$_3$ having an ether linkage.

SUMMARY OF THE INVENTION

In view of the above state of the art, the present invention has for its object to provide a compound having the activity to specifically inhibit proliferation of the causative virus HIV in the lymph node and yet a low toxic potential.

The inventors of the present invention discovered that a series of imidazole derivatives having herein-defined substituent groups meet the above object and completed the present invention Thus, the present invention is essentially directed to any of such imidazole derivatives and medicinal compositions comprising them as active ingredient

DETAILED DISCLOSURE OF THE INVENTION

The present invention is now described in detail

The imidazole derivatives of the present invention have the following formula (I)

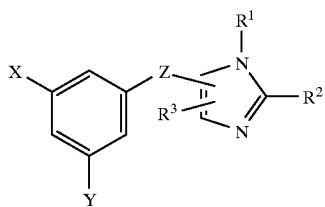

(I)

(wherein R$^1$ represents hydrogen, an alkyl group of 1 to 20 carbon atoms, an alkenyl group of 2 to 7 carbon atoms, a cycloalkylalkyl group of 4 to 12 carbon atoms, a haloalkyl group of 1 to 6 carbon atoms, an oxoalkyl group of 1 to 6 carbon atoms, an aroylalkyl group of 8 to 13 carbon atoms, a substituted or unsubstituted aralkyl group, a substituted or unsubstituted heteroarylalkyl group, a substituted or unsubstituted carbamoyloxyalkyl, carbamoylalkyloxyalkyl, or acyloxyalkyl group, or a branched hydroxyalkyl group;

R$^2$ represents an alkyl group of 1 to 6 carbon atoms, an acyl group of 1 to 6 carbon atoms, hydroxyiminomethyl, hydrazonomethyl, or a group of the formula —(CH$_2$)n—R$^4$ (where R$^4$ represents halogen, an alkoxy group, hydroxy, cyano, an acyloxy group, an aryloxycarbonyloxy group, an alkoxycarbonyloxy group, carboxy, a substituted or unsubstituted carbamoyl group, a substituted or unsubstituted hydroxyalkyloxy group, a substituted or unsubstituted benzyloxy group, a substituted or unsubstituted carbamoyloxy or thiocarbamoyloxy group, a substituted or unsubstituted-amino group, or azido; n represents an integer of 1 to 3);

R$^3$ represents a substituted or unsubstituted alkyl group of 1 to 6 carbon atoms;

X and Y independently represent hydrogen, an alkyl group of 1 to 3 carbon atoms, halogen, or nitro;

Z represents S, SO, SO$_2$ or CH$_2$).

In the above formula, the alkyl group of 1 to 20 carbon atoms for R$^2$ means a straight-chain or branched alkyl group, thus including methyl, ethyl, n-propyl, i-propyl, n-butyl, i-butyl, tert-butyl, n-pentyl, i-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, and the like.

The alkenyl group of 2 to 7 carbon atoms for R$^1$ is not particularly restricted but includes vinyl, allyl, propenyl, butenyl, pentenyl, hexenyl, heptenyl, and the like.

The cycloalkylalkyl group of 4 to 12 carbon atoms for R$^1$ is not particularly restricted but includes cyclopropylmethyl, 1- or 2-cyclopropylethyl, 1-, 2-, or 3-cyclopropylprop 1-, 2-, 3-, or 4-cyclopropylbutyl, 1-, 2-, 3-, 4-, or 5-cyclopropylpentyl, 1-, 2-, 3-, 4-, 5-, or 6-cyclopropylhexyl, 1-, 2-, 3-, 4-, 5-, 6-, or 7-cyclopropylheptyl, 1-, 2-, 3-, 4-, 5-, 6-, 7-, or 8-cyclopropyloctyl, 1-, 2-, 3-, 4-, 5-, 6-, 7-, 8-, or 9-cyclopropylnonyl, cyclobutylmethyl, 1- or 2-cyclobutylethyl, 1-, 2-, or 3-cyclobutylpropyl, 1-, 2-, 3-, or 4-cyclobutylbutyl, 1-, 2-, 3-, 4-, or 5-cyclobutylpentyl, 1-, 2-, 3-, 4-, 5-, or 6-cyclobutylhexyl, 1-, 2-, 3-, 4-, 5-, 6-, or 7-cyclobutylheptyl, 1-, 2-, 3-, 4-, 5-, 6-, 7-, or 8-cyclobutyloctyl, cyclopentylmethyl, 1- or 2-cyclopentylethyl, 1-, 2-, or 3-cyclopentylpropyl, 1-, 2-, 3-, or 4-cyclopentylbutyl, 1-, 2-, 3-, 4-, or 5-cyclopentylpentyl, 1-, 2-, 3-, 4-, 5-, or 6-cyclopentylhexyl, 1-, 2-, 3-, 4-, 5-, 6-, or 7-cyclopentylheptyl, cyclohexylmethyl, 1- or 2-cyclohexylethyl, 1-, 2-, or 3-cyclohexylpropyl, 1-, 2-, 3-, or 4-cyclohexylbutyl, 1-, 2-, 3-, 4-, or 5-cyclohexylpentyl, 1-, 2-, 3-, 4-, 5-, or 6-cyclohexylhexyl, cycloheptylmethyl, 1- or 2-cycloheptylethyl, 1-, 2-, or 3-cycloheptylpropyl, 1-, 2-, 3-, or 4-cycloheptylbutyl, 1-, 2-, 3-, 4-, or 5-cycloheptylpentyl, cyclooctylmethyl, 1- or 2-cyclooctylethyl, 1-, 2-, or 3-cyclooctylpropyl, 1-, 2-, 3-, or 4-cyclooctylbutyl, 1- or 2-cyclooctylethyl, 1-, 2-, or 3-cyclononylpropyl, and the like.

The haloalkyl group of 1 to 6 carbon atoms for $R^1$ is not particularly restricted but includes chloromethyl, 1- or 2-chloroethyl, 1-, 2-, or 3-chloropropyl, 1-, 2-, 3-, or 4-chlorobutyl, 1-, 2-, 3-, 4-, or 5-chloropentyl, 1-, 2-, 3-, 4-, 5-, or 6-chlorohexyl, bromomethyl, 1- or 2-bromoethyl, 1-, 2-, or 3-bromopropyl, 1-, 2-, 3-, or 4-bromobutyl, 1-, 2-, 3-, 4-, or 5-bromopentyl, 1-, 2-, 3-, 4-, 5-, or 6-bromohexyl, fluoromethyl, 1- or 2-fluoroethyl, 1-, 2-, or 3-fluoropropyl, 1-, 2-, 3-, or 4-fluorobutyl, 1-, 2-, 3-, 4-, or 5-fluoropentyl, 1-, 2-, 3-, 4-, 5-, or 6-fluorohexyl, iodomethyl, 1- or 2-iodoethyl, 1-, 2-, or 3-iodopropyl, 1-, 2-, 3-, or 4-iodobutyl, 1-, 2-, 3-, 4-, or 5-iodopentyl, 1-, 2-, 3-, 4-, 5-, or 6-iodohexyl, difluoromethyl, 1,2-difluoroethyl, trifluoromethyl, 2,2,2-trifluoroethyl, and the like.

The oxoalkyl group of 1 to 6 carbon atoms for $R^1$ is not particularly restricted but includes acetylmethyl, propionylmethyl, 2-oxoethyl, and the like.

The aralkyl group mentioned for $R^1$ means an aralkyl group of 7 to 12 carbon atoms, such as phenylmethlyl, 1- or 2-phenylethyl, 1-, 2-, or 3-phenylpropyl, 1-, 2-, 3-, or 4-phenylbutyl, 1-, 2-, 3-, 4-, or 5-phenylpentyl, 1-, 2-, 3-, 4-, 5-, or 6-phenylhexyl, 1-, 2-, 3-, 4-, 5-, 6-, or 7-phenylheptyl, naphthylmethyl, 1- or 2-naphthylethyl, and the like.

The aroylalkyl group of 8 to 13 carbon atoms for $R^1$ is not particularly restricted but includes benzoylmethyl, 1- or 2-benzoylethyl, 1-, 2-, or 3-benzoylpropyl, 1-, 2-, 3-, or 4-benzoylbutyl, 1-, 2-, 3-, 4-, or 5-benzoylpentyl, 1-, 2-, 3-, 4-, 5-, or 6-benzoylhexyl, 1-, 2-, 3-, 4-, 5-, 6-, or 7-benzoylheptyl, and the like.

The heteroarylalkyl group mentioned for $R^1$ is not particularly restricted but includes 2-pyridylmethyl, 3-pyridylmethyl, 4-pyridylmethyl, 1- or,2-(2-pyridyl)ethyl, 1- or 2-(3-pyridyl)ethyl, 1- or 2-(4-pyridyl)ethyl, 1-, 2-, or 3-(2-pyridyl)propyl, 2-thienylmethyl, 3-thienylmethyl, 4-thienylmethyl, 2-quinolylmethyl, 3-quinolylmethyl, 4-quinolylmethyl, and the like.

The carbamoyloxyalkyl group mentioned for $R^1$ is not particularly restricted but includes carbamoyloxymethyl, 1- or 2-carbamoyloxyethyl, 1-, 2-, or 3-carbamoyloxypropyl, 1-, 2-, 3-, or 4-carbamoyloxybutyl, and the like.

The carbamoylalkyloxyalkyl group mentioned for $R^1$ is not particularly restricted but includes carbamoylmethyloxymethyl, 1- or 2-carbamoylmethyloxyethyl, and the like.

The acyloxyalkyl group mentioned for $R^1$ is not particularly restricted but includes acetyloxymethyl, propionyloxymethyl, and the like.

The hydroxyalkyl group mentioned for $R^1$ is not particularly restricted but includes 2-hydroxy-1-propyl, 2-hydroxy-2-propyl, 2-hydroxy-3-propyl, and the like.

The substituent that may be present on said substituted or unsubstituted aralkyl, substituted or unsubstituted heteroarylalkyl, or substituted or unsubstituted carbamoyloxyalkyl, carbamoylalkyloxyalkyl, or acyloxyalkyl, all mentioned above for $R^1$, is not particularly restricted but includes alkyl (e.g. methyl, ethyl), alkenyl (e.g. allyl), cycloalkyl (e.g. cyclopropyl), haloalkyl(e.g. fluoromethyl), oxoalkyl (e.g. acetylmethyl), aralkyl (e.g. benzyl), aroylalkyl (e.g. benzoylmethyl), hydroxy, substituted or unsubstituted amino (e.g N-methylamino, N,N-dimethylamino, N-acetylamino, diaminomethyleneaminomethyl, ureidomethyl, methanesulfonamidomethyl).

In the above formula, the alkyl group of 1 to 6 carbon atoms for $R^2$ is a straight or branched alkyl group, thus including the alkyl groups of 1 to 6 carbon atoms mentioned for $R^1$. The acyl group of 1 to 6 carbon atoms for $R^2$ and $R^4$ is not particularly restricted but includes formyl, acetyl, propionyl, butyryl, valeryl, and the like.

The alkoxy group mentioned for $R^4$ is not particularly restricted but may for example be methoxy, ethoxy, propoxy, or butoxy.

The aryloxycarbonyloxy group mentioned for $R^4$ is not particularly restricted, either, thus including phenyloxycarbonyloxy as an example.

The alkoxycarbonyloxy group mentioned for $R^4$ is not particularly restricted, including ethoxycarbonyloxy as an example.

The hydroxyalkyloxy group for $R^4$ is not particularly restricted but includes hydroxymethyloxy, hydroxyethyloxy, and so on.

The substituent that may be present on said substituted or unsubstituted carbamoyl, substituted or unsubstituted hydroxyalkyloxy, substituted or unsubstituted benzyloxy, substituted or unsubstituted carbamoyloxy or thiocarbamoyloxy, or substituted or unsubstituted amino group for $R^4$ is not particularly restricted but includes alkyl, alkenyl, cycloalkylalkyl, haloalkyl, oxoalkcyl, acyl, carbamoyl, and substituted or unsubstituted amino (e.g. N-methylamino, N,N-dimethylamino, N-acetylamino, diaminomethyleneaminomethyl, ureidomethyl, methanesulfonamidomethyl).

The alkyl group of 1 to 6 carbon atoms for $R^3$ in the above formula is a straight or branched alkyl group and includes the same alkyl groups of 1 to 6 carbon atoms as mentioned for $R^1$. Preferred is isopropyl. The substituent for such alkyl group is not particularly restricted but includes hydroxy, alkoxy, acyloxy, alkenyl, cycloalkyl, halogen, oxoalkyl, aralkyl, aroylalkyl, cyano, carboxy, alkoxycarbonyl (e.g. methoxycarbonyl, ethoxycarbonyl), and the like.

In the above formula, the alkyl group of 1 to 3 carbon atoms for X is not particularly restricted but may for example be methyl, ethyl, or propyl. The halogen for X is not particularly restricted but includes chlorine, bromine, fluorine, and iodine. Preferred is chlorine.

The alkyl group of 1 to 3 carbon atoms for Y in the above formula is not particularly restricted but may for example be methyl, ethyl, or propyl. The halogen for Y is not particularly restricted but includes chlorine, bromine, fluorine, and iodine. Preferred is chlorine.

The following is a list of preferred species of the compounds according to the present invention.

(A-1) 2-Carbamoyloxymethyl-5-(3,5-dichlorophenylthio)-1-ethyl-4-isopropyl-1H-imidazole (A-2) 2-[5-(3,5-Dichlorophenylthio)-4-isopropyl-1-methyl-1H-imidazol-2-yl]ethanol (A-3) 2-Carbamoyloxymethyl-5-(3,5-dichlorophenylthio)-4-isopropyl-1-(pyridin-4-yl)methyl-1H-imidazole (A-4) [5-(3,5-Dichlorophenylthio)-1-ethyl-4-isopropyl-1H-imidazol-2-yl]methanol (A-5)[1-(2-Hydroxypropyl)-5-(3,5-dichlorophenylthio-4-isopropyl-1H-imidazol-2-yl]methanol (A-6)[5-(3,5-Dichlorophenylthio)-4-isopropyl-1-methyl-1H-imidazol-2-yl]acetonitrile (A-7)[5-(3,5-Dichlorophenylthio)-1-(4-aminobenzyl)-4-isopropyl-1H-imidazol-2-yl]methanol (A-8)[5-(3,5-Dichlorophenylthio)-1-(3-aminobenzyl)-4-isopropyl-1H-imidazol-2-yl]methanol (A-9)2-[5-(3,5-Dichlorophenylthio)-4-isopropyl-1H-imidazol-2-yl]ethanol (A-10)2-[2-(Carbamoyloxy)ethyl]-5-(3,5-dichlorophenylthio-1-ethyl-4-isopropyl-1H-imidazole (A-11)[5-(3,5-Dichlorophenylthio)-4-isopropyl-1-(5,6-dihydro-6-oxopyridin-3-yl)methyl-1H-imidazol-2-yl]methanol (A-12)2-Carbamoyloxymethyl-5-(3,5-dichlorophenylthio)-1-(5,6-dihydro-6-ocopyridin-3-yl)methyl-4-isopropyl-1H-imidazol In addition to the above species, the compound of the present invention includes the following species, for instance.

(1) 2-Carbamoyloxymethyl-5-isopropyl-1-methyl-4-phenylthio-1H-imidazole (2) 2-(5-(3-Chlorophenylthio)-4-isopropyl-1-(pyridin-4-yl]methyl))-1H-imidazole-2-carbaldehyde oxime (3) 4-(3,5-Difluorophenylthio)-5-isopropyl-1-methyl-1H-imidazole-2-carbaldehyde (4) Methyl 3-(5-(3,5-difluorophenylthio)-4-isopropyl-1-(pyridin-2-ylmethyl)-1H-imidazol-2-yl)propionate (5) 2-(5-(3-Nitrophenylthio)-4-isopropyl-1-pyridin-2-ylmethyl)-1H-imidazol-2-yl)ethanol (6) 5-(3-Chlorophenylthio)-4-isopropyl-1-(pyridin-3-ylmethyl)-1H-imidazole-2-carbaldehyde hydrazone (7) 2-(2-Carbamoyloxyethyl)-4-isopropyl-5-(phenylthio-1-(pyridin-4-ylmethyl)-1H-imidazole (8) 2-(2-Carbamoyloxyethyl)-5-(3,5-dimethylphenylthio)-4-isopropyl-1-methyl-1H-imidazole (9) 2-(2-Carbamoyloxyethyl)-5-(3,5-difluorophenylthio)-4-isopropyl-1-(2-phenylethyl)-1H-imidazole

(10) 2-(2-Carbamoyloxyethoxy)methyl-1-ethyl-4-isopropyl-5-phenylthio-1H-imidazole

(11) 2-(2-Carbamoyloxyethyl)-5-(3,5-dimethylphenylthio)-1-ethyl-4-isopropyl-1H-imidazole

(12) 2-(2-Carbamoyloxyethoxy)methyl-5-(3,5-difluorophenylthio)-4-isopropyl-1-(pyridin-3-ylmethyl)-1H-imidazole

(13) 2-(2-Carbamoyloxyethoxy)methyl-5-(3-nitrophenylthio)-1-ethyl-4-isopropyl-1H-imidazole

(14) 1,5-Dibenzyl-4-isopropyl-1H-imidazol-2-ylmethanol

(15) 2-Aminomethyl-5-(3-chlorophenylthio)-4-isopropyl-1-methyl-1H-imidazole

(16) 2-Azidomethyl-4-(3,5-(difluorophenylthio)-1-ethyl-5-isopropyl-1H-imidazole

(17) 4-Isopropyl-2-N-methyl(thiocarbamoyl)oxymethyl-5-phenylthio-1-(pyridin-4-ylmethyl)-1H-imidazole

(18) 5-(3,5-Dimethylphenylthio)-4-isopropyl-1-n-propyl-1H-imidazol-2-ylmethanol

(19) 2-(2-Carbamoyloxyethyl)-4-isopropyl-5-phenylthio-1-(pyridin-3-ylmethyl)-1H-imidazole

(20) 2-(2-Acetoxyethyl)-5-(3-chlorophenylthio)-4-isopropyl-1-(pyridin-4-ylmethyl)-1H-imidazole

(21) 3-(5-(3,5-Dichlorophenylthio)-4-isopropyl-1-(pyridin-2-ylmethyl)-1H-imidazol-2-yl)propanol

(22) 4-Isopropyl-2-N-methylcarbamoyloxymethyl-5-(3-fluorophenylthio)-1-(pyridin-4-ylmethyl)-1H-imidazole

(23) 4-Isopropyl-1-methyl-5-(3-fluorophenylthio)-1H-imidazol-2-ylacetonitrile

(24) 1-(5-(3,5-Dichlorophenylthio)-2-(3-carbamoyloxypropyl)-4-isopropyl-1H-imidazol-1-yl)-2-propanone

(25) 2-Carbamoyloxymethyl-5-(3,5-(difluorophenylthio)-1-fluoromethyl-4-isopropyl-1H-imidazole

(26) 2-Carbamoyloxymethyl-4-isopropyl-5-phenylthio-1-(pyridin-2-ylmethyl)-1H-imidazole

(27) 5-(3,5-Difluorophenylthio)-4-isopropyl-1-(pyridin-2-ylmethyl)-1H-imidazol-2-ylacetonitrile

(28) Methyl 3-(5-(3-chlorophenylthio)-4-isopropyl-1-(pyridin-2-ylmethyl)-1H-imidazol-2-yl)propionate

(29) 5-(3,5-Dichlorophenylthio)-4-isopropyl-1-pyridin-3-ylmethyl)-1H-imidazole-2-carbaldehyde hydrazone

(30) 5-(3,5-Difluorophenylthio)-4-isopropyl-1-methyl-1H-imidazol-2-ylmethanol

(31) 3-(1-Allyl-5-(3,5-dichlorophenylthio)-4-isopropyl-1H-imidazol-2-yl)propanol

(32) 1-Benzyl-5-(3,5-dichlorophenylthio)-4-isopropyl-1H-imidazol-2-ylmethanol

(33) 2-(2-Carbamoyloxyethoxy)methyl-5-(3,5-difluorophenylthio)-4-isopropyl-1-(pyridin-2-ylmethyl)-1H-imidazole

(34) 5-(3,5-Dichlorophenylthio)-4-isopropyl-1-(pyridin-2-ylmethyl)-1H-imidazol-2-ylmethanol

(35) 2-(2-Carbamoyloxyethyl)-5-(3,5-dimethylphenylthio)-4-isopropyl-1-(pyridin-2-ylmethyl)-1H-imidazole

(36) 2-Aminomethyl-4-isopropyl-5-(3-fluorophenylthio)-1-(pyridin-2-ylmethyl)-1H-imidazole

(37) 1-Benzyl-2-(3-carbamoyloxypropyl)-5-(3,5-difluorophenylthio)-4-isopropyl-1H-imidazole

(38) 5-(3,5-Difluorophenylthio)-2-dimethylaminomethyl-4-isopropyl-1-(pyridin-2-ylmethyl)-1H-imidazole

(39) 5-(3,5-Dichlorophenylthio)-2-(2-carbamoyloxyethyl)-4-isopropyl-1-n-propyl-1H-imidazole

(40) 2-2-(Acetoxyethyl)-5-(3,5-difluorophenylthio)-4-isopropyl-1-methyl-1H-imidazole

(41) 2-(2-Carbamoyloxyethyl)-5-(3,5-dimethylphenylthio)-1-hexyl-4-isopropyl-1H-imidazole

(42) 5-(3,5-Difluorophenylthio)-4-isopropyl-1-(2,2,2-trifluoroethyl)-1H-imidazol-2-ylmethyl

(43) 2-Carbamoyloxymethyl-5-(3,5-dimethylphenylthio)-4-isopropyl-1-(2,2,2-trifluoroethyl)-1H-imidazole

(44) 2-(2-Aminoethyl)-1-ethyl-4-isopropyl-5-phenylthio-1H-imidazol

(45) 1-Allyl-2-(3-carbamoyloxypropyl)-5-(3,5-difluorophenylthio)-4-isopropyl-1H-imidazole

(46) 2-(1-Allyl-5-(3,5-difluorophenylthio)-4-isopropyl-1H-imidazol-2-yl)ethanol

(47) 2-(5-(3-Chlorophenylthio)-4-isopropyl-1-(pyridin-2-ylmethyl)-1H-imidazol-2-ylmethoxy)ethanol

(48) α-(2-Carbamoyloxymethyl-5-(3,5-difluorophenylthio)-4-isopropyl-1H-imidazol-1-yl)acetophenone

(49) 3-(1-(4-Aminobenzyl)-5-(3,5-dichlorophenylthio)-4-isopropyl-1H-imidazol-2-yl)propanol

(50) 2-Carbamoyloxymethyl-1-cyclopropylmethyl-5-(3,5-difluorophenylthio)-4-isopropyl-1H-imidazole

(51) 2-Azidomethyl-4-(3-chlorophenylthio)-5-isopropyl-1-(pyridin-4-ylmethyl)-1H-imidazole

(52) N-(5-(3,5-Dichlorophenylthio)-1-ethyl-4-isopropyl-1H-imidazol-4-ylmethyl)acetamidine

(53) 2-(2-Carbamoyloxyethyl)-5-(3,5-difluorophenylthio)-4-isopropyl-1-methyl-1H-imidazole

(54) α-(2-(2-Hydroxyethyl)-5-(3,5-dichlorophenylthio)-4-isopropyl-1H-imidazol-1-yl)acetophenone

(55) 1-Allyl-2-(3-carbamoyloxypropyl)-5-(3,5-dimethylphenylthio)-4-isopropyl-1H-imidazole

(56) 2-(5-(3,5-Dichlorophenylthio)-4-isopropyl-1-(pyridin-3-ylmethyl))-1H-imidazole-2-carbaldehyde

(57) 5-(3,5-Dichlorophenylthio)-4-isopropyl-2-N-methylcarbamoyloxymethyl-1-(pyridin-4-ylmethyl)-1H-imidazole
(58) 2-Azidomethyl-4-isopropyl-5-phenylthio-1-(pyridin-4-ylmethyl)-1H-imidazole
(59) 2-(4-Isopropyl-5-phenylthio-1-(pyridin-4-ylmethyl)-1H-imidazol-2-ylmethoxy)ethanol
(60) 2-Acethylaminomethyl-5-(3,5-dichlorophenylthio)-4-isopropyl-1-(pyridin-4-ylmethyl)-1H-imidazole
(61) 2-(5-(3,5-Dichlorophenylthio)-1-hexyl-4-isopropyl-1H-imidazol-2-yl)ethanol
(62) 1-Ethyl-5-isopropyl-4-(3-fluorophenylthio)-1H-imidazol-2-ylmethanol
(63) 4-Isopropyl-2-N-methylthiocarbamoyloxymethyl-1-methyl-5-(3-fluorophenylthio)-1H-imidazole
(64) α-(5-(3,5-Difluorophenylthio)-2-(3-hydroxypropyl)-4-isopropyl-1H-imidazol-1-yl)acetophenone
(65) 5-(3,5-Dichlorophenylthio)-4-isopropyl-1-(3-(pyridin-4-yl)propyl-1H-imidazol-2-ylmethanol
(66) 5-(3-Chlorophenylthio)-2-dimethylaminomethyl-1-ethyl-4-isopropyl-1H-imidazole
(67) 2-(5-(3,5-Dichlorophenylthio)-4-isopropyl-1-(quinolin-3-ylmethyl)-1H-imidazol-2-yl)ethanol
(68) 2-Carbamoyloxymethyl)-4-isopropyl-5-(3-fluorophenylthio)-1-(pyridin-3-ylmethyl)-1H-imidazole
(69) 5-(3,5-Difluorophenylthio)-4-isopropyl-1-(pyridin-4-ylmethyl)-1H-imidazol-2-ylacetonitrile
(70) 2-Acetylaminomethyl-5-(3,5-difluorophenylthio)-1-ethyl-4-isopropyl-1H-imidazole
(71) 5-(3,5-Difluorophenylthio)-4-isopropyl-1-(pyridin-3-ylmethyl)-1H-imidazole-2-carbaldehyde oxime
(72) 5-(3,5-Dichlorophenylthio)-2-dimethylaminomethyl-4-isopropyl-1-methyl-1H-imidazole
(73) 2-Carbamoyloxymethyl-5-(3,5-difluorophenylthio)-1-ethyl-4-isopropyl-1H-imidazole
(74) 2-(1-Ethyl-4-isopropyl-5-(3-fluorophenylthio)-1H-imidazol-2-yl)ethanol
(75) 5-(3-Nitrophenylthio)-4-isopropyl-1-(pyridin-3-ylmethyl)-1H-imidazol-2-yl acetate
(76) 4-Isopropyl-1-methyl-5-phenylthio-1H-imidazol-2-yl acetate
(77) 1-Benzyl-2-carbamoyloxymethyl-5-(3,5-difluorophenylthio)-4-isopropyl-1H-imidazole
(78) 4-Isopropyl-2-N-methylcarbamoyloxymethyl-5-phenylthio-1-(pyridin-2-ylmethyl)-1H-imidazole
(79) 1-Benzyl-2-(2-carbamoyloxyethyl)-5-(3,5-difluorophenylthio)-4-isopropyl-1H-imidazole
(80) 2-Acetylaminomethyl-4-isopropyl-1-methyl-5-(3-fluorophenylthio)-1H-imidazole
(81) 2-(5-(3,5-Dichlorophenylthio)-4-isopropyl-1-(pyridin-4-ylmethyl)-1H-imidazole-2-carbaldehyde hydrazone
(82) 4-Isopropyl-1-methyl-5-phenylthio-1H-imidazol-2-ylmethyl acetate
(83) 2-Aminomethyl-4-(3,5-difluorophenylthio)-5-isopropyl-1-methyl-1H-imidazole
(84) 5-(3,5-Difluorophenylthio)-1-ethyl-4-isopropyl-1H-imidazole-2-carbaldehyde
(85) 4-Isopropyl-5-(3-fluorophenylthio)-1-(pyridin-2-ylmethyl)-1H-imidazol-2-yl acetate
(86) 2-(4-Isopropyl-5-(3-fluorophenylthio)-1-(pyridin-2-ylmethyl)-1H-imidazol-2-ylmethoxy)ethanol
(87) 4-Isopropyl-5-phenylthio-1-(pyridin-3-ylmethyl)-2-ureidomethyl-1H-imidazole
(88) 2-(5-(3,5-Difluorophenylthio)-1-hexyl-4-isopropyl-1H-imidazol-2-yl)ethanol
(89) 5-(3,5-Difluorophenylthio)-4-isopropyl-1-methyl-1H-imidazol-2-ylacetonitrile
(90) 2-Carbamoyloxymethyl-4-(3,5-difluorophenylthio)-1-ethyl-5-isopropyl-1H-imidazole
(91) 4-Isopropyl-2-N-methylcarbamoyloxymethyl-1-methyl-5-phenylthio-1H-imidazole
(92) 5-(3-Nitrophenylthio)-4-isopropyl-2-methanesulfonamidomethyl-1-methyl-1H-imidazole
(93) 5-(3,5-Difluorophenylthio)-4-isopropyl-1-methyl-2-N-methylthiocarbamoyloxymethyl-1H-imidazole
(94) α-(2-(2-Hydroxyethyl)-5-(3,5-difluorophenylthio)-4-isopropyl-1H-imidazol-1-yl)acetophenone
(95) 4-Isopropyl-2-N-methylcarbamoyloxymethyl-5-phenylthio-1-(pyridin-4-ylmethyl)-1H-imidazole
(96) 2-Carbamoyloxymethyl-5-(3-chlorophenylthio)-1-ethyl-4-isopropyl-1H-imidazole
(97) 2-(3-Carbamoyloxypropyl)-5-(3-nitrophenylthio)-1-ethyl-4-isopropyl-1H-imidazole
(98) 2-(4-(3-Nitrophenylthio)-1-ethyl-5-isopropyl]-1H-imidazol-2-ylmethoxy)ethanol
(99) 2-Acetylaminomethyl-5-(3-chlorophenylthio)-4-isopropyl-1-(pyridin-3-ylmethyl)-1H-imidazole
(100) 1-Ethyl-4-isopropyl-5-(3-fluorophenylthio)-1H-imidazole-2-carbaldehyde hydrazone
(101) 2-Dimethylaminomethyl-4-isopropyl-5-(3-fluorophenylthio)1-(pyridin-3-ylmethyl)-1H-imidazole
(102) 5-(3,5-Dichlorophenylthio)-4-isopropyl-2-N-methylcarbamoyloxymethyl-1-(pyridin-2-ylmethyl)-1H-imidazole
(103) 1,4-Dibenzyl-5-isopropyl-1H-imidazol-2-ylmethanol
(104) 5-(3,5-Difluorophenylthio)-4-isopropyl-1-methyl-1H-imidazol-2-ylmethyl acetate
(105) 2-Carbamoyloxymethyl-4-(3,5-difluorophenylthio)-5-isopropyl-1-methyl-1H-imidazole
(106) 5-(3,5-Dichlorophenylthio)-1-ethyl-4-isopropyl-2-N-methylaminomethyl-1H-imidazole
(107) 2-2-(Acetoxyethyl)-4-isopropyl-5-phenylthio-1-(pyridin-4-ylmethyl)-1H-imidazole
(108) 2-(5-(3,5-Dichlorophenylthio)-4-isopropyl-1-methyl)-1H-imidazole-2 -carbaldebyde hydrazone
(109) 1-(2-Aminobenzyl)-5-(3,5-dichlorophenylthio)-2-(2-carbamoyloxyethyl)-4-isopropyl-1H-imidazole
(110) 2-Carbamoyloxymethyl-5-(3-chlorophenylthio)-4-isopropyl-1-(pyridin-3-ylmethyl)-1H-imidazole
(111) 2-(2-Carbamoyloxyethyl)-5-(3,5-difluorophenylthio)-1-hexyl-4-isopropyl-1H-imidazole
(112) 1-(2-(2-Hydroxyethyl)-5-(3,5-dimethylphenylthio)-4-isopropyl-1H-imidazol-1-yl)-2-propanone
(113) 5-(3,5-Dichlorophenylthio)-1-n-butyl-2-(2-carbamoyloxyethyl)-4-isopropyl-1H-imidazole
(114) 2-(5-(3,5-Difluorophenylthio)-4-isopropyl-1-methyl-1H-imidazol-2-ylmethoxy)ethanol
(115) 2-(2-Carbamoyloxyethyl)-5-(3-nitrophenylthio)-1-ethyl-4-isopropyl-1H-imidazole
(116) 1-n-Butyl-5-(3,5-dimethylphenylthio)-4-isopropyl-1H-imidazol-2-ylmethanol
(117) 1-(2-Carbamoyloxyethyl)-2-(3-carbamoyloxypropyl)-5-(3,5-difluorophenylthio)-4-isopropyl-1H-imidazole
(118) 2-(4-Isopropyl-5-(3-fluorophenylthio)-I-(pyridin-3-ylmethyl)-1H-imidazol-2-yl)ethanol
(119) 4-Isopropyl-1-methyl-5-(3-fluorophenylthio-1H-imidazole-2-carbaldehyde hydrazone
(120) 1-n-Butyl-5-(3,5-difluorophenylthio)-4-isopropyl-1H-imidazol-2-ylmethanol
(121) 2-(5-(3,5-Dichlorophenylthio)-1,4-diisopropyl-1H-imidazol-2-yl)ethanol
(122) 5-(3,5-Difluorophenylthio)-4-isopropyl-2-methanesulfonamidomethyl-1-methyl-1H-imidazole
(123) 2-(3-Carbamoyloxypropyl)-5-(3,5-Difluorophenylthio)-4-isopropyl-1-(3-phenylpropyl)-1H-imidazole (124) 2-(2-Carbamoyloxyethyl)-5-(3,5-difluorophenylthio)-4-isopropyl-1-(pyridin-2-ylmethyl)-1H-imidazole
(125) 5-(3,5-Dichlorophenylthio)-2-carbamoyloxymethyl-4-isopropyl-1-n-propyl-1H-imidazole
(126) 4-(3,5-Dichlorophenylthio)-2-carbamoyloxymethyl-1-ethyl-5-isopropyl-1H-imidazole
(127) 2-(1-Ethyl-4-isopropyl-5-phenylthio-1H-imidazol-2-yl)ethanol
(128) 5-(3-Chlorophenylthio)-4-isopropyl-2-N-methylthiocarbamoyloxymethyl-1-(pyridin-4-ylmethyl)-1H-imidazole
(129) 2-(5-(3,5-Dimethyl phenylthio)-1-fluoromethyl-4-isopropyl-1H-imidazol-2-yl)ethanol
(130) 2-Aminomethyl-4-(3,5-dichlorophenylthio)-1-ethyl-5-isopropyl-1H-imidazole
(131) 2-(2-Carbamoyloxyethoxy)methyl-5-(3-nitrophenylthio)-4-isopropyl-1-(pyridin-4-ylmethyl)-1H-imidazole
(132) 2-Azidomethyl-5-(3,5-dichlorophenylthio)-4-isopropyl-1-(pyridin-4-ylmethyl)-1H-imidazole
(133) 2-(2-Aminoethyl)-5-(3,5-difluorophenylthio)-4-isopropyl-1-(pyridin-4-ylmethyl)-1H-imidazole
(134) 2-(3-Carbamoyloxypropyl)-5-(3,5-difluorophenylthio)-4-isopropyl-1-methyl-1H-imidazole
(135) 5-(3-Nitrophenylthio)-4-isopropyl-1-methyl-2-N-methylcarbamoyloxymethyl-1H-imidazole
(136) 5-(3-Chlorophenylthio)-4-isopropyl-1-(pyridin-3-ylmethyl)-1H-imidazol-2-ylmethyl acetate
(137) 5-(3,5-Difluorophenylthio)-4-isopropyl-1-methyl-1H-imidazol-2-yl acetate
(138) N-(5-(3-Chlorophenylthio)-4-isopropyl-1-(pyridin-4-ylmethyl)-1H-imidazol-4-ylmethyl)acetamidine
(139) 4-Isopropyl-5-(3-fluorophenylthio)-1-(pyridin-3-ylmethyl)-1H-imidazole-2-carbaldehyde hydrazone
(140) 5-(3,5-Dichlorophenylthio)-4-isopropyl-1-methyl-1H-imidazol-2-ylacetonitrile
(141) 2-(5-(3,5-Dichlorophenylthio)-1-ethyl-4-isopropyl-1-imidazol-2-ylmethoxy)ethyl acetate
(142) 2-(2-Carbamoyloxyethyl)-5-(3,5-dimethylphenylthio)-4-isopropyl-1-n-propyl-1H-imidazole
(143) 1-(3-Aminobenzyl)-5-(3,5-dichlorophenylthio)-4-isopropyl-1-imidazol-2-ylmethanol
(144) 5-(3-Nitrophenylthio)-4-isopropyl-2-N-methylaminomethyl-3-(pyridin-2-ylmethyl)-1H-imidazole
(145) 3-(5-(3,5-Difluorophenylthio)-4-isopropyl-1-(5,6-dihydro-6-oxopyridin-3-ylmethyl)-1H-imidazol-2-yl)propanol
(146) 3-(5-(3,5-Dichlorophenylthio)-4-isopropyl-1-(2-phenylethyl)-1H-imidazol-2-yl)propanol
(147) N-(5-(3,5-Dichlorophenylthio)-4-isopropyl-1-(pyridin-4-ylmethyl)-1H-imidazol-4-ylmethyl)acetamidine
(148) 5-(3,5-Dichlorophenylthio)-1-(2-carbamoyloxyethyl)-2-carbamoyloxymethyl-4-isopropyl-1H-imidazole
(149) 5-(3,5-Dichlorophenylthio)-2-carbamoyloxymethyl-4-isopropyl-1-(2-(pyridin-4-yl)ethyl)-1H-imidazole
(150) 2-(2-Azidoethyl)-5-(3-chlorophenylthio)-1-ethyl-4-isopropyl-1H-imidazole
(151) N-(4-Isopropyl-5-(3-fluorophenylthio)-1-(pyridin-2-ylmethyl)-1H-imidazol-4-ylmethyl)acetamide
(152) 2-Carbamoyloxymethyl-5-(3,5-difluorophenylthio)-4-isopropyl-1-(2,2,2-trifluoroethyl)-1H-imidazole
(153) N-(1-Ethyl-4-isopropyl-5-phenylthio-1H-imidazol-4-ylmethyl)acetamidine
(154) 5-(3,5-Dichlorophenylthio)-2-diaminomethyleneaminomethyl-4-isopropyl-1-(pyridin-4-ylmethyl)-1H-imidazole
(155) 5-(3,5-Dichlorophenylthio)-2-dimethylaminomethyl-4-isopropyl-1-(pyridin-3-ylmethyl)-1H-imidazole
(156) 5-(3,5-Difluorophenylthio)-4-isopropyl-1-(2-phenylethyl)-1H-imidazol-2-ylmethanol
(157) α-(2-(2-Carbamoyloxyethyl)-5-(3,5-dimethylphenylthio)-4-isopropyl-1H-imidazol-1-yl)acetophenone
(158) 2-Azidomethyl-4-(3-nitrophenylthio)-1-ethyl-5-isopropyl-1H-imidazol
(159) 5-(3,5-Difluorophenylthio)-4-isopropyl-1-methyl-1H-imidazol-2-ylmethanol
(160) 5-(3-Nitrophenylthio)-4-isopropyl-1-(pyridin-3-ylmethyl)-1H-imidazole-2-carbaldehyde hydrazone
(161) 2-Carbamoyloxymethyl-1-ethyl-5-isopropyl-4-phenylthio-1H-imidazol
(162) 2-(1-(2-Aminobenzyl)-5-(3,5-difluorophenylthio)-4-isopropyl-1H-imidazol-2-yl)ethanol
(163) 1-Cyclopropylmethyl-5-(3,5-dimethylphenylthio)-4-isopropyl-1H-imidazol-2-ylmethanol
(164) 2-(5-(3,5-Dimethylphenylthio)-4-isopropyl-1-methyl-1H-imidazol-2-yl)ethanol
(165) α-(5-(3,5-Dichlorophenylthio)-2-carbamoyloxymethyl-4-isopropyl-1H-imidazol-1-yl)acetophenone
(166) 2-Acetylaminomethyl-5-(3,5-difluorophenylthio)-4-isopropyl-1-methyl-11-1-imidazole
(167) 2-(3-Carbamoyloxypropyl)-5-(3,5-difluorophenylthio)-4-isopropyl-1-(pyridin-3-ylmethyl)-1H-imidazole
(168) Methyl 3-(5-(3,5-dichlorophenylthio)-4-isopropyl-1-(pyridin-4-ylmethyl)-1H-imidazol-2-yl)propionate
(169) 5-(3,5-Dichlorophenylthio)-4-isopropyl-1-(2,2,2-trifluoroethyl)-1H-imidazol-2-ylmethanol
(170) 2-(3-Carbamoyloxypropyl)-5-(3,5-difluorophenylthio)-4-isopropyl-1-(2-methylpyridin-3-ylmethyl)-1H-imidazole
(171) N-(4-Isopropyl-5-phenylthio-1-(pyridin-4-ylmethyl)-1H-imidazol-4-ylmethyl)acetamidine
(172) 1-(3-Aminobenzyl)-2-(2-carbamoyloxyethyl)-5-(3,5-difluorophenylthio)-4-isopropyl-1H-imidazole
(173) 5-(3,5-Difluorophenylthio)-4-isopropyl-1-(pyridin-3-ylmethyl)-1H-imidazol-2-yl acetate
(174) 1-(2-Aminobenzyl)-5-(3,5-Difluorophenylthio)-4-isopropyl-1H-imidazol-2-ylmethanol
(175) 2-(2-Carbamoyloxyethyl)-5-(3-chlorophenylthio)-4-isopropyl-1-(pyridin-4-ylmethyl)-1H-imidazole
(176) 2-(2-Azidoethyl)-5-(3-nitrophenylthio)-4-isopropyl-1-(pyridin-4-ylmethyl)-1H-imidazole
(177) 2-(3-Carbamoyloxypropyl)-1-cyclopropylmethyl-5-(3,5-difluorophenylthio)-4-isopropyl-1H-imidazole
(178) 2-(2-Carbamoyloxyethyl)-1-ethyl-4-isopropyl-5-(3-fluorophenylthio)-1H-imidazole
(179) 5-(3-Chlorophenylthio)-4-isopropyl-1-(pyridin-2-ylmethyl)-1H-imidazole-2-carbaldehyde hydrazone
(180) 2-Acetylaminomethyl-5-(3-chlorophenylthio)-4-isopropyl-1-(pyridin-2-ylmethyl)-1H-imidazole
(181) 2-Carbamoyloxymethyl-4-isopropyl-5-(3-fluorophenylthio)-1-(pyridin-4-ylmethyl)-1H-imidazole
(182) 2-(5-(3,5-Dimethylphenylthio)-4-isopropyl-1-n-propyl-1H-imidazol-2-yl)ethanol
(183) N-(4-Isopropyl-1-methyl-5-(3-fluorophenylthio)-1H-imidazol-4-ylmethyl)acetamidine
(184) 2-(2-Aminoethyl)-4-isopropyl-5-(3-fluorophenylthio)-1-(pyridin-3-ylmethyl)-1H-imidazole
(185) 2-Carbamoyloxymethyl-5-(3,5-difluorophenylthio)-4-isopropyl-1-(pyridin-3-ylmethyl)-1H-imidazole
(186) N-(5-(3,5-Dichlorophenylthio)-4-isopropyl-1-(pyridin-2-ylmethyl)-1H-imidazol-4-ylmethyl)acetamidine (187) 5-(3,5-Dimethylphenylthio)-1-fluoromethyl-4-isopropyl-1H-imidazol-2-ylmethanol
(188) 2-(2-Acetoxyethyl)-5-(3,5-difluorophenylthio)-4-isopropyl-1-(pyridin-3-ylmethyl)-1H-imidazole
(189) 4-(3,5-Dimethylphenylthio)-5-isopropyl-1-methyl-1H-imidazol-2-ylmethanol
(190) 5-(3-Nitrophenylthio)-4-isopropyl-1-methyl-2-N-methylaminomethyl-1H-imidazole
(191) 5-(3-Chlorophenylthio)-4-isopropyl-1-methyl-1H-imidazol-2-yl acetate
(192) 2-(2-Carbamoyloxyethyl)-5-(3-chlorophenylthio)-4-isopropyl-1-(pyridin-3-ylmethyl)-1H-imidazole
(193) 2-Carbamoyloxymethyl-5-(3,5-difluorophenylthio)-1-hexyl-4-isopropyl-1H-imidazole
(194) 2-Azidomethyl-5-(3-nitrophenylthio)-4-isopropyl-1-(pyridin-3-ylmethyl)-1H-imidazole
(195) 2-(5-(3,5-Dichlorophenylthio)-1-(2-carbamoyloxyethyl)-4-isopropyl-1H-imidazol-2-yl)ethanol
(196) 5-(3,5-Dichlorophenylthio)-4-isopropyl-1-(pyridin-3-ylmethyl)-2-ureidomethyl-1H-imidazole
(197) 1-(2-(2-Hydroxyethyl)-5-(3,5-difluorophenylthio)-4-isopropyl-1H-imidazol-2-yl)-2-propanone
(198) 5-(3,5-Dichlorophenylthio)-1-cyclopropylmethyl-4-isopropyl-1H-imidazol-2-ylmethanol
(199) 1-Allyl-2-carbamoyloxymethyl-5-(3,5-dimethylphenylthio)-4-isopropyl-1H-imidazole
(200) 5-(3,5-Dichlorophenylthio)-2-(3-carbamoyloxypropyl)-4-isopropyl-1-methyl-1H-imidazole
(201) 2-Carbamoyloxymethyl-4-isopropyl-1-methyl-5-phenylthio-1H-imidazole
(202) 3-(1-Cyclopropylmethyl-5-(3,5-difluorophenylthio)-4-isopropyl-1H-imidazol-2-yl)propanol
(203) 5-(3,5-Difluorophenylthio)-4-isopropyl-1-(pyridin-2-ylmethyl)-2-ureidomethyl-1H-imidazole
(204) 5-(3,5-Dichlorophenylthio)-4-isopropyl-1-(pyridin-3-ylmethyl)-1H-imidazol-2-ylmethyl acetate
(205) 2-Carbamoyloxymethyl-5-(3,5-difluorophenylthio)-4-isopropyl-1-methyl-1H-imidazole
(206) 5-(3,5-Dichlorophenylthio)-2-(3-carbamoyloxypropyl)-4-isopropyl-1-(2-phenylethyl)-1H-imidazole
(207) 2-(2-Azidoethyl)-5-(3,5-dichlorophenylthio)-4-isopropyl-1-(pyridin-3-ylmethyl)-1H-imidazole
(208) 4-Isopropyl-2-N-methylcarbamoyloxymethyl-1-methyl-5-(3-fluorophenylthio)-1H-imidazole
(209) 2-(4-Isopropyl-5-phenylthio-1-(pyridin-4-ylmethyl)-1H-imidazol-2-yl)ethanol
(210) 3-(5-(3,5-Dichlorophenylthio)-4-isopropyl-1-(5,6-dihydro-6-oxopyridin-3-ylmethyl)-1H-imidazol-2-yl)propanol
(211) 2-Diaminomethyleneaminomethyl-5-(3,5-difluorophenylthio)-4-isopropyl-1-(pyridin-2-ylmethyl)-1H-imidazole
(212) 2-(4-Isopropyl-5-phenylthio-1-(pyridin-3-ylmethyl)-1H-imidazol-2-ylmethoxy)ethyl acetate
(213) 2-Diaminomethyleneaminomethyl-5-(3-nitrophenylthio)-4-isopropyl-1-(pyridin-3-ylmethyl)-1H-imidazole
(214) 5-(3-Chlorophenylthio)-1-ethyl-4-isopropyl-2-ureidomethyl-1H-imidazole
(215) 3-(1,4-Diisopropyl-5-(3,5-difluorophenylthio)-1H-imidazol-2-yl)propanol
(216) 2-(2-Aminoethyl)-5-(3-chlorophenylthio)-4-isopropyl-1-(pyridin-2-ylmethyl)-1H-imidazole
(217) 1-(3-Aminobenzyl)-5-(3,5-difluorophenylthio)-4-isopropyl-1H-imidazol-2-ylmethanol
(218) 2-(5-(3,5-Difluorophenylthio)-4-isopropyl-1-(3-(pyridin-4-yl)propyl)-1H-imidazol-2-yl)ethanol
(219) 2-(4-Isopropyl-5-(3-fluorophenylthio)-1-(pyridin-4-ylmethyl))-1H-imidazole-2-carbaldehyde
(220) 3-(1-(2-Aminobenzyl)-5-(3,5-difluorophenylthio)-4-isopropyl-1H-imidazol-2-yl)propanol
(221) 2-(2-Carbamoyloxyethoxy)i-methyl-5-(3,5-difluorophenylthio)-4-isopropyl-ethyl-1H-imidazole
(222) 1-Allyl-5-(3,5-difluorophenylthio)-4-isopropyl-1H-imidazol-2-ylmethanol
(223) 2-(1-Benzyl-5-(3,5-difluorophenylthio)-4-isopropyl-1H-imidazol-2-yl)ethanol
(224) 2-(3-Carbamoyloxypropyl)-5-(3,5-difluorophenylthio)-4-isopropyl-1-(5,6-dihydro-6-oxopyridin-3-ylmethyl)-1H-imidazole
(225) 5-(3,5-Dichlorophenylthio)-2-(3-carbamoyloxypropyl)-1-hexyl-4-isopropyl-1H-imidazole
(226) 2-(2-Acetoxyethyl)-5-isopropyl-5-3-fluorophenylthio)-1-(pyridin-2-ylmethyl)-1H-imidazole
(227) 5-(3,5-Dichlorophenylthio)-1-ethyl-4-isopropyl-1H-imidazole-2-carbaldehyde
(228) 5-(3,5-Dichlorophenylthio)-1-ethyl-4-isopropyl-1H-imidazol-2-yl acetate
(229) 2-Acetylaminomethyl-5-(3,5-dichlorophenylthio)-4-isopropyl-1-methyl-1H-imidazole
(230) 2-(2-Acetoxyethyl)-4-isopropyl-5-(3-fluorophenylthio-1-(pyridin-4-ylmethyl)-1H-imidazole
(231) 2-Carbamoyloxymethyl-4-(3,5-dimethylpthenylthio)-5-isopropyl-1-(pyridin-4-ylmethyl)-1H-imidazole
(232) 2-(2-Azidoethyl)-4-isopropyl-5-phenylthio-1-(pyridin-3-ylmethyl)-1H-imidazole
(233) N-(5-(3,5-Dichlorophenylthio)-4-isopropyl-1-methyl-1H-imidazol-4-ylmethyl)acetamidine
(234) 5-(3-Nitrophenylthio 4-isopropyl-1-(pyridin-3-ylmethyl)-2-ureidomethyl-1H-imidazole
(235) 2-Aminomethyl-4-isopropyl-5-phenylthio-1-(pyridin-4-ylmethyl)-1H-imidazole
(236) 3-(5-(3,5-Dimethylphenylthio)-4-isopropyl-1-(pyridin-4-ylmethyl)-1H-imidazol-2-yl)propanol
(237) 2-(5-(3,5-Difluorophenylthio)-4-isopropyl-1-(2-(pyridin-4-yl)ethyl)-1H-imidazol-2-yl)ethanol
(238) 4-(3,5-Dichlorophenylthio)-5-isopropyl-1-methyl-1H-imidazol-2-ylmethyl acetate
(239) 5-(3,5-Dichlorophenylthio)-1,2-bis-(2-carbamoyloxyethyl)-4-isopropyl-1H-imidazole
(240) 2-(5-(3,5-Difluorophenylthio)-4-isopropyl-1-(pyridin-3-ylmethyl)-1H-imidazol-2-yl)ethanol
(241) 5-(3,5-Difluorophenylthio)-1-ethyl-4-isopropyl-1H-imidazole-2-carbaldehyde hydrazone
(242) 4-Isopropyl-2-N-methylcarbamoyloxymethyl-1-methyl-5-phenylthio-1H-imidazole
(243) 2-Carbamoyloxymethyl-5-(3,5-difluorophenylthio)-4-isopropyl-1-(pyridin-4-ylmethyl)-1H-imidazole
(244) 5-(3,5-Dichlorophenylthio)-2-carbamoyloxymethyl-1-fluoromethyl-4-isopropyl-1H-imidazole
(245) 4-(3,5-Dimethylphenylthio)-1-fluoromethyl-5-isopropyl-1H-imidazol-2-ylmethanol
(246) 2-Aminomethyl-5-(3-chlorophenylthio)-4-isopropyl-1-(pyridin-2-ylmethyl)-1H-imidazole
(247) 1-Ethyl-4-isopropyl-5-(3-fluorophenylthio)-1H-imidazole-2-carbaldehyde
(248) 5-(3-Nitrophenylthio)-4-isopropyl-1-(pyridin-3-ylmethyl)-1H-imidazol-2-ylacetonitrile
(249) 5-(3,5-Dichlorophenylthio)-4-isopropyl-2-N-methylthiocarbamoyloxymethyl-1-(pyridin-4-ylmethyl)-1H-imidazole
(250) 2-(5-(3,5-Difluorophenylthio)-1,4-diisopropyl-1H-imidazol-2-yl)ethanol (251) 5-(3,5-Dichlorophenylthio)-2-(3-carbamoyloxypropyl)-4-isopropyl-1-(pyridin-2-ylmethyl)-1H-imidazole
(252) Methyl 3-(4-isopropyl-5-(3-fluorophenylthio)-1-(pyridin-3-ylmethyl)-1H-imidazol-2-yl)propionate
(253) 2-(5-(3,5-Dimethylphenylthio)-1-ethyl-4-isopropyl-1H-imidazol-2-yl)ethanol
(254) 5-(3,5-Dichlorophenylthio)-1-ethyl-4-isopropyl-2-N-methylthiocarbamoyloxymethyl-1H-imidazole
(255) N-(4-Isopropyl-5-phenylthio-1-(pyridin-2-ylmethyl)-1H-imidazol-4-ylmethyl)acetamidine
(256) 5-(3-Nitrophenylthio)-4-isopropyl-2-N-methylcarbamoyl-oxymethyl-1-(pyridin-4-ylmethyl)-1H-imidazole
(257) 2-Aminomethyl-5-isopropyl-1-methyl-4-phenylthio-1H-imidazole
(258) 2-Carbamoyloxymethyl-4-(3-chlorophenylthio)-5-isopropyl-1-methyl-1H-imidazole
(259) 4-Isopropyl-1-methyl-5-(3-fluorophenylthio)-1H-imidazol-2-yl acetate
(260) 5-(3-Nitrophenylthio)-4-isopropyl-1-(pyridin-4-ylmethyl)-1H-imidazole-2-carbaldehyde hydrazone
(261) 2-(2-Carbamoyloxyethyl)-4-isopropyl-5-phenylthio-1-(pyridin-2-ylmethyl)-1H-imidazole
(262) 2-(3-Carbamoyloxypropyl)-5-(3-nitrophenylthio)-4-isopropyl-1-(pyridin-4-ylmethyl)-1H-imidazole
(263) 4-Isopropyl-2-N-methylaminomethyl-1-methyl-5-(3-fluorophenylthio)-1H-imidazole
(264) 2-(4-(3-Chlorophenylthio)-5-isopropyl-1-methyl-1H-imidazol-2-ylmethoxy)ethanol
(265) Methyl 3-(5-(3,5-dichlorophenylthio)-4-isopropyl-1-(pyridin-2-ylmethyl)-1H-imidazol-2-yl)propionate
(266) 1-(5-(3,5-Dichlorophenylthio)-2-hydroxymethyl-4-isopropyl-1H-imidazol-1-yl)-2-propanone
(267) 2-(1-(2-Carbamoyloxyethyl)-5-(3,5-difluorophenylthio)-4-isopropyl-1H-imidazol-2-yl)ethanol
(268) 4-(3-Chlorophenylthio)-1-ethyl-5-isopropyl-1H-imidazol-2-ylmethyl acetate
(269) 5-(3,5-Dichlorophenylthio)-2-dimethylaminomethyl-4-isopropyl-1-(pyridin-2-ylmethyl)-1H-imidazole
(270) 2-Aminomethyl-4-isopropyl-5-phenylthio-1-(pyridin-2-ylmethyl)-1H-imidazole
(271) 5-(3,5-Dichlorophenylthio)-4-isopropyl-1-(pyridin-2-ylmethyl)-2-ureidomethyl-1H-imidazole
(272) 2-(5-(3,5-Dichlorophenylthio)-4-isopropyl-1-methyl-1H-imidazol-2-ylmethoxy)ethyl acetate
(273) 5-(3-Nitrophenylthio)-4-isopropyl-1-(pyridin-2-ylmethyl)-1H-imidazole-2-carbaldehyde hydrazone
(274) N-(1-Ethyl-4-isopropyl-5-(3-fluorophenylthio)-1H-imidazol-4-ylmethyl)acetamidine
(275) 5-(3-Chlorophenylthio)-1-ethyl-4-isopropyl-1H-imidazole-2-carbaldehyde
(276) 5-(3,5-Dichlorophenylthio)-4-isopropyl-1-(pyridin-3-ylmethyl)-1H-imidazol-2-ylacetonitrile
(277) 1-(2-Aminobenzyl)-2-(3-carbamoyloxypropyl)-5-(3,5-difluorophenylthio)-4-isopropyl-1H-imidazole
(278) 2-Carbamoyloxymethyl-5-(3-chlorophenylthio)-4-isopropyl-1-(pyridin-4-ylmethyl)-1H-imidazole
(279) 5-(3-Nitrophenylthio)-1-ethyl-4-isopropyl-2-N-methylthiocarbamoyloxymethyl-1H-imidazole
(280) 5-(3-Chlorophenylthio)-4-isopropyl-2-N-methylaminomethyl-1-(pyridin-4-ylmethyl)-1H-imidazole
(281) 1-(4-Aminobenzyl)-5-(3,5-dichlorophenylthio)-2-(2-carbamoyloxyethyl)-4-isopropyl-1H-imidazole
(282) 4-Isopropyl-1-methyl-5-phenylthio-1H-imidazol-2-ylacetonitrile
(283) 2-(4-(3,5-Difluorophenylthio)-5-isopropyl-1-(pyridin-4-ylmethyl)-1H-imidazol-2-ylmethoxy)ethanol
(284) 5-(3,5-Dichlorophenylthio)-4-isopropyl-1-methyl-2-ureidomethyl-1H-imidazole
(285) 1-n-Butyl-5-(3,5-difluorophenylthio)-4-isopropyl-1H-imidazol-2-ylmethanol
(286) 2-(2-Carbamoyloxyethoxy)methyl-4-isopropyl-5-phenylthio-1-(pyridin-2-ylmethyl)-1H-imidazole
(287) 2-(2-Carbamoyloxyethyl)-4-isopropyl-1-methyl-5-(3-fluorophenylthio)-1H-imidazole
(288) 2-(5-(3-Nitrophenylthio)-4-isopropyl-1-(pyridin-2-ylmethyl))-1H-imidazole-2-carbaldehyde oxime
(289) 5-(3-Chlorophenylthio)-4-isopropyl-2-N-methylaminoethyl-1-(pyridin-2-ylmethyl)-1H-imidazole
(290) 5-(3-Chlorophenylthio)-2-dimethylaminomethyl-4-isopropyl-1-(pyridin-3-ylmethyl)-1H-imidazole
(291) 5-(3,5-Dichlorophenylthio)-4-isopropyl-2-N-methylaminomethyl-1-(pyridin-4-ylmethyl)-1H-imidazole
(292) 2-(2-Azidoethyl)-5-(3-nitrophenylthio)-1-ethyl-4-isopropyl-1H-imidazole
(293) 5-(3,5-Dimethylphenylthio)-4-isopropyl-1(2,2,2-trifluoroethyl)-1H-imidazol-2-ylmethanol
(294) 1-n-Butyl-2-carbamoyloxymethyl-5-(3,5-dimethylphenylthio)-4-isopropyl-1H-imidazole
(295) 2-(5-(3,5-Difluorophenylthio)-4-isopropyl-1-methyl-1H-imidazol-2-ylmethoxy)ethyl acetate
(296) 2-Diaminomethyleneaminomethyl-4-isopropyl-1-methyl-5-phenylthio-1H-imidazole
(297) 4-(3,5-Difluorophenylthio)-5-isopropyl-1-(pyridin-4-ylmethyl)-1H-imidazol-2-ylmethyl acetate
(298) 2-Carbamoyloxymethyl-4-(3,5-difluorophenylthio)-1-fluoromethyl-5-isopropyl-1H-imidazole
(299) 2-Carbamoyloxymethyl-4-(3-nitrophenylthio)-1-ethyl-5-isopropyl-1H-imidazole
(300) N-(4-Isopropyl-1-methyl-5-phenylthio-1H-imidazol-4-ylmethyl)acetamidine
(301) N-(4-Isopropyl-5-(3-fluorophenylthio)-I-(pyridin-3-ylmethyl)-1H-imidazol-4-ylmethyl)acetamidine
(302) 2-(3-Carbamoyloxypropyl)-1-ethyl-4-isopropyl-5-(3-fluorophenylthio)-1H-imidazole
(303) 2-Diaminomethyleneaminomethyl-5-(3,5-Difluorophenylthio)-4-isopropyl-1-methyl-1H-imidazole
(304) 5-(3-Chlorophenylthio)-4-isopropyl-2-N-methyl(thiocarbamoyl)oxymethyl-1-(pyridin-2-ylmethyl)-1H-imidazole
(305) 3-(5-(3-Nitrophenylthio)-4-isopropyl-1-(pyridin-4-ylmethyl)-1H-imidazol-2-yl)propanol
(306) 2-(5-(3-Chlorophenylthio)-1-ethyl-4-isopropyl)-1H-imidazole-2-carbaldehyde oxime
(307) 2-Acetylaminomethyl-5-(3,5-dichlorophenylthio)-4-isopropyl-1-(pyridin-2-ylmethyl)-1H-imidazole
(308) 2-(4-Isopropyl-5-(3-fluorophenylthio)-1-(pyridin-3-ylmethyl))-1H-imidazole-2-carbaldehyde
(309) 2-(5-(3-Chlorophenylthio)-4-isopropyl-1-methyl)-1H-imidazole,-2-carbaldehyde-hydrazone
(310) 2-Carbamoyloxymethyl-1-cyclopropylmethyl-5-(3,5-dimethylphenylthio)-4-isopropyl-1H-imidazole
(311) 4-(3-Chlorophenylthio)-5-isopropyl-1-(pyridin-4-ylmethyl)-1H-imidazol-2-ylmethyl acetate
(312) 3-(5-(3-Nitrophenylthio)-4-isopropyl-1-(pyridin-2-ylmethyl)-1H-imidazol-2-yl)propanol
(313) 2-(2-Aminoethyl)-5-(3-nitrophenylthio)-4-isopropyl-1-(pyridin-4-ylmethyl)-1H-imidazole
(314) 5-(3-Nitrophenylthio)-4-isopropyl-1-(pyridin-4-ylmethyl)-1H-imidazol-2-yl acetate
(315) 4-Isopropyl-5-(3-fluorophenylthio)-1-(pyridin-4-ylmethyl)-1H-imidazol-2-yl acetate (316) 5-(3,5-Difluorophenylthio)-4-isopropyl-1-(pyridin-3-ylmethyl)-2-ureidomethyl-1H-imidazole
(317) 2-(4-Isopropyl-5-(3-fluorophenylthio)-1-(pyridin-3-ylmethyl)-1H-imidazol-2-ylmethoxy)ethyl acetate
(318) 1-Ethyl-4-isopropyl-5-(3-fluorophenylthio)-2-ureidomethyl-1H-imidazole
(319) 2-(5-(3,5-Dichlorophenylthio)-4-isopropyl-1-(3-phenylpropyl)-1H-imidazol-2-yl)ethanol
(320) 5-(3,5-Dichlorophenylthio)-2-carbamoyloxymethyl-4-isopropyl-1-(2-phenylethyl)-1H-imidazole
(321) 5-(3,5-Difluorophenylthio)-1-fluoromethyl-4-isopropyl-1H-imidazol-2-ylmethanol
(322) 2-Aminomethyl-4-(3-nitrophenylthio)-5-isopropyl-1-methyl-1H-imidazole
(323) 5-(3,5-Difluorophenylthio)-1-ethyl-4-isopropyl-1H-imidazol-2-ylacetonitrile
(324) 2-Carbamoyloxymethyl-5-(3,5-dimethylphenylthio)-1-fluoromethyl-4-isopropyl-1H-imidazole
(325) 4-Isopropyl-5-phenylthio-1-(pyridin-4-ylmethyl)-1H-imidazol-2-ylacetonitrile
(326) 1-Benzyl-4-(3,5-dimethylphenylthio)-5-isopropyl-1H-imidazol-2-ylmethanol
(327) 2-(4-Isopropyl-5-(3-fluorophenylthio)-1-(pyridin-2-ylmethyl))-1H-imidazole-2-carbaldehyde
(328) 3-(4-Isopropyl-5-(3-fluorophenylthio)-1-(pyridin-3-ylmethyl)-1H-imidazol-2-yl)propanol
(329) 1-(3-Aminobenzyl)-2-(3-carbamoyloxypropyl)-5-(3,5-difluorophenylthio)-4-isopropyl-1H-imidazole
(330) 2-(1-Ethyl-5-isopropyl-4-(3-fluorophenylthio))-1H-imidazole-2-carbaldehyde
(331) 5-(3,5-Dichlorophenylthio)-2-(3-carbamoyloxypropyl)-4-isopropyl-1-(2-methylpyridin-3-ylmethyl)-1H-imidazole
(332) 1-Ethyl-4-isopropyl-2-methanesulfonamidomethyl-5-(3-fluorophenylthio)-1H-imidazole
(333) 2-Azidomethyl-4-isopropyl-5-phenylthio-1-(pyridin-3-ylmethyl)-1H-imidazole
(334) 5-(3-Chlorophenylthio)-2-diaminomethyleneaminomethyl-4-isopropyl-1-(pyridin-3-ylmethyl)-1H-imidazole
(335) 5-(3-Chlorophenylthio)-4-isopropyl-1-(pyridin-4-ylmethyl)-2-ureidomethyl-1H-imidazole
(336) 5-(3,5-Dichlorophenylthio)-2-(2-carbamoyloxyethyl)-4-isopropyl-1-(pyridin-3-ylmethyl)-1H-imidazole
(337) 2-Carbamoyloxymethyl-4-(3,5-dimethylphenylthio)-1-ethyl-5-isopropyl-1H-imidazole
(338) 2-(4-Isopropyl-5-phenylthio-1-(pyridin-4-ylmethyl)-1H-imidazole-2-carbaldehyde hydrazone
(339) 5-(3,5-Dichlorophenylthio)-4-isopropyl-1-(pyridin-4-ylmethyl)-2-ureidomethyl-1H-imidazole
(340) 5-(3-Chlorophenylthio)-4-isopropyl-1-(pyridin-3-ylmethyl)-1H-imidazol-2-ylacetonitrile
(341) 5-(3-Chlorophenylthio)-2-dimethylaminomethyl-4-isopropyl-1-(pyridin-4-ylmethyl)-1H-imidazole
(342) 2-(5-(3-Chlorophenylthio)-4-isopropyl-1-(pyridin-2-ylmethyl)-1H-imidazol-2-ylmethoxy)ethyl acetate
(343) 2-Acetylaminomethyl-5-(3-chlorophenylthio)-4-isopropyl-1-(pyridin-4-ylmethyl)-1H-imidazole
(344) 3-(1-(2-Carbamoyloxyethyl)-5-(3,5-difluorophenylthio)-4-isopropyl-1H-imidazol-2-yl)propanol
(345) 5-Isopropyl-1-methyl-4-(3-fluorophenylthio)-1H-imidazol-2-ylmethanol
(346) 2-Acetylaminomethyl-4-isopropyl-5-phenylthio-1-(pyridin-2-ylmethyl)-1H-imidazole
(347) 2-(2-Carbamoyloxyethyl)-1-cyclopropylethyl-5-(3,5-dimethylphenylthio)-4-isopropyl-1H-imidazole
(348) 2-Carbamoyloxymethyl-5-(3,5-difluorophenylthio)-4-isopropyl-1-(2-phenylethyl)-1H-imidazole
(349) 2-(2-Azidoethyl)-5-(3,5-difluorophenylthio)-4-isopropyl-1-(pyridin-4-ylmethyl)-1H-imidazole
(350) 2-(5-(3-Nitrophenylthio)-4-isopropyl1-methyl)-1H-imidazole-2-carbaldehyde
(351) 4-(3-Chlorophenylthio)-1-ethyl-5-isopropyl-1H-imidazole-2-carbaldehyde
(352) 5-(3,5-Difluorophenylthio)-4-isopropyl-1-(pyridin-3-ylmethyl)-1H-imidazol-2-ylacetonitrile
(353) 4-Isopropyl-2-methanesulfonamidomethyl-5-(3-fluorophenylthio)-1-(pyridin-2-ylmethyl)-1H-imidazole
(354) 2-Carbamoyloxymethyl-4-(3-chlorophenylthio)-1-ethyl-5-isopropyl-1H-imidazole
(355) 2-Aminomethyl-5-(3-nitrophenylthio)-4-isopropyl-1-methyl-1H-imidazole
(356) 5-(3-Nitrophenylthio)-4-isopropyl-2-methanesulfonamidomethyl-1-(pyridin-2-ylmethyl)-1H-imidazole
(357) 5-(3,5-Difluorophenylthio)-1-hexyl-4-isopropyl-1H-imidazol-2-ylmethanol
(358) 2-(3-Carbamoyloxypropyl)-5-(3,5-difluorophenylthio)-1-ethyl-4-isopropyl-1H-imidazole
(359) 2-Aminomethyl-5-(3-nitrophenylthio)-4-isopropyl-1-(pyridin-3-ylmethyl)-1H-imidazole
(360) 3-(5-(3,5-Dimethylphenylthio)-1-hexyl-4-isopropyl-1H-imidazol-2yl)propanol
(361) 2-(5-(3-Nitrophenylthio)-4-isopropyl-1-(pyridin-4-ylmethyl))-1H-imidazole-2-carbaldehyde oxime
(362) 2-(5-(3,5-Difluorophenylthio)-1-hexyl-4-isopropyl-1H-imidazol-2-yl)ethanol
(363) 2-(5-(3-Chlorophenylthio)-4-isopropyl-1-(pyridin-4-ylmethyl)-1H-imidazol-2-yl)ethanol
(364) 1-(2-(2-Cabamoyloxyethyl)-5-(3,5-dimethylphenylthio)-4-isopropyl-1H-imidazol-1-yl)-2-propanone
(365) 5-(3,5-Dichlorophenylthio)-4-isopropyl-1-(quinolin-3-ylmethyl)-1H-imidazol-2-ylmethanol
(366) Methyl 3-(1-ethyl-4-isopropyl-5-(3-fluorophenylthio)-1H-imidazol-2,-yl)propionate
(367) 2-Aminomethyl-4-isopropyl-5-phenylthio-1-(pyridin-3-ylmethyl)-1H-imidazole
(368) 1-(5-(3,5-Difluorophenylthio)-2-(3-hydroxypropyl)-4-isopropyl-1H-imidazol-1-yl)-2-propanone
(369) 2-(2-Carbamoyloxyethyl)-5-(3,5-dimethylphenylthio)-1-fluoromethyl-4-isopropyl-1H-imidazole
(370) 2-Carbamoyloxymethyl-5-(3,5-difluorophenylthio)-1,4-diisopropyl-1H-imidazole
(371) 4-Isopropyl-5-phenylthio-1-(pyridin-4-ylmethyl)-1H-imidazol-2-yl acetate
(372) 5-(3,5-Dichlorophenylthio)-2-(2-carbamoyloxyethyl)-1-ethyl-4-isopropyl-1H-imidazole
(373) 2-(5-(3,5-Difluorophenylthio)-4-isopropyl-1-methyl)-1H-imidazole-2-carbaldehyde hydrazone
(374) 2-(4-Isopropyl-5-(3-fluorophenylthio)-1-(pyridin-4-ylmethyl)-1H-imidazol-2-yl)ethanol
(375) 2-(2-Acetoxyethyl)-5-(3,5-difluorophenylthio)-4-isopropyl-1-(pyridin-4-ylmethyl)-1H-imidazole
(376) 5-(3,5-Dimethylphenylthio)-1-ethyl-4-isopropyl-1H-imidazol-2-ylmethanol
(377) 5-(3,5-Dichlorophenylthio)-2-carbamoyloxymethyl-4-isopropyl-1-(2-methylpyridin-3-ylmethyl)-1H-imidazole
(378) 2-Azidomethyl-4-(3-nitrophenylthio)-5-isopropyl-1-methyl-1H-imidazole
(379) 1-Allyl-5-(3,5-dichlorophenylthio)-2-(3-carbamoyloxypropyl)-4-isopropyl-1H-imidazole (380) 1-(5-(3,5-Dimethylphenylthio)-2-hydroxymethyl)-4-isopropyl-1H-imidazol-1-yl)-2-propanone
(381) 2-(3-Carbamoyloxypropyl)-5-(3-Chlorophenylthio)-1-ethyl-4-isopropyl-1H-imidazole
(382) 2-Carbamoyloxymethyl-4-3-nitrophenylthio)-5-isopropyl-1-methyl-1H-imidazole
(383) 1-(4-Aminobenzyl)-2-carbamoyloxymethyl-5-(3,5-difluorophenylthio)-4-isopropyl-1H-imidazole
(384) 5-(3,5-Dichlorophenylthio)-2-diaminomethyleneaminomethyl-4-isopropyl-1-(pyridin-2-ylmethyl)-1H-imidazole
(385) 2-Azidomethyl-5-(3-nitrophenylthio)-4-isopropyl-1-methyl-1H-imidazole
(386) 2-(5-(3,5-Dichlorophenylthio)-4-isopropyl-1-(2-phenylethyl)-1H-imidazol-2-yl)ethanol
(387) 2-Aminomethyl-5-isopropyl-4-(3-fluorophenylthio)-1-(pyridin-4-ylmethyl)-1H-imidazole
(388) 5-(3,5-Difluorophenylthio)-4-isopropyl-2-N-methylaminomethyl-1-(pyridin-2-ylmethyl)-1H-imidazole
(389) 2-Acetylaminomethyl-5-(3-chlorophenylthio)-1-ethyl-4-isopropyl-1H-imidazole
(390) 2-(2-Carbamoyloxyethyl)-5-(3,5-difluorophenylthio)-4-isopropyl-1-n-propyl-1H-imidazole
(391) 2-Aminomethyl-4-(3-chlorophenylthio)-5-isopropyl-1-methyl-1H-imidazole
(392) 3-(5-(3,5-Dichlorophenylthio)-4-isopropyl-1-(3-(pyridin-4-yl)propyl)-1H-imidazol-2-yl)propanol
(393) 2-Diaminomethyleneaminomethyl-4-isopropyl-5-phenylthio-1-(pyridin-4-ylmethyl)-1H-imidazole
(394) 2-(3-Carbamoyloxypropyl)-1,5-dibenzyl-4-isopropyl-1H-imidazole
(395) 5-(3,5-Dichlorophenylthio)-1-n-butyl-4-isopropyl-1H-imidazol-2-ylmethanol
(396) 2-(5-(3-Nitrophenylthio)-4-isopropyl-1-methyl-1H-imidazol-2-ylmethoxy)ethanol
(397) 1-(5-(3,5-Dichlorophenylthio)-2-carbamoyloxymethyl-4-isopropyl-1H-imidazol-1-yl)-2-propanone
(398) 2-(3-Carbamoyloxypropyl)-5-(3,5-difluorophenylthio)-1-hexyl-4-isopropyl-1H-imidazole
(399) 2-(5-(3,5-Dichlorophenylthio)-4-isopropyl1-1-methyl-1H-imidazol-2-yl)ethanol
(400) 5-(3-Nitrophenylthio)-4-isopropyl-2-N-methyl(thiocarbamoyl)oxymethyl-1-(pyridin-3-ylmethyl)-1H-imidazole
(401) 1-Benzyl-2-carbamoyloxymethyl-4-(3,5-difluorophenylthio)-5-isopropyl-1H-imidazole
(402) 2-(1,5-Dibenzyl-4-isopropyl-1H-imidazol-2-yl)ethanol
(403) 2-(4-(3,5-Dichlorophenylthio)-5-isopropyl-1-(pyridin-4-ylmethyl))-1H-imidazole-2-carbaldehyde
(404) 2-(4-(3,5-Dichlorophenylthio)-1-ethyl-5-isopropyl)-1H-imidazole-2-carbaldehyde
(405) 2(3-Carbamoyloxypropyl)-5-(3,5-difluorophenylthio)-4-isopropyl-1-(pyridin-3-ylmethyl)-1H-imidazole
(406) 2-Carbamoyloxymethyl-5-(3,5-dimethylphenylthio)-1-hexyl-4-isopropyl-1H-imidazole
(407) 5-(3-Nitrophenylthio)-1-ethyl-4-isopropyl-1H-imidazol-2-ylmethanol
(408) 2-(5-(3,5-Dichlorophenylthio)-4-isopropyl-1-methyl-1H-imidazol-2-ylmethoxy)ethanol
(409) 5-(3,5-Dichlorophenylthio)-2-(3-carbamoyloxypropyl)-4-isopropyl-1-(3-phenylpropyl)-1H-imidazole
(410) 2-(5-(3,5-Dichlorophenylthio)-4-isopropyl-1-(3-(pyridin-4-yl)propyl)-1H-imidazol-2-yl)ethanol
(411) 2-(3-Carbamoyloxypropyl)-5-(3,5-difluorophenylthio)-1,4-diisopropyl-1H-imidazole
(412) 2-Azidomethyl-5-(3-chlorophenylthio)-4-isopropyl-1-(pyridin-2-ylmethyl)-1H-imidazole
(413) 1-(4-Aminobenzyl)-2-(2-carbamoyloxyethyl)-5-(3,5-difluorophenylthio)-4-isopropyl-1H-imidazole
(414) 5-(3-Nitrophenylthio)-2-dimethylaminomethyl-4-isopropyl-1-(pyridin-2-ylmethyl)-1H-imidazole
(415) 2-(2-Carbamoyloxyethyl)-5-(3,5-dimethylphenylthio)-4-isopropyl-1-(2,2,2-trifluoroethyl-)-1H-imidazole
(416) 2-Carbamoyloxymethyl-4-(3,5-difluorophenylthio)-5-isopropyl-1-(pyridin-4-ylmethyl)-1H-imidazole
(417) 4-Isopropyl-2-N-methylaminomethyl-1-methyl-5-phenylthio-1H-imidazole
(418) 4-(3,5-Dichlorophenylthio)-1-fluoromethyl-5-isopropyl-1H-imidazol-2-ylmethanol
(419) 5-Isopropyl-1-methyl-4-phenylthio-1H-imidazol-2-ylmethanol
(420) 1-Benzyl-2-carbamoyloxymethyl-4-(3,5-dimethylphenylthio)-5-isopropyl-1H-imidazole
(421) 4-Isopropyl-5-phenylthio-1-(pyridin-2-ylmethyl)-1H-imidazol-2-ylmethanol
(422) Methyl 3-(5-(3-chlorophenylthio)-4-isopropyl-1-(pyridin-3-ylmethyl)-1H-imidazol-2-yl)propionate
(423) 5-(3,5-Dichlorophenylthio)-2-(3-carbamoyloxypropyl)-4-isopropyl-1-(2-(pyridin-4-yl)ethyl)-1H-imidazole
(424) 2-Aminomethyl-5-(3-nitrophenylthio)-4-isopropyl-1-(pyridin-2-ylmethyl)-1H-imidazole
(425) 2-Aminomethyl-4-isopropyl-5-(3-fluorophenylthio)-1-(pyridin-4-ylmethyl)-1H-imidazole
(426) 3-(5-(3,5-Dichlorophenylthio)-4-isopropyl-1-(2,2,2-trifluoroethyl)-1H-imidazol-2-yl)propanol
(427) 4-(3,5-Difluorophenylthio)-1-fluoromethyl-5-isopropyl-1H-imidazol-2-ylmethanol
(428) 2-Diaminomethyleneaminomethyl-4-isopropyl-1-methyl-5-(3-fluorophenylthio)-1H-imidazole
(429) 2-(5-(3,5-Difluorophenylthio)-1-ethyl-4-isopropyl-1H-imidazol-2-yl)ethanol
(430) α-(2-Carbamoyloxymethyl-5-(3,5-dimethylphenylthio)-4-isopropyl-1H-imidazol-1-yl)acetophenone
(431) 1-(2-(2-Carbamoyloxyethyl)-5-(3,5-difluorophenylthio)-4-isopropyl-1H-imidazol-1-yl)-2-propanone
(432) 3-(5-(3,5-Difluorophenylthio)-4-isopropyl-1-n-propyl-1H-imidazol-2-yl)propanol
(433) α-(2-(2-Hydroxyethyl)-5-(3,5-difluorophenylthio)-4-isopropyl-1H-imidazol-1-yl)acetophenone
(434) 2-Aminomethyl-4-isopropyl-1-methyl-5-(3-fluorophenylthio)-1H-imidazole
(435) 2-(2-Carbamoyloxyethoxy)methyl-5-(3-chlorophenylthio)-4-isopropyl-1-(pyridin-4-ylmethyl)-1H-imidazole
(436) 5-(3,5-Difluorophenylthio)-4-isopropyl-1-methyl-2-ureidomethyl-1H-imidazole
(437) 2-Diaminomethyleneaminomethyl-4-isopropyl-5-phenylthio-1-(pyridin-3-ylmethyl)-1H-imidazole
(438) 2-(2-Carbamoyloxyethoxy)methyl-5-(3,5-difluorophenylthio)-4-isopropyl-1-(pyridin-4-ylmethyl)-1H-imidazole
(439) 3-(5-(3-Chlorophenylthio)-4-isopropyl-1-(pyridin-2-ylmethyl)-1H-imidazol-2-yl)propanol
(440) 2-(2-Carbamoyloxyethyl)-1-cyclopropylmethyl-5-(3,5-difluorophenylthio)-4-isopropyl-1H-imidazole
(441) 5-(3-Chlorophenylthio)-4-isopropyl-1-(pyridin-4-ylmethyl)-1H-imidazol-2-ylacetonitrile (442) 2-(4-Isopropyl-1-methyl-5-phenylthio-1H-imidazol-2-yl)-ethanol
(443) 2-(5-Isopropyl-1-methyl-4-phenylthio-1H-imidazol-2-ylmethoxy)ethanol
(444) 5-(3-Nitrophenylthio)-4-isopropyl-1-(pyridin-2-ylmethyl)-1H-imidazol-2-ylacetonitrile
(445) 2-Aminomethyl-5-(3,5-dichlorophenylthio)-4-isopropyl-1-(pyridin-4-ylmethyl)-1H-imidazole
(446) 2-(5-(3,5-Dichlorophenylthio)-1-fluoromethyl-4-isopropyl-1H-imidazol-2-yl)ethanol
(447) 2-Carbamoyloxymethyl-5-(3,5-dimethylphenylthio)-1-ethyl-4-isopropyl-1H-imidazole
(448) N-(5-(3-Nitrophenylthio)-4-isopropyl-1-(pyridin-2-ylmethyl)-1H-imidazol-4-ylmethyl)acetamidine
(449) Methyl 3-(5-(3,5-difluorophenylthio)-1-ethyl-4-isopropyl-1H-imidazol-2-yl)propionate
(450) 5-(3,5-Difluorophenylthio)-4-isopropyl-1-(3-phenylpropyl)-1H-imidazol-2-ylmethanol
(451) 2-(2-Aminoethyl-5-(3,5-dichlorophenylthio)-1-ethyl-4-isopropyl-1H-imidazole
(452) 1-Benzyl-2-(2-carbamoyloxyethyl)-5-(3,5-dimethylphenylthio)-4-isopropyl-1H-imidazole
(453) 1-(4-Aminobenzyl)-5-(3,5-dichlorophenylthio)-2-carbamoyloxymethyl-4-isopropyl-1H-imidazole
(454) 3-(5-(3,5-Dichlorophenylthio)-1-ethyl-4-isopropyl-1H-imidazol-2-yl)propanol
(455) 5-(3,5-Dichlorophenylthio)-4-isopropyl-2-N-methylaminomethyl-1-(pyridin-2-ylmethyl)-1H-imidazole
(456) 5-(3,5-Dichlorophenylthio)-1-ethyl-4-isopropyl-2-methanesulfonamidomethyl-1H-imidazole
(457) 2-Carbamoyloxymethyl-5-(3-nitrophenylthio)-4-isopropyl-1-(pyridin-2-ylmethyl)-1H-imidazole
(458) 2-(1-n-Butyl-5-(3,5-difluorophenylthio)-4-isopropyl-1H-imidazol-2-yl)ethanol
(459) 2-(5-(3-Chlorophenylthio)-4-isopropyl-1-(pyridin-3-ylmethyl)-1H-imidazol-2-ylmethoxy)ethanol
(460) 5-(3-Chlorophenylthio)-4-isopropyl-1-(pyridin-2-ylmethyl)-1H-imidazol-2-ylacetonitrile
(461) 4-Isopropyl-5-phenylthio-1-(pyridin-4-ylmethyl)-2-ureidomethyl-1H-imidazole
(462) 2-(5-(3,5-Difluorophenylthio)-4-isopropyl-1-(pyridin-3-ylmethyl)-1H-imidazol-2-ylmethoxy)ethanol
(463) 2-(1-(4-Aminobenzyl)-5-(3,5-difluorophenylthio)-4-isopropyl-1H-imidazol-2-yl)ethanol
(464) 2-Diaminomethyleneaminomethyl-4-isopropyl-5-(3-fluorophenylthio)-1-(pyridin-4-ylmethyl)-1H-imidazole
(465) 2-(5-(3-Chlorophenylthio)-4-isopropyl-1-methyl-1H-imidazol-2-ylmethoxy)ethyl acetate
(466) 1-Ethyl-4-isopropyl-5-(3-fluorophenylthio)-1H-imidazol-2-ylacetonitrile
(467) 2-(5-(3-Nitrophenylthio)-4-isopropyl-1-(pyridin-3-ylmethyl)-1H-imidazol-2-ylmethoxy)ethyl acetate
(468) 2-(3-Carbamoyloxypropyl)-5-(3,5-dimethylphenylthio)-4-isopropyl-1-(pyridin-3-ylmethyl)-1H-imidazole
(469) 4-Isopropyl-2-N-methyl(thiocarbamoyl)oxymethyl-5-phenylthio-1-(pyridin-3-ylmethyl)-1H-imidazole
(470) 5-(3,5-Dichlorophenylthio)-1-fluoromethyl-4-isopropyl-1H-imidazol-2-ylmethanol
(471) 2-(5-(3-Nitrophenylthio)-1-ethyl-4-isopropyl-1H-imidazol-2-ylmethoxy)ethyl acetate
(472) 2-Diaminomethyleneaminomethyl-4-isopropyl-5-(3-fluorophenylthio)-1-(pyridin-3-ylmethyl)-1H-imidazole
(473) 5-(3,5-Difluorophenylthio)-4-isopropyl-2-N-methyl(thiocarbamoyl)oxymethyl-1-(pyridin-3-ylmethyl)-1H-imidazole
(474) 1-(3-Aminobenzyl)-2-carbamoyloxymethyl-5-(3,5-difluorophenylthio)-4-isopropyl-1H-imidazole
(475) 2-(2-Azidoethyl)-5-(3,5-dichlorophenylthio)-4-isopropyl-1-methyl-1H-imidazole
(476) 2-Carbamoyloxymethyl-1-cyclopropylmethyl-5-(3,5-difluorophenylthio)-4-isopropyl-1H-imidazole
(477) 1-n-Butyl-2-(2-carbamoyloxyethyl)-5-(3,5-difluorophenylthio)-4-isopropyl-1H-imidazole
(478) 5-(3,5-Difluorophenylthio)-4-isopropyl-1-(2-methylpyridin-3-ylmethyl)-1H-imidazol-2-ylmethanol
(479) 2-(1-Ethyl-4-isopropyl-5-phenylthio)-1H-imidazole-2-carbaldehyde
(480) 2-(5-Isopropyl-1-methyl-4-(3-fluorophenylthio)-1H-imidazol-2-ylmethoxy)ethanol
(481) 2-(3-Carbamoyloxypropyl)-5-(3,5-Difluorophenylthio)-4-isopropyl-1-(2,2,2-trifluoroethyl)-1H-imidazole
(482) 5-(3,5-Difluorophenylthio)-4-isopropyl-1-(pyridin-2-ylmethyl)-1H-imidazol-2-ylmethyl acetate
(483) 5-(3-Nitrophenylthio)-4-isopropyl-1-(pyridin-3-ylmethyl)-1H-imidazol-2-ylmethyl acetate
(484) 2-(2-Aminoethyl-5-(3-nitrophenylthio)-4-isopropyl-1-(pyridin-2-ylmethyl)-1H-imidazole
(485) 2-(5-(3-Chlorophenylthio)-4-isopropyl-1-methyl)-1H-imidazole-2-carbaldehyde
(486) 2-Acetylaminomethyl-5-(3,5-difluorophenylthio)-4-isopropyl-1-(pyridin-2-ylmethyl)-1H-imidazole
(487) 1-(4-Aminobenzyl)-5-(3 5-dichlorophenylthio)-2-(3-carbamoyloxypropyl)-4-isopropyl-1H-imidazole
(488) 2-(1-Ethyl-5-isopropyl-4-phenylthio-1H-imidazol-2-ylmethoxy)ethanol
(489) 2-Dimethylaminomethyl-4-isopropyl-5-(3-fluorophenylthio)-1-(pyridin-2-ylmethyl)-1H-imidazole
(490) 5-(3-Chlorophenylthio)-1-ethyl-4-isopropyl-2-N-methyl(thiocarbamoyloxymethyl-1H-imidazole
(491) 2-(5-(3,5-Difluorophenylthio)-4-isopropyl-1-methyl-1H-imidazol-2-yl)ethanol
(492) 2-(4-(3,5-Dichlorophenylthio)-5-isopropyl-1-(pyridin-4-ylmethyl)-1H-imidazol-2-ylmethoxy)ethanol
(493) 4-(3,5-Dichlorophenylthio)-2-carbamoyloxymethyl-5-isopropyl-1-(pyridin-4-ylmethyl)-1H-imidazole
(494) 2-(2-Aminoethyl)-5-(3-nitrophenylthio)-1-ethyl-4-isopropyl-1H-imidazole
(495) 2-Carbamoyloxymethyl-5-(3,5-Difluorophenylthio)-4-isopropyl-1-(2-(pyridin-4-yl)ethyl)-1H-imidazole
(496) 2-Aminomethyl-5-(3,5-dichlorophenylthio)-4-isopropyl-1-methyl-1H-imidazole
(497) 4-Isopropyl-5-phenylthio-1-(pyridin-3-ylmethyl)-1H-imidazol-2-ylacetonitrile
(498) 2-Azidomethyl-5-isopropyl-4-(3-fluorophenylthio)-1-(pyridin-4-ylmethyl)-1H-imidazole
(499) 5-(3-Nitrophenylthio)-4-isopropyl-1-(pyridin-2-ylmethyl)-1H-imidazol-2-ylmethanol
(500) 2-(2-Carbamoyloxyethyl)-5-(3,5-difluorophenylthio)-1-hexyl-4-isopropyl-1H-imidazole
(501) 5-(3,5-Dichlorophenylthio)-2-(2-carbamoyloxyethyl)-methyl-4-isopropyl-1-(pyridin-3-ylmethyl)-1H-imidazole
(502) 2-(5-(3,5-Difluorophenylthio)-4-isopropyl-1-(pyridin-4-ylmethyl)-1H-imidazol-2-ylmethoxy)ethyl acetate
(503) 2-(5-(3-Nitrophenylthio)-4-isopropyl-1-(pyridin-4-ylmethyl)-1H-imidazol-2-ylmethoxy)ethyl acetate
(504) 5-(3-Chlorophenylthio)-2-diaminomethyleneaminomethyl-4-isopropyl-1-(pyridin-2-ylmethyl)-1H-imidazole
(505) 2-(5-(3,5-Dichlorophenylthio)-4-isopropyl-1-n-propyl-1H-imidazol-2-yl)ethanol (506) 4-Isopropyl-5-phenylthio-1-(pyridin-3-ylmethyl)-H-imidazole-2-carbaldehyde oxime
(507) 2-(1-(3-Aminobenzyl)-5-(3,5-difluorophenylthio)-4-isopropyl-1H-imidazol-2-yl)ethanol
(508) 1-Allyl-2-carbamoyloxymethyl-5-(3,5-difluorophenylthio)-4-isopropyl-1H-imidazole
(509) 5-(3-Chlorophenylthio)-2-diaminomethyleneaminomethyl-4-isopropyl-1-methyl-1H-imidazole
(510) 2-Carbamoyloxymethyl-4-isopropyl-5-phenylthio-1-(pyridin-4-ylmethyl)-1H-imidazole
(511) 5-(3-Chlorophenylthio)-4-isopropyl-1-(pyridin-3-ylmethyl)-1H-imidazol-2-yl acetate
(512) 2-(2-Azidoethyl)-5-(3-chlorophenylthio)-4-isopropyl-1-(pyridin-2-ylmethyl)-1H-imidazole
(513) 2-(4-Isopropyl-5-phenylthio-1-(pyridin-2-ylmethyl)-1H-imidazol-2-ylmethoxy)ethanol
(514) 5-(3,5-Dichlorophenylthio)-2-carbamoyloxymethyl-1,4-diisopropyl-1H-imidazole
(515) 2-(5-(3,5-Dichlorophenylthio)-4-isopropyl-1-(pyridin-3-ylmethyl)-1H-imidazol-2-ylmethoxy)ethyl acetate
(516) 5-Isopropyl-1-1-methyl-4-phenylthio-1H-imidazole-2-carbaldehyde
(517) 2-(5-(3,5-Difluorophenylthio)-4-isopropyl-1-(3-phenylpropyl)-1H-imidazol-2-yl)ethanol
(518) 2-(2-Azidoethyl)-5-(3-nitrophenylthio)-4-isopropyl-1-(pyridin-3-ylmethyl)-1H-imidazole
(519) N-(5-(3,5-Difluorophenylthio)-4-isopropyl-1-(pyridin-3-ylmethyl)-1H-imidazol-4-ylmethyl)acetamidine
(520) 2-(5-(3,5-Difluorophenylthio)-1-fluoromethyl-4-isopropyl-1H-imidazol-2-yl)ethanol
(521) 2-Acetylaminomethyl-5-(3-nitrophenylthio)-4-isopropyl-(pyridin-4-ylmethyl)-1H-imidazole
(522) 2-Carbamoyloxymethyl-5-(3-chlorophenylthio)-4-isopropyl-1-methyl-1H-imidazole
(523) 1-Benzyl-5-(3,5-difluorophenylthio)-4-isopropyl-1H-imidazol-2-ylmethanol
(524) 1-Cyclopropylmethyl-5-(3,5-difluorophenylthio)-4-isopropyl-1H-imidazol-2-ylmethanol
(525) 5-(3,5-Dichlorophenylthio)-4-isopropyl-2-N-methylcarbamoyloxymethyl-1-(pyridin-3-ylmethyl)-1H-imidazole
(526) 2-(5-(3-Nitrophenylthio)-4-isopropyl-1-(pyridin-2-ylmethyl)-1H-imidazol-2-ylmethoxy)ethanol
(527) 2-Carbamoyloxymethyl-4-(3,5-dimethylphenylthio)-5-isopropyl-1-methyl-1H-imidazole
(528) 2-(5-(3,5-Dichlorophenylthio)-4-isopropyl-1-(pyridin-3-ylmethyl)-1H-imidazole-2-carbaldehyde oxime
(529) 2-Carbamoyloxymethyl-4-(3,5-difluorophenylthio)-1-ethyl-5-isopropyl-1H-imidazole
(530) 2-(5-(3,5-Dichlorophenylthio)-4-isopropyl-1-(2,2,2-trifluoroethyl)-1H-imidazol-2-yl)ethanol
(531) 5-(3,5-Difluorophenylthio)-1-ethyl-4-isopropyl-1H-imidazol-2-ylmethanol
(532) 3-(5-(3,5-Difluorophenylthio)-4-isopropyl-1-(pyridin-4-ylmethyl)-1H-imidazol-2-yl)propanol
(533) 2-(2-Carbamoyloxyethyl)-5-(3-chlorophenylthio)-4-isopropyl-1-(pyridin-2-ylmethyl)-1H-imidazole
(534) 2-(3-Carbamoyloxypropyl)-1-ethyl-4-isopropyl-5-phenylthio-1H-imidazole
(535) Methyl 3-(5-(3,5-difluorophenylthio)-4-isopropyl-1-methyl-1H-imidazol-2-yl)propionate
(536) 2-(4-Isopropyl-5-(3-fluorophenylthio)-1-(pyridin-2-ylmethyl)-1H-imidazol-2-yl)ethanol
(537) 1-Ethyl-4-isopropyl-5-phenylthio-1H-imidazol-2-yl acetate
(538) 3-(5-(3,5-Dichlorophenylthio)-4-isopropyl-1-(pyridin-3-ylmethyl)-1H-imidazol-2-yl)propanol
(539) 2-(3-Carbamoyloxypropyl)-4-isopropyl-1-methyl-5-phenylthio-1H-imidazole
(540) 2-Carbamoyloxymethyl-5-(3-nitrophenylthio)-4-isopropyl-1-(pyridin-4-ylmethyl)-1H-imidazole
(541) 4-Isopropyl-5-(3-fluorophenylthio)-1-(pyridin-2-ylmethyl)-1H-imidazol-2-ylacetonitrile
(542) N-(5-(3-Nitrophenylthio)-4-isopropyl-1-methyl-1H-imidazol-4-ylmethyl)acetamidine
(543) 2-Azidomethyl-4-(3,5-dichlorophenylthio)-1-ethyl-5-isopropyl-1H-imidazole
(544) 2-(5-(3-Chlorophenylthio)-4-isopropyl-1-(pyridin-3-5 ylmethyl))-1H-imidazole-2-carbaldehyde oxime
(545) 4-(3,5-Dimethylphenylthio)-1-ethyl-5-isopropyl-1H-imidazol-2-ylmethanol
(546) 4-(3,5-Difluorophenylthio)-5-isopropyl-1-methyl-1H-imidazol-2-ylmethyl acetate
(547) 4-Isopropyl-5-(3-fluorophenylthio)-1-(pyridin-4-ylmethyl)-1H-imidazol-2-ylmethyl acetate
(548) 2-(3-Carbamoyloxypropyl)-5-(3,5-dimethylphenylthio)-4-isopropyl-1-n-propyl-1H-imidazole
(549) 5-(3,5-Dichlorophenylthio)-4-isopropyl-2-methanesulfonamidomethyl-1-(pyridin-2-ylmethyl)-1H-imidazole
(550) 2-Carbamoyloxymethyl-5-(3-nitrophenylthio)-4-isopropyl-1-(pyridin-3-ylmethyl)-1H-imidazole
(551) 2-(4-isopropyl-5-phenylthio-1-(pyridin-4-ylmethyl))-1H-imidazole-2-carbaldehyde
(552) 4-(3,5-Dichlorophenylthio)-5-isopropyl-1-1-ethyl-1H-imidazol-2-ylmethanol
(553) 4-Isopropyl-5-(3-fluorophenylthio)-1-(pyridin-3-ylmethyl)-1H-imidazol-2-yl acetate
(554) 1-(2-Aminobenzyl)-5-(3,5-dichlorophenylthio)-4-isopropyl-1H-imidazol-2-ylmethanol
(555) 2-(3-Carbamoyloxypropyl)-5-(3-nitrophenylthio)-4-isopropyl-1-(pyridin-2-ylmethyl)-1H-imidazole
(556) 2-Azidomethyl-5-isopropyl--methyl-4-(3-fluorophenylthio)-1H-imidazole
(557) 1-Benzyl-2-carbamoyloxymethyl-5-(3,5-Difluorophenylthio)-4-isopropyl-1H-imidazole
(558) 2-(3-Carbamoyloxypropyl)-5-(3,5-difluorophenylthio)-4-isopropyl-1-n-propyl-1H-imidazole
(559) 3-(1-Ethyl-4-isopropyl-5-phenylthio-1H-imidazol-2-yl)propanol
(560) 5-(3,5-Difluorophenylthio)-4-isopropyl-1-(pyridin-2-ylmethyl)-1H-imidazole-2-carbaldehyde oxime
(561) 2-Carbamoyloxymethyl-5-(3,5-dimethylphenylthio)-4-isopropyl-1-(pyridin-4-ylmethyl)-1H-imidazole
(562) 2-Carbamoyloxymethyl-4-isopropyl-1-methyl-5-(3-fluorophenylthio)-1H-imidazole
(563) 2-2-(Acetoxyethyl)-5-(3,5-dichlorophenylthio)-4-isopropyl-1-(pyridin-3-ylmethyl)-1H-imidazole
(564) 3-(1,5-Dibenzyl-4-isopropyl-1H-imidazol-2-yl)propanol
(565) 1-(2-Aminobenzyl)-2-carbamoyloxymethyl-5-(3,5-difluorophenylthio)-4-isopropyl-1H-imidazole
(566) 4-(3,5-Difluorophenylthio)-1-fluoromethyl-5-isopropyl-1H-imidazol-2-ylmethanol
(567) 4-(3-Nitrophenylthio)-5-isopropyl-1-(pyridin-4-ylmethyl)-1H-imidazole-2-carbaldehyde
(568) 5-(3-Nitrophenylthio)-4-isopropyl-2-N-methylaminomethyl-1-(pyridin-3-ylmethyl)-1H-imidazole
(569) 4-(3,5-Difluorophenylthio)-5-isopropyl-1-ethyl-1H-imidazol-2-ylmethanol (570) 2-(5-(3,5-Difluorophenylthio)-4-isopropyl-1(pyridin-2-ylmethyl)-1H-imidazol-2-yl)ethanoi
(571) 5-(3,5-Dichlorophenylthio)-2-(2-carbamoyloxyethyl)-4-isopropyl-1-(3-phenylpropyl)-1H-imidazole
(572) 2-(2-Carbamoyloxyethoxy)methyl-5-(3-chlorophenylthio)-4-isopropyl-1-(pyridin-3-ylmethyl)-1H-imidazole
(573) 2-(5-(3,5-Difluorophenylthio)-4-isopropyl-1-(2(1H)-pyridin-5-ylmethyl)-1H-imidazol-2-yl)ethanol
(574) 2-(2-Carbamoyloxyethyl)-5-(3,5-difluorophenylthio)-4-isopropyl-1-(pyridin-4-ylmethyl)-1H-imidazole
(575) 5-(3,5-Difluorophenylthio)-4-isopropyl-2-N-dimethylaminomethyl-1-(pyridin-4-ylmethyl)-1H-imidazole
(576) 5-(3,5-Difluorophenylthio)-4-isopropyl-1-(pyridin-4-ylmethyl)-1H-imidazol-2-yl-acetate
(577) 3-(5-(3,5-Difluorophenylthio)-4-isopropyl-1-(pyridin-2-ylmethyl)-1H-imidazol-2-yl)propanol
(578) 2-2-(Acetoxyethyl)-5-(3,5-difluorophenylthio)-4-isopropyl-1-(pyridin-2-ylmethyl)-1H-imidazole
(579) 5-(3-Nitrophenylthio)-4-isopropyl-1-(pyridin-4-ylmethyl)-1H-imidazol-2-ylmethanol
(580) 2-(2-Azidoethyl)-5-(3,5-dichlorophenylthio)-4-isopropyl-1-(pyridin-2-ylmethyl)-1H-imidazole
(581) 2-(4-(3-Nitrophenylthio)-5-isopropyl-1-(pyridin-4-ylmethyl)-1H-imidazol-2-ylmethoxy)ethanol
(582) 2-(3-Carbamoyloxypropyl)-5-(3,5-difluorophenylthio)-4-isopropyl-1-(pyridin-2-ylmethyl)-1H-imidazole
(583) 5-(3-Nitrophenylthio)-4-isopropyl-2-N-methylcarbamoyloxymethyl-1-(pyridin-3-ylmethyl)-1H-imidazole
(584) 5-(3,5-Dichlorophenylthio)-2-(3-carbaiimoyloxypropyl)-1-cyclopropylmethyl-4-isopropyl-1H-imidazole
(585) 2-(1,4-Diisopropyl-5-(3,5-difluorophenylthio)-1H-imidazol-2-yl)ethanol
(586) 2-Azidomethyl-5-(3-chlorophenylthio)-1-ethyl-4-isopropyl-1H-imidazole
(587) 5-(3-Chlorophenylthio)-4-isopropyl-1-(pyridin-3-ylmethyl)-1H-imidazol-2-ylmethanol
(588) 5-Isopropyl-4-(3-fluorophenylthio)-1-(pyridin-4-ylmethyl)-1H-imidazol-2-ylmethanol
(589) 1-(2-(2-Hydroxyethyl)-5-(3,5-difluorophenylthio)-4-isopropyl-1H-imidazol-1-yl)-2-propanone
(590) 2-Carbamoyloxymethyl-5-(3,5-difluorophenylthio)-1-hexyl-4-isopropyl-1H-imidazole
(591) 2-Diaminomethyleneaminomethyl-5-(3-nitrophenylthio)-1-ethyl-4-isopropyl-1H-imidazole
(592) 2-Acetylaminomethyl-5-(3,5-dichlorophenylthio)-4-isopropyl-1-(pyridin-3-ylmethyl)-1H-imidazole
(593) 2-Diaminomethyleneaminomethyl-5-(3,5-difluorophenylthio)-1-ethyl-4-isopropyl-1H-imidazole
(594) 4-Isopropyl-1-methyl-5-(3-fluorophenylthio)-1H-imidazol-2-ylmethyl acetate
(595) 5-(3,5-Difluorophenylthio)-1-ethyl-4-isopropyl-2-methanesulfonamidomethyl-1H-imidazole
(596) 2-Diaminomethyleneaminomethyl-4-isopropyl-5-phenylthio-1-(pyridin-2-ylmehtyl)-1H-imidazole
(597) 2-(3-Carbamoyloxypropyl)-5-(3-nitrophenylthio)-4-isopropyl-1-methyl-1H-imidazole
(598) 2-Acetylaminomethyl-5-(3,5-dichlorophenylthio)-1-ethyl-4-isopropyl-1H-imidazole
(599) 2-2-(Acetoxyethyl)-5-(3-chlorophenylthio)-4-isopropyl-1-methyl-1H-imidazole
(600) 2-Aminomethyl-4-isopropyl-5-(3-fluorophenylthio)-1-(pyridin-3-ylmethyl)-1H-imidazole
(601) 2-Aminomethyl-1-ethyl-4-isopropyl-5-phenylthio-1H-imidazole
(602) 4-Isopropyl-2-methanesulfonamidomethyl-5-phenylthio-1-(pyridin-4-ylmethyl)-1H-imidazole
(603) 2-(2-Carbamoyloxyethyl)-5-(3,5-difluorophenylthio)-4-isopropyl-1-(3-phenylpropyl)-1H-imidazole
(604) 1-(2-(3-Carbamoyloxypropyl)-5-(3,5-difluorophenylthio)-4-isopropyl-1H-imidazol-1-yl)-2-propanone
(605) 3-(4-Isopropyl-5-(3-fluorophenylthio)-1-(pyridin-2-ylmethyl)-1H-imidazol-2-yl)propanol
(606) 3-(1-Cyclopropylmethyl-5-(3,5-difluorophenylthio)-4-isopropyl-1H-imidazol-2-yl)propanol
(607) 5-(3,5-Dichlorophenylthio)-4-isopropyl-1-(pyridin-4-ylmethyl)-1H-imidazol-2-ylmethanol
(608) 2-(2-Carbamoyloxyethyl)-5-(3-chlorophenylthio)-1-ethyl-4-isopropyl-1H-imidazole
(609) 5-(3-Nitrophenylthio)-4-isopropyl-1-methyl)-1H-imidazole-2-carbaldehyde oxime
(610) 1-Ethyl-4-isopropyl-2-N-methylthiocarbamoyloxymethyl-5-(3-fluorophenylthio)-1H-imidazole
(611) 2-(5-(3,5-Difluorophenylthio)-4-isopropyl-1-(quinolin-3-ylmethyl)-1H-imidazol-2-yl)ethanol
(612) 1-(5-(3,5-Dimethylphenylthio)-2-(3-hydroxypropyl)-4-isopropyl-1H-imidazol-1-yl)-2-propanone
(613) 2-(5-(3,5-Dimethylphenylthio)-4-isopropyl-1-(pyridin-4-ylmethyl)-1H-imidazol-2-yl)ethanol
(614) 3-(5-(3,5-Difluorophenylthio)-4-isopropyl-1-(2-(pyridin-4-yl)ethyl)-1H-imidazol-2-yl)propanol
(615) 2-(5-(3-Nitrophenylthio)-4-isopropyl-1-(pyridin-3-ylmethyl)-1H-imidazol-2-ylmethoxy)ethanol
(616) 4-Isopropyl-5-(3-fluorophenylthio)-1-(pyridin-3-ylmethyl)-1H-imidazol-2-ylmethyl acetate
(617) 5-(3-Nitrophenylthio)-4-isopropyl-1-methyl-1H-imidazol-2-yl acetate
(618) 5-(3,5-Dimethylphenylthio)-1-hexyl-4-isopropyl-1H-imidazol-2-ylmethanol
(619) 2-(5-Isopropyl-4-phenylthio-1-(pyridin-4-ylmethyl))-1H-imidazole-2-carbaldehyde
(620) Methyl 3-(5-(3,5-dichlorophenylthio)-4-isopropyl-1-methyl-1H-imidazol-2-yl)propionate
(621) 4-(3-Chlorophenylthio)-5-isopropyl-1-methyl-1H-imidazol-2-ylmethanol
(622) 2-Aminomethyl-5-(3-nitrophenylthio)-1-ethyl-4-isopropyl-1H-imidazole
(623) 5-(3,5-Difluorophenylthio)-4-isopropyl-2-N-methylcarbamoyloxymethyl-1-(pyridin-4-ylmethyl)-1H-imidazole
(624) 2-(5-(3-Nitrophenylthio)-1-ethyl-4-isopropyl-1H-imidazol-2-ylmethoxy)ethanol
(625) 2-(2-Carbamoyloxyethyl)-5-(3,5-difluorophenylthio)-4-isopropyl-1-(pyridin-2-ylmethyl)-1H-imidazole
(626) 5-(3-Nitrophenylthio)-4-isopropyl-2-methanesulfonamidomethyl-1-(pyridin-3-ylmethyl)-1H-imidazole
(627) 3-(5-(3,5-Dichlorophenylthio)-4-isopropyl-1-(3-phenylpropyl)-1H-imidazol-2-yl)propanol
(628) 2-(5-(3-Chlorophenylthio)-4-isopropyl-1-methyl-1H-imidazol-2-yl)ethanol
(629) 2-(2-Aminoethyl)-5-(3,5-difluorophenylthio)-4-isopropyl-1-(pyridin-2-ylmethyl)-1H-imidazole
(630) 5-(3,5-Difluorophenylthio)-4-isopropyl-1-(pyridin-4-ylmethyl)-1H-imidazole-2-carbaldehyde oxime
(631) 2-(3-Carbamoyloxypropyl)-5-(3,5-difluorophenylthio)-1,4-diisopropyl-1H-imidazole
(632) 2-Aminomethyl-4-(3,5-dichlorophenylthio)-5-isopropyl-1-methyl-1H-imidazole (633) 1-Allyl-5-(3,5-difluorophenylthio)-4-isopropyl-1H-imidazol-2-ylmethanol
(634) 2-Carbamoyloxymethyl-5-(3,5-difluorophenylthio)-4-isopropyl-1-n-propyl-1H-imidazole
(635) 2-Azidomethyl-5-(3,5-difluorophenylthio)-1-ethyl-4-isopropyl-1H-imidazole
(636) 2-Diaminomethyleneaminomethyl-5-(3-nitrophenylthio)-4-isopropyl-1-(pyridin-4-ylmethyl)-1H-imidazole
(637) 5-(3,5-Dichlorophenylthio)-2-(2-carbamoyloxyethyl)-4-isopropyl-1-(2-(pyridin-4-yl)ethyl)-1H-imidazole
(638) 1-(4-Aminobenzyl)-2-(3-carbamoyloxypropyl)-5-(3,5-difluorophenylthio)-4-isopropyl-1H-imidazole
(639) 2-Aminomethyl-5-isopropyl-4-phenylthio-.-(pyridin-4-ylmethyl)-1H-imidazole
(640) 5-(3,5-Difluorophenylthio)-4-isopropyl-1-n-propyl-1H-imidazol-2-ylmethanol
(641) 2-(2-Acetoxyethyl)-5-(3-nitrophenylthio)-1-ethyl-4-isopropyl-1H-imidazole
(642) 2-(2-Carbamoyloxyethyl)-5-(3-nitrophenylthio)-4-isopropyl-1-(pyridin-2-ylmethyl)-1H-imidazole
(643) 3-(5-(3-Chlorophenylthio)-4-isopropyl-1-methyl-1H-imidazol-2-yl)propanol
(644) 5-(3,5-Dichlorophenylthio)-1-ethyl-4-isopropyl-2-ureidomethyl-1H-imidazole
(645) 4-Isopropyl-5-phenylthio-1-(pyridin-2-ylmethyl)-1H-imidazole-2-carbaldehyde hydrazone
(646) 3-(5-(3-Chlorophenylthio)-1-ethyl-4-isopropyl-1H-imidazol-2-yl)propanol
(647) 1-(3-Aminobenzyl)-5-(3,5-dichlorophenylthio)-2-carbamoyloxymethyl-4-isopropyl-1H-imidazole
(648) N-(5-(3-Nitrophenylthio)-1-ethyl-4-isopropyl-1H-imidazol-4-ylmethyl)acetamidine
(649) 5-(3-Nitrophenylthio)-1-ethyl-4-isopropyl-2-N-methylaminomethyl-1H-imidazole
(650) 2-(3-Carbamoyloxypropyl)-4-isopropyl-5-(3-fluorophenylthio)-1-(pyridin-3-ylmethyl)-1H-imidazole
(651) Methyl 3-(4-isopropyl-5-phenylthio-1-(pyridin-3-ylmethyl)-1H-imidazol-2-yl)propionate
(652) 5-(3-Chlorophenylthio)-4-isopropyl-1-methyl-2-N-methylthiocarbamoyloxymethyl-1H-imidazole
(653) 2-(2-Carbamoyloxyethyl)-5-(3,5-dimethylphenylthio)-4-isopropyl-1-(pyridin-4-ylmethyl)-1H-imidazole
(654) α-(5-(3,5-Dichlorophenylthio)-2-hydroxymethyl-4-isopropyl-1H-imidazol-1-yl)acetophenone
(655) 2-(3-Carbamoyloxypropyl)-5-(3,5-difluorophenylthio)-4-isopropyl-1-(3-(pyridin-4-yl)propyl)-1H-imidazole
(656) 2-(2-Aminoethyl)-5-(3-chlorophenylthio)-4-isopropyl-1-(pyridin-4-ylmethyl)-1H-imidazole
(657) 2-Dimethylaminomethyl-4-isopropyl-5-phenylthio-1-(pyridin-4-ylmethyl)-1H-imidazole
(658) 3-(1-Ethyl-4-isopropyl-5-(3-fluorophenylthio)-1H-imidazol-2-yl)propanol
(659) 4-Isopropyl-2-methanesulfonamidomethyl-1-methyl-5-phenylthio-1H-imidazole
(660) 1-Allyl-5-(3,5-dimethylphenylthio)-4-isopropyl-1H-imidazol-2-ylmethanol
(661) 2-(2-Carbamoyloxyethyl)-1,5-dibenzyl-4-isopropyl-1H-imidazole
(662) 4-Isopropyl-2-N-methylaminomethyl-5-phenylthio-1-(pyridin-4-ylmethyl)-1H-imidazole
(663) 5-(3,5-Dichlorophenylthio)-4-isopropyl-1-(pyridin-3-ylmethyl)-1H-imidazol-2-yl acetate
(664) 2-(2-Azidoethyl)-4-isopropyl-5-phenylthio-1-(pyridin-2-ylmethyl)-1H-imidazole
(665) 2-(4-Isopropyl-5-phenylthio-1-(pyridin-4-ylmethyl))-1H-imidazolecarbaldehyde oxime
(666) 3-(5-(3,5-Difluorophenylthio)-1-fluoromethyl-4-isopropyl-1H-imidazol-2-yl)propanol
(667) 5-(3,5-Dichlorophenylthio)-2-(2-carbamoyloxyethyl)-4-isopropyl-1-(2-phenylethyl)-1H-imidazole
(668) 1-n-Butyl-2-(2-carbamoyloxyethyl)-5-(3,5-difluorophenylthio)-4-isopropyl-1H-imidazole
(669) 2-(3-Carbamoyloxypropyl)-5-(3,5-difluorophenylthio)-4-isopropyl-1-(pyridin-4-ylmethyl)-1H-imidazole
(670) 2-Carbamoyloxymethyl-5-(3,5-difluorophenylthio)-1-ethyl-4-isopropyl-1H-imidazole
(671) 2-(3-Carbamoyloxypropyl)-5-(3-chlorophenylthio)-4-isopropyl-1-methyl-1H-imidazole
(672) 2-(2-Carbamoyloxyethoxy)methyl-5-(3-nitrophenylthio)-4-isopropyl-1-(pyridin-3-ylmethyl)-1H-imidazole
(673) 2-Diaminomethyleneaminomethyl-5-(3,5-difluorophenylthio)-4-isopropyl-1-(pyridin-4-ylmethyl)-1H-imidazole
(674) 2-(4-Isopropyl-1-methyl-5-(3-fluorophenylthio)-1H-imidazol-2-ylmethoxy)ethanol
(675) 3-(5-(3,5-Dimethylphenylthio)-1-fluoromethyl-4-isopropyl-1H-imidazol-2-yl)propanol
(676) 5-(3,5-Dichlorophenylthio)-4-isopropyl-1-(2-phenylethyl)-1H-imidazol-2-ylmethanol
(677) 1-Ethyl-4-isopropyl-5-(3-fluorophenylthio)-1H-imidazol-2-yl acetate
(678) 2-(2-Carbamoyloxyethyl)-5-(3,5-difluorophenylthio)-1-fluoromethyl-4-isopropyl-1H-imidazole
(679) 5-(3-Nitrophenylthio)-2-dimethylaminomethyl-4-isopropyl-1-(pyridin-4-ylmethyl)-1H-imidazole
(680) 4-Isopropyl-5-phenylthio-1-(pyridin-4-ylmethyl)-1H-imidazol-2-ylmethyl acetate
(681) 2-Carbamoyloxymethyl-5-(3,5-Difluorophenylthio)-4-isopropyl-1-methyl-1H-imidazole
(682) 4-(3-Chlorophenylthio)-5-isopropyl-1-methyl-1H-imidazol-2-ylmethyl acetate
(683) 2-(2-Azidoethyl)-4-isopropyl-5-phenylthio-1-(pyridin-4-ylmethyl)-1H-imidazole
(684) 2-(2-Azidoethyl)-4-isopropyl-1-methyl-5-phenylthio-1H-imidazole
(685) 1-Ethyl-4-isopropyl-5-(3-fluorophenylthio)-1H-imidazol-2-ylmethyl acetate
(686) 2-(3-Carbamoyloxypropyl)-1-cyclopropylmethyl-5-(3,5-dimethylphenylthio)-4-isopropyl-1H-imidazole
(687) 4-Isopropyl-2-N-methylaminomethyl-5-(3-fluorophenylthio)-1-(pyridin-3-ylmethyl)-1H-imidazole
(688) Methyl 3-(4-isopropyl-5-phenylthio-1-(pyridin-4-ylmethyl)-1H-imidazol-2-yl)propionate
(689) 2-Diaminomethyleneaminomethyl-5-(3-nitrophenylthio)-4-isopropyl-1-methyl-1H-imidazole
(690) 1,4-Diisopropyl-5-(3,5-dimethylphenylthio)-1H-imidazol-2-ylmethanol
(691) 2-(3-Carbamoyloxypropyl)-4-isopropyl-5-phenylthio-1-(pyridin-3-ylmethyl)-1H-imidazole
(692) 2-Azidomethyl-5-(3-nitrophenylthio)-4-isopropyl-1-(pyridin-2-ylmethyl)-1H-imidazole
(693) 1-Ethyl-4-isopropyl-2-N-methylthiocarbamoyloxymethyl-5-phenylthio-1H-imidazole
(694) 2-(5-(3-Nitrophenylthio)-4-isopropyl-1-(pyridin-4-ylmethyl)-1-imidazol-2-yl)ethanol
(695) 5-(3,5-Dichlorophenylthio)-2-(3-carbamoyloxypropyl)-1-ethyl-4-isopropyl-1H-imidazole
(696) Methyl 3-(5-(3-nitrophenylthio)-4-isopropyl-1-methyl-1H-imidazol-2-yl)propionate (697) 2-(2-Acetoxyethyl)-5-(3,5-dichorophenylthio)-4-isopropyl-1-(pyridin-2-ylmethyl)-1H-imidazole (698) 2-2-(Acetoxyethyl)-5-(3,5-dichlorophenylthio)-4-isopropyl-1-methyl-1H-imidazole (699) 2-Azidomethyl-4-(3-chlorophenylthio)-1-ethyl-5-isopropyl-1H-imidazole (700) 3-(5-(3,5-Difluorophenylthio)-4-isopropyl-1-(2-phenylethyl)-1H-imidazol-2-yl)propanol (701) 2-(1-n-Butyl-5-(3,5-dimethylphenylthio)-4-isopropyl-1H-imidazol-2-yl)ethanol (702) 1-(2-Carbamoyloxyethyl)-5-(3,5-difluorophenylthio)-4-isopropyl-1H-imidazol-2-ylmethanol (703) α-(2-(2-Carbamoyloxyethyl)-5-(3,5-difluorophenylthio)-4-isopropyl-1H-imidazol-1-yl)acetophenone (704) 5-(3,5-Difluorophenylthio)-4-isopropyl-1-(pyridin-3-ylmethyl)-1H-imidazole-2-carbaldehyde (705) 5-(3,5-Dichlorophenylthio)-2-diaminomethyleneaminomethyl-1-ethyl-4-isopropyl-1H-imidazole (706) 2-(5-(3,5-Dichlorophenylthio)-1-ethyl-4-isopropyl-1H-imidazol-2-ylmethoxy)ethanol (707) 5-(3,5-Dichlorophenylthio)-4-isopropyl-1-(3-phenylpropyl)-1H-imidazol-2-ylmethanol (708) 2-(2-Aminoethyl)-4-isopropyl-5-phenylthio-1-(pyridin-2-ylmethyl)-1H-imidazole (709) 2-Carbamoyloxymethyl-5-(3,5-dimethylphenylthio)-4-isopropyl-1-n-propyl-1H-imidazole (710) 5-(3,5-Dichlorophenylthio)-2-(3-carbamoyloxypropyl)-1,4-diisopropyl-1H-imidazole (711) 1-(2-Aminobenzyl)-5-(3,5-dichlorophenylthio)-2-(3-carbamoyloxypropyl)-4-isopropyl-1H-imidazole (712) 2-Carbamoyloxymethyl-4-(3,5-difluorophenylthio)-5-isopropyl-1-methyl-1H-imidazole (713) 2-(3-Carbamoyloxypropyl)-5-(3,5-dimethylphenylthio)-4-isopropyl-1-(2,2,2-trifluoroethyl)-1H-imidazole (714) 2-Carbamoyloxymethyl-5-(3-nitrophenylthio)-1-ethyl-4-isopropyl-1H-imidazole (715) 2-Azidomethyl-5-(3,5-difluorophenylthio)-4-isopropyl-1-(pyridin-2-ylmethyl)-1H-imidazole (716) 3-(5-(3,5-Difluorophenylthio)-1-hexyl-4-isopropyl-1H-imidazol-2-yl)propanol (717) 2-(5-(3-Nitrophenylthio)-4-isopropyl-1-methyl-1H-imidazol-2-yl)ethanol (718) 1-Benzyl-2-(3-carbamoyloxypropyl)-5-(3,5-dimethylphenylthio)-4-isopropyl-1H-imidazole (719) 5-(3-Chlorophenylthio)-1-ethyl-4-isopropyl-1H-imidazol-2-ylacetonitrile (720) 2-(5-(3,5-Difluorophenylthio)-4-isopropyl-1-(pyridin-2-ylmethyl)-1H-imidazol-2-yl)ethanol (721) 2-(4-(3,5-Dichlorophenylthio)-1-ethyl-5-isopropyl-1H-imidazol-2-ylmethoxy)ethanol (722) 4-Isopropyl-2-N-methylaminomethyl-5-(3-fluorophenylthio)-1-(pyridin-2-ylmethyl)-1H-imidazole (723) 4-Isopropyl-5-phenylthio-1-(pyridin-2-ylmethyl)-1H-imidazole-2-carbaldehyde (724) 5-(3-Nitrophenylthio)-4-isopropyl-1-methyl-1H-imidazol-2-ylmethanol (725) 5-(3,5-Dichlorophenylthio)-1-n-butyl-2-carbamoyloxymethyl-4-isopropyl-1H-imidazole (726) 5-(3,5-Difluorophenylthio)-1-ethyl-4-isopropyl-2-N-methylcarbamoyloxymethyl-1H-imidazole (727) 2-Dimethylaminomethyl-4-isopropyl-1-methyl-5-phenyl-1H-imidazole (728) 2-Carbamoyloxymethyl-1-ethyl-4-isopropyl-5-(3-fluorophenylthio)-1H-imidazole (729) 5-(3,5-Difluorophenylthio)-4-isopropyl-2-N-methylcarbamoyloxymethyl-1-(pyridin-3-ylmethyl)-1H-imidazole (730) 2-(5-(3,5-Dichlorophenylthio)-4-isopropyl-1-(pyridin-4-ylmethyl)-1H-imidazol-2-yl)ethanol (731) 2-Carbamoyloxymethyl-5-(3,5-dimethylphenylthio)-4-isopropyl-1-methyl-1H-imidazole (732) 2-(2-Aminoethyl)-5-(3-chlorophenylthio)-4-isopropyl-1-(pyridin-3-ylmethyl)-1H-imidazole (733) 2-(3-Carbamoyloxypropyl)-4-isopropyl-5-(3-fluorophenylthio)-1-(pyridin-4-ylmethyl)-1H-imidazole (734) 5-(3,5-Dichlorophenylthio)-2-(2-carbamoyloxyethyl)-4-isopropyl-1-methyl-1H-imidazole (735) 2-Acetylaminomethyl-5-(3-nitrophenylthio)-4-isopropyl-1-(pyridin-2-ylmethyl)-1H-imidazole (736) 2-(1-Allyl-5-(3,5-dichlorophenylthio)-4-isopropyl-1H-imidazol-2-yl)ethanol (737) 5-(3,5-Dichlorophenylthio)-2-(3-carbamoyloxypropyl)-4-isopropyl-1-(3-(pyridin-4-yl)propyl)-1H-imidazole (738) 5-(3,5-Dichlorophenylthio)-4-isopropyl-1-(pyridin-4-ylmethyl)-1H-imidazol-2-yl acetate (739) 2-(2-Carbamoyloxyethyl)-5-(3,5-difluorophenylthio)-4-isopropyl-1-(pyridin-3-ylmethyl)-1H-imidazole (740) 1-Benzyl-2-(3-carbamoyloxypropyl)-5-(3,5-difluorophenylthio)-4-isopropyl-1H-imidazole (741) 4-Isopropyl-2-N-methyl(thiocarbamoyl)oxymethyl-5-(3-fluorophenylthio)-1-(pyridin-4-ylmethyl)-1H-imidazole (742) 3-(5-(3,5-Dichlorophenylthio)-1,4-diisopropyl-1H-imidazol-2-yl)propanol (743) 2-(2-Azidoethyl)-5-(3-nitrophenylthio)-4-isopropyl-1-(pyridin-2-ylmethyl)-1H-imidazole (744) 2-(2-Carbamoyloxyethoxy)methyl-4-isopropyl-5-phenylthio-1-(pyridin-3-ylmethyl)-1H-imidazole (745) 2-Acetylaminomethyl-5-(3-nitrophenylthio)-1-ethyl-4-isopropyl-1H-imidazole (746) 2-Carbamoyloxymethyl-4-(3,5-difluorophenylthio)-5-isopropyl-1-(pyridin-4-ylmethyl)-1H-imidazole (747) 2-(3-Carbamoyloxypropyl)-5-(3,5-dimethylphenylthio)-4-isopropyl-1-(pyridin-4-ylmethyl)-1H-imidazole (748) 2-Carbamoyloxymethyl-5-(3,5-difluorophenylthio)-4-isopropyl-1-(quinolin-3-ylmethyl)-1H-imidazole (749) 5-(3,5-Difluorophenylthio)-4-isopropyl-1-(pyridin-4-ylmethyl)-1H-imidazol-2-ylmethanol (750) Methyl 3-(4-isopropyl-5-(3-fluorophenylthio)-1-(pyridin-4-ylmethyl)-1H-imidazol-2-yl)propionate (751) 5-(3,5-Dichlorophenylthio)-2-(2-Carbamoyloxyethoxy)-methyl-4-isopropyl-1-(pyridin-4-ylmethyl)-1H-imidazole (752) 5-(3,5-Difluorophenylthio)-4-isopropyl-2-methanesulfonamidomethyl-1-(pyridin-4-ylmethyl)-1H-imidazole (753) 2-(2-Carbamoyloxyethoxy)methyl-4-isopropyl-5-(3-fluorophenylthio)-1-(pyridin-2-ylmethyl)-1H-imidazole (754) 4-(3,5-Dichlorophenylthio)-5-isopropyl-1-(pyridin-4-ylmethyl)-1H-imidazol-2-ylmethanol (755) 4-Isopropyl-5-(3-fluorophenylthio)-1-(pyridin-3-ylmethyl)-2-ureidomethyl-1H-imidazole (756) 5-(3,5-Dichlorophenylthio)-1-n-butyl-2-(3-carbamoyloxypropyl)-4-isopropyl-1H-imidazole (757) 2-Aminomethyl-5-(3-chlorophenylthio)-4-isopropyl-1-(pyridin-4-ylmethyl)-1H-imidazole (758) 2-Aminomethyl-4-(3-chlorophenylthio)-1-ethyl-5-isopropyl-1H-imidazole (759) 4-(3,5-Dichlorophenylthio)-5-isopropyl-1-(pyridin-4-ylmethyl)-1H-imidazol-2-ylmethyl acetate (760) 2-(2-Aminoethyl)-4-isopropyl-1-methyl-5-(3-fluorophenylthio)-1H-imidazole
(761) 4-Isopropyl-2-N-methylcarbamoyloxymethyl-5-phenylthio-1-(pyridin-3-ylmethyl)-1H-imidazole
(762) 4-(3-Nitrophenylthio)-5-isopropyl-1-(pyridin-4-ylmethyl)-1H-imidazol-2-ylmethanol
(763) 4-Isopropyl-1-methyl-5-(3-fluorophenylthio)-1H-imidazole-2-carbaldehyde
(764) 5-Isopropyl-1-methyl-4-(3-fluorophenylthio)-1H-imidazol-ylmethyl acetate
(765) 2-Aminomethyl-5-(3-nitrophenylthio)-4-isopropyl-1-(pyridin-4-ylmethyl)-1H-imidazole
(766) 2-(2-Azidoethyl)-4-isopropyl-5-(3-fluorophenylthio)-1-(pyridin-3-ylmethyl)-1H-imidazole
(767) 1-n-Butyl-2-carbamoyloxymethyl-5-(3,5-difluorophenylthio)-4-isopropyl-1H-imidazole
(768) 2-(2-Acetoxyethyl)-1-ethyl-4-isopropyl-5-(3-fluorophenylthio)-1H-imidazole
(769) 4-(3,5-Difluorophenylthio)-5-isopropyl-1-(pyridin-4-ylmethyl)-1H-imidazol-2-ylmethanol
(770) 3-(5-(3,5-Difluorophenylthio)-4-isopropyl-1-(2-methylpyridin-3-ylmethyl)-1H-imidazol-2-yl)propanol
(771) α-(5-(3,5-Dichlorophenylthio)-2-(3-hydroxypropyl)-4-isopropyl-1H-imidazol-1-yl)acetophenone
(772) 4-(3,5-Dichlorophenylthio)-2-carbamoyloxymethyl-1-fluoromethyl-5-isopropyl-1H-imidazole
(773) 3-(5-(3,5-Difluorophenylthio)-4-isopropyl-1-(quinolin-3-ylmethyl)-1H-imidazol-2-yl)propanol
(774) 2-(1-Cyclopropylmethyl-5-(3,5-difluorophenylthio)-4-isopropyl-1H-imidazol-2-yl)ethanol
(775) 5-(3,5-Difluorophenylthio)-4-isopropyl-1-(3-(pyridin-4-yl)propyl)-1H-imidazol-2-ylmethanol
(776) 5-(3-Chlorophenylthio)-4-isopropyl-1-methyl-1H-imidazole-2-carbaldehyde oxime
(777) 2-Azidomethyl-5-(3,5-difluorophenylthio)-4-isopropyl-1-(pyridin-3-ylmethyl)-1H -imidazole
(778) 5-(3-Chlorophenylthio)-4-isopropyl-1-methyl-2-N-methylaminomethyl-1H-imidazole
(779) 2-Carbamoyloxymethyl-5-(3,5-difluorophenylthio)-4-isopropyl-1-(2-methylpyridin-3-ylmethyl)-1H-imidazole
(780) 5-(3-Chlorophenylthio)-4-isopropyl-1-(pyridin-2-ylmethyl)-1H-imidazole-2-carbaldehyde oxime
(781) 2-(1-Cyclopropylmethyl-5-(3,5-difluorophenylthio)-4-isopropyl-1H-imidazol-2-yl)ethanol
(782) 2-Dimethylaminomethyl-1-ethyl-4-isopropyl-5-(3-fluorophenylthio)-1H-imidazole
(783) 2-Aminomethyl-5-(3,5-difluorophenylthio)-1-ethyl-4-isopropyl-1H-imidazole
(784) 1-Allyl-2-(3-carbamoyloxypropyl)-5-(3,5-difluorophenylthio)-4-isopropyl-1H-imidazole
(785) 2-Acetylaminomethyl-4-isopropyl-5-phenylthio-1-(pyridin-3-ylmethyl)-1H-imidazole
(786) 5-(3,5-Dichlorophenylthio)-2-(3-carbamoyloxypropyl)-4-isopropyl-1-(pyridin-4-ylmethyl)-1H-imidazole
(787) 3-(5-(3,5-Difluorophenylthio)-4-isopropyl-1-methyl-1H-imidazol-2-yl)propanol
(788) 2-Carbamoyloxymethyl-5-(3,5-difluorophenylthio)-4-isopropyl-1-(2,2,2-trifluoroethyl)-1H-imidazole
(789) 1-Ethyl-4-isopropyl-5-phenylthio-1H-imidazole-2-carbaldehyde oxime
(790) Methyl 3-(5-(3,5-difluorophenylthio)-4-isopropyl-1-(pyridin-4-ylmethyl)-1H-imidazol-2-yl)propionate
(791) 2-(5-Isopropyl-4-phenylthio-1-(pyridin-4-ylmethyl)-1H-imidazol-2-ylmethoxy)ethanol
(792) 5-(3,5-Dichlorophenylthio)-2-dimethylaminomethyl-1-ethyl-4-isopropyl-1H-imidazole
(793) 2-(4-(3-Chlorophenylthio)-1-ethyl-5-isopropyl-1H-imidazol-2-ylmethoxy)ethanol
(794) 2-(2-Carbamoyloxyethoxy)methyl-4-isopropyl-1-methyl-5-phenylthio-1H-imidazole
(795) 4-Isopropyl-2-methanesulfonamidomethyl-1-methyl-5-(3-fluorophenylthio)-1H-imidazole
(796) 5-(3,5-Dichlorophenylthio)-4-isopropyl-1-(5,6-dihydro-6-oxopyridin-3-ylmethyl)-1H-imidazol-2-ylmethanol
(797) 1-n-Butyl-2-carbamoyloxymethyl-5-(3,5-difluorophenylthio)-4-isopropyl-1H-imidazole
(798) 3-(1-(2-Aminobenzyl)-5-(3,5-dichlorophenylthio)-4-isopropyl-1H-imidazol-2-yl)propanol
(799) 5-(3,5-Dichlorophenylthio)-1-ethyl-4-isopropyl-1H-imidazol-2-ylacetonitrile
(800) 4-Isopropyl-1-methyl-5-(3-fluorophenylthio)-2-ureidomethyl-1H-imidazole
(801) 2-(2-Carbamoyloxyethyl)-5-(3-nitrophenylthio)-4-isopropyl-1-(pyridin-4-ylmethyl)-1H-imidazole
(802) 1-Benzyl-2-carbamoyloxymethyl-4-(3,5-difluorophenylthio)-5-isopropyl-1H-imidazole
(803) 5-(3,5-Difluorophenylthio)-1-ethyl-4-isopropyl-1H-imidazole-2-carbaldehyde oxime
(804) 5-(3,5-Difluorophenylthio)-1-ethyl-4-isopropyl-2-ureidomethyl-1H-imidazole
(805) 5-(3,5-Dichlorophenylthio)-2-(2-carbamoyloxyethoxy)-methyl-1-ethyl-4-isopropyl-1H-imidazole
(806) 5-(3,5-Dimethylphenylthio)-4-isopropyl1-(pyridin-3-ylmethyl)-1H-imidazol-2-ylmethanol
(807) N-(5-(3,5-Difluorophenylthio)-4-isopropyl-1-methyl-1H-imidazol-4-ylmethyl)acetamidine
(808) α-(5-(3,5-Dimethylphenylthio)-2-(3-hydroxypropyl)-4-isopropyl-1H-imidazol-1-yl)acetophenone
(809) 2-Azidomethyl-4-isopropyl-1-methyl-5-phenylthio-1H-imidazole
(810) 2-2-(Acetoxyethyl)-5-(3,5-difluorophenylthio)-1-ethyl-4-isopropyl-1H-imidazole
(811) 2-(3-Carbamoyloxypropyl)-5-(3,5-difluorophenylthio)-4-isopropyl-1-n-propyl-1H-imidazole
(812) 5-(3,5-Dichlorophenylthio)-2-(3-carbamoyloxypropyl)-4-isopropyl-1-(pyridin-3-ylmethyl)-1H-imidazole
(813) 2-(2-Aminoethyl)-4-(3-chlorophenylthio)-1-ethyl-4-isopropyl-1H-imidazole
(814) 2-Carbamoyloxymethyl-1,4-dibenzyl-5-isopropyl-1H-imidazole
(815) 5-(3,5-Dichlorophenylthio)-2-(3-carbamoyloxypropyl)-4-isopropyl-1-n-propyl-1H-imidazole
(816) 1-(5-(3,5-Difluorophenylthio)-2-hydroxymethyl-4-isopropyl-1H-imidazol-1-yl)-2-propanone
(817) 2-Azidomethyl-5-isopropyl-1-methyl-4-phenylthio-1H-imidazole
(818) 5-(3,5-Difluorophenylthio)-1-hexyl-4-isopropyl-1H-imidazol-2-ylmethanol
(819) 2-Acetylaminomethyl-5-(3-chlorophenylthio)-4-isopropyl-1-methyl-1H-imidazole
(820) 4-(3,5-Dichlorophenylthio)-1-ethyl-5-isopropyl-1H-imidazol-2-ylmethyl acetate
(821) 2-Carbamoyloxymethyl-4-(3,5-difluorophenylthio)-1-fluoromethyl-5-isopropyl-1H-imidazole
(822) 1-Ethyl-4-isopropyl-5-phenylthio-1H-imidazol-2-ylmethyl acetate
(823) 2-(5-(3-Chlorophenylthio)-1-ethyl-4-isopropyl-1H-imidazol-2-yl)ethanol (824) 5-(3,5-Dichlorophenylthio)-4-isopropyl-1-(2-methylpyridin-3-ylmethyl)-1H-imidazol-2-ylmethanol
(825) 5-Isopropyl-1-methyl-4-phenylthio-1H-imidazol-2-ylmethyl acetate
(826) 2-Acetylaminomethyl-5-(3-nitrophenylthio)-4-isopropyl-1-methyl-1H-imidazole
(827) 4-(3-Chlorophenylthio)-5-isopropyl-1-(pyridin-4-ylmethyl)-1H-imidazole-2-carbaldehyde
(828) 1-(2-Carbamoyloxyethyl)-2-carbamoyloxymethyl-5-(3,5-difluorophenylthio)-4-isopropyl-1H-imidazole
(829) 5-(3,5-Dichorophenylthio)-2-(2-carbamoyloxyethyl)-1-cyclopropylmethyl-4-isopropyl-1H-imidazole
(830) 2-(2-Carbamoyloxyethyl)-5-(3,5-dimethylphenylthio)-4-isopropyl-1-(pyridin-3-ylmethyl)-1H-imidazole
(831) 2-(5-(3-Nitrophenylthio)-4-isopropyl-1-(pyridin-2-ylmethyl)-1H-imidazol-2-ylmethoxy)ethyl acetate
(832) Methyl 3-(1-ethyl-4-isopropyl-5-phenylthio-1H-imidazol-2-yl)propionate
(833) 2-(5-(3,5-Difluorophenylthio)-1-ethyl-4-isopropyl-1H-imidazol-2-ylmethoxy)ethyl acetate
(834) 2-(2-Carbamoyloxyethyl)-5-(3,5-difluorophenylthio)-4-isopropyl-1-(pyridin-3-ylmethyl)-1H-imidazole
(835) 2-(2-Carbamoyloxyethyl)-5-(3,5-difluorophenylthio)-4-isopropyl-1-(2-methylpyridin-3-ylmethyl)-1H-imidazole
(836) 2-(4-Isopropyl-1-methyl-5-phenylthio)-1H-imidazole-2-carbaldehyde
(837) 2-(3-Carbamoyloxypropyl)-5-(3-chlorophenylthio)-4-isopropyl-1-(pyridin-2-ylmethyl)-1H-imidazole
(838) 4-Isopropyl-2-methanesulfonamidomethyl-5-(3-fluorophenylthio)-1-(pyridin-4-ylmethyl)-1H-imidazole
(839) 2-2-(Acetoxyethyl)-4-isopropyl-1-ethyl-5-phenylthio-1H-imidazole
(840) 2-(5-(3-Chlorophenylthio)-4-isopropyl-1-(pyridin-4-ylmethyl)-1H-imidazol-2-ylmethoxy)ethyl acetate
(841) N-(5-(3,5-Dichlorophenylthio)-4-isopropyl-1-(pyridin-3-ylmethyl)-1H-imidazol-4-ylmethyl)acetamidine
(842) 5-(3,5-Difluorophenylthio)-4-isopropyl-1-(pyridin-4-ylmethyl)-2-ureidomethyl-1H-imidazole
(843) 2-(2-Aminoethyl)-4-isopropyl-5-(3-fluorophenylthio)-1-(pyridin-4-ylmethyl)-1H-imidazole
(844) 2-(5-(3-Nitrophenylthio)-1-ethyl-4-isopropyl)-1H-imidazole-2-carbaldehyde oxime
(845) 5-(3-Nitrophenylthio)-4-isopropyl-1-methyl-1H-imidazol-2-ylacetonitrile
(846) 4-Isopropyl-5-(3-fluorophenylthio)-1-(pyridin-2-ylmethyl)-2-ureidomethyl-1H-imidazole
(847) 2-(2-Azidoethyl)-5-(3,5-dichlorophenylthio)-4-isopropyl-1-(pyridin-4-ylmethyl-1H-imidazole
(848) 2-Aminomethyl-4-(3,5-difluorophenylthio)-1-ethyl-5-isopropyl-1H-imidazole
(849) 4-(3-Nitrophenylthio)-1-ethyl-5-isopropyl-1H-imidazol-2-ylmethyl acetate
(850) 3-(5-(3,5-Difluorophenylthio)-4-isopropyl-1-(pyridin-4-ylmethyl)-1H-imidazol-2-yl)propanol
(851) 2-Diaminomethyleneaminomethyl-5-(3-nitrophenylthio)-4-isopropyl-1-(pyridin-2-ylmethyl)-1H-imidazole
(852) 5-(3,5-Difluorophenylthio)-4-isopropyl-1-(pyridin-2-ylmethyl)-1H-imidazole-2-carbaldehyde hydrazone
(853) 4-Isopropyl-5-(3-fluorophenylthio)-1-(pyridin-2-ylmethyl)-1H-imidazole-2-carbaldehyde hydrazone
(854) 2-(5-(3,5-Difluorophenylthio)-4-isopropyl-1-(2,2,2-trifluoroethyl)-1H-imidazol-2-yl)ethanol
(855) 2-(2-Carbamoyloxyethyl)-5-(3,5-difluorophenylthio)-4-isopropyl-1-n-propyl-1H-imidazole
(856) 5-(3,5-Difluorophenylthio)-4-isopropylmethyl-1H-imidazole-2-carbaldehyde oxime
(857) 3-(5-(3,5-Difluorophenylthio)-4-isopropyl-1-(2,2,2-trifluoroethyl)-1H-imidazol-2-yl)propanol
(858) 2-Azidomethyl-5-(3,5-difluorophenylthio)-4-isopropyl-1-(pyridin-4-ylmethyl)-1H-imidazole
(859) 1-Ethyl-5-isopropyl-4-phenylthio-1H-imidazol-2-ylmethanol
(860) 2-(5-(3,5-Difluorophenylthio)-4-isopropyl-1-n-propyl-1H-imidazol-2-yl)ethanol
(861) 5-(3-Nitrophenylthio)-4-isopropyl-1-methyl-2-N-methylthiocarbamoyloxymethyl-1H-imidazole
(862) 5-(3,5-Difluorophenylthio)-4-isopropyl-1-(pyridin-4-ylmethyl)-1H-imidazole-2-carbaldehyde
(863) 5-(3-Nitrophenylthio)-4-isopropyl-1-methyl-1H-imidazole-2-carbaldehyde hydrazone
(864) 2-(2-Azidoethyl)-5-(3-chlorophenylthio)-4-isopropyl-1-methyl-1H-imidazole
(865) 2-Azidomethyl-5-(3,5-difluorophenylthio)-4-isopropyl-1-methyl-1H-imidazole
(866) 2-(2-Aminoethyl)-5-(3,5-difluorophenylthio)-1-ethyl-4-isopropyl-1H-imidazole
(867) 2-(4-(3-Nitrophenylthio)-5-isopropyl-1-methyl-1H-imidazol-2-ylmethoxy)ethanol
(868) 2-(2-Carbamoyloxyethyl)-5-(3,5-difluorophenylthio)-4-isopropyl-1-(quinolin-3-ylmethyl)-1H-imidazole
(869) 2-Azidomethyl-5-(3-chlorophenylthio)-4-isopropyl-1-(pyridin-3-ylmethyl)-1H-imidazole
(870) 5-(3,5-Dichlorophenylthio)-2-carbamoyloxymethyl-1-hexyl-4-isopropyl-1H-imidazole
(871) 5-(3,5-Dichlorophenylthio)-2-carbamoyloxymethyl-4-isopropyl-1-(2,2,2-trifluoroethyl)-1H-imidazole
(872) 3-(5-(3,5-Dimethylphenylthio)-4-isopropyl-1-(pyridin-2-ylmethyl)-1H-imidazol-2-yl)propanol
(873) 2-(2-Carbamoyloxyethyl)-5-(3,5-difluorophenylttlio)-1,4-diisopropyl-1H-imidazole
(874) Methyl 3-(5-(3,5-dichlorophenylthio)-1-ethyl-4-isopropyl-1H-imidazol-2-yl)propionate
(875) 5-(3,5-Dichlorophenylthio)-2-(2-carbamoyloxyethyl)-1-fluoromethyl-4-isopropyl-1H-imidazole
(876) 2-(4-(3,5-Dichlorophenylthio)-5-isopropyl-1-methyl-1H-imidazol-2-ylmethoxy)ethanol
(877) N-(5-(3-Chlorophenylthio)-4-isopropyl-1-(pyridin-2-ylmethyl)-1H-imidazole -4-ylmethyl)acetamidine
(878) 2-2-(Acetoxyethyl)-4-isopropyl-5-(3-fluorophenylthio)-1-(pyridin-3-ylmethyl)-1H-imidazole
(879) 1-Ethyl-4-isopropyl-5-(3-fluorophenylthio)-1H-imidazole-2-carbaldehyde oxime
(880) 4-Isopropyl-5-(3-fluorophenylthio)-1-(pyridin-3-ylmethyl)-1H-imidazole-2-carbaldehyde oxime
(881) 2-Carbamoyloxymethyl-5-isopropyl-4-phenylthio-1-(pyridin-4-ylmethyl)-1H-imidazole
(882) 2-Aminomethyl-4-(3-nitrophenylthio)-5-isopropyl-1-(pyridin-4-ylmethyl)-1H-imidazole
(883) 4-Isopropyl-2-N-methylaminomethyl-5-phenylthio-1-(pyridin-2-ylmethyl)-1H-imidazole
(884) 5-(3,5-Dichlorophenylthio)-4-isopropyl-1-(pyridin-2-ylmethyl)-1H-imidazole-2-carbaldehyde hydrazone
(885) 5-(3,5-Dichlorophenylthio)-4-isopropyl-1-methyl-1H-imidazol-2-ylmethyl acetate
(886) N-(4-Isopropyl-5-phenylthio-1-(pyridin-3-ylmethyl)-1H-imidazol-4-ylmethyl)acetamidine
(887) 5-(3,5-Difluorophenylthio)-4-isopropyl-1-(quinolin-3-ylmethyl)-1H-imidazol-2-ylmethanol
(888) 5-(3-Nitrophenylthio)-1-ethyl-4-isopropyl-1H-imidazol-2-ylacetonitrile
(889) 4-(3,5-Dimethylphenylthio)-5-isopropyl-1-(pyridin-4-ylmethyl)-1H-imidazol-2-ylmethanol (890) 1-n-Butyl-2-(2-carbamoyloxyethyl-5-(3,5-dimethylphenylthio)-4-isopropyl-1H-imidazole
(891) 2-(5-(3-Chlorophenylthio)-4-isopropyl-1-(pyridin-4-ylmethyl))-1H-imidazole-2-carbaldehyde
(892) 5-(3-Chlorophenylthio)-4-isopropyl-1-(pyridin-4-ylmethyl)-1H-imidazole-2-carbaldehyde hydrazone
(893) 5-(3-Chlorophenylthio)-1-ethyl-4-isopropyl-1H-imidazole-2-carbaldehyde hydrazone
(894) 1-Ethyl-4-isopropyl-2-N-methylaminomethyl-5-(3-fluorophenylthio)-1H-imidazole
(895) 2-Azidomethyl-1-ethyl-5-isopropyl-4-phenylthio-1H-imidazole
(896) 5-(3,5-Difluorophenylthio)-4-isopropyl-2-N-methylaminomethyl-1-(pyridin-3-ylmethyl)-1H-imidazole
(897) 2-(3-Carbamoyloxypropyl)-5-(3-chlorophenylthio)-4-isopropyl-1-(pyridin-4-ylmethyl)-H-imidazole
(898) 2-(1-(2-Aminobenzyl)-5-(3,5-dichlorophenylthio)-4-isopropyl-1H-imidazol-2-yl)ethanol
(899) 2-(2-Carbamoyloxyethoxy)methyl-5-(3-chlorophenylthio)-4-isopropyl-1-(pyridin-2-ylmethyl)-1H-imidazole
(900) 5-(3,5-Difluorophenylthio)-4-isopropyl-1-(pyridin-3-ylmethyl)-1H-imidazol-2-ylmethanol
(901) 5-Isopropyl-4-phenylthio-1-(pyridin-4-ylmethyl)-1H-imidazol-2-ylmethanol
(902) 2-(2-Aminoethyl)-5-(3,5-difluorophenylthio)-4-isopropyl-1-(pyridin-3-ylmethyl)-1H-imidazole
(903) 2-(1-Ethyl-4-isopropyl-5-phenylthio)-1H-imidazole-2-carbaldehyde hydrazone
(904) 5-(3,5-Difluorophenylthio)-4-isopropyl-1-(pyridin-2-ylmethyl)-1H-imidazol-2-ylmethanol
(905) 3-(5-(3,5-Dimethylphenylthio)-4-isopropyl-1-n-propyl-1H-imidazol-2-yl)propanol
(906) 1-(2-Carbamoyloxymethyl-5-(3,5-difluorophenylthio)-4-isopropyl-1H-imidazol-1-yl)-2-propanone
(907) 5-(3,5-Dichlorophenylthio)-2-(2-carbamoyloxyethoxy)methyl-4-isopropyl-1-methyl-1H-imidazole
(908) 3-(5-(3,5-Dichlorophenylthio)-4-isopropyl-1-(2-(pyridin-4-yl)ethyl)-1H-imidazol-2-yl)propanol
(909) 2-(5-(3-Nitrophenylthio)-4-isopropyl-1-(pyridin-2-ylmethyl)-1H-imidazol-2-yl)ethanol
(910) 1-(5-(3,5-Difluorophenylthio)-2-(3-hydroxypropyl)-4-isopropyl-1H-imidazol-1-yl)-2-propanone
(911) 2-(5-(3,5-Dichlorophenylthio)-1-cyclopropylmethyl-4-isopropyl-1H-imidazol-2-yl)ethanol
(912) 4-Isopropyl-5-(3-fluorophenylthio)-1-(pyridin-2-ylmethyl)-1H-imidazol-2-ylmethanol
(913) 2-(2-Acetoxyethyl)-5-(3-1-nitrophenylthio)-4-isopropyl-1-(pyridin-2-ylmethyl)-1H-imidazole
(914) 5-(3,5-Difluorophenylthio)-4-isopropyl-1-(pyridin-3-ylmethyl)-1H-imidazol-2-ylmethanol
(915) 5-(3.,5-Dichlorophenylthio)-4-isopropyl-1-(pyridin-3-ylmethyl)-1H-imidazol-2-ylmethanol
(916) 2-Carbamoyloxymethyl-5-(3,5-difluorophenylthio)-4-isopropyl-1-(5,6-dihydro-6-oxopyridin-3-ylmethyl)-1H-imidazole
(917) 2-Carbamoyloxymethyl-1,5-dibenzyl-4-isopropyl-1H-imidazole
(918) 2-(1-Cyclopropylmethyl-5-(3,5-dimethylphenylthio)-4-isopropyl-1H-imidazol-2-yl)ethanol
(919) 5-(3-Chlorophenylthio)-4-isopropyl-2-N-methylaminomethyl-1-(pyridin-3-ylmethyl)-1H-imidazole
(920) 5-(3-Chlorophenylthio)-4-isopropyl-2-methanesulfonamidomethyl-1-(pyridin-4-ylmethyl)-1H-imidazole
(921) Methyl 3-(5-(3-nitrophenylthio)-4-isopropyl-1-(pyridin-2-ylmethyl)-1H-imidazol-2-yl)propionate
(922) 3-(5-(3,5-Dichlorophenylthio)-4-isopropyl-1-(pyridin-4-ylmethyl)-1H-imidazol-2-yl)propanol
(923) 2-(3-Carbamoyloxypropyl)-1-cyclopropylmethyl-5-(3,5-difluorophenylthio)-4-isopropyl-1H-imidazole
(924) 2-(4-Isopropyl-5-phenylthio-1-(pyridin-4-ylmethyl)-1H-imidazol-2-ylmethoxy)ethyl acetate
(925) 5-(3-Nitrophenylthio)-4-isopropyl-1-methyl-1H-imidazol-2-ylmethyl acetate
(926) 2-(2Acetoxyethyl)-5-(3-nitrophenylthio)-4-isopropyl-1-methyl-1H-imidazole
(927) 3-(1,4-Diisopropyl-5-(3,5-dimethyl)phenylthio)-1H-imidazol-2-yl)propanol
(928) 5-(3,5-Difluorophenylthio)-4-isopropyl-1-(pyridin-2-ylmethyl)-1H-imidazole-2-carbaldehyde
(929) 2-Aminomethyl-5-(3-chlorophenylthio)-4-isopropyl-1-(pyridin-3-ylmethyl)-1H-imidazole
(930) 1-Allyl-5-(3,5-dichlorophenylthio)-4-isopropyl-1H-imidazol-2-ylmethanol
(931) 5-(3,5-Dichlorophenylthio)-4-isopropyl-2-methanesulfonamidomethyl-1-(pyridin-3-ylmethyl)-1H-imidazole
(932) 2-Carbamoyloxymethyl-5-(3,5-difluorophenylthio)-4-isopropyl-1-n-propyl-1H-imidazole
(933) 5-(3,5-Dichlorophenylthio)-2-carbamoyloxymethyl-4-isopropyl-1-(3-(pyridin-4-yl)propyl-1H-imidazole
(934) 2-(3-Carbamoyloxypropyl-5-(3,5-dichorophenylthio)-4-isopropyl-1-(quinolin-3-ylmethyl)-1H-imidazole
(935) 2-(5-(3,5-Dichlorophenylthio)-1-n-butyl-4-isopropyl-1H-imidazol-2-yl)ethanol
(936) 5-(3,5-Dichlorophenylthio)-4-isopropyl-1-methyl-1H-imidazole-2-carbaldehyde
(937) 2-(3-Carbamoyloxypropyl)-5-(3,5-difluorophenylthio)-1-ethyl-4-isopropyl-1H-imidazole
(938) 3-(5-(3,5-Dimethylphenylthio)-1-ethyl-4-isopropyl-1H-imidazol-2-yl)propanol
(939) 5-(3,5-Difluorophenylthio)-4-isopropyl-1-(2-(pyridin-4-yl)ethyl)-1H-imidazol-2-ylmethanol
(940) 4-Isopropyl-5-phenylthio-1-(pyridin-3-ylmethyl)-1H-imidazol-2-ylmethyl acetate
(941) 2-(4-Isopropyl-5-(3-fluorophenylthio)-1-(pyridin-3-ylmethyl)-1H-imidazol-2-ylmethoxy)ethanol
(942) 4-Isopropyl-5-phenylthio-1-(pyridin-3-ylmethyl)-1H-imidazol-2-yl acetate
(943) 5-(3,5-Dichlorophenylthio)-2-carbamoyloxymethyl-4-isopropyl-1-(5,6-dihydro-6-oxopyridin-3-ylmethyl)-1H-imidazole
(944) 2-(2-Carbamoyloxyethlyl)-4-isopropyl-1-methyl-5-phenylthio-1H-imidazole
(945) 2-Dimethylaminomethyl-4-isopropyl-1-methyl-5-(3-fluorophenylthio)-1H-imidazole
(946) 4-(3,5-Difluorophenylthio)-1-ethyl-5-isopropyl-1H-imidazol-2-ylmethanol.
(947) 2-(3-Carbamoyloxypropyl)-5-(3,5-difluorophenylthio)-1-hexyl-4-isopropyl-1H-imidazole
(948) 5-(3,5-Difluorophenylthio)-4-isopropyl-1-(2(1H)-pyridin-5-ylmethyl)-1H-imidazol-2-ylmethanol
(949) 2-(2-Aminoethyl)-4-isopropyl-5-phenylthio-1-(pyridin-3-ylmethyl)-1H-imidazole
(950) 5-(3-Chlorophenylthio)-1-ethyl-4-isopropyl-2-methanesulfonamidomethyl-1H-imidazole
(951) 5-(3,5-Dichlorophenylthio)-2-(2-carbamoyloxyethyl)-4-isopropyl-1-(5,6-dihydro-6-oxopyridin-3-ylmethyl)-1H-imidazole
(952) 5-(3-Chlorophenylthio)-4-isopropyl-1-methyl-2-N-methylcarbamoyloxymethyl-1H-imidazole (953) 5-(3,5-Difluorophenylthio)-4-isopropyl-1-(pyridin-2-ylmethyl)-1H-imidazol-2-ylmethanol
(954) 5-(3,5-Dichlorophenylthio)-4-isopropyl-1-methyl-1H-imidazol-2-ylmethanol
(955) α-(5-(3,5-Dichlorophenylthio)-2-(2-carbamoyloxyethyl)-4-isopropyl-1H-imidazol-1-yl)acetophenone
(956) 1-Benzyl-5-(3,5-dimethylphenylthio)-4-isopropyl-1H-imidazol-2-ylmethanol
(957) Methyl 3-(4-isopropyl-1-methyl-5-phenylthio-1H-imidazol-2-yl)propionate
(958) 1-(5-(3,5-Dichlorophenylthio)-2-(3-hydroxypropyl)-4-isopropyl-1H-imidazol-1-yl)-2-propanone
(959) 5-(3,5-Difluorophenylthio)-4-isopropyl-1-(pyridin-4-ylmethyl)-1H-imidazol-2-ylmethyl acetate
(960) 2-(4-Isopropyl-1-methyl-5-phenylthio-1H-imidazol-2-ylmethoxy)ethyl acetate
(961) 3-(5-(3-Nitrophenylthio)-4-isopropyl-1-(pyridin-3-ylmethyl)-1H-imidazol-2-yl)propanol
(962) 2-Azidomethyl-4-isopropyl-5-(3-fluorophenylthio)-1-(pyridin-2-ylmethyl)-1H-imidazole
(963) 5-(3,5-Difluorophenylthio)-4-isopropyl-1-(2,2,2-trifluoroethyl)-1H-imidazol-2-ylmethanol
(964) 2-Carbamoyloxymethyl-5-(3,5-difluorophenylthio)-1,4-diisopropyl-1H-imidazole
(965) 2-(2-Aminoethyl)-4-isopropyl-5-(3-fluorophenylthio)-1-(pyridin-2-ylmethyl)-1H-imidazole
(966) 4-Isopropyl-2-N-methylthiocarbamoyloxymethyl-5-(3-fluorophenylthio)-1-(pyridin-2-ylmethyl)-1H-imidazole
(967) 2-(5-(3-Nitrophenylthio)-1-ethyl-4-isopropyl)-1H-imidazole-2-carbaldehyde
(968) 2-(5-(3,5-Difluorophenylthio)-4-isopropyl-1-(pyridin-2-ylmethyl)-1H-imidazol-2-ylmethoxy)ethyl acetate
(969) 3-(5-(3-Nitrophenylthio)-4-isopropyl-1-methyl-1H-imidazol-2-yl)propanol
(970) α-(2-(3-Carbamoyloxypropyl)-5-(3,5-difluorophenylthio)-4-isopropyl-1H-imidazol-1-yl)acetophenone
(971) 2-Aminomethyl-5-(3,5-difluorophenylthio)-4-isopropyl-1-methyl-1H-imidazole
(972) 2-(3-Carbamoyloxypropyl)-5-(3-chlorophenylthio)-4-isopropyl-1-(pyridin-3-ylmethyl)-1H-imidazole
(973) α-(2-Carbamoyloxymethyl-5-(3,5-difluorophenylthio)-4-isopropyl-1H-imidazol-1-yl)acetophenone
(974) 5-(3,5-Difluorophenylthio)-1-ethyl-4-isopropyl-2-N-dimethylaminomethyl-1H-imidazole
(975) 2-(4-Isopropyl-5-(3-fluorophenylthio)-1-(pyridin-2-ylmethyl))-1H-imidazole-2-carbaldehyde oxime
(976) 2-(5-(3,5-Dichlorophenylthio)-4-isopropyl-1-(2-methylpyridin-3-ylmethyl)-1H-imidazol-2-yl)ethanol
(977) 2-(2-Aminoethyl)-5-(3,5-dichlorophenylthio)-4-isopropyl-methyl-1H-imidazole
(978) 1-(2-Aminobenzyl)-2-(2-carbamoyloxyethyl)-5-(3,5-difluorophenylthio)-4-isopropyl-1H-imidazole
(979) 5-(3,5-Dichlorophenylthio)-2-(2-carbamoyloxyethyl)-4-isopropyl-1-(quinolin-3-ylmethyl)-1H-imidazole
(980) 3-(5-(3,5-Difluorophenylthio)-4-isopropyl-1-(3-phenylpropyl)-1H-imidazol-2-yl)propanol
(981) 2-(5-(3,5-Dichlorophenylthio)-4-isopropyl-1-(pyridin-4-ylmethyl)-1H-imidazol-2-ylmethoxy)ethyl acetate
(982) 2-(2-Acetoxyethyl)-5-(3,5-dichlorophenylthio)-1-ethyl-4-isopropyl-1H-imidazole
(983) 3-(5-(3,5-Difluorophenylthio)-1-ethyl-4-isopropyl-1H-imidazol-2-yl)propanol
(984) α-(2-(3-Carbamoyloxypropyl)-5-(3,5-dimethylphenylthio)-4-isopropyl-1H-imidazol-1-yl)acetophenone
(985) 2-Azidomethyl-4-(3,5-difluorophenylthio)-5-isopropyl-1-(pyridin-4-ylmethyl)-1H-imidazole
(986) 5-(3,5-Dichlorophenylthio)-2-(2-carbamoyloxyethyl)-1-hexyl-4-isopropyl-1H-imidazole
(987) 1-(4-Aminobenzyl)-5-(3,5-dichlorophenylthio)-4-isopropyl-1H-imidazol-2-ylmethanol
(988) 2-(5-(3,5-Dichlorophenylthio)-4-isopropyl-1-(pyridin-4-ylmethyl)-1H-imidazol-2-ylmethoxy)ethanol
(989) 5-(3-Nitrophenylthio)-2-dimethylaminomethyl-4-isopropyl-1-(pyridin-3-ylmethyl)-1H-imidazole
(990) 2-(5-(3,5-Difluorophenylthio)-1-ethyl-4-isopropyl-1H-imidazol-2-yl)ethanol
(991) 5-(3-Nitrophenylthio)-4-isopropyl-2-N-methylthiocarbamoyloxymethyl-1-(pyridin-4-ylmethyl)-1H-imidazole
(992) 2-(3-Carbamoyloxypropyl)-5-(3,5-dimethylphenylthio)-4-isopropyl-1-(pyridin-2-ylmethyl)-1H-imidazole
(993) 5-(3-Chlorophenylthio)-4-isopropyl-2-methanesulfonamidomethyl-1-methyl-1H-imidazole
(994) 2-(2-Carbamoyloxyethlyl)-5-(3,5-difluorophenylthio)-4-isopropyl-1-methyl-1H-imidazole
(995) 2-Azidomethyl-5-(3-chlorophenylthio)-4-isopropyl-1-(pyridin-4-ylmethyl)-1H-imidazole
(996) 4-Isopropyl-5-(3-fluorophenylthio)-1-(pyridin-4-ylmethyl)-1H-imidazol-2-ylmethanol
(997) 5-(3-Chlorophenylthio)-4-isopropyl-1-methyl-2-ureidomethyl-1H-imidazole
(998) 2-(3-Carbamoyloxypropyl)-5-(3,5-difluorophenylthio)-4-isopropyl-1-(2-(pyridin-4-yl)ethyl)-1H-imidazole
(999) 5-(3,5-Dichlorophenylthio)-4-isopropyl-1-(pyridin-4-ylmethyl)-1H-imidazol-2-ylacetonitrile (1000) 3-(1-Benzyl-5-(3,5-difluorophenylthio)-4-isopropyl-1H-imidazol-2-yl)propanol
(1001) 5-(3-Chlorophenylthio)-4-isopropyl-1-(pyridin-2-ylmethyl)-1H-imidazole-2-carbaldehyde
(1002) 2-Carbamoyloxymethyl-5-(3-nitrophenylthio)-4-isopropyl-1-methyl-1H-imidazole
(1003) 4-(3-Nitrophenylthio)-5-isopropyl-1-(pyridin-4-ylmethyl)-1H-imidazol-2-ylmethyl acetate
(1004) 2-(1,4-Diisopropyl-5-(3,5-dimethylphenylthio)-1H-imidazol-2-yl)ethanol
(1005) 4-Isopropyl-2-methanesulfonamidomethyl-5-phenylthio-1-(pyridin-3-ylmethyl)-1H-imidazole
(1006) 4-Isopropyl-5-(3-fluorophenylthio)-1-(pyridin-2-ylmethyl)-1H-imidazol-2-ylmethyl acetate
(1007) 2-(2-Carbamoyloxyethyl)-4-isopropyl-5-(3-fluorophenylthio)-1-(pyridin-2-ylmethyl)-1H-1-imidazole
(1008) 5-(3-Nitrophenylthio)-1-ethyl-4-isopropyl-2-N-methylcarbamoyloxymethyl-1H-imidazole
(1009) 4-Isopropyl-1-methyl-5-(3-fluorophenylthio)-1H-imidazole-2-carbaldehyde oxime
(1010) 2-(2-Acetoxyethyl)-5-(3-chlorophenylthio)-1-ethyl-4-isopropyl-1H-imidazole
(1011) α-(5-(3,5-Difluorophenylthio)-2-(3-hydroxypropyl)-4-isopropyl-1H-imidazol-1-yl)acetophenone
(1012) 2-Aminomethyl-5-(3-chlorophenylthio)-1-ethyl-4-isopropyl-1H-imidazole
(1013) 4-Isopropyl-2-N-methylcarbamoyloxymethyl-5-(3-fluorophenylthio)-1-(pyridin-1-2-ylmethyl)-1H-imidazole
(1014) 2-(5-(3,5-Dichlorophenylthio)-4-isopropyl-1-(pyridin-2-ylmethyl)-1H-imidazole-2-carbaldehyde oxime
(1015) 4-Isopropyl-2-N-methyl,(thiocarbamoyl)oxymethyl-5-(3-fluorophenylthio)-1-(pyridin-3-ylmethyl)-1H-imidazole (1016) 2-(5-(3,5-Dimethylphenylthio)-1-hexyl-4-isopropyl-1H-imidazol-2-yl)ethanol
(1017) 2-(5-(3-Chlorophenylthio)-1-ethyl-4-isopropyl-1H-imidazol-2-ylmethoxy)ethanol
(1018) 3-(5-(3,5-Dimethylphenylthio)-4-isopropyl-1-methyl-1H-imidazol-2-yl)propanol
(1019) 2-Aminomethyl-1-ethyl-4-isopropyl-5-(3-fluorophenylthio)-1H-imidazole
(1020) 2-(2-Carbamoyloxyethyl)-5-(3,5-difluorophenylthio)-4-isopropyl-1-(2,2,2-trifluoroethyl)-1H-imidazole
(1021) 2-(2-Carbamoyloxyethoxy)methyl-4-isopropyl-1-methyl-5-(3-fluorophenylthio)-1H-imidazole
(1022) 1-Benzyl-4-(3,5-difluorophenylthio)-5-isopropyl-1H-imidazol-2-ylmethanol
(1023) 1-Allyl-5-(3,5-dichlorophenylthio)-2-(2-carbamoyloxyethyl)-4-isopropyl-1H-imidazole
(1024) 5-(3,5-Difluorophenylthio)-2-dimethylaminomethyl-4-isopropyl-1-(pyridin-2-ylmethyl)-1H-imidazole
(1025) 2-(5-(3,5-Difluorophenylthio)-4-isopropyl-1-(2-methylpyridin-3-ylmethyl)-1H-imidazol-2-yl)ethanol
(1026) 1-(2-Carbamoyloxymethyl-5-(3,5-difluorophenylthio)-4-isopropyl-1H-imidazol-1-yl)-2-propanone
(1027) 3-(4-Isopropyl-5-phenylthio-1-(pyridin-4-ylmethyl)-1H-imidazol-2-yl)propanol
(1028) 5-(3,5-Dichlorophenylthio)-2-carbamoyloxymethyl-1-ethyl-4-isopropyl-1H-imidazole
(1029) 2-Carbamoyloxymethyl-5-isopropyl-4-(3-fluorophenylthio)-1-(pyridin-4-ylmethyl)-1H-imidazole
(1030) 1-Allyl-5-(3,5-dichlorophenylthio)-2-carbamoyloxymethyl-4-isopropyl-1H-imidazole
(1031) 2-(5-(3,5-Dichlorophenylthio)-4-isopropyl-1-(pyridin-2-ylmethyl)-1H-imidazol-2-ylmethoxy)ethanol
(1032) 2-(2-Carbamoyloxyethyl)-5-(3,5-difluorophenylthio)-1-ethyl-4-isopropyl-1H-imidazole
(1033) 2-(3-Carbamoyloxypropyl)-5-(3,5-dimethylphenylthio)-1-hexyl-4-isopropyl-1H-imidazole
(1034) 2-Carbamoyloxymethyl-5-(3,5-difluorophenylthio)-4-isopropyl-1-(pyridin-4-ylmethyl)-1H-imidazole
(1035) 2-Aminomethyl-1-ethyl-5-isopropyl-4-phenylthio-1H-imidazole
(1036) 2-Aminomethyl-5-isopropyl-1-methyl-4-(3-fluorophenylthio)-1H-imidazole
(1037) 1-Ethyl-4-isopropyl-2-N-methylcarbamoyloxymethyl-5-phenylthio-1H-imidazole
(1038) 1-Benzyl-4-(3,5-difluorophenylthio)-5-isopropyl-1H-imidazol-2-ylmethanol
(1039) 2-(5-(3,5-Difluorophenylthio)-4-isopropyl-1-(pyridin-2-ylmethyl)-1H-imidazol-2-ylmethoxy)ethanol
(1040) 2-Carbamoyloxymethyl-1-ethyl-5-isopropyl-4-(3-fluorophenylthio)-1H-imidazole
(1041) α-(2-(2-Carbamoyloxyethyl)-5-(3,5-difluorophenylthio)-4-isopropyl-1H-imidazol-1-yl)acetophenone
(1042) 2-Acetylaminomethyl-4-isopropyl-5-phenylthio-1-(pyridin-4-ylmethyl)-1H-imidazole
(1043) 2-(2-Carbamoyloxyethoxy)methyl-5-(3-chlorophenylthio)-4-isopropyl-1-methyl-1H-imidazole
(1044) 2-Acetylaminomethyl-5-(3,5-difluorophenylthio)-4-isopropyl-1-(pyridin-3-ylmethyl)-1H-imidazole
(1045) 2-(5-(3,5-Dimethylphenylthio)-4-isopropyl-1-(pyridin-3-ylmethyl)-1H-imidazol-2-yl)ethanol
(1046) 5-(3,5-Difluorophenylthio)-4-isopropyl-2-N-methyl(thiocarbamoyl)oxymethyl-1-(pyridin-2-ylmethyl)-1H-imidazole
(1047) 3-(5-(3,5-Dichlorophenylthio)-4-isopropyl-1-methyl-1H-imidazol-2-yl)propanol
(1048) 2-(2-Carbamoyloxyethyl)-5-(3,5-difluorophenylthio)-4-isopropyl-1-(5,6-dihydro-6-oxopyridin-3-ylmethyl)-1H-imidazole
(1049) 5-(3-Nitrophenylthio)-1-ethyl-4-isopropyl-1H-imidazol-2-yl acetate
(1050) 2-(1-Allyl-5-(3,5-difluorophenylthio)-4-isopropyl-1H-imidazol-2-yl)ethanol
(1051) 2-(5-(3-Chlorophenylthio)-1-ethyl-4-isopropyl-1H-imidazol-2-ylmethoxy)ethyl acetate
(1052) 4-(3-Nitrophenylthio)-5-isopropyl-1-methyl-1H-imidazole-2-carbaldehyde
(1053) 2-(2-Azidoethyl)-5-(3,5-difluorophenylthio)-1-ethyl-4-isopropyl-1H-imidazole
(1054) 5-(3,5-Dichlorophenylthio)-2-(2-carbamoyloxyethyl)-4-isopropyl-1-(2,2,2-trifluoroethyl)-1H-imidazole
(1055) 2-(5-(3,5-Difluorophenylthio)-4-isopropyl-1-n-propyl-1H-imidazol-2-yl)ethanol
(1056) 1-(3-Aminobenzyl)-5-(3,5-dichlorophenylthio)-2-(2-carbamoyloxyethyl)-4-isopropyl-1H-imidazole
(1057) 5-(3-Nitrophenylthio)-4-isopropyl-1-(pyridin-2-ylmethyl)-1H-imidazole-2-carbaldehyde
(1058) 1-(2-Aminobenzyl)-5-(3,5-dichlorophenylthio)-2-carbamoyloxymethyl-4-isopropyl-1H-imidazole
(1059) 3-(4-Isopropyl-5-phenylthio-1-(pyridin-3-ylmethyl)-1H-imidazol-2-yl)propanol
(1060) 1-Allyl-2-(2-carbamoyloxyethyl)-5-(3,5-dimethylphenylthio)-4-isopropyl-1H-imidazole
(1061) 5-(3-Chlorophenylthio)-4-isopropyl-methyl-1H-imidazol-2-ylacetonitrile
(1062) 3-(5-(3,5-Difluorophenylthio)-4-isopropyl-1-(pyridin-3-ylmethyl)-1H-imidazol-2-yl)propanol
(1063) 2-Aminomethyl-5-(3,5-Difluorophenylthio)-1-ethyl-4-isopropyl-1H-imidazole
(1064) 3-(1-Allyl-5-(3,5-dimethylphenylthio)-4-isopropyl-1H-imidazol-2-yl)propanol
(1065) Methyl 3-(5-(3-nitrophenylthio)-4-isopropyl-1-(pyridin-3-ylmethyl)-1H-imidazol-2-yl)propionate
(1066) 2-(2-Aminoethyl)-5-(3,5-dichlorophenylthio)-4-isopropyl-1-(pyridin-3-ylmethyl)-1H-imidazole
(1067) 5-(3,5-Difluorophenylthio)-1-ethyl-4-isopropyl-1H-imidazol-2-yl acetate
(1068) 5-(3-Chlorophenylthio)-1-ethyl-4-isopropyl-1H-imidazol-2-yl acetate
(1069) 4-(3-Nitrophenylthio)-5-isopropyl-1-methyl-1H-imidazol-2-ylmethyl acetate
(1070) Methyl 3-(4-isopropyl-1-methyl-5-(3-fluorophenylthio)-1H-imidazol-2-yl)propionate
(1071) 2-(2-Azidoethyl)-5-(3-chlorophenylthio)-4-isopropyl-1-(pyridin-3-ylmethyl)-1H-imidazole
(1072) 3-(5-(3,5-Dimethylphenylthio)-4-isopropyl-1-(2,2,2-trifluoroethyl)-1H-imidazol-2-yl)propanol
(1073) 5-(3-Nitrophenylthio)-4-isopropyl-1-(pyridin-2-ylmethyl)-2-ureidomethyl-1H-imidazole
(1074) 2-(S-(3-Nitrophenylthio)-4-isopropyl-1-(pyridin-4-ylmethyl)-1H-imidazol-2-ylmethoxy)ethanol
(1075) 2-(5-(3,5-Difluorophenylthio)-4-isopropyl-1-(pyridin-3-ylmethyl)-1H-imidazol-2-ylmethoxy)ethyl acetate
(1076) 2-(3-Carbamoyloxypropyl)-4-isopropyl-5-phenylthio-1-(pyridin-2-ylmethyl)-1H-imidazole
(1077) 2-Azidomethyl-5-(3-nitrophenylthio)-4-isopropyl-1-(pyridin-4-ylmethyl)-1H-imidazole
(1078) 5-(3,5-Dimethylphenylthio)-4-isopropyl-1-methyl-1H-imidazol-2-ylmethanol
(1079) 2-Acetylaminomethyl-4-isopropyl-5-(3-fluorophenylthio)-1-(pyridin-4-ylmethyl)-1H-imidazole (1080) 5-(3,5-Dichlorophenylthio)-4-isopropyl-1-(pyridin-2-ylmethyl)-1H-imidazole-2-carbaldehyde
(1081) 3-(1-Allyl-5-(3,5-difluorophenylthio)-4-isopropyl-1H-imidazol-2-yl)propanol
(1082) 5-(3,5-Difluorophenylthio)-2-dimethylaminomethyl-4-isopropyl-1-(pyridin-4-ylmethyl)-1H-imidazole
(1083) 5-(3-Nitrophenylthio)-4-isopropyl-1-(pyridin-2-ylmethyl)-1H-imidazol-2-ylmethyl acetate
(1084) 4-Isopropyl-1-methyl-5-(3-fluorophenylthio)-1-imidazol-2-ylmethanol
(1085) 2-(5-(3-Chlorophenylthio)-4-isopropyl-1-(pyridin-3-ylmethyl)-1H-imidazol-2-yl)ethanol
(1086) 2-(5-(3,5-Difluorophenylthio)-1-fluoromethyl-4-isopropyl-1H-imidazol-2-yl)ethanol
(1087) 5-(3,5-Dichlorophenylthio)-2-carbamoyloxymethyl-4-isopropyl-1-methyl-1H-imidazole
(1088) 1-(5-(3,5-Dichlorophenylthio)-2-(2-carbamoyloxyethyl)-4-isopropyl-1H-imidazol-1-yl)-2-propanone
(1089) 5-(3-Chlorophenylthio)-2-diaminomethyleneaminomethyl-4-isopropyl-1-(pyridin-4-ylmethyl)-1H-imidazole
(1090) N-(5-(3-Chlorophenylthio)-4-isopropyl-1-(pyridin-3-ylmethyl)-1H-imidazol-4-ylmethyl)acetamidine
(1091) Methyl 3-(5-(3-chlorophenylthio)-1-ethyl-4-isopropyl-1H-imidazol-2-yl)propionate
(1092) 5-(3-Nitrophenylthio)-4-isopropyl-1-(pyridin-2-ylmethyl)-1H-imidazol-2-yl acetate
(1093) 2-(2-Azidoethyl)-4-isopropyl-5-(3-fluorophenylthio)-1-(pyridin-4-ylmethyl)-1H-imidazole
(1094) 2-(2-Carbamoyloxyethyl)-5-(3,5-difluorophenylthio)-1,4-diisopropyl-1H-imidazole
(1095) 2-Azidomethyl-4-(3,5-difluorophenylthio)-5-isopropyl-1-methyl-1H-imidazole
(1096) 2-(2-Aminoethyl)-4-isopropyl-5-phenylthio-1-(pyridin-4-ylmethyl)-1H-imidazole
(1097) 2-Azidomethyl-5-(3-nitrophenylthio)-1-ethyl-4-isopropyl-1H-imidazole
(1098) 5-(3-Chlorophenylthio)-4-isopropyl-2-ethanesulfonamidomethyl-1-(pyridin-2-ylmethyl)-1H-imidazole
(1099) 5-(3,5-Dichlorophenylthio)-1-ethyl-4-isopropyl-1H-imidazol-2-ylmethyl acetate
(1100) 4-Isopropyl-5-phenylthio-1-(pyridin-2-ylmethyl)-1H-imidazol-2-ylacetonitrile
(1101) α-(2-(3-Carbamoyloxypropyl)-5-(3,5-difluorophenylthio)-4-isopropyl-1H-imidazol-1-yl)acetophenone
(1102) 2-Azidomethyl-4-isopropyl-5-phenylthio-1-(pyridin-2-ylmethyl)-1H-imidazole
(1103) 2-(2-Carbamoyloxyethoxy)methyl-4-isopropyl-5-(3-fluorophenylthio)-1-(pyridin-3-ylmethyl)-1H-imidazole
(1104) 2-(2-Aminoethyl)-5-(3,5-dichlorophenylthio)-4-isopropyl-1-(pyridin-4-ylmethyl)-1H-imidazole
(1105) 5-(3,5-Dichlorophenylthio)-2-(3-carbamoyloxypropyl)-4-isopropyl-1-5,6-dihydro-6-oxopyridin-3-ylmethyl)-1H-imidazole
(1106) N-(5-(3-Chlorophenylthio)-4-isopropyl-1-methyl-1H-imidazol-4-ylmethyl)acetamidine
(1107) 4-Isopropyl-2-N-methylaminomethyl-5-(3-fluorophenylthio)-1-(pyridin-4-ylmethyl)-1H-imidazole
(1108) 2-Dimethylaminomethyl-4-isopropyl-5-phenylthio-1-(pyridin-2-ylmethyl)-1H-imidazole
(1109) 2-(2-Carbamoyloxyethyl)-5-(3,5-difluorophenylthio)-4-isopropyl-1-(pyridin-4-ylmethyl)-1H-imidazole
(1110) 1-Allyl-2-(2-carbamoyloxyethyl)-5-(3,5-difluorophenylthio)-4-isopropyl-1H-imidazole
(1111) 2-Azidomethyl-5-(3,5-dichlorophenylthio)-1-ethyl-4-isopropyl-1H-imidazole
(1112) 5-(3-Chlorophenylthio)-1-ethyl-4-isopropyl-1H-imidazol-2-ylmethanol
(1113) 4-Isopropyl-5-(3-fluorophenylthio)-1-(pyridin-4-ylmethyl)-2-ureidomethyl-1H-imidazole
(1114) 5-(3,5-Dichlorophenylthio)-2-(2-carbamoyloxyeLyl)-4-isopropyl-1-(2-methylpyridin-3-ylmethyl)-1H-imidazole
(1115) 4-Isopropyl-5-(3-fluorophenylthio)-1-(pyridin-4-ylmethyl)-1H-imidazole-2-carbaldehyde hydrazone
(1116) 2-(2-Aminoethyl)-5-(3,5-dichlorophenylthio)-4-isopropyl-1-(pyridin-2-ylmethyl)-1H-imidazole
(1117) 5-(3-Nitrophenylthio)-1-ethyl-4-isopropyl-2-methanesulfonamidomethyl-1H-imidazole
(1118) 1-Ethyl-5-isopropyl-4-phenylthio-1H-imidazol-2-ylmethylacetate
(1119) 2-(5-(3-Nitrophenylthio)-4-isopropyl-1-methyl-1H-imidazol-2-ylmethoxy)ethyl acetate
(1120) 2-(2-Azidoethyl)-5-(3,5-difluorophenylthio)-4-isopropyl-1-(pyridin-2-ylmethyl)-1H-imidazole
(1121) N-(5-(3,5-Difluorophenylthio)-4-isopropyl-1-(pyridin-2-ylmethyl)-1H-imidazol-4-ylmethyl)acetamidine
(1122) 2-(5-isopropyl-4-(3-fluorophenylthio)-1-(pyridin-4-ylmethyl))-1H-imidazole-2-carbaldehyde
(1123) 3-(5-(3,5-Difluorophenylthio)-4-isopropyl-1-(2,2,2-trifluoroethyl)-1H-imidazol-2-yl)propanol
(1124) 2-(2-Carbamoyloxyethyl)-4-isopropyl-5-(3-fluorophenylthio)-1-(pyridin-4-ylmethyl)-1H-imidazole
(1125) 2-(1-Ethyl-4-isopropyl-5-(3-fluorophenylthio)-1H-imidazol-2-ylmethoxy)ethyl acetate
(1126) 2-(5-(3-Chlorophenylthio)-4-isopropyl-1-methyl-1H-imidazol-2-ylmethoxy)ethanol
(1127) 5-(3,5-Dichlorophenylthio)-2-carbamoyloxymethyl-4-isopropyl-1-(pyridin-3-ylmethyl)-1H-imidazole
(1128) 2-(5-(3,5-Dichlorophenylthio)-4-isopropyl-1-(2-(pyridin-4-yl)ethyl)-1H-imidazol-2-yl)ethanol
(1129) 2-(1-Allyl-5-(3,5-dimethylphenylthio)-4-isopropyl-1H-imidazol-2-yl)ethanol
(1130) 2-(2-Carbamoyloxyethyl)-5-(3,5-difluorophenylthio)-4-isopropyl-1-(3-(pyridin-4-yl)propyl)-1H-imidazole
(1131) 2-(3-Carbamoyloxypropyl)-5-(3,5-dimethylpthenylthio)-1-fluoromethyl-4-isopropyl-1H-imidazole
(1132) 5-(3-Chlorophenylthio)-2-dimethylaminomethyl-4-isopropyl-1-(pyridin-2-ylmethyl)-1H-imidazole
(1133) 4-(3,5-Difluorophenylthio)-5-isopropyl-1-(pyridin-4-ylmethyl)-1H-imidazol-2-ylmethanol
(1134) 2-Acetylaminomethyl-4-isopropyl-1-methyl-5-phenylthio-1H-imidazole
(1135) 3-(5-(3,5-Difluorophenylthio)-4-isopropyl-1-n-propyl-1H-imidazol-2-yl)propanol
(1136) 2-(2-Acetoxyethyl)-4-isopropyl-5-phenylthio-1-(pyridin-2-ylmethyl)-1H-imidazole
(1137) 3-(1-(4-Aminobenzyl)-5-(3,5-difluorophenylthio)-4-isopropyl-1H-imidazol-2-yl)propanol
(1138) 5-(3-Nitrophenylthio)-2-dimethylaminomethyl-1-ethyl-4-isopropyl-1H-imidazole
(1139) 2-Carbamoyloxymethyl-5-(3,5-difluorophenylthio)-4-isopropyl-1-(3-(pyridin-4-yl)propyl)-1H-imidazole
(1140) 2-(5-(3,5-Difluorophenylthio)-4-isopropyl-1-(pyridin-3-ylmethyl)-1H-imidazol-2-yl)ethanol
(1141) 5-(3,5-Difluorophenylthio)-1-ethyl-4-isopropyl-1H-imidazol-2-ylmethanol
(1142) 4-Isopropyl-2-methanesulfonamidomethyl-5-(3-fluorophenylthio)-1-(pyridin-3-ylmethyl)-1H-imidazole (1143) 2-(1-Ethyl-4-isopropyl-5-phenylthio-1H-imidazol-2-ylmethoxy)ethyl acetate
(1144) 5-(3-Nitrophenylthio)-4-isopropyl-2-N-methyl(thiocarbamoyl)oxymethyl-1-(pyridin-2-ylmethyl)-1H-imidazole
(1145) 2-(5-(3,5-Dichlorophenylthio)-4-isopropyl-1-(pyridin-3-ylmethyl)-1H-imidazol-2-yl)ethanol
(1146) 5-(3,5-Dichlorophenylthio)-4-isopropyl-2-methanesulfonamidomethyl-1-(pyridin-4-ylmethyl)-1H-imidazole
(1147) 2-2-(Acetoxyethyl)-5-(3-nitrophenylthio)-4-isopropyl-1-(pyridin-3-ylmethyl)-1H-imidazole
(1148) 4-Isopropyl-2-N-methylaminomethyl-5-phenylthio-1-(pyridin-3-ylmethyl)-1H-imidazole
(1149) 5-(3,5-Dichlorophenylthio)-4-isopropyl-1-(pyridin-2-ylmethyl)-1H-imidazol-2-ylacetonitrile
(1150) 4-Isopropyl-5-phenylthio-1-(pyridin-2-ylmethyl)-2-ureidomethyl-1H-imidazole
(1151) Methyl 3-(4-isopropyl-5-phenylthio-1-(pyridin-2-ylmethyl)-1H-imidazol-2-yl)propionate
(1152) 5-(3-Nitrophenylthio)-2-dimethylaminomethyl-4-isopropyl-1-methyl-1H-imidazole
(1153) 5-(3-Chlorophenylthio)-4-isopropyl-2-N-methylcarbamoyloxymethyl-1-(pyridin-4-ylmethyl)-1H-imidazole
(1154) 2-Carbamoyloxymethyl-5-(3,5-difluorophenylthio)-4-isopropyl-1-(3-phenylpropyl)-1H-imidazole
(1155) 4-(3-Chlorophenylthio)-1-ethyl-5-isopropyl-1H-imidazol-2-ylmethanol
(1156) 3-(5-(3,5-Dichlorophenylthio)-4-isopropyl-1-n-propyl-1H-imidazol-2-yl)propanol
(1157) 3-(5-(3,5-Difluorophenylthio)-1-hexyl-4-isopropyl-1H-imidazol-2-yl)propanol
(1158) 5-(3-Chlorophenylthio)-4-isopropyl-1-(pyridin-4-ylmethyl)-1H-imidazol-2-ylmethyl acetate
(1159) 5-(3-Chlorophenylthio)-4-isopropyl-1-(pyridin-3-ylmethyl)2-ureidomethyl-1H-imidazole
(1160) 5-(3,5-Dichlorophenylthio)-4-isopropyl-1-(pyridin-4-ylmethyl)-1H-imidazole-2-carbaldehyde oxime
(1161) 5-(3,5-Dichlorophenylthio)-4-isopropyl-2-N-methylthiocarbamoyloxymethyl-1-(pyridin-3-ylmethyl)-1H-imidazole
(1162) 5-(3,5-Difluorophenylthio)-1-ethyl-4-isopropyl-1H-imidazol-2-ylmethyl acetate
(1163) 2-(3-Carbamoyloxypropyl)-5-(3,5-difluorophenylthio)-4-isopropyl-1-methyl-1H-imidazole
(1164) 3-(5-(3,5-Difluorophenylthio)-4-isopropyl-1-(3-(pyridin-4-yl)propyl)-1H-imidazol-2-yl)propanol
(1165) 2-Dimethylaminomethyl-4-isopropyl-5)-phenylthio-1-(pyridin-3-ylmethyl)-1H-imidazole
(1166) 5-(3,5-Dimethylphenylthio)-4-isopropyl-1-(pyridin-4-ylmethyl)-1H-imidazol-2-ylmethanol
(1167) 2-(2-Carbamoyloxyethoxy)methyl-5-(3,5-difluorophenylthio)-1-ethyl-4-isopropyl-1H-imidazole
(1168) 2-Diaminomethyleneaminomethyl-1-ethyl-4-isopropyl-5-phenylthio-1H-imidazole
(1169) 2-(4-Isopropyl-5-phenylthio-1-(pyridin-3-ylmethyl)-1H-imidazol-2-ylmethoxy)ethanol
(1170) 1-(2-(2-Carbamoyloxyethlyl)-5-(3,5-difluorophenylthio)-4-isopropyl-1H-imidazol-1-yl))-2-propanone
(1171) 3-(4-Isopropyl-1-methyl-5-phenylthio-1H-imidazol-2-yl)propanol
(1172) 2-Carbamoyloxymethyl-5-(3,5-dimethylphenylthio)-4-isopropyl-1-(pyridin-2-ylmethyl)-1H-imidazole
(1173) 5-(3-Nitrophenylthio)-4-isopropyl-1-(pyridin-3-ylmethyl)-1H-imidazole-2-carbaldehyde oxime
(1174) N-(5-(3-Nitrophenylthio)-4-isopropyl-1-(pyridin-3-ylmethyl)-1H-imidazol-4-ylmethyl)acetamidine
(1175) 2-(2-Acetoxyethyl)-5-(3-chlorophenylthio)-4-isopropyl-1-(pyridin-3-ylmethyl)-1H-imidazole
(1176) 3-(5-(3,5-Difluorophenylthio)-1-fluoromethyl-4-isopropyl-1H-imidazol-2-yl)propanol
(1177) α-(5-(3,5-Difluorophenylthio)-2-hydroxymethyl-4-isopropyl-1H-imidazol-1-yl)acetophenone
(1178) 2-Carbamoyloxymethyl-5-(3,5-difluorophenylthio)-4-isopropyl-1-(pyridin-2-ylmethyl)-1H-imidazole
(1179) 1-Ethyl-4-isopropyl-5-phenylthio-1H-imidazol-2-ylacetonitrile
(1180) 5-(3 5-Dichlorophenylthio)-1-ethyl-4-isopropyl-1H-imidazole-2-carbaldehyde hydrazone
(1181) 2-(5-(3,5-Difluorophenylthio)-4-isopropyl-1-(pyridin-4-ylmethyl)-1H-imidazol-2-yl)ethanol
(1182) 5-(3,5-Dichlorophenylthio)-2-diaminomethyleneaminomethyl-4-isopropyl-1-(pyridin-3-yl-methyl)-1H-imidazole
(1183) 2-Aminomethyl-4-(3,5-difluorophenylthio)-5-isopropyl-1-(pyridin-4-ylmethyl)-1H-imidazole
(1184) 1-n-Butyl-2-(3-carbamoyloxypropyl)-5-(3,5-dimethylphenylthio)-4-isopropyl-1H-imidazole
(1185) 2-(4-isopropyl-1-methyl-5-(3-fluorophenylthio)-1H-imidazol-2-yl)ethanol
(1186) 1-Allyl-2-(2-carbamoyloxyethyl)-5-(3,5-difluorophenylthio)-4-isopropyl-1H-imidazole
(1187) 2-(5-(3,5-Dichlorophenylthio)-4-isopropyl-1-(5,6-dihydro-6-oxopyridin-3-ylmethyl)-1H-imidazol-2-yl)ethanol
(1188) 5-(3,5-Dichlorophenylthio)-2-carbamoyloxymethyl-4-isopropyl-1-(quinolin-3-ylmethyl)-1H-imidazole
(1189) 2-(1-(4-Aminobenzyl)-5-(3,5-dichlorophenylthio)-4-isopropyl-1H-imidazol-2-yl)ethanol
(1190) 5-(3,5-Dichlorophenylthio)-2-(3-carbamoyloxypropyl)-1-fluoromethyl-4-isopropyl-1H-imidazole
(1191) 2-(4-Isopropyl-5-phenylthio-1-(pyridin-2-ylmethyl)-1H-imidazol-2-ylmethoxy)ethyl acetate
(1192) 2-(5-(3,5-Dichlorophenylthio)-4-isopropyl-1-(pyridin-2-ylmethyl)-1H-imidazol-2-ylmethoxy)ethyl acetate
(1193) 2-Azidomethyl-1-ethyl-4-isopropyl-5-phenylthio-1H-imidazole
(1194) 5-(3-Chlorophenylthio)-1-ethyl-4-isopropyl-2-N-methylcarbamoyloxymethyl-1H-imidazole
(1195) 2-(1-(3-Aminobenzyl)-5-(3,5-dichlorophenylthio)-4-isopropyl-1H-imidazol-2-yl)ethanol
(1196) 2-Aminomethyl-4-(3-chlorophenylthio)-5-isopropyl-1-(pyridin-4-ylmethyl)-1H-imidazole
(1197) 4-(3,5-Difluorophenylthio)-1-ethyl-5-isopropyl-1H-imidazol-2-ylmethyl acetate
(1198) 2-Dimethylaminomethyl-4-isopropyl-5-(3-fluorophenylthio)-1-(pyridin-4-ylmethyl)-1H-imidazole
(1199) 2-Aminomethyl-4-(3-nitrophenylthio)-1-ethyl-5-isopropyl-1H-imidazole
(1200) α-(5-(3,5-Dimethylphenylthio)-2-hydroxymethyl-4-isopropyl-1H-imidazol-2-yl)acetophenone
(1201) 5-(3,5-Difluorophenylthio)-4-isopropyl-2-N-methyl(thiocarbamoyl)oxymethyl-1-(pyridin-4-ylmethyl-1H-imidazole
(1202) 2-(2-Carbamoyloxyethyl)-1-cyclopropylmethyl-5-(3,5-difluorophenylthio)-4-isopropyl-1H-imidazole
(1203) 2-Azidomethyl-4-isopropyl-5-(3-fluorophenylthio)-1-(pyridin-3-ylmethyl)-1H-imidazole
(1204) 2-(5-Isopropyl-4-(3-fluorophenylthio)-1-(pyridin-4-ylmethyl)-1H-imidazol-2-ylmethoxy)ethanol (1205) 5-(3,5-Dichlorophenylthio)-2-(3-carbamoyloxypropyl)-4-isopropyl-1-(2,2,2-trifluoroethyl)-1H-imidazole
(1206) 4-Isopropyl-5-phenylthio-1-(pyridin-3-ylmethyl)-1H-imidazol-2-ylmethanol
(1207) 3-(5-(3-Chlorophenylthio)-4-isopropyl-1-(pyridin-3-ylmethyl)-1H-imidazol-2-yl)propanol
(1208) 3-(1-(3-Aminobenzyl)-5-(3,5-dichlorophenylthio)-4-isopropyl-1H-imidazol-2-yl)propanol
(1209) 5-(3,5-Dichlorophenylthio)-2-dimethylaminomethyl-4-isopropyl-1-(pyridin-4-ylmethyl)-1H-imidazole
(1210) 4-Isopropyl-1-methyl-5-phenylthio-1H-imidazole-2-carbaldehyde hydrazone
(1211) 2-(5-(3-Chlorophenylthio)-4-isopropyl-1-(pyridin-4-ylmethyl)-1H-imidazol-2-ylmethoxy)ethanol
(1212) 4-(3-Chlorophenylthio)-5-isopropyl-1-methyl-1H-imidazole-2-carbaldehyde
(1213) 2-(5-(3,5-Difluorophenylthio)-4-isopropyl-1-(pyridin-4-ylmethyl)-1H-imidazol-2-yl)ethanol
(1214) 5-isopropyl-4-(3-fluorophenylthio)-1-(pyridin-4-ylmethyl)-1H-imidazol-2-ylmethyl acetate
(1215) 2-(3-Carbamoyloxypropyl)-4-isopropyl-5-phenylthio-1-(pyridin-4-ylmethyl)-1H-imidazole
(1216) 4-Isopropyl-5-(3-fluorophenylthio)-1-(pyridin-3-ylmethyl)-1H-imidazol-2-ylacetonitrile
(1217) 4-Isopropyl-5-phenylthio-1-(pyridin-2-ylmethyl)-1H-imidazole-2-carbaldehyde oxime
(1218) 1-Ethyl-4-isopropyl-2-N-methylcarbamoyloxymethyl-5-(3-fluorophenylthio)-1H-imidazole
(1219) 5-Isopropyl-1-methyl-4-(3-fluorophenylthio)-1H-imidazole-2-carbaldehyde
(1220) 5-(3,5-Dichlorophenylthio)-1-ethyl-4-isopropyl-2-N-methylcarbamoyloxymethyl-1H-imidazole
(1221) 3-(1-(3-Aminobenzyl)-5-(3,5-difluorophenylthio)-4-isopropyl-1H-imidazol-2-yl)propanol
(1222) 3-(5-(3,5-Difluorophenylthio)-1,4-diisopropyl-1H-imidazol-2-yl)propanol
(1223) 2-(2-Carbamoyloxyethyl)-1-ethyl-4-isopropyl-5-phenylthio-1H-imidazole
(1224) 3-(5-(3,5-Dichlorophenylthio)-l1-hexyl-4-isopropyl-1H-imidazol-2-yl)propanol
(1225) 5-(3.,5-Dichlorophenylthio)-4-isopropyl-1-(pyridin-2-ylmethyl)-1H-imidazol-2-ylmethyl acetate
(1226) 4-(3-Nitrophenylthio)-5-isopropyl-1-methyl-1H-imidazol-2-ylmethanol
(1227) 5-(3,5-Difluorophenylthio)-1-fluoromethyl-4-isopropyl-1H-imidazol-2-ylmethanol
(1228) 5-(3-Chlorophenylthio)-1-ethyl-4-isopropyl-2-N-methylaminoethyl-1H-imidazole
(1229) 1-n-Butyl-2-(3-carbamoyloxypropyl)-5-(3,5-difluorophenylthio)-4-isopropyl-1H-imidazole
(1230) 5-(3,5-Difluorophenylthio)-4-isopropyl-1-(pyridin-4-ylmethyl)-1H-imidazol-2-ylmethanol
(1231) 5-(3,5-Dichlorophenylthio)-4-isopropyl-1-(pyridin-2-ylmethyl)-1H-imidazol-2-yl acetate
(1232) 2-Carbamoyloxymethyl-5-isopropyl-1-methyl-4-(3-fluorophenylthio)-1H-imidazole
(1233) 4-(3,5-Difluorophenylthio)-1-ethyl-5-isopropyl-1H-imidazole-2-carbaldehyde
(1234) 5-(3,5-Dichlorophenylthio)-1-ethyl-4-isopropyl-1H-imidazole-2-carbaldehyde oxime
(1235) 2-(3-Carbamoyloxypropyl)-5-(3,5-dimethylphenylthio)-1-ethyl-4-isopropyl-1H-imidazole
(1236) 2-(5-(3-Nitrophenylthio)-4-isopropyl-1-(pyridin-3-ylmethyl))-1H-imidazole -2-carbaldehyde
(1237) 2-(2-Aminoethyl)-5-(3-nitrophenylthio)-4-isopropyl-1-(pyridin-3-ylmethyl)-1H-imidazole
(1238) 5-(3-Nitrophenylthio)-1-ethyl-4-isopropyl-2-ureidomethyl-1H-imidazole
(1239) 2-(5-(3,5-Dichlorophenylthio)-4-isopropyl-1-(pyridin-2-ylmethyl)-1H-imidazol-2-yl)ethanol
(1240) 3-(4-Isopropyl-1-methyl-5-(3-fluorophenylthio)-1H-imidazol-2-yl)propanol
(1241) Methyl 3-(5-(3-chlorophenylthio)-4-isopropyl-1-(pyridin-4-ylmethyl)-1H-imidazol-2-yl)propionate
(1242) 2-(3-Carbamoyloxypropyl)-4-isopropyl-5-(3-fluorophenylthio)-1-(pyridin-2-ylmethyl)-1H-imidazole
(1243) 4-(3,5-Difluorophenylthio)-5-isopropyl-1-methyl-1H-imidazol-2-ylmethanol
(1244) 2-(4-Isopropyl-5-phenylthio-1-(pyridin-2-ylmethyl)-1H-imidazol-2-yl)ethanol
(1245) 4-Isopropyl-1-methyl-5-phenylthio-1H-imidazol-2-ylmethanol
(1246) 2-(2-Aminoethyl)-1-ethyl-4-isopropyl-5-(3-fluorophenylthio)-1H-imidazole
(1247) 2-Carbamoyloxymethyl-4-(3,5-dimethylphenylthio)-1-fluoromethyl-5-isopropyl-1H-imidazole
(1248) 2-Aminomethyl-1-ethyl-5-isopropyl-4-(3-fluorophenylthio)-1H-imidazole
(1249) 2-Carbamoyloxymethyl-4-isopropyl-5-(3-fluorophenylthio)-1-(pyridin-2-ylmethyl)-1H-imidazole
(1250) 2-(2-Acetoxyethyl)-1-ethyl-4-isopropyl-5-phenylthio-1H-imidazole
(1251) 5-(3,5-Difluorophenylthio)-4-isopropyl-1-(pyridin-2-ylmethyl)-1H-imidazol-2-yl acetate
(1252) 5-(3,5-Dichlorophenylthio)-4-isopropyl-1-methyl-2-N-methylcarbamoyloxymethyl-1H-imidazole
(1253) 2-(2-Carbamoyloxyethyl)-5-(3,5-difluorophenylthio)-4-isopropyl-1-(2,2,2-trifluoroethyl)-1H-imidazole
(1254) 4-(3,5-Difluorophenylthio)-1-ethyl-5-isopropyl-1H-imidazol-2-ylmethanol
(1255) 2-Carbamoyloxymethyl-5-(3-chlorophenylthio)-4-isopropyl-1-(pyridin-2-ylmethyl)-1H-imidazole
(1256) 4-Isopropyl-5-phenylthio-1-(pyridin-3-ylmethyl)-1H-imidazole-2-carbaldehyde
(1257) 2-Azidomethyl-5-(3,5-dichlorophenylthio)-4-isopropyl-1-(pyridin-3-ylmethyl)-1H-imidazole
(1258) 2-(5-(3,5-Dimethylphenylthio)-4-isopropyl-1-(2,2,2-trifluoroethyl)-1H-imidazol-2-yl)ethanol
(1259) 2-(2-Aminoethyl)-5-(3-chlorophenylthio)-4-isopropyl-1-methyl-1H-imidazole
(1260) 2-(5-(3-Nitrophenylthio)-1-ethyl-4-isopropyl-1H-imidazol-2-yl)ethanol
(1261) 4-(3,5-Difluorophenylthio)-5-isopropyl-1-(pyridin-4-ylmethyl)-1H-imidazole-2-carbaldehyde
(1262) 5-(3-Chlorophenylthio)-4-isopropyl-1-(pyridin-2-ylmethyl)-1H-imidazol-2-ylmethanol
(1263) 3-(5-(3,5-Difluorophenylthio)-4-isopropyl-1-(pyridin-3-ylmethyl)-1H-imidazol-2-yl)propanol
(1264) 2-(2-Aminoethyl)-5-(3,5-difluorophenylthio)-4-isopropyl-1-methyl-1H-imidazole
(1265) 5-(3,5-Difluorophenylthio)-2-dimethylaminomethyl-4-isopropyl-1-methyl-1H-imidazole
(1266) 5-(3,5-Dichlorophenylthio)-1-(2-carbamoyloxyethyl)-2-(3-carbamoyloxypropyl)-4-isopropyl-1H-imidazole
(1267) 1,2-Di-(2-carbamoyloxyethyl)-5-(3,5-difluorophenylthio)-4-isopropyl-1H-imidazole
(1268) 2-Azidomethyl-4-(3,5-dichlorophenylthio)-5-isopropyl-1-(pyridin-4-ylmethyl)-1H-imidazole
(1269) 2-Aminomethyl-5-(3,5-dichlorophenylthio)-4-isopropyl-1-(pyridin-2-ylmethyl)-1H-imidazole
(1270 ) 2-Acetylaminomethyl-5-(3-nitrophenylthio)-4-isopropyl-1-(pyridin-3-ylmethyl)-1H-imidazole (1271) 2-Acetylaminomethyl-4-isopropyl-5-(3-fluorophenylthio)-1-(pyridin-2-ylmethyl)-1H-imidazole (1272) 2-Acetylaminomethyl-4-isopropyl-5-(3-fluorophenylthio)-1-(pyridin-3-ylmethyl)-1H-imidazole (1273) 2-Carbamoyloxymethyl-5-(3,5-difluorophenylthio)-4-isopropyl-1-(pyridin-3-ylmethyl)-1H-imidazole (1274) α-(2-(2-Hydroxyethyl)-5-(3,5-dimethylphenylthio)-4-isopropyl-1H-imidazol-1-yl)acetophenone (1275) α-(5-(3,5-Dichlorophenylthio)-2-(3-carbamoyloxypropyl)-4-isopropyl-1H-imidazol-1-yl) acetophenone (1276) 5-(3,5-Dichlorophenylthio)-1-ethyl-4-isopropyl-1H-imidazol-2-ylmethanol (1277) N-(5-(3,5-Difluorophenylthio)-1-ethyl-4-isopropyl-1H-imidazol-4-ylmethyl)acetamidine (1278) 1-Cyclopropylmethyl-5-(3,5-difluorophenylthio)-4-isopropyl-1H-imidazol-2-ylmethanol (1279) 1-Allyl-2-carbamoyloxymethyl-5-(3,5-difluorophenylthio)-4-isopropyl-1H-imidazole (1280) 2-Dimethylaminomethyl-1-ethyl-4-isopropyl-5-phenylthio-1H-imidazole (1281) 5-(3,5-Dichlorophenylthio)-2-carbamoyloxymethyl-4-isopropyl-1-(3-phenylpropyl)-1H-imidazole (1282) 4-(3-Chlorophenylthio)-5-isopropyl-1-(pyridin-4-ylmethyl)-1H-imidazol-2-ylmethanol (1283) 5-(3,5-Dichlorophenylthio)-2-carbamoyloxymethyl-4-isopropyl-1-(pyridin-4-ylmethyl)-1H-imidazole (1284) 2-Acetylaminomethyl-5-(3,5-difluorophenylthio)-4-isopropyl-1-(pyridin-4-ylmethyl)-1H-imidazole (1285) 3-(5-(3,5-Difluorophenylthio)-1-ethyl-4-isopropyl-1H-imidazol-2-yl)propanol (1286) N-(5-(3,5-Difluorophenylthio)-4-isopropyl-1-(pyridin-4-ylmethyl)-1H-imidazol-4-ylmethyl)acetamide (1287) 4-Isopropyl-2-N-methyl(thiocarbamoyl)oxymethyl-5-phenylthio-1-(pyridin-2-ylmethyl)-1H-imidazole (1288) Methyl 3-(5-(3-chlorophenylthio)-4-isopropyl-1-methyl-1H-imidazol-2-yl)propionate (1289) 2-(1-Ethyl-5-isopropyl-4-(3-fluorophenylthio)-1H-imidazol-2-ylmethoxy)ethanol (1290) 1-Benzyl-2-carbamoyloxymethyl-5-(3,5-dimethylphenylthio)-4-isopropyl-1H-1-imidazole (1291) 5-(3-Nitrophenylthio)-4-isopropyl-1-methyl-2-ureidomethyl-1H-imidazole (1292) 2-(2-Carbamoyloxyethoxy)methyl-4-isopropyl-5-(3-fluorophenylthio)-1-(pyridin-4-ylmethyl)-1H-imidazole (1293) 2-(2-Carbamoyloxyethyl)-4-isopropyl-5-(3-fluorophenylthio)-1-(pyridin-3-ylmethyl)-1H-imidazole (1294) 2-(2-Azidoethyl)-5-(3-nitrophenylthio)-4-isopropyl-1-methyl-1H-imidazole (1295) 2-(2-Azidoethyl)-1-ethyl-4-isopropyl-5-phenylthio-1H-imidazole (1296) 2-Aminomethyl-5-(3,5-difluorophenylthio)-4-isopropyl-1-(pyridin-2-ylmethyl)-1H-imidazole (1297) 5-(3,5-Difluorophenylthio)-4-isopropyl-2-methanesulfonamidomethyl-1-(pyridin-2-ylmethyl)-1H-imidazole (1298) 1-(2-(3-Carbamoyloxypropyl)-5-(3,5-difluorophenylthio)-4-isopropyl-1H-imidazol-1-yl)-2-propanone (1299) 3-(5-(3,5-Dichlorophenylthio)-4-isopropyl-1-(2-methylpyridin-3-ylmethyl)-1H-imidazol-2-yl)propanol (1300) 2-Aminomethyl-5-(3,5-dichlorophenylthio)-4-isopropyl-1-(pyridin-3-ylmethyl)-1H-imidazole (1301) 2-Aminomethyl-4-isopropyl-1-methyl-5-phenylthio-1H-imidazole (1302) 2-(1-Ethyl-4-isopropyl-5-phenylthio-1H-imidazol-2-ylmethoxy)ethanol (1303) 2-(4-(3,5-Difluorophenylthio)-1-ethyl-5-isopropyl-1H-imidazol-2-ylmethoxy)ethanol (1304) 2-(2-Carbamoyloxyethyl)-1,4-diisopropyl-5-(3,5-dimethylphenylthio)-1H-imidazole (1305) 2-(l-Benzyl-5-(3,5-difluorophenylthio)-4-isopropyl-1H-imidazol-2-yl)ethanol (1306) 5-(3,5-Difluorophenylthio)-4-isopropyl-2-methanesulfonamidomethyl-1-(pyridin-3-ylmethyl)-1H-imidazole (1307) Methyl 3-(4-isopropyl-5-(3-fluorophenylthio)-1-(pyridin-2-ylmethyl)-1H-imidazol-2-yl)propionate (1308) 2-(1-Ethyl-4-isopropyl-5-(3-fluorophenylthio)-1H-imidazol-2-ylmethoxy)ethanol (1309) Methyl 3-(5-(3-nitrophenylthio)-4-isopropyl-1-(pyridin-4-ylmethyl)-1H-imidazol-2-yl-)propionate (1310) 2-(5-(3-Chlorophenylthio)-4-isopropyl-1-(pyridin-2-ylmethyl)-1H-imidazol-2-yl)ethanol (1311) 2-(2-Acetoxyethyl)-5-(3,5-dichlorophenylthio)-4-isopropyl-1-(pyridin-4-ylmethyl)-1H-imidazole (1312) 5-(3,5-Dichlorophenylthio)-2-(2-carbamoyloxyethoxy)-methyl-4-isopropyl-(pyridin-2-ylmethyl)-1H-imidazole (1313) 2-Aminomethyl-5-(3,5-difluorophenylthio)-4-isopropyl-1-(pyridin-3-ylmethyl)-1H-imidazole (1314) 2-(1-Ethyl-5-isopropyl-4-phenylthio)-1H-imidazole-2-carbaldehyde (1315) 2-(5-(3,5-(Difluorophenylthio)-4-isopropyl1-methyl-1H-imidazol-2-yl)ethanol (1316) 3-(1-Allyl-5-(3,5-difluorophenylthio)-4-isopropyl-1H-imidazol-2-yl)propanol (1317) 2-(4-Isopropyl-1-methyl-5-(3-fluorophenylthio)-1H-imidazol-2-ylmethoxy)ethyl acetate (1318) 5-(3,5-Dichlorophenylthio)-1,4-diisopropyl-1H-imidazol-2-ylmethanol (1319) 2-Azidomethyl-4-(3-nitrophenylthio)-5-isopropyl-1-(pyridin-4-ylmethyl)-1H-imidazole (1320) 5-(3-Chlorophenylthio)-4-isopropyl-1-(pyridin-2-ylmethyl)-1H-imidazol-2-yl acetate (1321) 5-(3,5-Dichlorophenylthio)-2-diaminomethyleneaminomethyl-4-isopropyl-1-methyl-1H-imidazole (1322) 5-(3,5-Dichlorophenylthio)-2-(2-carbamoyloxyethyl)-4-isopropyl-1-(3-(pyridin-4-yl)propyl)-1H-imidazole (1323) 5-(3-Chlorophenylthio)-4-isopropyl-1-(pyridin-4-ylmethyl)-1H-imidazol-2-ylmethanol (1324) 2-(3-Carbamoyloxypropyl)-5-(3,5-difluorophenylthio)-1-fluoromethyl-4-isopropyl-1H-imidazole (1325) 5-(3,5-Difluorophenylthio)-1,4-diisopropyl-1H-imidazol-2-ylmethanol (1326) 3-(5-(3,5-Dichlorophenylthio)-4-isopropyl-1-(quinolin-3-ylmethyl)-1H-imidazol-2-yl)propanol (1327) 4-Isopropyl-5-phenylthio-1-(pyridin-3-ylmethyl)-1H-imidazole-2-carbaldehyde hydrazone (1328) 4-Isopropyl-5-(3-fluorophenylthio)-1-(pyridin-4-ylmethyl)-1H-imidazol-2-ylacetonitrile (1329) 2-Aminomethyl-5-(3,5-difluorophenylthio)-4-isopropyl-1-(pyridin-4-ylmethyl)-1H-imidazole (1330) 5-(3,5-Difluorophenylthio)-4-isopropyl-1-(pyridin-3-ylmethyl)-1H-imidazol-2-ylmethyl acetate (1331) 2-(5-(3,5-Difluorophenylthio)-4-isopropyl-1-(pyridin-4-ylmethyl)-1H-imidazol-2-ylmethoxy)ethanol (1332) 2-(4-(3-Chlorophenylthio)-5-isopropyl-1-(pyridin-4-ylmethyl)-1H-imidazol-2-ylmethoxy)ethanol (1333) 5-(3-Nitrophenylthio)-4-isopropyl-2-N-methylaminomethyl-1-(pyridin-4-ylmethyl)-1H-imidazole (1334) N-(5-(3-Chlorophenylthio)-1-ethyl-4-isopropyl-1H-imidazol-4-ylmethyl)acetamidine
(1335) 5-(3-Nitrophenylthio)-4-isopropyl-1-(pyridin-4-ylmethyl)-1H-imidazol-4-ylmethyl acetate
(1336) 3-(5-(3-Nitrophenylthio)-1-ethyl-4-isopropyl-1H-imidazol-2-yl)propanol
(1337) 3-(1-n-Butyl-5-(3,5-difluorophenylthio)-4-isopropyl-1H-imidazol-2-yl)propanol
(1338) 2-(2-Carbamoyloxyethyl)-5-(3,5-difluorophenylthio)-1-fluoromethyl-4-isopropyl-1H-imidazole
(1339) 5-(3,5-Dichlorophenylthio)-4-isopropyl-2-N-methyl(thiocarbamoyl)oxymethyl-1-(pyridin-2-ylmethyl)-1H-imidazole
(1340) 2-(2-Acetoxyethyl)-4-isopropyl-1-methyl-5-(3-fluorophenylthio)-1H-imidazole
(1341) 5-(3,5-Difluorophenylthio)-1-ethyl-4-isopropyl-2-N-methylthiocarbamoyloxymethyl-1H-imidazole
(1342) 2-(3-Carbamoyloxypropyl)-5-(3,5-dimethylphenylthio)-4-isopropyl-1-methyl-1H-imidazole
(1343) 2-(2-Carbamoyloxyethoxy)methyl-4-isopropyl-5-phenylthio-1-(pyridin-4-ylmethyl)-1H-imidazole
(1344) 3-(5-(3,5-Dichlorophenylthio)-1-fluoromethyl-4-isopropyl-1H-imidazol-2-yl)propanol
(1345) 5-(3,5-Difluorophenylthio)-4-isopropyl-1-(pyridin-3-ylmethyl)-1H-imidazole-2-carbaldehyde hydrazone
(1346) N-(5-(3-Nitrophenylthio)-4-isopropyl-1-(pyridin-4-ylmethyl)-1H-imidazol-4-ylmethyl)acetamidine
(1347) 5-(3,5-Dichlorophenylthio)-2-(2-carbamoyloxyethyl)-4-isopropyl-1-(pyridin-2-ylmethyl)-1H-imidazole
(1348) 5-(3,5-Dichlorophenylthio)-4-isopropyl-1-methyl-2-N-methylaminomethyl-1H-imidazole
(1349) 2-Carbamoyloxymethyl-4-isopropyl-5-phenylthio-1-(pyridin-3-ylmethyl)-1H-imidazole
(1350) 5-(3-Nitrophenylthio)-1-ethyl-4-isopropyl-1H-imidazol-2-ylmethyl acetate
(1351) 5-(3-Chlorophenylthio)-4-isopropyl-1-(pyridin-3-ylmethyl)-1H-imidazole-2-carbaldehyde
(1352) 2-(4-Isopropyl-5-(3-fluorophenylthio)-1-(pyridin-4-ylmethyl)-1H-imidazol-2-ylmethoxy)ethanol
(1353) 2-Carbamoyloxymethyl-5-(3,5-difluorophenylthio)-4-isopropyl-1-(pyridin-2-ylmethyl)-1H-imidazole
(1354) 5-(3,5-Dichlorophenylthio)-2-(-2-carbamoyloxyethyl)-4-isopropyl-1-(pyridin-4-ylmethyl)-1H-imidazole
(1355) 2-(4-(3-Nitrophenylthio)-1-ethyl-5-isopropyl)-1H-imidazole-2-carbaldehyde
(1356) 2-(4-Isopropyl-5-(3-fluorophenylthio)-1-(pyridin-4-ylmethyl)-1H-imidazol-2-ylmethoxy)ethyl acetate
(1357) 2-(5-(3,5-Dichlorophenylthio)-4-isopropyl-1-(pyridin-3-ylmethyl)-1H-imidazol-2-ylmethoxy)ethanol
(1358) 5-(3-Nitrophenylthio)-4-isopropyl-2-methanesulfonamidomethyl-1-(pyridin-4-ylmethyl)-1H-imidazole
(1359) 5-(3,5-Difluorophenylthio)-4-isopropyl-2-N-methylcarbamoyloxymethyl-1-(pyridin-2-ylmethyl)-1H-imidazole
(1360) 5-(3,5-Difluorophenylthio)-4-isopropyl-1-methyl-2-N-methylcarbamoyloxymethyl-1H-imidazole
(1361) 3-(1-Benzyl-5-(3,5-dimethylphenylthio)-4-isopropyl-1H-imidazol-2-yl)propanol
(1362) 2-(4-(3,5-Difluorophenylthio)-5-isopropyl-1-methyl-1H-imidazol-2-ylmethoxy)ethanol
(1363) 5-(3-Chlorophenylthio)-4-isopropyl-2-methanesulfonamidomethyl-1-(pyridin-3-ylmethyl)-1H-imidazole
(1364) 2-(2-Azidoethyl)-1-ethyl-4-isopropyl-5-(3-fluorophenylthio)-1H-imidazole
(1365) 3-(1-Benzyl-5-(3,5-difluorophenylthio)-4-isopropyl-1H-imidazol-2-yl)propanol
(1366) 2-(5-(3,5-Dichlorophenylthio)-4-isopropyl-1-(pyridin-4-ylmethyl))-1H-imidazole-2-carbaldehyde
(1367) 5-(3,5-Difluorophenylthio)-4-isopropyl-1-n-propyl-1H-imidazol-2-ylmethanol
(1368) 4-Isopropyl-2-N-methylcarbamoyloxymethyl-5-(3-fluorophenylthio)-1-(pyridin-3-ylmethyl)-1H-imidazole
(1369) 2-Acetylaminomethyl-1-ethyl-4-isopropyl-5-phenylthio-1H-imidazole
(1370) 2-Carbamoyloxymethyl-1-ethyl-4-isopropyl-5-phenylthio-1H-imidazole
(1371) 5-(3,5-Dichlorophenylthio)-4-isopropyl-1-methyl-1H-imidazol-2-yl acetate
(1372) 1-(2-Carbamoyloxymethyl-5-(3,5-dimethylphenylthio)-4-isopropyl-1H-imidazol-1-yl)-2-propanone
(1373) 2-(4-Isopropyl-5-(3-fluorophenylthio)-1-(pyridin-2-ylmethyl)-1H-imidazol-2-ylmethoxy)ethyl acetate
(1374) 2-(5-(3,5-Dichlorophenylthio)-1-ethyl-4-isopropyl-1H-imidazol-2-yl)ethanol
(1375) 3-(1-n-Butyl-5-(3,5-dimethylphenylthio)-4-isopropyl-1H-imidazol-2-yl)propanol
(1376) 2-(2-Azidoethyl)-5-(3,5-difluorophenylthio)-4-isopropyl-1-(pyridin-3-ylmethyl)-1H-imidazole
(1377) 2-(2-Carbamoyloxyethyl)-5-(3-nitrophenylthio)-4-isopropyl-1-methyl-1H-imidazole
(1378) 2-(3-Carbamoyloxypropyl)-5-(3-nitrophenylthio)-4-isopropyl-1-(pyridin-3-ylmethyl)-1H-imidazole
(1379) 5-(3-Chlorophenylthio)-4-isopropyl-1-methyl-1H-imidazol-2-ylmethyl acetate
(1380) 2-Azidomethyl-4-isopropyl-1-methyl-5-(3-fluorophenylthio)-1H-imidazole
(1381) 2-(3-Carbamoyloxypropyl)-5-(3,5-difluorophenylthio)-4-isopropyl-1-(2,2,2-trifluoroethyl)-1H-imidazole
(1382) 2-Azidomethyl-5-(3-chlorophenylthio)-4-isopropyl-1-methyl-1H-imidazole
(1383) 5-(3,5-Dichlorophenylthio)-4-isopropyl-1-(2-(pyridin-4-yl)ethyl)-1H-imidazol-2-ylmethanol
(1384) 5-(3,5-Dichlorophenylthio)-4-isopropyl-2-N-methylaminomethyl-1-(pyridin-3-ylmethyl)-1H-imidazole
(1385) 5-(3,5-Dichlorophenylthio)-2-(3-carbamoyloxypropyl)-4-isopropyl-1-(quinolin-3-ylmethyl)-1H-imidazole
(1386) 2-(5-(3,5-Difluorophenylthio)-4-isopropyl-1-(2,2,2-trifluoroethyl)-1H-imidazol-2-yl)ethanol
(1387) 2-Carbamoyloxyethlyl-4-(3-chlorophenylthio)-5-isopropyl-1-(pyridin-4-ylmethyl)-1H-imidazole
(1388) 5-(3,5-Dichlorophenylthio)-2-carbamoyloxymethyl-1-cyclopropylethyl-4-isopropyl-1H-1-imidazole
(1389) 2-Carbamoyloxymethyl-5-(3,5-difluorophenylthio)-1-fluoromethyl-4-isopropyl-1H-imidazole
(1390) 2-(2-Azidoethyl)-4-isopropyl-5-(3-fluorophenylthio)-1-(pyridin-2-ylmethyl)-1H-imidazole
(1391) 5-(3-Nitrophenylthio)-1-ethyl-4-isopropyl-1H-imidazole-2-carbaldehyde hydrazone
(1392) 5-(3,5-(Dichlorophenylthio)-4-isopropyl-1-(pyridin-4-ylmethyl)-1H-imidazol-2-ylmethyl acetate
(1393) 2-(3-Carbamoyloxypropyl)-5-(3,5-difluorophenylthio)-4-isopropyl-1-(pyridin-4-ylmethyl)-1H-imidazole
(1394) 2-(2-Carbamoyloxyethoxy)methyl-5-(3-nitrophenylthio)-4-isopropyl-1-(pyridin-2-ylmethyl)-1H-imidazole (1395) 2-(3-Carbamoyloxypropyl)-1,4-diisopropyl-5-(3,5-dimethylphenylthio)-1H-imidazole
(1396) 1-Ethyl-4-isopropyl-5-(3-fluorophenylthio)-1H-imidazol-2-ylmethanol
(1397) 2-(2-Carbamoyloxyethyl)-5-(3,5-difluorophenylthio)-4-isopropyl-1-(2-(pyridin-4-yl)ethyl)-1H-imidazole
(1398) 5-(3-Chlorophenylthio)-4-isopropyl-1-(pyridin-2-ylmethyl)-1H-imidazol-2-ylmethyl acetate
(1399) 1-Ethyl-5-isopropyl-4-(3-fluorophenylthio)-1H-imidazol-2-ylmethyl acetate
(1400) 2-(5-(3,5-Dimethylphenylthio)-4-isopropyl-1-(pyridin-2-ylmethyl)-1H-imidazol-2-yl)ethanol
(1401) 1-Ethyl-4-isopropyl-2-methanesulfonamidomethyl-5-phenylthio-1H-imidazole
(1402) 2-Aminomethyl-4-(3,5-dichlorophenylthio)-5-isopropyl-1-(pyridin-4-ylmethyl)-1H-imidazole
(1403) 2-(2-Azidoethyl)-4-isopropyl-1-methyl-5-(3-fluorophenylthio)-1H-imidazole
(1404) 2-Diaminomethyleneaminomethyl-1-ethyl-4-isopropyl-5-(3-fluorophenylthio)-1H-imidazole
(1405) 2-Azidomethyl-5-(3,5-dichlorophenylthio)-4-isopropyl-1-(pyridin-2-ylmethyl)-1H-imidazole
(1406) 5-(3,5-Dichlorophenylthio)-4-isopropyl-1-methyl-2-N-methyl(thiocarbamoyl)oxymethyl-1H-imidazole
(1407) 2-(3-Carbamoyloxypropyl)-5-(3,5-difluorophenylthio)-4-isopropyl-1-(2-phenylethyl)-1H-imidazole
(1408) 5-(3-Chlorophenylthio)-2-diaminomethyleneaminomethyl-1-ethyl-4-isopropyl-1H-imidazole
(1409) 5-(3,5-Dichlorophenylthio)-2-(2-carbamoyloxyethyl)-1,4-diisopropyl-1H-imidazole
(1410) 2-(2-Azidoethyl)-5-(3,5-difluorophenylthio)-4-isopropyl-1-methyl-1H-imidazole
(1411) 2-(2-Carbamoyloxyethoxy)methyl-5-(3-chlorophenylthio)-1-ethyl-4-isopropyl-1H-imidazole
(1412) 2-Azidomethyl-4-(3,5-dichlorophenylthio)-5-isopropyl-1-methyl-1H-imidazole
(1413) 3-(5-(3,5-Difluorophenylthio)-4-isopropyl-1-methyl-1H-imidazol-2-yl)propanol
(1414) 2-2-(Acetoxyethyl)-5-(3-chlorophenylthio)-4-isopropyl-1-(pyridin-2-ylmethyl)-1H-imidazole
(1415) 2-(1-Benzyl-5-(3,5-dimethylphenylthio)-4-isopropyl-1H-imidazol-2-yl)ethanol
(1416) 2-Azidomethyl-4-(3-chlorophenylthio)-5-isopropyl-1-methyl-1H-imidazole
(1417) 5-(3-Nitrophenylthio)-4-isopropyl-1-(pyridin-4-ylmethyl)-1H-imidazol-2-ylacetonitrile
(1418) 2-(2-Acetoxyethyl)-4-isopropyl-5-phenylthio-1-(pyridin-3-ylmethyl)-1H-imidazole
(1419) - 5-(3,5-Difluorophenylthio)-4-isopropyl-1-(pyridin-4-ylmethyl)-1H-imidazole-2-carbaldehyde hydrazone
(1420) 4-Isopropyl-5-phenylthio-1-(pyridin-2-ylmethyl)-1H-imidazol-2-yl acetate
(1421) 2-Diaminomethyleneaminomethyl-4-isopropyl-5-(3-fluorophenylthio)-1-(pyridin-2-ylmethyl)-1H-imidazole
(1422) 2-Acetylaminomethyl-1-ethyl-4-isopropyl-5-(3-fluorophenylthio)-1H-imidazole
(1423) 1-Ethyl-4-isopropyl-5-phenylthio-2-ureidomethyl-1H-imidazole
(1424) 2-Carbamoyloxymethyl-1,4-diisopropyl-5-(3,5-dimethylphenylthio)-1H-imidazole
(1425) 3-(5-(3,5-Difluorophenylthio)-4-isopropyl-1-(pyridin-2-ylmethyl)-1H-imidazol-2-yl)propanol
(1426) 4-Isopropyl-1-methyl-5-phenylthio-1H-imidazole-2-carbaldehyde oxime
(1427) 5-(3,5-Dimethylphenylthio)-4-isopropyl-1-(pyridin-2-ylmethyl)-1H-imidazol-2-ylmethanol
(1428) 3-(1-Cyclopropylmethyl-5-(3,5-dimethylphenylthio)-4-isopropyl-1H-imidazol-2-yl)propanol
(1429) 5-(3,5-Dichlorophenylthio)-4-isopropyl-1-1-propyl-1H-imidazol-2-ylmethanol
(1430) 1-(3-Aminobenzyl)-5-(3,5-chlorophenylthio)-2-(3-carbamoyloxypropyl)-4-isopropyl-1H-imidazole
(1431) 5-(3,5-Dichorophenylthio)-4-isopropyl-1-methyl-1H-imidazole-2-carbaldehyde oxime
(1432) 5-(3-Chlorophenylthio)-4-isopropyl-2-N-methyl(thiocarbamoyl)oxymethyl-1-(pyridin-3-ylmethyl)-1H-imidazole
(1433) 1-(2-(3-Carbamoyloxypropyl)-5-(3,5-dimethylphenylthio)-4-isopropyl-1H-imidazol-1-yl)-2-propanone
(1434) 2-(3-Carbamoyloxypropyl)-4-isopropyl-1-methyl-5-(3-fluorophenylthio)-1H-imidazole
(1435) 5-(3,5-Difluorophenylthio)-4-isopropyl-1-methyl-2-N-methylaminomethyl-1H-imidazole
(1436) 4-(3,5-Dichlorophenylthio)-1-ethyl-5-isopropyl-1H-imidazol-2-ylmethanol
(1437) α-(5-(3,5-Difluorophenylthio)-2-hydroxymethyl-4-isopropyl-1H-imidazol-1-yl)acetophenone
(1438) Methyl 3-(5-(3-nitrophenylthio)-1-ethyl-4-isopropyl-1H-imidazol-2-yl)propionate
(1439) 2-Azidomethyl-1-ethyl-4-isopropyl-5-(3-fluorophenylthio)-1H-imidazole
(1440) 2-(2-Carbamoyloxyethyl)-5-(3-chlorophenylthio)-4-isopropyl-1-methyl-1H-imidazole
(1441) 3-(5-(3,5-Dichlorophenylthio)-1-n-butyl-4-isopropyl-1H-imidazol-2-yl)propanol
(1442) 5-(3-Chlorophenylthio)-4-isopropyl-1-(pyridin-2-ylmethyl)-2-ureidomethyl-1H-imidazole
(1443) 3-(5-(3,5-Dichlorophenylthio)-1-cyclopropylethyl-4-isopropyl-1H-imidazol-2-yl)propanol
(1444) 2-(2Acetoxyethyl)-5-(3-nitrophenylthio)-4-isopropyl-1-(pyridin-4-ylmethyl)-1H-imidazole
(1445) 4-Isopropyl-5-phenylthio-1-(pyridin-2-ylmethyl)-1H-imidazol-2-ylmethyl acetate
(1446) 4-(3,5-Dichlorophenylthio)-5-isopropyl-1-methyl-1H-imidazole-2-carbaldehyde
(1447) 5-(3-Chlorophenylthio)-4-isopropyl-1-methyl-1H-imidazol-2-ylmethanol
(1448) 5-(3-Chlorophenylthio)-2-dimethylaminomethyl-4-isopropyl-1-methyl-1H-imidazole
(1449) 2-(4-Isopropyl-1-methyl-5-phenylthio-1H-imidazol-2-ylmethoxy)ethanol
(1450) 3-(5-(3-Chlorophenylthio)-4-isopropyl-1-(pyridin-4-ylmethyl)-1H-imidazol-2-yl)propanol
(1451) 5-(3-Nitrophenylthio)-4-isopropyl-1-(pyridin-4-ylmethyl)-1H-imidazole-2-carbaldehyde
(1452) 1-Ethyl-4-isopropyl-5-phenylthio-1H-imidazol-2-ylmethanol
(1453) 2-(2-Carbamoyloxyethoxy)methyl-5-(3-nitrophenylthio)-4-isopropyl-1-methyl-1H-imidazole
(1454) 2-Azidomethyl-1-ethyl-5-isopropyl-4-(3-fluorophenylthio)-1H-imidazole
(1455) 3-(5-(3,5-Dimethylphenylthio)-4-isopropyl-1-(pyridin-3-ylmethyl)-1H-imidazol-2-yl)propanol
(1456) 2-(5-(3,5-Difluorophenylthio)-1-ethyl-4-isopropyl-1H-imidazol-2-ylmethoxy)ethanol
(1457) 2-(2-Aminoethyl)-5-(3-nitrophenylthio)-4-isopropyl-1-methyl-1H-imidazole
(1458) 2-(3-Carbamoyloxypropyl)-5-(3,5-difluorophenylthio)-4-isopropyl-1-(pyridin-2-ylmethyl)-1H-imidazole (1459) 5-(3,5-Dichlorophenylthio)-2-carbamoyloxymethyl-4-isopropyl-1-(pyridin-2-ylmethyl)-1H-imidazole
(1460) 1-Ethyl-4-isopropyl-2-N-methylaminomethyl-5-phenylthio-1H-imidazole
(1461) 5-(3-Chlorophenylthio)-4-isopropyl-2-N-methylcarbamoyloxymethyl-1-(pyridin-3-ylmethyl)-1H-imidazole
(1462) 5-(3,5-Difluorophenylthio)-4-isopropyl-1-methyl-1H-imidazole-2-carbaldehyde
(1463) 2-Diaminomethyleneaminomethyl-5-(3,5-difluorophenylthio)-4-isopropyl-1-(pyridin-3-ylmethyl)-1H-imidazole
(1464) 2-Azidomethyl-4-isopropyl-5-(3-fluorophenylthio)-1-(pyridin-4-ylmethyl)-1H-imidazole
(1465) 2-(1-n-Butyl-5-(3,5-difluorophenylthio)-4-isopropyl-1H-imidazol-2-yl)ethanol
(1466) 2-(2-Carbamoyloxyethyl)-5-(3-nitrophenylthio)-4-isopropyl-1-(pyridin-3-ylmethyl)-1H-1-imidazole
(1467) 3-(4-Isopropyl-5-phenylthio-1-(pyridin-2-ylmethyl)-1H-imidazol-2-yl)propanol
(1468) 2-(3-Carbamoyloxypropyl)-5-(3,5-difluorophenylthio)-1-fluoromethyl-4-isopropyl-1H-imidazole
(1469) 5-(3-Nitrophenylthio)-4-isopropyl-2-N-methylcarbamoyloxymethyl-1-(pyridin-2-ylmethyl.)-1H-imidazole
(1470) 2-Carbamoyloxymethyl-4-(3-nitrophenylthio)-5-isopropyl-1-(pyridin-4-ylmethyl)-1H-imidazole
(1471) 5-(3-Chlorophenylthio)-4-isopropyl-2-N-methylcarbamoyloxymethyl-1-(pyridin-2-ylmethyl)-1H-imidazole
(1472) 4-(3-Nitrophenylthio)-1-ethyl-5-isopropyl-1H-imidazol-2-ylmethanol
(1473) 2-(2-Azidoethyl)-5-(3-chlorophenylthio)-4-isopropyl-1-(pyridin-4-ylmethyl)-1H-imidazole
(1474) 2-(4-Isopropyl-5-phenylthio-1-(pyridin-3-ylmethyl)-1H-imidazol-2-yl)ethanol
(1475) Methyl 3-(5-(3,5-dichlorophenylthio)-4-isopropyl-1-(pyridin-3-ylmethyl)-1H-imidazol-2-yl)propionate
(1476) 5-Isopropyl-4-phenylthio-1-(pyridin-4-ylmethyl)-1H-imidazol-2-ylmethyl acetate
(1477) 2-(2-Azidoethyl)-5-(3,5-dichlorophenylthio)-1-ethyl-4-isopropyl-1H-imidazole
(1478) 1-n-Butyl-2-(3-carbamoyloxypropyl)-5-(3,5-difluorophenylthio)-4-isopropyl-1H-imidazole
(1479) 3-(1-n-Butyl-5-(3,5-difluorophenylthio)-4-isopropyl-1H-imidazol-2-yl)propanol
(1480) 4-Isopropyl-1-methyl-5-phenylthio-2-ureidomethyl-1H-imidazole
(1481) 5-(3,5-Difluorophenylthio)-2-dimethylaminomethyl-1-ethyl-4-isopropyl-1H-imidazole
(1482) 1-(2-(2-Hydroxyethyl)-5-(3,5-dichlorophenylthio)-4-isopropyl-1H-imidazol-1-yl)-2-propanone
(1483) 2-(2-Carbamoyloxyethyl)-5-(3,5-difluorophenylthio)-1-ethyl-4-isopropyl-1H-imidazole
(1484) 5-(3-Nitrophenylthio)-4-isopropyl-1-(pyridin-3-ylmethyl)-1H-imidazol-2-ylmethanol
(1485) 5-(3,5-Dichlorophenylthio)-4-isopropyl-2-methanesulfonamidomethyl-1-methyl-1H-imidazole
(1486) 2-(5-(3,5-Difluorophenylthio)-4-isopropyl-1-(2-phenylethyl)-1H-imidazol-2-yl)ethanol
(1487) 1-(4-Aminobenzyl)-5-(3,5-difluorophenylthio)-4-isopropyl-1H-imidazol-2-ylmethanol
(1488) 4-Isopropyl-5-(3-fluorophenylthio)-1-(pyridin-4-ylmethyl)-1H-imidazole-2-carbaldehyde oxime
(1489) 2-Carbamoyloxymethyl-5-(3,5-dimethylphenylthio)-4-isopropyl-1-(pyridin-3-ylmethyl)-1H-imidazole
(1490) 3-(4-Isopropyl-5-(3-fluorophenylthio)-1-(pyridin-4-ylmethyl)-1H-imidazol-2-yl)propanol
(1491) 2-Azidomethyl-5-(3,5-dichlorophenylthio)-4-isopropyl-1-methyl-1H-imidazole
(1492) 5-(3,5-Dichlorophenylthio)-1-(2-carbamoyloxyethyl)-4-isopropyl-1H-imidazol-2-ylmethanol
(1493) 5-(3,5-Dichlorophenylthio)-1-hexyl-4-isopropyl-1H-imidazol -2-ylmethanol
(1494) 5-(3-Chlorophenylthio)-4-isopropyl-1-(pyridin-4-ylmethyl)-1H-imidazol-2-yl acetate
(1495) 4-(3,5-Dichlorophenylthio)-2-carbamoyloxymethyl-5-isopropyl-1-methyl-1H-imidazole
(1496) 1,4-Diisopropyl-5-(3,5-difluorophenylthio)-1H-imidazol-2-ylmethanol
(1497) 2-(5-(3-Chlorophenylthio)-4-isopropyl-1-(pyridin-3-ylmethyl)-1H-imidazol-2-ylmethoxy)ethyl acetate
(1498) N-(4-Isopropyl-5-(3-fluorophenylthio)-1-(pyridin-4-ylmethyl)-1H-imidazol-4-ylmethyl)acetamidine
(1499) 2-Azidomethyl-5-isopropyl-4-phenylthio-1-(pyridin-4-ylmethyl)-1H-imidazole
(1500) 2-(2-Carbamoyloxyethoxymethyl-1-ethyl-4-isopropyl-5-(3-fluorophenylthio)-1H-imidazole
(1501) 3-(5-(3,5-Dichlorophenylthio)-1-(2-carbamoyloxyethyl)-4-isopropyl-1H-imidazol-2-yl)propanol
(1502) 4-Isopropyl-2-methanesulfonamidomethyl-5-phenylthio-1(pyridin-2-ylmethyl)-1H-imidazole
(1503) 1-Benzyl-2-(2-carbamoyloxyethyl)-5-(3,5-difluorophenylthio)-4-isopropyl-1H-imidazole
(1504) Methyl 3-(5-(3,5-difluorophenylthio)-4-isopropyl-1-(pyridin-3-ylmethyl)-1H-imidazol-2-yl)propionate
(1505) 5-(3-Chlorophenylthio)-1-ethyl-4-isopropyl-1H-imidazol-2-ylmethyl acetate
(1506) 4-Isopropyl-5-phenylthio-1-(pyridin-4-ylmethyl)-1H-imidazol-2-ylmethanol
(1507) 1-(5-(3,5-Difluorophenylthio)-2-hydroxymethyl-4-isopropyl-1H-imidazol-1-yl)-2-propanone
(1508) 5-(3-Nitrophenylthio)-4-isopropyl-1-(pyridin-4-ylmethyl)-2-ureidomethyl-1H-imidazole
(1509) 4-Isopropyl-5-(3-fluorophenylthio)-1-(pyridin-3-ylmethyl)-1H-imidazol-2-ylmethanol
(1510) 2-(2-Azidoethyl)-4-isopropyl-1-methyl-5-phenylthio-1H-imidazole The salts of above-mentioned compounds of the present invention are not particularly restricted only if they are pharmacologically acceptable. Thus, for example, salts with mineral acids such as hydrochloric acid, sulfuric acid, nitric acid, phosphoric acid, hydrofluoric acid, hydrobromic acid, etc.; salts with organic acids such as formic acid, acetic acid, tartaric acid, lactic acid, citric acid, fumaric acid, maleic acid, succinic acid, methanesulfonic acid, methanesulfonic acid, benzenesulfonic acid, toluenesulfonic acid, naphthalenesulfonic acid, camphorsulfonic acid, etc., and salts with alkali metals or alkaline earth metals such as sodium, potassium, calcium, etc. can be mentioned.

The compounds of the present invention are novel ones discovered by the present inventors and, as will be described hereinafter, are non-nucleic acid low-molecular-weight compounds which specifically inhibit the reverse transcriptase of HIV-1 (NNRTI).

The activity of the above compounds is comparable with that of AZT and, in an assay system using human peripheral blood lymphocytes infected with a fresh isolate of the virus, exhibits greater activity than AZT. The above compound further has potent activity against AZT-resistant strains and mutants showing cross resistance to many NNRTIs, and the occurrence of resistant strains in vitro is slower than in nevirapine, in which the locus of mutation is also different.

Moreover, the above compound is very efficiently transferred to the lymph node and the concentration is maintained in the lymph node sufficiently higher than the in vitro 90% inhibitory concentration. In addition, the above compound is a highly safe drug with a very low toxicity.

Thus, the compounds of the invention are of great use as anti-HIV drugs showing a Synergism with AZT in the treatment of AIDS.

All the above-described species of the compounds of the present invention can be chemically synthesized by the known processes starting with known compounds. A general technology for the production of the compounds of the invention is now described in detail.

The base compounds of the invention can be synthesized by condensing imidazoles 2 with a thiophenol 3 in accordance with the following reaction scheme.

Furthermore, starting with the base compounds (represented by general formula 5 or 6), a variety of the compounds of the invention having various 2-substituent groups can be synthesized by modifying the 2-side chain of the imidazole ring.

In this route of synthesis, where any substituent is reactive, the reaction may be conducted with preliminary protection of the substituent with a suitable protective group.
Base route of synthesis (1)
Where Z=S

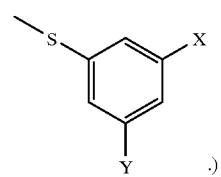

(Step 1)

In this step, halogen (e.g. chlorine, bromine, or iodine) is introduced into the imidazole derivative 1 in the presence of a base. As the halogen, iodine is particularly preferred.

Thus, iodine can be permitted to react in the presence of a base (e.g. sodium hydroxide or potassium hydroxide)in a solvent such as methylene chloride or ethylene chloride. Compound 1 can be synthesized according to the process described in EP-585014.

(Step 2)

In this step, compound 2 is condensed with a thiophenol derivative of the compound 3. The thiophenol derivative (a thiophenol or the corresponding disulfide)is dissolved in a suitable solvent (e.g. N,N-dimethylformamide, tetrahydrofuran, dimethyl sulfoxide), and the imidazole iodide 2 prepared in the preceding step is added thereto in the presence of a strong base such as lithium hydride, sodium hydride, or potassium hydride. In this step, a phenylthioimidazole of the formula 4 and its tautomer are obtained.

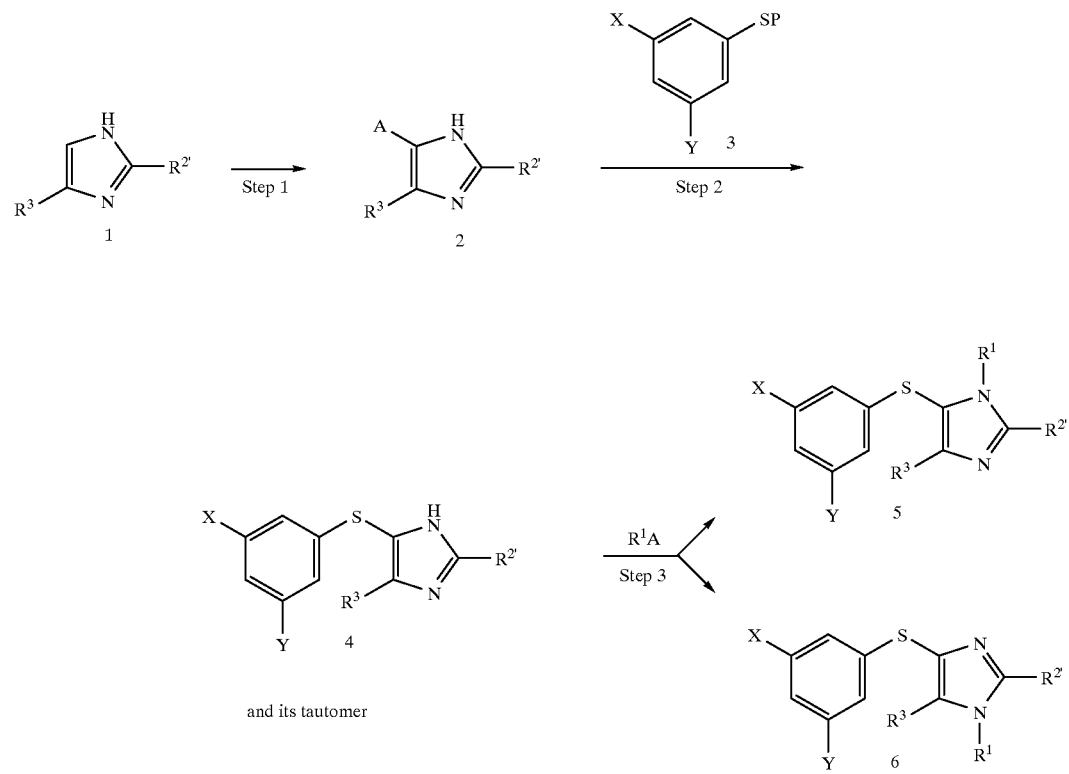

and its tautomer (In the above reaction scheme, $R^1$, $R^3$, X, and Y are as defined hereinbefore. A represents halogen. $R^2$' represents a species of $R^2$ which can be used in this reaction or hydrogen.

P represents hydrogen or a group of the following formula:

(Step 3)

In this step, $R^1$ is introduced into the N-position of the imidazole moiety. Thus, a desired substituent is introduced into the N-position. For example, a halide of the desired substituent (i.e. $R^1$A)is reacted with the phenylthioimidazole 4 or its tautomer as obtained in the preceding step. This reaction is carried out in the presence of a strong base (e.g. lithium hydride or sodium hydride)in an aprotic solvent such as N,N-dimethylformamide or dimethyl sulfoxide. In this step, the compounds 5 and 6 which are position isomers with respect to $R^1$ are obtained. Starting with this compound 5 or 6, other species of the compounds of the invention having various 2-substituents can be obtained by selecting desired substituents for the 2-position of the imidazole ring. The synthetic routes [A] to [D] are now described referring to the respective reaction schemes below.

Synthetic route [A]

Where $R^2$=CHO, $CH_2OH$ or CH=NR$^a$

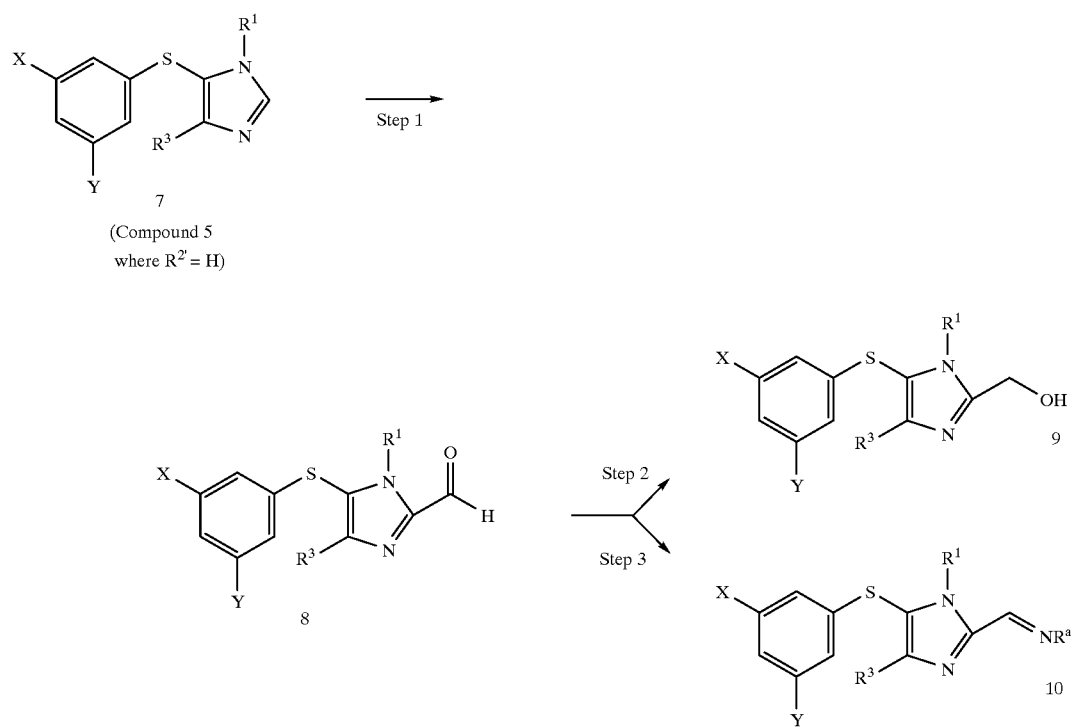

(In the above reaction scheme, $R^1$, $R^3$, X and Y are as defined hereinbefore. $R^a$ represents hydroxy or substituted or unsubstituted amino.)

(Step 1)

In this step, a formyl group is introduced into the 2-position of the imidazole moiety. This step is carried out by reacting compound 7 with N,N-dimethylformamide in the presence of a strong base, e.g. butyllithium, in a solvent such as tetrahydrofuran.

(Step 2)

In this step, the formyl group in the 2-position of the imidazole moiety is transformed into a hydroxymethyl group. This step is carried out by reducing the compound 8 with a reducing agent such as sodium borohydride in a solvent such as ethanol or methanol.

(Step 3)

In this step, the formyl group in the 2-position of the imidazole moiety is converted into an oxime or a hydrazono group. Thus, the compound 8 is reacted with hydroxylamine hydrochloride or hydrazine hydrate in a solvent such as methanol or ethanol.

Synthetic route [B]

Where $R^2$=$CH_2OR^{2a}$, $CH_2OCONH_2$, or $CH_2O(CH_2)_2OR^{2a}$

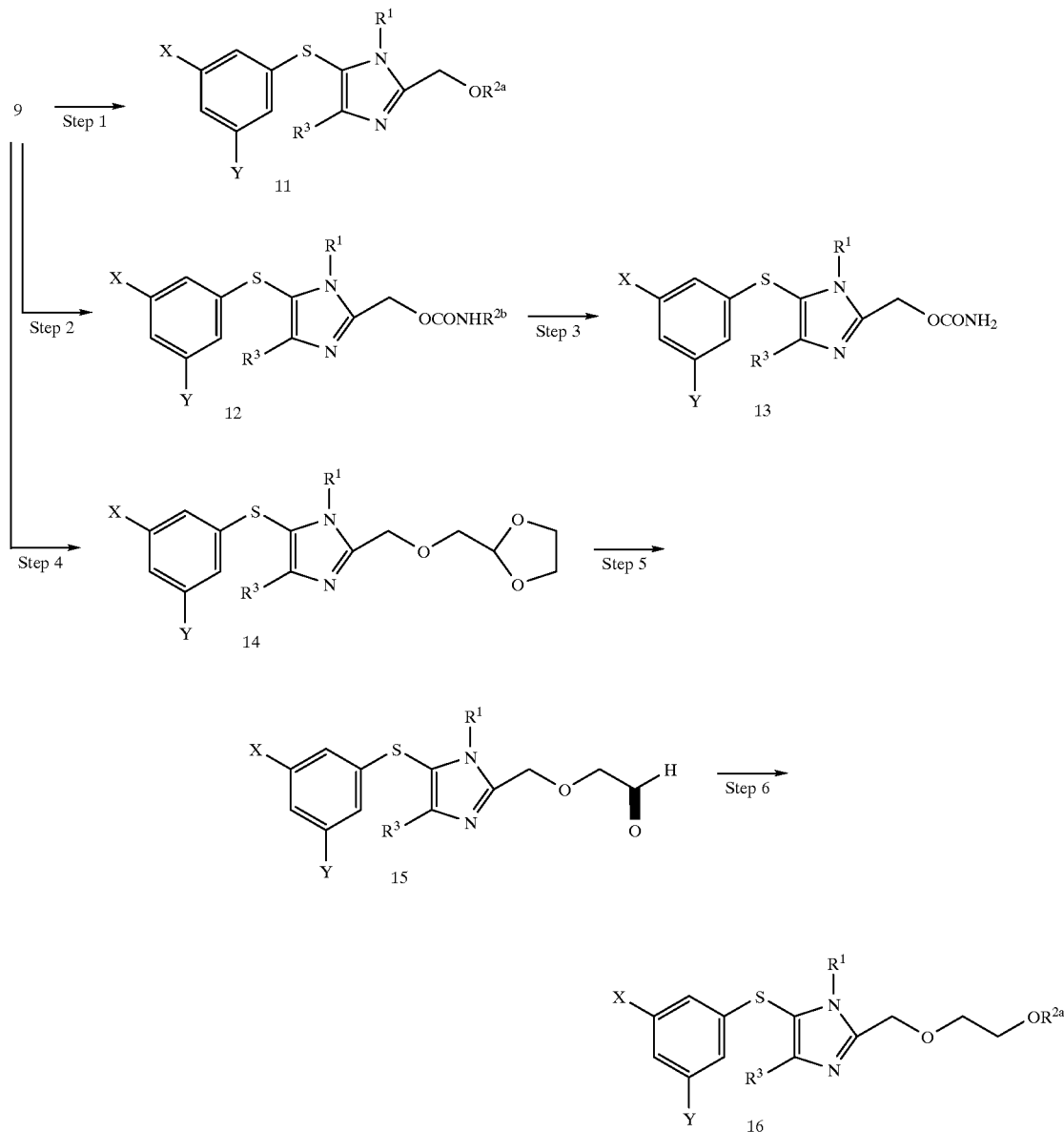

(In the above reaction scheme, $R^1$, $R^3$, X, and Y are as defined hereinbefore. $R^{2a}$ represents hydrogen, acyl, or substituted or unsubstituted carbamoyl or thiocarbamoyl. $R^{2b}$ represents alkyl.)

(Step 1)

In this step, the 2-hydroxymethyl group of the imidazole moiety of the compounds 9 is acylated. This step can be carried out by reacting the compounds 9 with an acylating agent (e.g. an acid chloride such as acetyl chloride or propionyl chloride or an acid anhydride such as acetic anhydride)in the presence of a base (e.g. triethylamine)in a solvent such as methylene chloride or ethylene chloride.

(Step 2)

In this step, the 2-hydroxymethyl group of the imidazole moiety of the compounds 9 is carbamoylated. This step can be carried out by reacting the compounds 9 with a carbamoylating agent (e.g. trichloroacetyl isocyanate or chlorosulfonyl isocyanate)in a solvent such as tetrahydrofuran or glyme.

(Step 3)

In this step, the acyl moiety of the acylamino group of the compounds 12 is hydrolytically eliminated to give the free carbamoyl compounds 13. This step can be carried out by heating the compounds 12 in the presence of an organic base (e.g. triethylamine or N,N-dimethylaniline)in a solvent such as methanol or ethanol.

(Step 4)

In this step through the next step, an acetaldehyde group is introduced into the 2-hydroxy group of the imidazole moiety of the compounds 9. First, the compounds 9 are reacted with 2-bromo-1,3-dioxolane in the presence of a strong base such as sodium hydride or potassium hydride in a solvent such as N,N-dimethylformamide, tetrahydrofuran, or dimethyl sulfoxide.

(Step 5)

The aldehyde-protecting group in the 2-side chain of the imidazole ring in the compounds 14 obtained in the preceding step is eliminated by acidic hydrolysis. This step can be carried out by treating the compounds 14 with a mineral acid such as hydrochloric acid in methanol.

(Step 6)

In this step, the aldehyde group of the compounds 15 obtained in the preceding step is reduced to the corresponding alcohols 16 ($R^{2a}$=H) and, where desired, followed by introducing a substitute such as an acyl, carbamoyl, or thiocarbamoyl group. For example, the compounds 15 are reduced with a reducing agent such as sodium borohydride in a solvent such as ethanol or methanol to give the alcohols 16 ($R^{2a}$=H). When the alcohols 16 are acylated, carbamoylated, or thiocarbamoylated by the well-known technology in the art, the corresponding acyl derivatives ($R^{2a}$=acyl), carbamoyl derivatives ($R^{2a}$=carbamoyl), or thiocarbamoyl derivatives ($R^{2a}$=thiocarbamoyl) is obtained. Specific procedures are described in the examples.

Synthetic Route [C]

Where $R^2$=substituted or unsubstituted aminomethyl

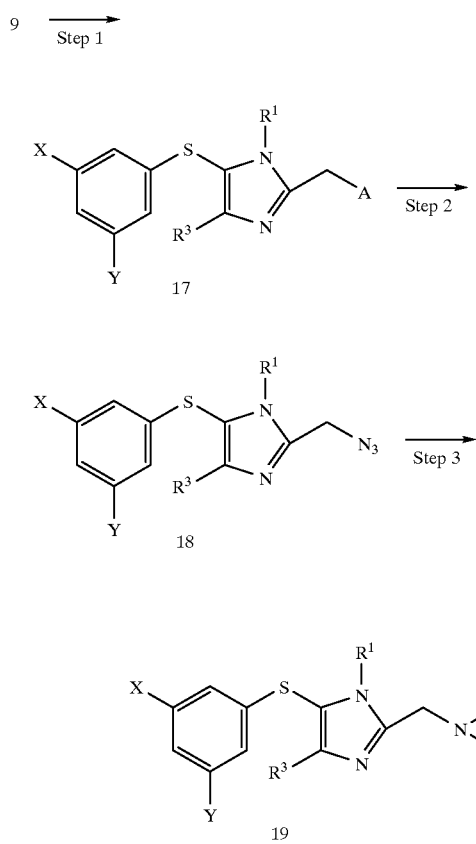

(In the above reaction scheme, $R^1$, $R^3$, A, X, and Y are as defined hereinbefore. $R^{2c}$ and $R^{2d}$ independently represent hydrogen or alkyl)

(Step 1)

In this step, halogen is introduced into the hydroxymethyl group in 2-position of the imidazole moiety. This step is carried out by reacting the compounds 9 with a chlorinating agent such as thionyl chloride, phosphorus oxychloride, or phosphorus trichloride in a solvent such as N,N-dimethylformamide, tetrahydrofuran, or dimethyl sulfoxide.

(Step 2)

In this step, the halide obtained in the preceding step is converted into an azide. This step is carried out by reacting the compounds 17 with an azide such as sodium azide or potassium azide in a solvent such as N,N-dimethylformamide or dimethyl sulfoxide.

(Step 3)

In this step, the azide compounds obtained in the preceding step are reducted to amino compounds. Thus, the compounds 18 are reacted with triphenylphosphine in a solvent such as tetrahydrofuran, N,N-dimethylformamide, or dimethyl sulfoxide.

Synthetic Route [D]

Where $R^2$=$CH_2COOR^{2c}$

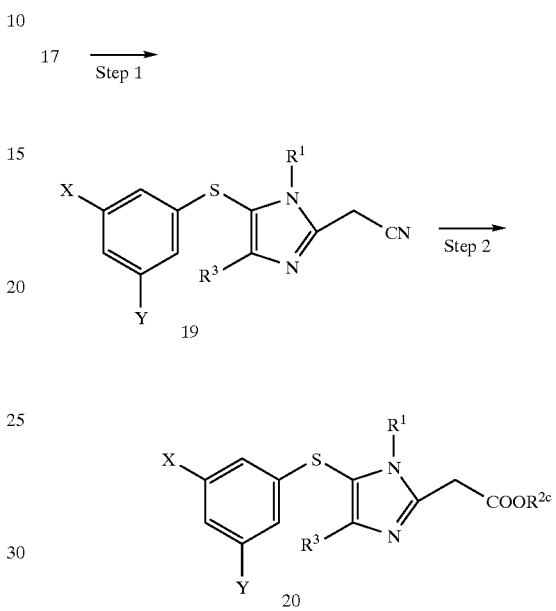

(In the above reaction scheme, $R^1$, $R^{2c}$, $R^3$, X, and Y are as defined hereinbefore.)

(Step 1)

In this step, the halomethyl group in the 2-position of the imidazole moiety obtained by Synthetic route [C] is cyanated. This step is carried out by reacting the compounds 17 with a cyanating agent such as potassium cyanide or sodium cyanide in a solvent such as N,N-dimethylformamide, tetrahydrofuran, or dimethyl sulfoxide.

(Step 2)

In this step, the cyano compounds 19 obtained in the preceding step are carboxylated or esterified. Thus, the compounds 19 are treated with dry hydrogen chloride gas in a solvent such as methanol or ethanol and neutralized with, for example, sodium hydrogen carbonate or potassium hydrogen carbonate to give the methyl or ethyl esters 20 ($R^{2c}$=methyl or ethyl). Subjecting this ester to the routine alkaline hydrolysis gives the free carboxylic acids 20 ($R^{2c}$=H).

Basal Route of Synthesis (2)

Z=SO or $SO_2$

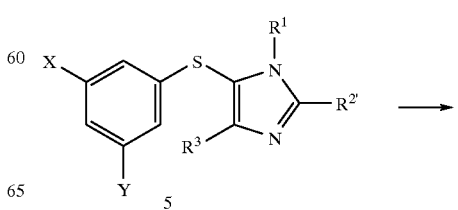

-continued

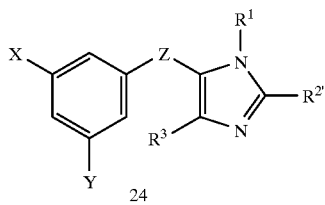

(In the above reaction scheme, $R^1$, $R^{2'}$, $R^3$, X, Y and Z are as defined hereinbefore.)

The compounds in which Z is SO or $SO_2$ can be produced by reacting the sulfide compounds with one or more equimolar amount of an oxidizing agent such as sodium periodate, m-chloroperbenzoic acid, aqueous hydrogen peroxide, sodium dichromate, potassium permanganate, chromic acid, or selenium dioxide in a solvent such as methylene chloride or acetonitrile and, where necessary, followed by separating the reaction product by silica gel or alumina column chromatography.

Moreover, by modifying the 2-side chain of the imidazole ring in the same manner as in the base route of synthesis (1), species of the compounds of the invention having various substituents in the 2-position can be obtained.

Base Route of Synthesis (3)
Where $Z=CH_2$

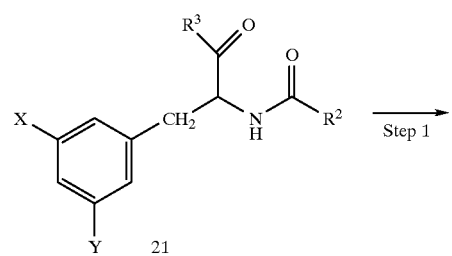

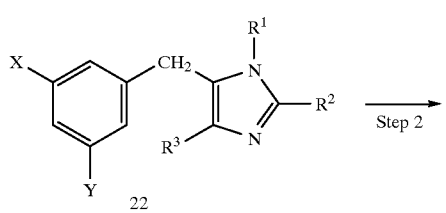

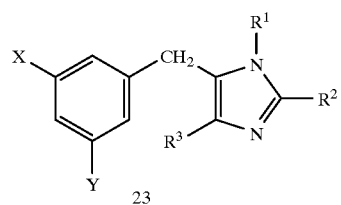

(In the above reaction scheme, $R^1$, $R^2$, $R^3$, X, and Y are as defined hereinbefore.)
(Step 1)
In the base route of synthesis (3), a suitable α-acylamino-α-substituted ketone compound 21 is used as the starting compound. Compound 21 is subjected to dehydrative cyclization by heating with ammonia or its salt of organic or inorganic acid in an organic solvent, e.g. acetic acid, at room temperature or under reflux, to form an imidazole ring.
(Step 2)
This step is carried out in the same manner as Step 3 in the base route of synthesis (1).

By modifying the 2-side chain of the imidazole ring in the same manner as in the base route of synthesis (1), species of the compounds of the invention having various substituents in the 2-position can be obtained.

The compounds of the present invention can be administered orally or parenterally. For oral administration, the compounds of the invention can be used in any of the conventional dosage forms, e.g. solid dosage forms such as tablets, powders, granules, capsules, etc.; solutions, oily suspensions; and liquid dosage forms such as syrups, elixirs. For parenteral administration, the compounds of the invention can be used in the form of an injectable aqueous or oily suspension. In the manufacture of such dosage forms, the conventional excipients, binders, lubricants, aqueous solvents, oily solvents, emulsifiers, suspending agents, etc. can be selectively employed. Moreover, other additives such as preservatives and stabilizers can also be incorporated. The dosage of the compound or salt thereof of the present invention depends on the route of administration, the patient's age and body weight and clinical condition, and type of disease. Usually, however, a daily oral dose of 0.05 to 3000 mg, preferably 0.1 to 1000 mg, or a daily parenteral dose of 0.01 to 1000 mg, preferably 0.05 to 500 mg, can be administered in 1 to 5 divided doses.

BEST MODE OF CARRYING OUT THE INVENTION

The following examples, formulation examples, and test examples are intended to describe the present invention in further detail and should by no means be construed as defining the scope of the invention.

EXAMPLE 1

Synthesis of 5-(3,5-Dichlorophenylthio)-1,2-dimethyl-4-isopropyl-1H-imidazole (Compound I-1)

4-Isopropyl-2-methylimidazole (3a)was synthesized in accordance with the procedure described in EP-A 585014, while 5-iodo-4-isopropyl-2-methylimidazole (4a)and 5-(3,5-dichlorophenylthio)-4-isopropyl-2-methyl-1H-imidazole (5a)were synthesized in accordance with the procedure described in Japanese Kokai Hei-5-255270.

In dry N,N-dimethylformamide (8 ml)was dissolved 400 mg (1.3 mmol)of 5-(3,5-dichlorophenylthio)-4-isopropyl-2-methyl-1H-1-imidazole (5a), followed by addition of 80 mg (2.0 mmol)of sodium hydride under ice-cooling. After 5 minutes, 245 mg (1.73 mmol)of methyl iodide was added. After 30 minutes, the reaction mixture was poured in ice-water and extracted with diethyl ether. The extract was washed with water, dried over sodium sulfate, filtered, and concentrated under reduced pressure. The residue was purified by silica gel chromatography (ethyl acetate:n-hexane= 1:2)and recrystallized from n-hexane to provide 313 mg (yield 75%)of 5-(3,5-dichlorophenylthio)-1,2-dimethyl-4-isopropyl-1H-imidazole (Compound I-1). mp 95 to 96° C.
$^1$H-NMR ($CDCl_3$—TMS)δ ppm: 1.23 (d, J=6.8 Hz, 6H), 2.47 (s, 3H), 3.10 (sept, 1H), 3.42 (s, 3H), 6.82 (m, 2H), 7.10 (m, 1H) Elementary analysis ($C_{14}H_{16}Cl_2N_2S$) Calc. (%):C, 53.34: H, 5.12: Cl, 22.49: N, 8.89 Found (%):C, 53.05: H, 5.21: Cl, 22.40: N, 8.96

EXAMPLE 2

Synthesis of 5-(3,5-Dimethylphenylthio)-1,2-dimethyl-4-isopropyl-1H-imidazole (Compound I-2)

Compound I-2 was obtained by the same synthetic process as that for Compound I-1 in Example 1.

¹H-NMR (CDCl₃—TMS)δ ppm: 1.25 (d, J=7.0 Hz, 6H), 2.22 (s, 6H), 2.46 (s, 3H), 3.16 (sept, 1H), 3.42 (s, 3H), 6.58 (s, 2H), 6.75 (s, 1H)

EXAMPLE 3

Synthesis of 5-(3-Chlorophenylthio)-1,2-dimethyl-4-isopropylimidazole (Compound I-3)

Compound I-3 was obtained from 5-(3-chlorophenylthio)-4-isopropyl-2-methylimidazole by the same synthetic process as that for Compound I-1 in Example 1 (yield 47%). mp 91 to 94° C.

¹H-NMR (CDCl₃—TMS)δ ppm: 1.25 (d, J=7.2 Hz, 6H), 2.46 (s, 3H), 3.08–3.2 (m, 1H), 3.42 (s, 3H), 6.80–6.84 (m, 1H), 6.94 (t, J=2.4 Hz, 1H), 7.1~7.2 (m, 1H)

EXAMPLE 4

Synthesis of 1-Benzyl-5-(3,5-dimethylphenylthio)-4-isopropyl-2-methylimidazole (Compound I-4)

Compound I-4 was obtained by the same synthetic process as that for Compound I-1 in Example 1. mp 94 to 97° C.

¹H-NMR (CDCl₃—TMS)δ ppm: 1.28 (d, J=6.6 Hz, 6H), 2.45 (s, 3H), 3.05–3.2 (m, 1H), 5.06, (s, 2H), 6.68 (d, J=1.8 Hz, 2H), 6.9 (dd, J=0.9, 1.8 Hz, 2H), 6.99 (t, J=1.8 Hz, 1H), 7.1–7.3 (m, 4H) Elementary analysis ($C_{20}H_{20}Cl_2N_2S$) Calc. (%):C, 61.38: H, 5.15: Cl, 18.12: N, 7.16: S, 8.19 Found (%):C, 61.28: H, 5.21: Cl, 18.35: N, 7.10: S, 8.25

EXAMPLE 5

Synthesis of 1,2-Dimethyl-5-(3,5-dimethylphenylthio)-4-ethylimidazole (Compound I-5)

In dry dimethylformamide (4 ml)was dissolved 200 mg (0.8 mmol)of 5-(3,5-dimethylphenylthio)-4-ethyl-2-methylimidazole (5c), followed by addition of 49 mg (1.2 mmol)of 60% sodium hydride under ice-cooling, and the mixture was stirred for 5 minutes. Then, 138 mg (1.00 mmol)of methyl iodide was added and stirred for 30 minutes. The reaction mixture was poured in ice-water and extracted with diethyl ether, and the organic layer was dried over sodium sulfate. The solvent was concentrated under reduced pressure. The residue was purified by silica gel chromatography (ethyl acetate:methylene chloride=1:1). From the first fraction, 40 mg (yield 19%)of positional isomer (6e')of the target compound was obtained as oil. From the latter fraction, 140 mg of 1,2-dimethyl-5-(3,5-dimethylphenylthio)-4-ethylimidazole (Compound I-5)was obtained as oil (yield 66%).

(6e')oil ¹H-NMR (CDCl₃—TMS)δ ppm: 1.09 (t, J=7.4 Hz, 3H), 2.21 (s, 6H), 2.40 (s, 3H), 2.70 (q, J=7.4 Hz, 2H), 3.51 (s, 3H), 6.70 (m, 1H), 6.77 (m, 2H)

Compound I-5 oil ¹H-NMR (CDCl₃—TMS)δ ppm: 1.22 (t, J=7.6 Hz, 3H), 2.22 (s, 6H), 2.44 (s, 3H), 2.66 (q, J=7.4 Hz, 2H), 3.42 (s, 3H), 6.59 (m, 1H), 6.75 (m, 2H)

EXAMPLE 6

Synthesis of 5-(3,5-Dimethylphenylthio)-4-isopropyl-1-methyl-1H-imidazole-2-carbaldehyde (Compound I-6)

In 350 ml of acetonitrile was dissolved 70 g (0.452 mol) of 2,2-dichloro-3-methylbutyraldehyde (1), followed by addition of 74 g (0.913 mol)of 37% formalin. Under ice-cooling, 616 ml of 28% aqueous ammonia was added and the mixture was stirred at room temperature for 66 hours. This reaction mixture was concentrated under reduced pressure and the residue was extracted with methylene chloride. The extract was dried over sodium sulfate, filtered, and concentrated under reduced pressure, whereupon a mixture of 4-isopropylimidazole (3b)and (4-isopropyl-1H-imidazol-2-yl) isopropyl ketone (3b')was obtained as yellow oil. In 199 ml of methylene chloride was dissolved 39.5 g of the above oil, and a solution of sodium hydroxide (28.7 g)in water (287 ml) was added to the above solution. Then, under ice-cooling and stirring, a solution of iodine (182 g, 0.716 mol)in methylene chloride (910 ml)-methanol (455 ml)was added dropwise. After completion of dropwise addition, the mixture was further stirred on ice for 30 minutes. To this solution was added an aqueous solution of sodium thiosulfate and the mixture was neutralized with hydrochloric acid and extracted with methylene chloride. The extract was washed with water and the organic layer was dried over anhydrous sodium sulfate, filtered, and concentrated under reduced pressure. The residue was recrystallized from diisopropyl ether to provide 55.9 g (yield 43%)of 2,5-diiodo-4-isopropyl-1H-imidazole (7).

The filtrate obtained in the filtration of 2,5-diiodo-4-isopropyl-1H-imidazole (7)was concentrated under reduced pressure and the residue was subjected to silica gel chromatography (eluted with 1% methanol-methylene chloride followed by 5% methanol-methylene chloride). The eluate was recrystallized from ethyl acetate-isopropyl ether to provide 7.6 g (yield 6%)of (5-iodo-4-isopropyl-1H-imidazol-2-yl) isopropyl ketone (8). mp 138–140° C.

¹H-NMR (CDCl₃—TMS)δ ppm: 1.24 (d, J=7.0 Hz, 6H), 1.35 (d, J=7.0 Hz, 6H), 3.14 (sept, 1H), 3.88 (sept, 1H), 11.35 (br, 1H)IR (film)cm⁻¹: 3232, 1655 Elementary analysis ($C_{10}H_{15}N_2IO$) Calc. (%):C, 39.23: H, 4.94: N, 9.15: I, 41.45 Found (%):C, 39.15: H, 4.95: N, 9.12: I, 41.43

In 240 ml of ethanol was dissolved 48.1 g (0.144 mol)of 2,5-diiodo-4-isopropyl-1H-imidazole (7), followed by addition of 240 ml of water and 20.1 g (0.159 mol)of sodium sulfite. The mixture was heated at 85° C. for 35 minutes. This reaction mixture was concentrated and extracted with methylene chloride and the extract was washed with water and dried over sodium sulfate. After filtration, the solvent was distilled off under reduced pressure and the residue was washed with ethyl acetate-diisopropyl ether and filtered to provide 26.9 g (yield 86%)of 4-isopropyl-5-iodo-1H-imidazole (4b).

¹H-NMR (CDCl₃—TMS)δ ppm: 1.32 (d, J=7.2 Hz, 6H), 3.08 (sept, 1H), 7.86 (s, 1H), 8.74 (br, 1H)

In 30 ml of dry N,N-dimethylformamide was dissolved 4.0 g (16.9. mmol)of 4-isopropyl-5-iodo-1H-imidazole (4b), followed by addition of 4.68 g (33.9 mmol)of 3,5-dimethylthiophenol and 2.1 g (52.5 mmol)of 60% sodium hydride. The mixture was heated at 140° C. for 7 hours. The N,N-dimethylformamide was then distilled off under reduced pressure and, after addition of dry ice, the residue was extracted with methylene chloride. The organic layer was washed with water and dried over sodium sulfate. The solvent was then distilled off under reduced pressure and the residue was fractionated by silica gel chromatography (3% methanol-methylene chloride). The eluted crude compound was recrystallized from ethyl acetate-diisopropyl ether to provide 2.2 g (yield 53%)of 5-(3,5-dimethylphenylthio)-4-isopropyl-1H-imidazole (X=Y=Me) (9).

¹H-NMR (CDCl₃—TMS)δ ppm: 1.25 (d, J=7.0 Hz, 6H), 2.19 (s, 6H), 3.25 (sept, 1H), 6.52 (s, 2H), 6.72 (s, 1H), 7.66 (s, 1H), 8.30 (br, 1H)

In 10 ml of dry N,N-dimethylformamide was dissolved 1.0 g (4.1 mmol)of 5-(3,5-dimethylphenylthio)-4-isopropyl-1H-imidazole (X=Y=Me)(9), followed by addition of 330 mg (8.3 mmol)of 60% sodium hydride under ice-cooling. After 5 minutes, 690 mg (4.9 mmol)of methyl iodide was added and the mixture was stirred for 10 minutes. This reaction mixture was poured in ice-water and extracted with diethyl ether. The organic layer was washed with water and dried over sodium sulfate. The solvent was then distilled off under reduced pressure and the residue was fractionated by alumina chromatography (ethyl acetate:n-hexane,=1:1). From the first fraction, 833 mg (yield 79%)of 5-(3,5-dimethylphenylthio)-4-isopropyl-1-methyl-1H-imidazole (X=Y=Me) (10)was recovered as oil.

$^1$H-NMR (CDCl$_3$—TMS)δ ppm: 1.26 (d, J=6.8 Hz, 3H), 1.27 (d, J=6.8 Hz, 3H), 2.22 (s, 6H), 3.17 (sept, 1H), 3.53 (s, 3H), 6.57 (s, 2H), 6.76 (s, 1H), 7.65 (s, 1H)

From the polar fraction, 201 mg (yield 19%)of methyl position isomer (10')was obtained as oil.

$^1$H-NMR (CDCl$_3$—TMS)δ ppm: 1.31 (d, J=7.2 Hz, 6H), 2.21 (s, 6H), 3.30 (sept, 1H), 3.67 (s, 3H), 6.71 (s, 2H), 6.75 (s, 2H), 7.42 (s, 1H)

In 16 ml of dry tetrahydrofuran was dissolved 800 mg (3.1 mmol)of 5-(3,5-dimethylphenylthio)-4-isopropyl-1-methyl-1H-imidazole (X=Y=Me)(10). This solution was cooled to −78° C. and 2.2 ml of n-butyllithium-n-hexane (1.66 molar) was added dropwise under nitrogen. After 5 minutes, 680 mg (9.3 mmol) of dry N,N-dimethylformamide was added and the reaction was further conducted at the same temperature for 15 minutes. This reaction mixture was poured in ice-water and extracted with diethyl ether. The organic layer was washed with water and dried over sodium sulfate. The solvent was then distilled off under reduced pressure and the residue was purified by silica gel chromatography (ethyl acetate:n-hexane=1:5)to provide 644 mg (yield 73%)of Compound I-6. mp 93 to 94° C.

$^1$H-NMR (CDCl$_3$—TMS)δ ppm: 1.29 (d, J=7.0 Hz, 6H ), 2.23 (s, 6H), 3.26 (sept, 1H), 3.91 (s, 3H), 6.59 (s, 2H), 6.81 (s, 1H), 9.83 (s, 1H)

EXAMPLE 7

Synthesis of 5-(3,5-Dichlorophenylthio)-4-isopropyl-1 -methyl-1H-imidazole-2-carbaldehyde (Compound I-7)

Compound I-7 was obtained by the same synthetic process as that for Compound I-6 in Example 6.

Oil $^1$H-NMR (CDCl$_3$—TMS)δ ppm: 1.29 (d, J=7.0 Hz, 6H), 3.19 (sept, 1H), 6.81 (m, 2H), 7.18 (m, 1H), 9.86 (s, 1H)

EXAMPLE 8

Synthesis of [5-(3,5-Dichlorophenylthio)-4-isopropyl-1-methyl-1H-imidazol-2-yl]methanol (Compound I-8)

In 4 ml of ethanol was dissolved 440 mg (1.3 mmol)of 5-(3,5-dichlorophenylthio)-4-isopropyl-1-methyl-1H-imidazole-2-carbaldehyde (Compound I-6), followed by addition of 51 mg (1.3 mmol)of sodium borohydride at room temperature. After 10 minutes, the mixture was neutralized by acetic acid and sodium bicarbonate, and extracted with methylene chloride. The organic layer was washed with water and dried over sodium sulfate. The solvent was then concentrated under reduced pressure and the residue was recrystallized by isopropyl ether:n-hexane to provide 340 mg (yield 77%)of Compound I-8. mp 157 to 158° C.

$^1$H-NMR (CDCl$_3$—TMS)δ ppm: 1.18 (d, J=7.0 Hz, 6H), 3.09 (sept, 1H), 3.59 (s, 3H), 4.76 (s, 2H), 4.76 (br, 1H), 6.81 (m, 2H), 7.12 (m, 1H) Elementary analysis (C$_{14}$H$_{16}$Cl$_2$N$_2$OS) Calc. (%):C, 50.76: H, 4.87: N, 8.46 Found (%):C, 50.81: H, 4.92: N, 8.44

EXAMPLE 9

Synthesis of [5-(3,5-Dimethylphenylthio)-4-isopropyl-1-methyl-1H-imidazol-2-yl]methanol (Compound I-9)

Compound I-9 was obtained by the same synthetic process as that for Compound I-8 in Example 8. mp 131~133° C.

$^1$H-NMR (CDCl$_3$—TMS)δ ppm: 1.23 (d, J=7.0 Hz, 6H), 2.23 (s, 6H), 3.19 (sept, 1H), 3.58 (s, 3H), 4.65 (s, 2H), 6.75 (br, 1H), 6.59 (s, 2H), 6.77 (s, 1H)

EXAMPLE 10

Synthesis of 5-(3,5-Dimethylphenylthio)-4-isopropyl-1-methyl-1H-imidazole-2-carbaldehyde Oxime (Compound I-10)

In 2 ml of ethanol was dissolved 50 g (0.17 mmol)of 5-(3,5-dimethylphenylthio)-4-isopropyl-1-methyl-1H-imidazole-2-carbaldehyde (Compound I-6), followed by addition of 36 mg (0.5 mmol)of hydroxylamine hydrochloride and 43 mg (0.5 mmol) of sodium acetate, and the mixture was stirred for 30 minutes at room temperature. To this reaction mixture, water was added, and the mixture was extracted with methylene chloride. The organic layer was washed with water, dried over sodium sulfate, and the solvent was concentrated under reduced pressure. The residue was washed with ethyl acetate to precipitate the product, and 32 mg (yield 60%)of Compound I-10 was obtained by the filtration. mp 240–241° C.

$^1$H-NMR (d6-DMSO—TMS)δ ppm: 1.14 (d, J=6.8 Hz, 6H), 2.19 (s, 6H), 3.08 (sept, 1H), 3.69 (s, 3H), 6.60 (s, 2H), 6.81 (s, 1H), 8.11 (s, 1H), 11.67 (s, 1H)

EXAMPLE 11

Synthesis of 5-(3,5-Dimethylphenylthio)-4-isopropyl-1-methyl-1H-imidazole-2-carbaldehyde Hydrazone (Compound I-11)

In 2 ml of ethanol was dissolved 50 mg (0.17 mmol)of 5-(3,5-dimethylphenylthio)-4-isopropyl-1-methyl-1H-imidazole-2-carbaldehyde (Compound I-6), followed by addition of 26 mg (0.5 mmol)of hydrazine hydrate, and the mixture was stirred at room temperature for 15 minutes. To this reaction mixture, water was added, and the mixture was extracted with methylene chloride. The organic layer was washed with water, dried over sodium sulfate, and the solvent was concentrated under reduced pressure. The residue was washed with n-hexane to precipitate the product, and 34 mg (yield 65%)of Compound I-11 was obtained by the filtration. mp 118–119° C.

$^1$H-NMR (CDCl$_3$—TMS)δ ppm: 1.27 (d, J=6.8 Hz, 6H), 2.23 (s, 6H), 3.21 (sept, 1H), 3.77 (s, 3H), 5.67 (br, 2H), 6.59 (s, 2H), 6.77 (s, 1H), 7.88 (s, 1H)

EXAMPLE 12

Synthesis of [5-(3,5-Dichlorophenylthio)-4-isopropyl-1-methyl-1H-imidazol-2-yl]isopropyl Ketone (Compound I-12)

(1)To dry N,N-dimethylformamide solution containing 2.70 g (15 mmol)of 3,5-dichlorophenylthiophenol and 0.36 g (15 mmol)of sodium hydoxide, 3.06 g (10 mmol)of 5-iodo-2-isobutyryl-4-isopropylimidazole (8)was added under stirring at room temperature. The mixture was stirred at room temperature for 30 minutes, and then, was stirred with heating at 150° C. for 3 hours. The reaction mixture was concentrated under reduced pressure, and to the residue was added water-ethyl acetate, to extract. The organic layer was washed with water, dried over sodium sulfate, and the solvent was concentrated under reduced pressure. The residue was purified by silica gel chromatography (ethyl acetate:n-hexane=1:9) to provide 1.70 g (yield 48%)of [5-(3,5-dichlorophenylthio)-4-isopropyl-1H-imidazol-2-yl] isopropyl ketone (14)as oil.

$^1$H-NMR (CDCl$_3$—TMS)δ ppm: 1.25–1.35 (m, 18H), 1.81 (s, 6H ), 3.29 (sept 1H ), 3.89 (sept, 1H), 6.98 (d, J=1.8 Hz, 2H), 7.10 (m, 2H), 7.18 (m, 1H), 7.30 (m, 1H)

(2)In 10 ml of acetone was dissolved 340 mg ((0.66 mmol)of [5-(3,5-dichlorophenylthio)-4-isopropyl-1H-imidazol-2-yl]isoprpyl ketone (14)and, at room temperature, 181 mg (13.0 mmol)of potassium carbonate and 191 mg (13.0 mmol)of methyl iodide were added with stirring. The mixture was allowed to stand overnight. This reaction mixture was concentrated under reduced pressure and the residue was extracted with methylene chloride. The organic layer was washed with water and dried over sodium sulfate and the solvent was distilled off under reduced pressure. The residue was purified by silica gel chromatography (ethyl acetate:n-hexane=1:9)to provide 123 mg (yield 50%)of Compound I-12 as oil.

$^1$H-NMR (CDCl$_3$—TMS)δ ppm: 1.23 (d, J=5.6 Hz, 6H), 1.26 (d, J=5.6 Hz, 6H), 3.36 (sept, 1H), 3.88 (s, 3H), 4.00 (sept, 1H), 6.80 (d, J=1.8 Hz, 2H), 7.15 (t, J=1.8 Hz, 1H)

REFERENCE EXAMPLE 1

Synthesis of [5-(3,5-Dichlorophenylthio)-4-isopropyl-1-methyl-1H-imidazol-2-yl]methanol
(Compound I-8)

(1)Benzyloxyacetaldehyde (2C)was synthesized in accordance with the procedure described in Synthetic Communications, 18, 359 (1988).

In 200 ml of acetonitrile was dissolved 53 g (339 mmol) of 2,2-dichloro-3-methylbutyraldehyde (1). Then, at 0° C., 45 g of benzyloxyacetaldehyde (2c)and 400 ml of aqueous ammonia (28%)were added. The mixture was stirred at room temperature for 15 hours. This reaction mixture was concentrated under reduced pressure and the residue was extracted with methylene chloride. The extract was washed with saturated brine, dried over sodium sulfate, and filtered. The filtrate was concentrated under reduced pressure to provide 2-(benzyloxymethyl)-4-isopropyl-1H-imidazole (3c). Yield 77 g (98.5%).

$^1$H-NMR (CDCl$_3$—TMS)δ ppm: 1.24 (d, J=6.8 Hz, 6H), 2.89 (m, 1H), 4.54 (s, 2H ), 4.61 (s, 2H ), 6.66 (s, 1H ), 7.31 (s, 5H)

(2)In 250 ml of methylene chloride was dissolved 70 g (304 mmol)of 2-(benzyloxymethyl)-4-isopropyl-1H-imidazole (3c). Then, an aqueous solution prepared by dissolving 13 g of sodium hydroxide in 160 ml of water was added at 0° C. and the mixture was stirred for 5 minutes. Then, a solution of iodine (49 g, 386 mmol)in methylene chloride (350 ml)-methanol (150 ml)was added at 0° C. and the mixture was then stirred at room temperature for 20 minutes. To this reaction mixture was added an aqueous solution of sodium sulfite and the mixture was extracted with methylene chloride. The extract was washed with saturated brine, dried over dry sodium sulfate, and filtered. The filtrate was concentrated under reduced pressure to provide 2-benzyloxymethyl-5-iodo-4-isopropylimidazole (4c). Yield 93 g (85.5%).

$^1$H-NMR (CDCl$_3$—TMS)δ ppm: 1.20 (d, J=7.0 Hz, 6H), 2.98 (m, 1H), 4.54 (s, 2H), 4.57 (s, 2H), 7.31 (s, 5H)

(3)In 100 ml of dimethyl sulfoxide was dissolved 23 g (65 mmol)of 2-benzyloxymethyl-5-iodo-4-isopropyl-1H-imidazole (4c). At room temperature, 620 mg (78 mmol)of lithium hydride and, then, 14 g (39 mmol)of di-3,5-dichlorophenyl disulfide were added. The mixture was stirred under heating at 60° C. for 5 hours. This reaction mixture was poured in ice-water and extracted twice with ethyl ether. The pooled organic layer was washed twice with water and dried over sodium sulfate and the solvent was distilled off under reduced pressure. The residue was dissolved in ethanol and 5.85 g (65 mmol)of oxalic acid was added. The salt that separated out was collected by filtration, neutralized with aqueous ammonia, and extracted with ethyl acetate. The organic layer was washed twice with water and dried over sodium sulfate and the solvent was distilled off under reduced pressure. The residue was rinsed with isopropyl alcohol to provide 20 g (yield 86%)of 2-benzyloxymethyl-5-(3,5-dichlorophenylthio)-4-isopropyl-1H-imidazole (16a).

$^1$H-NMR (CDCl$_3$—TMS)δ ppm: 1.22 (d, J=7.2 Hz, 6H), 3.64 (sept, 1H), 4.62 (s, 2H), 4.67 (s, 2H), 6.92 (bs, 2H), 7.07 (bs, 1H), 7.36 (s, 5H), 9.2 (b, 1H)

(4)In 50 ml of dry tetrahydrofuran was dissolved 15 g (44 mmol)of 2-benzyloxymethyl-5-(3,5-dichlorophenylthio)-4-isopropyl-1H-imidazole (16a). To this solution was added 6.87 g (48.4 mmol)of methyl iodide under ice-cooling, further followed by addition of 1.94 g (48.4 mmol)of sodium hydroxide and 100 mg of tetrabutylammonium bromide. After the ice-water bath was removed, the mixture was stirred for 1 hour. This reaction mixture was concentrated under reduced pressure and the residue was neutralized with hydrochloric acid and sodium hydrogen carbonate to be weakly basic and extracted twice with ethyl acetate. The pooled organic layer was washed with water and dried over sodium sulfate. The solvent was then distilled off under reduced pressure and the residue was fractionated by silica gel chromatography (3% ethyl acetate in methylene chloride). From the first fraction, 3.5 g (yield 22%)of the objective position isomer (17a')was obtained as oil. From the subsequent fraction, 10.4 g (yield 67%)of the objective 2-benzyloxymethyl-5-(3,5-dichlorophenylthio)-4-isopropyl-1-methyl-1H-imidazole (17a) was obtained as oil.

(17a')$^1$H-NMR (CDCl$_3$—TMS)δ ppm: 1.30 (d, J=7.2 Hz, 6H), 3.19 (sept, 1H), 3.66 (s, 3H), 4.55 (s, 2H), 4.66 (s, 2H), 6.97 (d, J=1.8 Hz, 2H), 7.05 (t, J=1.8 Hz, 1H), 7.31–7.40 (m, 5H)

(17a)$^1$H-NMR (CDCl$_3$—TMS)δ ppm: 1.26 (d, J=7.0 Hz, 6H), 3.12 (sept, 1H), 3.51 (s, 3H), 4.55 (s, 2H), 4.70 (s, 2H), 6.79 (d, J=1.8 Hz, 2H), 7.11 (t, J=1.8 Hz, 1H), 7.31–7.38 (m, 5H)

(5)In 20 ml of ethanol was dissolved 10.4 g (29.3 mmol)of 2-benzyloxymethyl-5-(3,5-dichlorophenylthio)-4-isopropyl-1-methyl-1H-imidazole (17a), followed by addition of 50 ml of concentrated hydrochloric acid. The mixture was refluxed under heating for 3 hours. This reaction mixture was concentrated under reduced pressure and the residue was neutralized with an aqueous sodium bicarbonate solution and extracted with ethyl acetate. The organic layer was washed with water and dried over sodium sulfate and the solvent was distilled off under reduced pressure. The residue was rinsed with isopropyl alcohol to provide 7.1 g (yield 92%)of the objective compound [5-(3,5-dichlorophenylthio)-4-isopropyl-1 -methyl-1H-imidazol-2-yl]methanol (Compound I-8). mp 157–158° C.

$^1$H-NMR (CDCl$_3$—TMS)δ ppm: 1.18 (d, J=7.0 Hz, 6H), 3.09 (sept, 1H), 3.59 (s, 3H), 4.76 (s, 2H), 4.76 (br, 1H), 6.81 (m, 2H), 7.12 (m, 1H) Elementary analysis (C$_{14}$H$_{16}$Cl$_2$N$_2$OS) Calc. (%):C, 50.76: H, 4.87: N, 8.46 Found (%):C, 50.81: H, 4.92: N, 8.44

REFERENCE EXAMPLE 2

Synthesis of [5-(3,5-Dichlorophenylthio)-4-isopropyl-1-methyl-1H-imidazol-2-yl]methanol (Compound I-8)

(1)1-p-methoxybenzylglycerol was synthesized in accordance with the procedure described in Synthetic Communications, 18, 359 (1988). The compound, 205.5 g (0.968 mol), was dissolved in 1060 ml of methylene chloride. To this solution was added an aqueous solution (1883 ml)of sodium periodate (269 g) dropwise at room temperature and the mixture was stirred overnight. This reaction mixture was diluted with 200 ml of water and extracted with methylene chloride. The organic layer was dried over magnesium sulfate and concentrated under reduced pressure to provide 175 g (yield 100%)of p-methoxybenzyloxyacetaldehyde (2d)as oil.

$^1$H-NMR (CDCl$_3$—TMS)δ ppm: 3.81 (s. 3H), 4.07 (s, 2H), 4.57 (s, 2H ), 6.89–6.92 (m, 2H ), 7.28–7.31 (m, 2H), 9.71 (s, 1H)

(2)In 970 ml of acetonitrile was dissolved 175 g (0.968 mol) of p-methoxybenzyloxyacetaldehyde (2d), followed by addition of 150 g (0.968 mol)of 2,2-dichloro-3-methylbutyraldehyde (1). Then, 1300 ml of 28% aqueous ammonia was further added dropwise under ice-cooling. After completion of dropwise addition, the mixture was allowed to stand at room temperature for 4 days. This reaction mixture was concentrated under reduced pressure and extracted with methylene chloride. The organic layer was washed with saturated brine and dried over MgSO$_4$ and the solvent was distilled off under reduced pressure. The crude product was dissolved in ethyl acetate. To this solution was added a solution of oxalic acid (89.8 g, 0.968 mol)in ethyl acetate (70 ml)and the resulting oxalate was collected by filtration and rinsed with ethyl acetate. This oxalate was neutralized with 2N-sodium hydroxide and extracted with ethyl acetate. The organic layer was washed with water and dried over magnisium sulfate. The solvent was then distilled off under reduced pressure to provide 165 g (yield 69%)of 4-isopropyl-2-(p-methoxybenzyloxymethyl)-1H-imidazole (3d)as oil.

$^1$H-NMR (CDCl$_3$—TMS)δ ppm: 3.81 (s. 3H), 4.07 (s, 2H), 4.57 (s, 2H ), 6.89–6.92 (m, 2H ), 7.28–7.31 (m, 2H), 9.71 (s, 1H)

(3)In methylene chloride (60 ml)-methanol (660 ml) dissolved 165 g (0.67 mol)of 4-isopropyl-2-(p-methoxybenzyloxymethyl)-1H-imidazole (3d), followed by addition of 170 g of solid iodine. Then, an aqueous solution prepared by dissolving 27.3 g (0.67 mol)of sodium hydroxide in 85 ml of water was added dropwise under ice-cooling. After completion of dropwise addition, the reaction mixture was stirred at room temperature for 1.5 hours. This reaction mixture was extracted with methylene chloride and the organic layer was washed with an aqueous solution of sodium sulfite and dried over anhydrous magnesium sulfate. The solvent was then distilled off under reduced pressure and the residue was rinsed with isopropyl ether and collected by filtration to provide 209.5 g (yield 81%)of 5-iodo-4-isopropyl-2-(p-methoxybenzyloxymethyl)-1H-imidazole (4d). mp 78–79° C.

$^1$H-NMR (CDCl$_3$—TMS)δ ppm: 1.20 (d, J=7.0 Hz, 6H), 2.99 (sept, 1H), 3.81 (s, 3H), 4.49 (s, 2H), 4.56 (s, 2H), 6.88 (d, J=8.6 Hz, 2H), 7.25 (d, J=8.6 Hz, 2H), 9.18 (bs, 1H)

(4)In 140 ml of dimethyl sulfoxide was suspended 30 g (84 mmol)of di-3,5-dichlorophenyl disulfide as well as 1.34 g (168 mmol)of lithium hydride powder and 59.1 g (153 mmol)of solid 5-iodo-4-isopropyl-2-(p-methoxybenzyloxymethyl)-1H-imidazole (4d)was added in small portions at 50° C. under nitrogen gas. After completion of addition, the mixture was stirred under heating at 60° C. for 45 minutes. This reaction mixture was poured in ice-water and extracted twice with ethyl ether. The pooled organic layer was washed twice with water and dried over magnesium, sulfate and the solvent was distilled off under reduced pressure. The residue was dissolved in ethyl acetate and a solution of oxalic acid (13.8 g, 65 mmol) in ethyl acetate (140 ml)was added. The salt that separated out was collected by filtration and rinsed with about 100 ml of ethyl acetate. This salt was neutralized with 2N-NaOH and extracted with diethyl ether. The organic layer was washed twice with water and dried over magnesium sulfate and the solvent was distilled off under reduced pressure to provide 51 g (yield 76%)of 5-(3,5-dichlorophenylthio)-4-isopropyl-2-(p-methoxybenzyloxymethyl)-1H-imidazole (16b)mp 96–97° C.

$^1$H-NMR (CDCl$_3$—TMS)δ ppm: 1.21 (d, J=7.2 Hz, 6H), 3.18 (sept, 1H), 3.81 (s, 3H), 4.54 (s, 2H), 4.64 (s, 2H), 6.88–6.92 (m, 4H), 7.07 (m, 1H), 7.26–7.30 (m, 2H) Elementary analysis (C$_{21}$H$_{22}$Cl$_2$N$_2$O$_2$S) Calc. (%):C, 57.67: H, 5.07: Cl, 16.21: N, 6.40: S, 7.33 Found (%):C, 57.62: H, 5.09: Cl, 16.32: N, 6.43: S, 7.27

(5)In 25 ml of dry N,N-dimethylformamide was dissolved 11.0 g (25.1 mmol)of 5-(3,5-dichlorophenylthio)-4-isopropyl-2-(p-methoxybenzyloxymethyl)-1H-imidazole (16b), followed by addition of 5.2 g (38 mmol)of potassium carbonate powder. Then, 3.90 g (27.7 mmol)of methyl iodide was further added and the mixture was stirred at room temperature for 8 hours. This reaction mixture was concentrated under reduced pressure and the residue was diluted with water and extracted with diethyl ether. The organic layer was washed with water and dried over magnesium sulfate. The solvent was distilled off under reduced pressure and the residue was fractionated by silica gel chromatography (ethyl acetate:methylene chloride=1:9). From the first fraction, 1.7 g (yield 15%)of the objective position isomer (17b')was obtained as oil. From the subsequent fraction, 9.14 g (yield 80%)of the objective 5-(3,5-dichlorophenylthio)-1-methyl-4-isopropyl-2-(p-methoxybenzyloxymethyl)-1H-imidazole (17b)was obtained. mp 79–80° C.

(17b')$^1$H-NMR (CDCl$_3$—TMS)δ ppm: 1.30 (d, J=7.2 Hz, 6H), 3.18 (sept, 1H), 3.64 (s, 3H), 3.80 (s, 3H), 4.48 (s, 2H), 4.64 (s, 2H), 6.84–7.27 (m, 7H)

(17b)$^1$H-NMR (CDCl$_3$—TMS)δ ppm: 1.26 (d, J=7.0 Hz, 6H), 3.12 (sept, 1H), 3.51 (s, 3H), 3.80 (s, 3H), 4.48 (s, 2H), 4.66 (s, 2H), 6.79–7.27 (m, 7H)

(6)In 45 ml of ethanol was dissolved 9.10 g (20.1 mmol)of 5-(3,5-dichlorophenylthio)-1-methyl-4-isopropyl-2-(p-methoxybenzyloxymethyl)-1H-imidazole (17b), followed by addition of 90 ml of 6N-hydrochloric acid, and the mixture was refluxed for 1 hour. This reaction mixture was concentrated under reduced pressure to remove ethanol and the residue forming a couple of layers was extracted twice with n-hexane to remove p-methoxybenzyl chloride. The aqueous layer was extracted with methylene chloride and the extract was neutralized with an aqueous sodium bicarbonate solution and dried over magnesium sulfate. The solvent was then distilled off under reduced pressure and the residue was rinsed with isopropyl ether to provide 6.3 g (yield 95%)of [5-(3,5-dichlorophenylthio)-4-isopropyl-1-methyl-1H-imidazol-2-yl]methanol (12=Compound I-8). mp 157–158° C.

$^1$H-NMR (CDCl$_3$—TMS)δ ppm: 1.18 (d, J=7.0 Hz, 6H), 3.09 (sept, 1H), 3.59 (s, 3H), 4.76 (s, 2H), 4.76 (br, 1H), 6.81 (m, 2H), 7.12 (m, 1H) Elementary analysis (C$_{14}$H$_{16}$Cl$_2$N$_2$OS) Calc. (%):C, 50.76: H, 4.87: N, 8.46 Found (%):C, 50.81: H, 4.92: N, 8.44

EXAMPLE 13

Synthesis of [5-(3-Chlorophenylthio)-4-isopropyl-1-methyl-1H-imidazol-2-yl]methanol (Compound I-13)

(1)By the same procedures as in Reference Example 2 (1) through (4), 5-(3-chlorophenylthio)-4-isopropyl-2-(p-methoxybenzyloxymethyl)-1H-imidazole (16c)was obtained. Oxalate: mp 124–125° C.

$^1$H-NMR (CDCl$_3$—TMS)δ ppm: 1.21 (d, J=7.0 Hz, 6H), 3.20 (sept, 1H), 4.53 (s, 2H), 4.63 (s, 2H), 6.89 (d, J=8.6 Hz, 2H), 7.27 (d, J=8.6 Hz, 2H), 6.90–7.20 (m, 4H) Elementary analysis (C$_{22}$H$_{25}$ClN$_2$O$_2$S.(COOH)$_2$.0.5.H$_2$O) Calc. (%):C, 55.86: H, 5.46: Cl, 6.87: N, 5.43: S, 6.21 Found (%):C, 55.56: H, 5.08: Cl, 7.27: N, 5.62: S, 6.40

(2)By the same procedures as in Reference Example 2 (5), from 5-(3-chlorophenylthio)-4-isopropyl-2-(p-methoxybenzyloxymethyl)-1H-imidazole (16c), 2-(p-methoxybenzyloxymethyl)-5-(3-chlorophenylthio)-1-methyl-4-isopropyl-1H-imidazole (17c) and its positional isomer (17c')were obtained in yields of 46% and 8%, respectively.

(17c')$^1$H-NMR (CDCl$_3$—TMS)δ ppm: 1.29 (d, J=7.0 Hz, 6H), 3.21 (sept, 1H), 3.63 (s, 3H), 3.80 (s, 3H), 4.48 (s, 2H), 4.62 (s, 2H), 6.87 (d, J=8.6 Hz, 2H), 7.25 (d, J=8.6 Hz, 2H), 6.90~7.20 (m, 4H)

(17c)$^1$H-NMR (CDCl$_3$—TMS)δ ppm: 1.26 (d, J=7.2 Hz, 6H), 3.15 (sept, 1H), 3.50 (s, 3H), 3.80 (s, 3H), 4.48 (s, 3H), 4.65 (s, 3H), 6.86 (d, J=8.8 Hz, 2H), 7.25 (d, J=8.8 Hz, 2H), 6.75–7.20 (m, 4H)

(3)By the same procedures as in Reference Example 2 (6), from 2-(p-methoxybenzyloxymethyl)-5-(3-chlorophenylthio)-1-methyl-4-isopropyl-1H-imidazole (17c), [5-(3-chlorophenylthio)-4-isopropyl-1-methyl-1H-imidazol-2-yl]methanol (Compound I-13)was obtained.

$^1$H-NMR (CDCl$_3$—TMS)δ ppm: 1.18 (d, J=7.2 Hz, 6H), 3.12 (sept, 1H), 3.58 (s, 3H), 4.75 (s, 2H), 6.70–7.25 (m, 4H) Elementary analysis (C$_{14}$H$_{17}$ClN$_2$OS) Calc. (%):C, 56.65: H, 5.77: Cl: 11.94: N, 9.43: S, 10.80 Found (%):C, 56.81: H, 5.78: Cl, 11.88: N, 9.16: S, 10.47

EXAMPLE 14

Synthesis of [4-Isopropyl-1-methyl-5-(3-nitrophenylthio)-1H-imidazol-2-yl]methanol (Compound I-14)

(1)By the same procedures as in Reference Example 2 (16b), 4-isopropyl-2-(p-methoxybenzyloxymethyl)-5-(3-nitrophenylthio)-1H-imidazole (16d)was obtained.

$^1$H-NMR (CDCl$_3$—TMS)δ ppm: 1.22 (d, J=7.2 Hz, 6H), 3.21 (sept, 1H), 3.81 (s, 3H), 4.55 (s, 2H), 4.64 (s, 2H), 6.90 (dJ=8.6 Hz, 2H), 7.29 (d, J=8.6 Hz, 2H), 7.30–8.00 (m, 4H)

(2)By the same procedures as in Reference Example 2 (17c), 4-isopropyl-2-(p-methoxybenzyloxymethyl)-1-methyl-5-(3-nitrophenylthio)-1H-imidazole (17d)was obtained. Yields of 4-isopropyl-2-(p-methoxybenzyloxymethyl)-1-methyl-5-(3-nitrophenylthio)-1H-imidazole (17d)and its positional isomer (17d')are 58% and 7%, respectively.

(17d)oil $^1$H-NMR (CDCl$_3$—TMS)δ ppm: 1.31 (d, J=7.0 Hz, 6H), 3.21 (sept, 1H), 3.67 (s, 3H), 3.80 (s, 3H), 4.49 (s, 2H), 4.63 (s, 2H), 6.88 (d, J=8.6 Hz, 2H), 7.26 (d, J=8.6 Hz, 2H), 7.30–8.00 (m, 4H) (17d)mp 89~90° C.

$^1$H-NMR (CDCl$_3$—TMS)δ ppm: 1.26 (d, J=7.0 Hz, 6H), 2.14 (sept, 1H), 3.80 (s, 3H), 4.50 (s, 2H), 4.67 (s, 2H), 6.87 (d, J=8.6 Hz, 2H), 7.25 (d, J=8.6 Hz, 2H), 7.41 (t, J=7.8 Hz, 1H), 7.83 (t, J=2.0 Hz, 1H), 7.98 (m, 1H) Elementary analysis (C$_{22}$H$_{25}$N$_3$O$_4$S) Calc. (%):C, 61.81: H, 5.89: N, 9.83: S, 7.50 Found (%):C, 61.78: H, 5.86: N, 9.80: S, 7.48

(3)By the same procedures as in Reference Example 2, Compound I-8, from 4-isopropyl-2-(p-methoxybenzyloxymethyl)-1-methyl-5-(3-nitrophenylthio)-1H-imidazole (17d), Compound I-14 was obtained.

$^1$H-NMR (CDCl$_3$—TMS)δ ppm: 1.19 (d, J=6.8 Hz, 6H), 3.12 (sept, 1H), 3.61 (s, 3H), 4.77 (s, 2H), 7.21 (dd, J=8.0, 2.0 Hz, 1H), 7.99 (dd, J=8.0, 2.0 Hz, 1H), 7.42 (t, J=8.0 Hz, 1H), 7.85 (t, J=2.0 Hz, 1H)

EXAMPLE 15

Synthesis of [1-n-Butyl-5-(3,5-dichlorophenylthio)-4-isopropyl-1H-imidazol-2-yl]methanol (Compound I-15)

By the same procedure as in Reference Example 2 for 5-(3,5-dichlorophenylthio)-1-methyl-4-isopropyl-2-(p-methoxybenzyloxymethyl)-1H-imidazole (17b), 2-(benzyloxymethyl)-1-n-butyl-5-(3,5-dichlorophenylthio)-4-isopropyl-1H-imidazole (17e)was obtained. Yields of 2-(benzyloxymethyl)-1-n-butyl-5-(3,5-dichlorophenylthio)-4-isopropyl-1H-imidazole (17e)and its positional isomer (17e') were 91% and 6%, respectively.

(17e')oil $^1$H-NMR (CDCl$_3$—TMS)δ ppm: 0.93 (t, J=7.2 Hz, 3H), 1.33 (d, J=7.2 Hz, 6H), 1.58–1.75 (m, 4H), 3.01 (sept, 1H ), 3.90–3.98 (m, 2H), 4.54 (s, 2H), 4.65 (s, 2H), 6.92 (s, 2H), 7.04 (s, 1H), 7.24–7.36 (m, 5H)

(17e)oil $^1$H-NMR (CDCl$_3$—TMS)δ ppm: 0.80 (t, J=7.0 Hz, 3H), 1.25 (d, J=7.0 Hz, 6H), 1.1–1.3 (m, 2H), 1.42~1.60 (m, 2H), 3.09 (sept, 1H), 3.84–3.92 (m, 2H), 4.55 (s, 2H), 4.67 (s, 2H), 6.79 (d, J=2 Hz, 2H), 7.10 (t, J=2 Hz, 1H), 7.30–7.39 (m, 5H)

By the same procedure as in Reference Example 2 for Compound I-8, Compound I-15 was obtained from 2-(benzyloxymethyl)-1-n-butyl-5-(3,5-dichlorophenylthio)-4-isopropyl-1H-imidazole (17e). mp 104–106° C.

$^1$H-NMR (CDCl$_3$—TMS)δ ppm: 0.86 (t, J=7.4 Hz, 3H), 1.17 (d, J=6.8 Hz, 6H), 1.20–1.40 (m, 2H), 1.50~1.65 (m, 2H), 3.06 (sept, 1H), 3.92–4.00 (m, 2H), 4.75 (s, 2H), 5.70 (s, 2H), 6.80 (d, J=1.8 Hz, 2H), 7.11 (t, J=1.8 Hz, 1H)

EXAMPLE 16

Synthesis of [1-Benzyl-5-(3,5-dichlorophenylthio)-4-isopropyl-1H-imidazol-2-yl]methanol (Compound I-16)

(1)In 10 ml of dry tetrahydrofuran was dissolved 423 mg (1.00 mmol)of 5-(3,5-dichlorophenylthio)-4-isopropyl-2-(p- methoxybenzyloxymethyl)-1H-imidazole (16b), followed by addition of 205 mg (1.20 mmol)of benzyl bromide, 48 mg (1.2 mmol)of sodium hydroxide and 5 mg (0.015 mg)of tetrabutylammonium bromide at room temperature with stirring, and the mixture was stirred at the same temperature for 3 hours. This reaction mixture was concentrated under reduced pressure and the residue was diluted with water and extracted with methylene chloride. The organic layer was washed with water and dried over sodium sulfate. The solvent was distilled off under reduced pressure and the residual oil was fractionated by silica gel chromatography (ethyl acetate:methylene chloride=1:9). From the first fraction, 33 mg (yield 6.5%)of the objective position isomer (17f')was obtained. From the subsequent fraction, 450 mg (yield 88%) of 1-benzyl-5-(3,5-dichlorophenylthio)-4-isopropyl-2-(p-methoxybenzyloxymethyl)-1H-imidazole (17f)was obtained.

(17f')oil $^1$H-NMR (CDCl$_3$—TMS)δ ppm: 1.28 (d, J=6.6 Hz, 6H), 2.95 (sept, 1H), 3.79 (s, 3H), 4.50 (s, 2H), 4.55 (s, 2H), 5.28 (s, 2H), 6.83 (d, J=6 Hz, 2H), 6.94–6.95 (m, 3H), 7.06 (m, 3H), 7.17 (d, J=5.8 Hz, 2H), 7.26–7.40 (m, 4H)

(17f)oil $^1$H-NMR (CDCl$_3$—TMS)δ ppm: 1.26 (d, J=6.6 Hz, 6H), 3.13 (sept, 1H), 3.80 (s, 3H), 4.47 (s, 2H), 4.61 (s, 2H), 5.18 (s, 2H), 6.63 (d, J=1.6 Hz, 2H), 6.83 (d, J=2 Hz, 2H), 6.90–6.93 (m, 2H), 6.99 (s, 1H), 7.11–7.21 (m, 4H), 7.26 (s, 4H)

To 25 ml of methanol was dissolved 1.41 g (2.67 mmol)of 1-benzyl-5-(3,5-dichlorophenylthio )-4-isopropyl-2-(p-methoxybenzyloxymethyl)-1H-imidazole (17f), followed by addition of 12.5 ml of 6N-hydrochloric acid at room temperature with stirring, and the mixture was stirred under heating at 60° C. for 3 hour. This reaction mixture was concentrated under reduced pressure, the residual solution was neutralized with a saturated aqueous solution of sodium bicarbonate to be weakly basic, and was extracted with methylene chloride. The extract was rinsed with water, and then, was dried over magnesium sulfate, and the solvent was concentrated under reduced pressure. The residue was crystalized from n-hexane and collected by filtration to give 1.0 g (yield 92%)of [1-benzyl-5-(3,5-dichlorophenylthio)-4-isopropyl-1H-imidazol-2-yl]methanol (Compound I-16). mp 121–124° C.

$^1$H-NMR (CDCl$_3$—TMS)δ ppm: 1.28 (d, J=6.9 Hz, 6H), 3.15 (sept, 1H), 4.79 (s, 2H), 5.25 (s, 2H), 6.64 (d, J=1.2 Hz, 2H), 6.9–7.0 (m, 3H), 7.18–7.26 (m, 4H)

EXAMPLE 17

Synthesis of [1-allyl-5-(3-chlorophenylthio)-4-isopropyl-1H-imidazol-2-yl]methanol (Compound I-17)

(1)In 10 ml of dry tetrahydrofuran was dissolved 744 mg (2.00 mmol)of 2-(benzyloxymethyl)-5-(3-chlorophenylthio)-4-isopropyl-1H-imidazole (16e), followed by addition of 410 mg (2.40 mmol)of allyl bromide, 96 mg (2.40 mmol)of sodium hydroxide and 5 mg (0.015 mg)of tetrabutylammoniumbromide at room temperature with stirring, and the mixture was stirred at room temperature for 3 hours. This reaction mixture was concentrated under reduced pressure, the residue was extracted with methylene chloride, the organic layer was washed with water and dried over sodium sulfate. The solvent was concentrated under reduced pressure and the residual oil was fractionated by silica gel chromatography (ethyl acetate:methylene chloride=1:9). From the first fraction, 50 mg (yield 6.7%)of the objective position isomer (17g')was obtained, and then, 480 mg (yield 58%)of 1-allyl-2-benzyloxymethyl-5-(3-chlorophenylthio)-4-isopropyl-1H-imidazole (17g)was obtained.

(17g')oil $^1$H-NMR (CDCl$_3$—TMS)δ ppm: 1.30 (d, J=7.2 Hz, 6H), 3.00 (sept, 1H), 4.53 (s, 2H), 4.66 (s, 2H), 4.67 (d, J=6.3 Hz, 2H), 4.83 (d, J=17.4 Hz, 1H), 5.21 (d, J=11.1 Hz, 1H), 5.85–5.95 (m, 1H), 6.97–7.04 (m, 3H), 7.09–7.14 (m, 1H), 7.25–7.40 (m, 5H)

(17g)oil $^1$H-NMR (CDCl$_3$—TMS)δ ppm: 1.26 (d, J=6.9 Hz, 6H), 3.13 (sept, 1H), 4.54 (s, 2H), 4.55–4.65 (m, 2H), 4.79 (s, 2H), 4.82 (d, J=18.3 Hz, 1H), 5.01 (d, J=11.4 Hz, 1H), 5.60–5.75 (m, 1H), 6.81 (d, J=10.5 Hz, 2H), 6.93 (s, 1H), 7.05–7.50 (m, 2H), 7.30–7.40 (m, 5H)

(2)In 5 ml of methylene chloride was dissolved 470 mg (1.13 mmol)of 1-allyl-2-benzyloxymethyl-5-(3-chlorophenylthio)-4-isopropyl-1H-imidazole (17g), with cooling to −40° C., 0.7 ml (1.36 mmol)of methylene chloride solution of boron trichloride (1.94 molar)was addled with stirring, and the mixture was stirred for 30 minutes. To this reaction mixture, a saturated aqueous solution of sodium bicarbonate was added for neutralization, methylene chloride layer was washed with water and dried over sodium sulfate. The solvent was concentrated under reduced pressure and the residue was fractionated by silica gel chromatography (ethyl acetate:methylene chloride=1:4). From the first fraction, 50 mg (yield 13%)of 1-allyl-2-chloromethyl-5-(3-chlorophenylthio)-4-isopropylimidazole (28a)was obtained as oil, and then, 155 mg (yield 43%)of Compound I-17 was obtained. mp 84–86° C.

(28a)$^1$H-NMR (CDCl$_3$—TMS)δ ppm: 1.26 (d, J=6.9 Hz, 6H), 3.16 (sept, 1H), 4.66–4.68 (m, 2H), 4.69 (s, 2H), 4.98 (d, J=18 Hz, 1H), 5.12 (d, J=12.6 Hz, 1H), 5.65–5.80 (m, 1H), 6.8 (d, J=10.5 Hz, 1H), 6.95 (s, 1H), 7.1–7.2 (m, 2H)

Compound I-17 $^1$H-NMR (CDCl$_3$—TMS)δ ppm: 1.23 (d, J=6.8 Hz, 6H), 3.16 (sept, 1H), 4.61–4.66 (m, 2H), 4.74 (s, 2H), 4.92 (d, J=18 Hz, 1H), 5.10 (d, J=12 Hz, 1H), 5.6–5.8 (m, 1H), 6.80–6.84 (m, 1H), 6.95 (t, J=2.7 Hz, 1H), 7.1–7.2 (m, 2H)

EXAMPLE 18

Synthesis of [5-(3,5-Dichlorophenylthio)-1-dodecyl-4-isopropyl-1H-imidazol-2-yl]methanol (Compound I-18)

(1)5-(3,5-dichlorophenylthio)-1-dodecyl-4-isopropyl-2-(p-methoxybenzyloxymethyl)-1H-imidazole (17h)was obtained by the same synthetic process as that for (17f)in Example 16 (yield 43%).

(17h)oil $^1$H-NMR (CDCl$_3$—TMS)δ ppm: 0.87 (t, J=6.0 Hz, 3H), 1.26 (d, J=6.9 Hz, 6H), 1.1–1.4 (m, 18H), 1.5 (br, 2H), 3.07 (sept, 1H), 3.81 (s, 3H), 3.85–3.90 (m, 2H), 4.48 (s, 2H), 4.64 (s, 2H), 6.80 (s, 2H), 6.87 (d, J=8.4 Hz, 2H), 7.11 (s, 1H), 7.27 (s, 2H)

(2)Compound I-18 was obtained from 5-(3,5-dichlorophenylthio)-1-dodecyl-4-isopropyl-2-(p-methoxybenzyloxymethyl)-1H-imidazole (17h)by the same synthetic process as that for Compound I-16 in Example 16 (yield 68%).

$^1$H-NMR (CDCl$_3$—TMS)δ ppm: 0.89 (t, J=7.5 Hz, 3H), 1.21 (d, J=7 Hz, 6H), 1.2–1.3 (m, 18H), 1.6 (br, 2H), 3.10 (sept, 1H), 3.92 (t, J=10 Hz, 2H), 4.76 (s, 2H), 6.82 (d, J=1.6 Hz, 2H), 7.12 (t, J=1.6 Hz, 1H)

EXAMPLE 19

Synthesis of [1-Allyl-5-(3,5-dichlorophenylthio)-4-isopropyl-1H-imidazol-2-yl]methanol (Compound I-19)

(1)1-Allyl-5-(3,5-dichlorophenylthio)-4-isopropyl-2-(p-methoxybenzyloxymethyl)-1H-imidazole (17i)was obtained by the same synthetic process as that for (17f) in Example 16. Yields of (17i) and its position isomer (17i') were 83% and 8%, respectively.

(17i')oil $^1$H-NMR (CDCl$_3$—TMS)δ ppm: 1.29 (d, J=7.5 Hz, 6H), 3.05 (sept, 1H), 3.80 (s, 3H), 4.46 (s, 2H), 4.58 (s, 2H), 4.62–4.7 (m, 2H), 4.82 (d, J=15 Hz, 1H), 5.22 (d, J=11 Hz, 1H), 5.82–5.98 (m, 1H), 6.87 (d, J=6 Hz, 2H)

(17i)oil $^1$H-NMR (CDCl$_3$—TMS)δ ppm: 1.26 (d, J=7.2 Hz, 6H), 3.10 (sept, 1H), 3.81 (s, 3H), 4.47 (s, 2H), 4.62 (s, 2H), 4.57–4.62 (m, 2H), 4.82 (d, J=18 Hz, 1H), 5.03 (d, J=10 Hz, 1H), 5.58–5.80 (m, 1H), 6.87 (d, J=2 Hz, 2H), 6.8–6.9 (m, 2H), 7.1 (t, J=3.4 Hz, 1H), 7.23 (s, 2H)

(2)[1-Allyl-4-(3,5-dichlorophenylthio)-4-isopropyl-1H-imidazol-2-yl]methanol (Compound I-19) was obtained from 1-allyl-5-(3,5-dichlorophenylthio)-4-isopropyl-2-(p-methoxybenzyloxymethyl)imidazole (17i) by the same synthetic process as that for Compound I-16 in Example 16 (yield 71%). mp 100–102° C.

Elementary analysis (C$_{16}$H$_{18}$N$_2$Cl$_2$OS) Calc. (%):C, 53.79: H, 5.08: N, 7.75: Cl, 19.85: S, 8.90 Found (%):C, 53.68: H, 5.16: N, 7.75: Cl, 19.57: S, 8.99

EXAMPLE 20

Synthesis of [1-Benzyl-5-(3-chlorophenylthio)-4-isopropyl-1H-imidazol-2-yl]methanol (Compound I-20)

(1) 1-Benzyl-5-(3-chlorophenylthio)-4-isopropyl-2-benzyloxymethyl-1H-imidazole (17j) was obtained by the same synthetic process as that for (17g) in Example 17. Yields of (17j) and its position isomer (17j') were 88% and 3%, respectively.

(17j')oil $^1$H-NMR (CDCl$_3$—TMS)δ ppm: 1.17 (d, J=7 Hz, 6H), 2.97 (sept, 1H), 4.53 (s, 2H), 4.60 (s, 2H), 5.30 (s, 2H), 6.9–7.2 (m, 8H), 7.2–7.4 (m, 5H)

(17j)oil $^1$H-NMR (CDCl$_3$—TMS)δ ppm: 1.28 (d, J=7 Hz, 6H), 3.16 (sept, 1H), 4.51 (s, 2H), 4.58 (s, 2H), 5.19 (s, 2H), 6.72–6.80 (m, 2H), 6.88–6.93 (m, 2H), 7.02–7.05 (m, 2H), 7.14–7.26 (m, 2H), 7.23–7.32 (m, 5H)

(2) 2-[1-Benzyl-5-(3-chlorophenylthio)-4-isopropyl-1H-imidazol-2-yl]methanol (Compound I-20) was obtained from 1-benzyl-5-(3-chlorophenylthio)-4-isopropyl-2-benzyloxymethyl-1H-imidazole (17j) by the same synthetic process as that for Compound I-17 in Example 17 (yield 35%). mp 120–122° C.

$^1$H-NMR (CDCl$_3$—TMS)δ ppm: 1.25 (d, J=6.6 Hz, 6H), 3.16 (sept, 1H), 4.70 (s, 2H), 5.22 (s, 2H), 6.75–6.82 (m, 2H), 6.90–7.06 (m, 4H), 7.1–7.3 (m, 3H) Elementary analysis (C$_{20}$H$_{21}$N$_2$ClOS) Calc. (%):C, 64.42: H, 5.68: N, 7.51: Cl, 9.51: S, 8.60 Found (%):C, 63.99: H, 5.69: N, 7.41: Cl, 9.39: S, 8.37

EXAMPLE 21

Synthesis of [1-Benzyl-4-isopropyl-5-(3-nitrophenylthio)-1H-imidazol-2-yl]methanol (Compound I-21)

(1) 1-Benzyl-5-(3-nitrophenylthio)-4-isopropyl-2-benzyloxymethyl-1H-imidazole (17k) was obtained by the same synthetic process as that for (17g) in Example 17. Yields of (17k) and its position isomer (17k') were 92% and 2%, respectively.

(17k')oil $^1$H-NMR (CDCl$_3$—TMS)δ ppm: 1.17 (d, J=7.2 Hz, 6H), 2.96 (sept, 1H), 4.53 (s, 2H), 4.59 (s, 2H), 5.30 (s, 2H), 6.98 (d, J=6.9 Hz, 2H), 7.23–7.41 (m, 8H), 7.49 (d, J=9.3 Hz, 1H), 7.80 (t, J=1.8 Hz, 1H), 7.92 (d, J=10 Hz, 1H)

(17k)oil $^1$H-NMR (CDCl$_3$—TMS)δ ppm: 1.30 (d, J=6.9 Hz, 6H), 3.15 (sept, 1H), 4.57 (s, 2H), 4.67 (s, 2H), 5.22 (s, 2H), 6.90–6.93 (m, 2H), 7.04–7.13 (m, 4H), 7.22–7.33 (m, 5H), 7.56 (t, J=2.1 Hz, 1H), 7.82–7.86 (m, 1H)

(2)[1-Benzyl-4-isopropyl-5-(3-nitrophenylthio)-1H-imidazol-2-yl]methanol (Compound I-21) was obtained from 1-benzyl-5-(3-nitrophenylthio)-4-isopropyl-2-benzyloxymethyl-1H-imidazole (17k) by the same synthetic process as that for Compound I-17 in Example 17 (yield 37%). mp 152–155° C.

As a by-product, 1-benzyl-2-chloromethyl-5-(3-nitrophenylthio)-4-isopropyl-1H-imidazole (28b) was obtained (yield 9%).

(28b)oil $^1$H-NMR (CDCl$_3$—TMS)δ ppm: 1.29 (d, J=6.6 Hz, 6H), 3.15 (sept, 1H), 4.63 (s, 2H), 5.29 (s, 2H), 6.89–6.92 (m, 2H), 7.05–7.14 (m, 5H), 7.63–7.90 (m, 2H)

Compound I-21 $^1$H-NMR (CDCl$_3$—TMS)δ ppm: 1.27 (d, J=6.9 Hz, 6H), 3.17 (sept, 1H), 4.78 (s, 2H), 5.26 (s, 2H), 6.93–6.97 (m, 2H), 7.08–7.13 (m, 2H), 7.22–7.26 (m, 3H), 7.57 (t, J=1.8 Hz, 1H), 7.84 (dd, J=11 Hz, 3 Hz, 1H) Elementary analysis (C$_{20}$H$_{21}$N$_3$O$_3$S) Calc. (%):C, 62.64: H, 5.52: N, 10.96: S, 8.36 Found (%):H, 5.66: N, 10.58: S, 8.05

EXAMPLE 22

Synthesis of [1-Allyl-4-isopropyl-5-(3-nitrophenylthio)-1H-imidazol-2-yl]methanol (Compound I-22)

(1) 1-Allyl-5-(3-nitrophenylthio)-4-isopropyl-2-benzyloxymethyl)-1H-imidazole (17l) was obtained by the same synthetic process as that for (17g) in Example 17. Yields of (17l) and its position isomer (17l') were 82% and 9%, respectively.

(17l')oil $^1$H-NMR (CDCl$_3$—TMS)δ ppm: 1.31 (d, J=7.2 Hz, 6H), 3.00 (sept, 1H), 4.55 (s, 2H), 4.63 (s, 2H), 4.69–4.73 (m, 2H), 4.86 (dt, J=15 Hz, 2 Hz, 1H), 5.24 (dt, J=11 Hz, 2 Hz, 1H), 5.80–6.00 (m, 1H), 7.26–7.48 (m, 7H), 7.83 (t, J=2 Hz, 1H), 7.92 (dt, J=9 Hz, 1.4 Hz, 1H)

(17l)oil $^1$H-NMR (CDCl$_3$—TMS)δ ppm: 1.27 (d, J=7.2 Hz, 6H), 3.11 (sept, 1H), 4.56 (s, 2H), 4.56–4.66 (m, 2H), 4.66 (s, 2H), 5.55–5.75 (m, 1H), 7.19–7.43 (m, 7H), 7.83 (t, J=2 Hz, 1H), 7.96 (dt, J=8.2 Hz, 1.2 Hz, 1H)

(2) Compound I-22 was obtained from (17l) by the same synthetic process as that for Compound I-17 in Example 17 (yield 37%). mp 117–120° C.

As a by-product, 1-allyl-2-chloromethyl-5-(3-nitrophenylthio)-4-isopropyl-1H-imidazole (28c) was obtained (yield 11%).

(28c)oil $^1$H-NMR (CDCl$_3$—TMS)δ ppm: 1.27 (d, J=8.4 Hz, 6H), 3.14 (sept, 1H), 4.64 (s, 2H), 4.70 (s, 2H), 4.9–5.0 (m, 2H), 5.6–5.8 (m, 1H), 7.2–7.5 (m, 2H), 7.8–8.0 (m, 2H)

Compound I-22 $^1$H-NMR (CDCl$_3$—TMS)δ ppm: 1.24 (d, J=7.2 Hz, 6H), 3.14 (sept, 1H), 4.64–4.69 (m, 2H), 4.71 (s, 2H), 4.9 (d, J=19.8 Hz, 1H), 5.08 (d, J=12 Hz, 1H), 5.65–5.63 (m, 1H), 7.23–7.26 (m, 1H), 7.42 (t, J=8.1 Hz, 1H), 7.87 (s, 1H), 7.99 (d, J=9 Hz, 1H) Elementary analysis (C$_{16}$H$_{19}$N$_3$O$_3$S) Calc. (%):C, 57.64: H, 5.74: N, 12.60: S, 9.62 Found (%):C, 57.45: H, 5.84: N, 12.70: S, 9.33

EXAMPLE 23

Synthesis of [1-Ethyl-4-isopropyl-5-(3-nitrophenylthio)-1H-imidazol-2-yl]methanol (Compound I-23)

(1) By the same synthetic process as that for (17g) in Example 17, 1-ethyl-5-(3-nitrophenylthio)-4-isopropyl-2- benzyloxymethyl-1H-imidazole (17m)was obtained. Yields of (17m)and its position isomer (17m')were 89% and 12%, respectively.

(17m')oil $^1$H-NMR (CDCl$_3$—TMS)δ ppm: 1.36 (d, J=7.2 Hz, 6H), 1.36 (t, 6.9 Hz, 3H), 3.07 (sept, 1H), 4.09 (q, J=6.9 Hz, 2H), 4.57 (s, 2H), 4.67 (s, 2H), 7.26–7.45 (m, 7H), 7.86 (t, J=2.1 Hz, 1H), 7.91 (dt, J=9 Hz, 1.2 Hz, 1H)

(17m)oil $^1$H-NMR (CDCl$_3$—TMS)δ ppm: 1.18 (d, J=7.5 Hz, 6H), 1.26 (t, 7.5 Hz, 3H), 3.12 (sept, 1H), 3.99 (q, J=7.5 Hz, 2H), 4.58 (s, 2H), 4.69 (s, 2H), 7.20 (dd J=8.1 Hz, 0.9 Hz, 1H), 7.30–7.42 (m, 6H), 7.84 (d, J=2.1 Hz), 7.96 (dd, J=8.1 Hz, 0.9 Hz, 1H)

(2)Compound I-23 was obtained from 1-ethyl-5-(3-nitrophenylthio)-4-isopropyl-2-benzyloxymethyl-1H-imidazole (17m)by the same synthetic process as that for Compound I-17 in Example 17 (yield 52%). mp 121–123° C.

As a by-product, 1-ethyl-2-chloromethyl-5-(3-nitrophenylthio)-4-isopropyl-1H-imidazole (28d)was obtained (yield 13%).

(28d)oil $^1$H-NMR (CDCl$_3$—TMS)δ ppm: 1.26 (d, J=6.9 Hz, 6H), 1.28 (t, J=7 Hz, 3H), 3.12 (sept, 1H), 4.03 (q, J=7 Hz, 2H), 4.60 (s, 2H), 4.72 (s, 2H), 7.18–7.45 (m, 2H), 7.84–7.95 (m, 2H)

Compound I-23 $^1$H-NMR (CDCl$_3$—TMS)δ ppm: 1.25 (d, J=6.9 Hz, 6H), 1.24 (t, J=7.2 Hz, 3H), 3.11 (sept, 1H), 4.06 (q, J=7.2 Hz, 2H), 4.77 (s, 2H), 7.22 (d, J=11 Hz, 1H), 7.40 (t, J=7 Hz, 1H), 7.87 (t, J=2 Hz, 1H), 7.97 (dd, J=11 Hz, 1 Hz, 1H) Elementary analysis (C$_{15}$H$_{19}$N$_3$O$_3$S.0.2.H$_2$O) Calc. (%):C, 55.44: H, 6.02: N, 12.93: S, 9.86 Found (%):C, 55.36: H, 5.90: N, 12.91: S, 9.70

EXAMPLE 24

Synthesis of [4-Isopropyl-5-(3-nitrophenylthio)-1-n-propyl-1H-imidazol-2-yl]methanol (Compound I-24)

(1)By the same synthetic process as that for (17g)in Example 17, 2-benzyloxymethyl-4-isopropyl-5-(3-nitrophenylthio)-1-n-propyl-1H-imidazole (17n)was obtained. Yields of (17n)and its position isomer (17n')were 93% and 7.5%, respectively.

(17n')oil $^1$H-NMR (CDCl$_3$—TMS)δ ppm: 0.96 (t, J=10 Hz, 3H), 1.34 (d, J,=7.2 Hz, 6H), 1.7–1.8 (m, 2H), 3.04 (sept, 1H), 3.93–3.98 (m, 2H), 4.55 (s, 2H), 4.65 (s, 2H), 7.26–7.43 (m, 7H), 7.83 (t, J=2.1 Hz, 1H), 7.90 (dd, J=7.8 Hz, 1.2 Hz, 1H)

(17n)oil $^1$H-NMR (CDCl$_3$—TMS)δ ppm: 0.80 (t, J=7.2 Hz, 3H), 1.25 (d, J=6.9 Hz, 6H), 1.50–1.62 (m, 2H), 3.11 (sept, 1H), 3.84–3.89 (m, 2H), 4.57 (s, 2H), 4.67 (s, 2H), 7.18 (dd, J=4.8 Hz, 0.9 Hz, 1H), 7.26–7.41 (m, 4H), 7.82 (t, J=2.1 Hz, 1H), 7.96 (dd, J=9.3 Hz, 1.2 Hz, 1H)

(2)Compound I-24 was obtained from 2-benzyloxymethyll-4-isopropyl-5-(3-nitrophenylthio)-1-n-propyl-1H-imidazole (17n) by the same synthetic process as that for Compound I-17 in Example 17 (yield 65%). Oil.

$^1$H-NMR (CDCl$_3$—TMS)δ ppm: 0.88 (t, J=7.2 Hz, 3H), 1.19 (d, J=6.9 Hz, 6H), 1.58–1.70 (m, 2H), 3.10 (sept, 1H), 3.93 (t, J=7.2 Hz, 2H), 4.76 (s, 2H), 7.20 (d, J=9 Hz, 1H), 7.40 (t, J=8.1 Hz, 1H), 7.85 (t, J=2.1 Hz, 1H), 7.97 (dd, J=11 Hz, J=0.9 Hz, 1H)

EXAMPLE 25

Synthesis of 2-[5-(3,5-Dichlorophenylthio)-1-ethyl-4-isopropyl-1H-imidazol-2-yl]methanol (Compound I-25)

(1)5-(3,5-Dichlorophenylthio)-1-ethyl-4-isopropyl-2-(p-methoxybenzyloxymethyl)-1H-imidazole (17o)was obtained by the same synthetic process as that for (17f)in Example 16 (yield 35%). Oil.

$^1$H-NMR (CDCl$_3$—TMS)δ ppm: 1.18 (t, J=7.0 Hz, 3H), 1.25 (d, J=7.0 Hz, 6H), 3.09 (sept, 1H), 3.80 (s, 3H), 3.96 (q, J=7.0 Hz, 2H), 4.48 (s, 2H), 4.64 (s, 2H), 6.80 (d, J=1.4 Hz, 2H), 6.85–6.89 (m, 2H), 7.11 (t, J=1.8 Hz, 1H), 7.24–7.28 (m, 2H)

(2)Compound I-25 was obtained from 5-(3,5-dichlorophenylthio)-1-ethyl-4-isopropyl-2-(p-methoxybenzyloxymethyl)-1H-imidazole (17o)by the same synthetic process as that for Compound I-8 in Reference Example 2 (yield 80%). mp 120–121° C.

$^1$H-NMR (CDCl$_3$—TMS)δ ppm: 1.17 (d, J=6.6 Hz, 6H), 1.25 (t, J=7.0 Hz, 3H), 3.07 (sept, 1H), 4.05 (t, J=7.0 Hz, 2H), 4.76 (s, 2H), 5.79 (br, 1H), 6.81 (d, J=1.6 Hz, 2H), 7.11 (t, J=1.6 Hz, 1H)

EXAMPLE 26

Synthesis of [5-(3,5-Dichlorophenylthio)-4-isopropyl-1-n-propyl-1H-imidazol-2-yl]methanol (Compound I-26)

(1)5-(3,5-Dichlorophenylthio)-4-isopropyl-2-(p-methoxybenzyloxymethyl)-1-n-propyl-1H-imidazole (17p) was obtained by the same synthetic process as that for (17f)in Example 16 (yield 41%). Oil.

$^1$H-NMR (CDCl$_3$—TMS)δ ppm: 0.81 (t, J=7.6 Hz, 3H), 1.24 (d, J=7.0 Hz, 6H), 1.51–1.64 (m, 3H), 3.08 (sept, 1H), 3.81 (s, 3H), 3.80–3.87 (m, 2H), 4.48 (s, 2H), 4.63 (s, 2H), 6.78 (d, J=8 Hz, 2H), 6.86–6.90 (m, 2H), 7.11 (t, J=1.8 Hz, 1H), 7.24–7.28 (m, 2H)

(2)Compound I-26 was obtained from 5-(3,5-dichlorophenylthio)-4-isopropyl-2-(p-methoxybenzyloxymethyl)-1-n-propyl-1H-imidazole (17p) by the same synthetic process as that for Compound I-8 in Reference Example 2 (yield 72%). mp 104–107° C.

$^1$H-NMR (CDCl$_3$—TMS)δ ppm: 1.17 (d, J=6.6 Hz, 6H), 1.25 (t, J=7.0 Hz, 3H), 3.07 (sept, 1H), 4.05 (t, J=7.0 Hz, 2H), 4.76 (s, 2H), 5.79 (br, 1H), 6.81 (d, J=1.6 Hz, 2H), 7.11 (t, J=1.6 Hz, 1H) Elementary analysis (C$_{16}$H$_{20}$Cl$_2$N$_2$OS.0.1.H$_2$O) Calc. (%):C, 53.22: H, 5.64: N, 7.76: S, 8.88: Cl, 19.63 Found (%):C, 53.27: H, 5.63: N, 7.77: S, 8.89: Cl, 19.96

EXAMPLE 27

Synthesis of [5-(3,5-Dichlorophenylthio)-1,4-diisopropyl-1H-imidazol-2-yl]methanol (Compound I-27)

(1)5-(3,5-dichlorophenylthio)-1,4-diisopropyl-2-(p-methoxybenzyloxymethyl)-1H-imidazole (17q)was obtained by the same synthetic process as that for (17f)in Example 16 (yield 43%).

$^1$H-NMR (CDCl$_3$—TMS)δ ppm: 1.23 (d, J=7.0 Hz, 6H), 1.42 (d, J=7.2 Hz, 6H), 3.07 (sept, 1H), 3.81 (s, 3H), 4.48 (s, 2H), 4.60–4.74 (m, 1H), 4.67 (s, 2H), 6.79 (d, J=1.8 Hz, 2H), 6.85–6.90 (m, 2H), 7.00 (t, J=1.8 Hz, 1H), 7.24–7.29 (m, 2H(2)

Compound I-27 was obtained from 5-(3,5-dichlorophenylthio)-1,4-diisopropyl-2-(p-methoxybenzyloxymethyl)-1H-imidazole (17q)by the same synthetic process as that for Compound I-8 in Reference Example 2 (yield 64%). mp 136–137° C.

$^1$H-NMR (CDCl$_3$—TMS)δ ppm: 1.19 (d, J=6.6 Hz, 6H), 1.45 (d, J=7.0 Hz, 6H), 2.99–3.13 (m, 1H), 4.31 (br, 1H), 4.62–4.77 (m, 1H), 4.79 (s, 2H), 6.8 (d, J=1.4 Hz, 2H), 7.11 (d, J=1.6 Hz, 1H)

EXAMPLE 28

Synthesis of [1-Ethyl-5-(3-chlorophenylthio)-4-isopropyl-1H-imidazol-2-yl]methanol (Compound I-28)

(1) 2-Benzyloxymethyl-5-(3-chlorophenylthio)-1-ethyl-4-isopropyl-1H-imidazole (17r) was obtained by the same synthetic process as that for (17g) in Example 17.

$^1$H-NMR (CDCl$_3$—TMS)δ ppm: 1.17 (t, J=7.4 Hz, 3H), 1.25 (d, J=6.6 Hz, 3H), 3.13 (sept, 1H), 3.98 (q, J=7.4 Hz, 2H), 4.56 (s, 2H), 4.67 (s, 2H), 6.79–7.20 (m, 4H), 7.24–7.40 (m, 5H)

(2) Compound I-28 was obtained from 2-benzyloxymethyl-5-(3-chlorophenylthio)-1-ethyl-4-isopropyl-1H-imidazole (17r) by the same synthetic process as that for Compound I-8 in Reference Example 1 (yield 64%). mp 99–100° C.

$^1$H-NMR (CDCl$_3$—TMS)δ ppm: 1.19 (d, J=6.6 Hz, 6H), 1.24 (t, J=7.0 Hz, 3H), 3.12 (sept, 1H), 4.05 (q, J=7.0 Hz, 2H), 4.77 (m, 2H), 6.78–7.19 (m, 4H) Elementary analysis (C$_{15}$H$_{19}$ClN$_2$OS.0.15.H$_2$O) Calc. (%):C, 57.46: H, 6.20: N, 8.93 Found (%):C, 57.25: H, 6.05: N, 8.92

EXAMPLE 29

Synthesis of [5-(3-Chlorophenylthio)-4-isopropyl-1-n-propyl-1H-imidazol-2-yl]methanol (Compound I-29)

(1) Compound I-29 was obtained by the same synthetic process as that for Compound I-16 in Example 16 (yield 73%). mp 85–88° C.

$^1$H-NMR (CDCl$_3$—TMS)δ ppm: 0.87 (t, J=7.2 Hz, 3H), 1.18 (d, J=6.6 Hz, 6H), 1.57–1.69 (m, 2H), 3.09 (sept, 1H), 3.88–3.94 (m, 2H), 4.74 (s, 2H), 5.0 (br, 1H), 6.80–7.18 (m, 4H) Elementary analysis (C$_{16}$H$_{21}$ClN$_2$OS) Calc. (%):C, 59.15: H, 6.52: N, 8.62: S, 9.87: Cl, 10.91 Found (%):C, 58.92: H, 6.51: N, 8.67: S, 9.89: Cl, 10.79

EXAMPLE 30

Synthesis of [1-cyclopropylmethyl-5-(3,5-dichlorophenylthio)-4-isopropyl-1H-imidazol-2-yl]methanol (Compound I-30)

(1) 2-Benzyloxymethyl-1-cyclopropylmethyl-5-(3,5-dichlorophenylthio)-4-isopropyl-1H-imidazole (17t) was obtained by the same synthetic process as that for (17g) in Example 17. Yields of (17t) and its position isomer (17t') were 86% and 10%, respectively.

(17t')oil $^1$H-NMR (CDCl$_3$—TMS)δ ppm: 0.28–0.36 (m, 2H), 0.55–0.64 (m, 2H), 0.99–1.16 (m, 1H), 1.35 (d, J=7.2 Hz, 6H), 3.04 (sept, 1H), 3.91 (d, J=6.6 Hz, 2H), 4.54 (s, 2H), 4.65 (s, 2H), 6.94 (d, J=2.0 Hz, 2H), 7.04 (t, J=2.0 Hz, 1H), 7.26–7.36 (m, 5H)

(17t)oil $^1$H-NMR (CDCl$_3$—TMS)δ ppm: 0.18–0.26 (m, 2H), 0.35–0.44 (m, 2H), 0.95–1.12 (m, 1H), 1.25 (d, J=7.0 Hz, 6H), 3.09 (sept, 1H), 3.82 (d, J=6.6 Hz, 2H), 4.55 (s, 2H), 4.70 (s, 2H), 6.78 (d, J=2.0 Hz, 2H), 7.09 (t, J=2.0 Hz, 1H), 7.27–7.40 (m, 5H)

Compound I-30 was obtained from 2-benzyloxymethyl-1-cyclopropylmethyl-5-(3,5-dichlorophenylthio)-4-isopropyl-1H-imidazole (17t) by the same synthetic process as that for Compound I-17 in Example 17 (yield 84%). mp 120–121° C.

$^1$H-NMR (CDCl$_3$—TMS)δ ppm: 0.29–0.37 (m, 2H), 0.41–0.53 (m, 2H), 1.00–1.20 (m, 1H), 1.17 (d, J=7.0 Hz, 6H), 3.05 (sept, 1H), 3.88 (d, J=6.6 Hz, 2H), 4.79 (s, 2H), 5.52 (br, 1H), 6.79 (d, J=1.8 Hz, 2H), 7.10 (t, J=1.8 Hz, 1H) Elementary analysis (C$_{17}$H$_{20}$Cl$_2$N$_2$OS) Calc. (%):C, 54.99: H, 5.43: N, 7.54: S, 8.64: Cl, 19.09 Found (%):C, 54.91: H, 5.42: N, 7.53: S, 8.68: Cl, 19.28

EXAMPLE 31

Synthesis of [1-Benzyloxymethyl-5-(3,5-dichlorophenylthio)-4-isopropyl-1H-imidazol-2-yl]methanol (Compound I-31)

(1) 1-Benzoylmethyl-5-(3,5-dichlorophenylthio)-4-isopropyl-2-(p-methoxybenzyloxymethyl)-1H-imidazole (17u) was obtained by the same synthetic process as that for (17f) in Example 16 (yield 88%).

(17u)oil. $^1$H-NMR (CDCl$_3$—TMS)δ ppm: 1.72 (d, J=7.2 Hz, 6H), 3.14 (sept, 1H), 3.74 (s, 3H), 4.36 (s, 2H), 4.64 (s, 3H), 7.03 (t, J=0.9 Hz, 1H), 7.09 (d, J=8.4 Hz, 2H), 7.46 (t, J=7.5 Hz, 2H), 7.59 (t, J=7.5 Hz, 1H), 7.79 (dd, J=7.5 Hz, 0.9 Hz, 2H)

(2) Compound I-31 was obtained from 1-benzoylmethyl-5-(3,5-dichlorophenylthio)-4-isopropyl-2-(p-methoxybenzyloxymethyl)-1H-imidazole (17u) by the same synthetic process as that for Compound I-16 in Example 16 (yield 75%). mp 205–211° C.

$^1$H-NMR (CDCl$_3$—TMS)δ ppm: 1.26 (d, J=7.0 Hz, 6H), 3.13 (sept, 1H), 4.72 (s, 2H), 5.51 (s, 2H), 6.77 (d, J=2 Hz, 2H), 7.01 (t, J=1.8 Hz, 1H), 7.40–7.65 (m, 3H), 7.87 (dt, J=5.6 Hz, 1.4 Hz, 2H)

EXAMPLE 32

Synthesis of [1-Acetylmethyl-5-(3,5-dichlorophenylthio)-4-isopropyl-1H-imidazol-2-yl]methanol (Compound I-32)

(1) In acetone (2 ml) was dissolved 111 mg (1.20 mmol) of chloroacetone, followed by addition of 200 mg (1.2 mmol) of potassium iodide, and the mixture was stirred at room temperature for 15 minutes. Then, 437 mg (1.00 mmol) of 5-(3,5-dichlorophenylthio)-4-isopropyl-2-(p-methoxybenzyloxymethyl)-1H-imidazole (16b) and 170 mg (1.20 mmol) of potassium carbonate were added in order, and the mixture was stirred for 5 hours and was left overnight. This reaction mixture was concentrated under reduced pressure and the residue was extracted with methylene chloride. The organic layer was washed with water, dried over anhydrous sodium sulfate and the solvent was concentrated under reduced pressure. The residue was fractionated by silica gel chromatography (ethyl acetate:methylene chloride=1:9). The oil was crystallized from ether to provide 270 mg (yield 62%) of 1-acetylmethyl-5-(3,5-dichlorophenylthio)-4-isopropyl-2-(p-methoxybenzyloxymethyl)-1H-imidazole (17v). mp 87–90° C.

$^1$H-NMR (CDCl$_3$—TMS)δ ppm: 1.26 (d, J=6.8 Hz, 6H), 1.97 (s, 3H), 3.80 (s, 3H), 4.38 (s, 2H), 4.60 (s, 2H), 4.74 (s, 2H), 6.81 (d, J=2 Hz, 2H), 6.84 (s, 1H), 6.89 (t, J=1.8 Hz, 2H), 7.11 (t, J=2 Hz, 1H), 7.21 (d, J=8.6 Hz, 2H) Elementary analysis (C$_{24}$H$_{26}$Cl$_2$N$_2$O$_3$S) Calc. (%):C, 58.42: H, 5.31: N, 5.68: S, 6.50: Cl, 14.37 Found (%):C, 58.23: H, 5.32: N, 5.81: S, 6.55: Cl, 14.69

(2) Compound I-32 was obtained from 1-acetylmethyl-5-(3,5-dichlorophenylthio)-4-isopropyl-2-(p-methoxybenzyloxymethyl)-1H-imidazole (17v) by the same synthetic process as that for Compound I-16 in Example 16 (yield 45%). mp 165–167° C.

¹H-NMR (CDCl₃—TMS)δ ppm: 1.21–1.27 (m, 6H), 1.56 (s, 2H), 2.16 (s, 1H), 3.11 (sept, 1H), 3.55, 3.92 (q, J=12.9 Hz, 2H), 4.59 (s), 4.80, 4.96 (q, J=15.6 Hz), 4.93 (s), 6.83 (t, J=1.8 Hz, 2H), 7.13 (t, J=1 Hz, 1H) Elementary analysis ($C_{16}H_{18}Cl_2N_2O_2S.0.5.H_2O$) Calc. (%):C, 50.25: H, 5.02: N, 7.35: Cl, 18.57 Found (%):C, 50.36: H, 4.87: N, 7.29: Cl, 18.94

EXAMPLE 32'

Synthesis of [1-(2-Hydroxypropyl)-5-(3,5-dichlorophenylthio)-4-isopropyl-1H-imidazol-2-yl] methanol (Compound I-32')

In methanol (5 ml)was dissolved 371 mg (0.8 mmol)of 1-acetylmethyl-2-benzyloxymethyl-5-(3,5-dichlorophenylthio)-4-isopropyl-1H-imidazole (17v"), followed by addition of 38 mg (1.0 mmol)of sodium borohydride with stirring at room temperature, and the mixture was stirred for 1.5 hours. This reaction mixture was concentrated under reduced pressure, and to the residue were added water and methylene chloride to extract. The organic layer was washed with water and was dried over sodium sulfate. The solvent was concentrated under reduced pressure, and the residue was purified by silica gel chromatography (ethyl acetate:methylene chloride=1:9), to obtain 2-benzyloxymethyl-5-(3,5-dichlorophenylthio)-1-(2-hydroxypropyl)-4-isopropyl-1H-imidazole (17v''')as oil quantitatively.

¹H-NMR (CDCl₃—TMS)δ ppm: 1.14 (d, J=5.7 Hz, 3H), 1.25 (t, J=6.9 Hz,), 2.72 (d, J=4.8 Hz, 1H), 3.10 (sept, 1H), 3.83–3.93 (m, 2H), 4.61 (dd, J=15.6 Hz, 10.2 Hz, 2H), 4.71 (dd, J=42.3 Hz, 12 Hz, 2H), 6.38 (s, 2H), 7.11 (s, 1H), 7.26–7.37 (m, 5H)

Compound I-32' was obtained from 2-benzyloxymethyl-5-(3,5-dichlorophenylthio)-1-(2-hydroxypropyl)-4-isopropyl-1H-imidazole (17v''')by the same synthetic process as that for Compound I-17 in Example 17 (yield 59%). mp 155–157° C.

¹H-NMR (CDCl₃—TMS)δ ppm: 1.21 (t, J=6.9 Hz,), 1.24 (d, J=5.4 Hz, 3H), 3.09 (sept, 1H), 3.72 (b, 1H), 3.93 (b, 2H ), 3.97 (dd, J=34.8 Hz, 11.7 Hz, 2H), 4.72 (dd, J=32.4 Hz, 13.5 Hz, 2H ), 6.79 (b, 1H), 6.79 (d, J=1.8 Hz, 2H), 7.13 (t, J=1.8 Hz) Elementary analysis ($C_{16}H_{20}Cl_2N_2O_2S$) Calc. (%):C, 51.20: H, 5.37: N, 7.46: Cl, 18.89: S, 8.54 Found (%):C, 51.25: H, 5.32: N, 7.38: Cl, 18.82: S, 8.56

EXAMPLE 33

Synthesis of 2-[5-(3,5-Dichlorophenylthio)-4-isopropyl-1-(1,1,1-trifluoroethyl)-1H-imidazol-2-yl] methanol (Compound I-33)

(1)5-(3,5-Dichlorophenylthio)-4-isopropyl-2-(p-methoxybenzyloxymethyl)-1-(1,1,1-trifluoroethyl)-1H-imidazole (17w)was obtained by the same synthetic process as that for 17f in Example 16. Yields of 17w and its position isomer 17w' were 58% and 6.4%, respectively.

17w' oil ¹H-NMR (CDCl₃—TMS)δ ppm: 1.33 (d, J=7 Hz, 6H), 2.90 (sept, 1H), 3.80 (s, 3H), 4.48 (s, 2H), 4.69 (s, 2H), 4.71 (q, J=18 Hz, 2H), 6.88 (d, J=8.6 Hz, 2H), 6.95 (d, J=2 Hz, 2H), 7.08 (d=1 Hz, 1H), 7.24 (d, J=8 Hz, 2H)

17w oil ¹H-NMR (CDCl₃—TMS)δ ppm: 1.25 (d, J=7.2 Hz, 6H), 3.10 (sept, 1H), 3.81 (s, 3H), 4.47 (s, 2H), 4.69 (q, J=17 Hz, 2H), 4.74 (s, 2H), 6.77 (d, J=1.8 Hz, 2H), 6.88 (d, J=8.7 Hz, 2H), 7.12 (s, 1H), 7.23 (d, J=8.7 Hz, 2H)

Compound I-33 was obtained from 5-(3,5-dichlorophenylthio)-4-isopropyl-2-(p-methoxybenzyloxymethyl)-1-(1,1,1-trifluoroethyl)-1H-imidazole (17w)by the same synthetic process as that for Compound I-16 in Example 16 (yield 82%). mp 134–136° C.

¹H-NMR (CDCl₃—TMS)δ ppm: 1.22 (d, J=6.9 Hz, 6H), 3.06 (sept, 1H), 3.30–3.38 (m, 1H), 4.72 (q, J=8.4 Hz, 2H), 4.84 (d, J=6 Hz, 2H), 6.79 (d, J=1.8 Hz, 2H), 7.14 (d, J=2 Hz, 1H) Elementary analysis ($C_{15}H_{15}Cl_2F_3N_2S$) Calc. (%):C, 45.12: H, 3.79: N, 7.02: Cl, 17.76: F, 14.27: S, 8.03 Found (%):C, 45.30, H, 3.85: N, 7.00: Cl, 17.98: F, 14.26: S, 7.95

EXAMPLE 34

Synthesis of [1-Fluoromethyl-5-(3,5-dichlorophenylthio)-4-isopropyl-1H-imidazol-2-yl] methanol (Compound I-34)

In dimethylsulfoxide (20 ml)was dissolved 814 mg (2.0 mmol)of 2-benzyloxymethyl-5-(3,5-dichlorophenylthio)-4-isopropylimidazole (16a), with cooling to 0 to 3° C., followed by addition of 1.44 g (10.4 mmol)of potassium carbonate with stirring, and the mixture was stirred at the same temperature for 15 minutes. Then, 270 mg (2.40 mmol)of bromofluoromethane was added, and the mixture was stirred for 30 minutes at the same temperature and then for 3 hours at room temperature, and left overnight. The reaction mixture was diluted with water, extracted with ethyl acetate, and the organic layer was washed with water and dried over sodium sulfate. The solvent was concentrated under reduced pressure, and the crude product was fractionated by silica gel column chromatography (ethyl acetate:methylene chloride=1:19). From the first fraction, 137 mg (yield 16%)of positional isomer (17x')of the target compound was obtained as oil. From the subsequent fraction, 700 mg of 2-benzyloxymethyl-5-(3,5-dichlorophenylthio)-1-fluoromethyl-4-isopropyl-1H-imidazole (17x)of the target compound was obtained as oil (yield 80%).

17x' oil ¹H-NMR (CDCl₃—TMS)δ ppm: 1.35 (d, J=6.9 Hz, 6H), 3.23 (sept, 1H), 4.56 (s, 2H), 4.73 (s, 2H), 6.04 (d, J=52.2 Hz, 2H), 6.97 (d, J=1.5 Hz, 2H), 7.09 (d, J=1.5 Hz, 1H), 7.3–7.4 (m, 5H)

17x oil ¹H-NMR (CDCl₃—TMS)δ ppm: 1.26 (d, J=7.2 Hz, 6H), 3.12 (sept, 1H), 4.57 (s, 2H), 4.78 (s, 2H), 5.99 (d, J=52.2 Hz, 2H), 6.85 (d, J=1.8 Hz, 2H), 7.13 (d, J=1.8 Hz, 1H), 7.30–7.76 (m, 5H)

Compound I-34 was obtained from 2-benzyloxymethyl-5-(3,5-dichlorophenylthio)-1-fluoromethyl-4-isopropyl-1H-imidazole (17x)by the same synthetic process as that for Compound I-17 in Example 17 (yield 86%). mp 115–117° C.

¹H-NMR (CDCl₃—TMS)δ ppm: 1.21 (d, J=7.2 Hz, 6H), 3.12 (sept, 1H), 3.98 (t, J=6.3 Hz, 1H), 4.86 (d, J=6.3 Hz, 2H), 6.04 (d, J=52.2 Hz, 2H), 6.86 (d. J=1.8 Hz, 2H), 7.14 (d, J=1.8 Hz, 1H) Elementary analysis ($C_{14}H_{15}Cl_2FN_2OS$) Calc. (%):C, 48.15: H, 4.33: N, 8.02: Cl, 20.30: F, 5.33: S, 9.18 Found (%):C, 48.01: H, 4.36: N, 7.96: Cl, 20.36: F, 5.63: S, 9.25

EXAMPLE 35

Synthesis of [5-(3,5-Dichlorophenylthio)-1-(1-fluoroethyl)-4-isopropyl-1H-imidazol-2-yl]methanol (Compound I-35)

2-Benzyloxymethyl-5-(3,5-dichlorophenylthio)-1-fluoroethyl-4-isopropyl-1H-imidazole (17y)was obtained by the same synthetic process as that for Compound 17f in Example 17. Yields of (17y) and its position isomer (17y') were 95% and 4%, respectively.

17y' oil $^1$H-NMR (CDCl$_3$—TMS)δ ppm: 1.33 (d, J=7 Hz, 6H), 3.02 (sept, ]H), 4.27 (t, J=3 Hz, 1H), 4.38 (t, J=4.8 Hz, 1H), 4.50 (t, J=4.8 Hz, 1H), 4.74 (t, J=5.4 Hz, 1H)

17y oil $^1$H-NMR (CDCl$_3$—TMS)δ ppm: 1.26 (d, J=7 Hz, 6H), 3.10 (sept, 1H), 4.25 (d, J=4.8 Hz, 1H), 4.20–4.56 (m, 2H), 4.56 (s, 2H), 4.56–4.60 (m, 2H), 4.73 (s, 2H), 6.80 (d, J=3 Hz, 2H), 7.11 (t, J=3 Hz, 1H), 7.29–7.35 (m, 5H)

Compound I-35 was obtained from 2-benzyloxymethyl-5-(3,5-dichlorophenylthio)-1-fluoroethyl-4-isopropyl-1H-imidazole (17y) by the same synthetic process as that for Compound I-17 in Example 17 (yield 58%). mp 131–132° C.

$^1$H-NMR (CDCl$_3$—TMS)δ ppm: 1.23 (d, J=5.6 Hz, 6H), 3.09 (sept, 1H), 4.0 (t, J=7.5 Hz, 1H), 4.29 (t, J=5.4 Hz, 1H), 4.37 (t, J=5.4 Hz, 1H), 4.52 (t, J=5.1 Hz, 1H), 4.61 (t, J=5.1 Hz, 1H), 6.80 (d, J=2.1 Hz, 2H), 7.13 (t, J=2.1 Hz, 1H) Elementary analysis (C$_{15}$H$_{17}$Cl$_2$FN$_2$OS.0.1.H$_2$O) Calc. (%):C, 49.33: H, 4.76: N, 7.67: F, 5.20: S, 8.78 Found (%):C, 49.07: H, 4.69: N, 7.72: F, 5.60: S, 8.86

EXAMPLE 36

Synthesis of [5-(3,5-Difluorophenylthio)-1-ethyl-4-isopropyl-1H-imidazol-2-yl]methanol (Compound I-36)

In dimethylformamide (10 ml) was dissolved 432 mg (1.2 mmol) of 2-benzyloxymethyl-5-(3,5-difluorophenylthio)-4-isopropyl-1H-imidazole (-16f), followed by addition of 192 mg (1.4 mmol) of potassium carbonate and 153 mg (1.4 mmol) of bromoethane at room temperature with stirring, the mixture was stirred at the same temperature for 3 days. The reaction mixture was extracted with ether, and the ether layer was washed with water, dried over magnesium sulfate, and filtered. The ether layer was concentrated under reduced pressure, and the residual oil was purified by silica gel column chromatography (methanol:methylene chloride= 3:97). From the first fraction, 20 mg (yield 4.3%) of positional isomer (17z') of the target compound was obtained. From the subsequent fraction, 300 mg of 2-benzyloxymethyl-5-(3,5-difluorophenylthio)-1-ethyl-4-isopropyl-1H-imidazole (17z), which was useful compound for the next reaction, was obtained (yield 65%). Oil.

17z' oil $^1$H-NMR (CDCl$_3$—TMS)δ ppm: 1.34 (d, J=6.9 Hz, 6H), 1.35 (t, J=7.0 Hz, 3H), 3.00–3.10 (m, 1H), 4.05 (q, J=7.0 Hz, 2H), 4.55 (s, 2H), 4.65 (s, 2H), 6.46–6.65; (m, 3H), 7.25–7.40 (m, 5H)

17z oil $^1$H-NMR (CDCl$_3$—TMS)δ ppm: 1.19 (t, J=7.0 Hz, 3H), 1.25 (d, J=6.6 Hz, 6H), 3.00–3.20 (m, 1H), 3.90–4.00(q, J=7.0 Hz, 2H), 4.57 (s, 2H), 4.67 (s, 2H), 6.44–6.60 (m, 3H), 7.20–7.40 (br, 5H)

$^1$H-NMR (CDCl$_3$)d 3a 1.34 (d, J=6.9 Hz, 6H), 1.35 (t, J=7.0 Hz, 3H), 3.00–3.10 (m, 1H), 4.05 (q, J=7.0 Hz, 2H), 4.55 (s, 2H), 4.65 (s, 2H), 6.46–6.65, (m, 3H), 7.25–7.40 (m, 5H)

In 5 ml of ethanol was dissolved 300 mg (0.75 mmol) of 2-benzyloxymethyl-5-(3,5-difluorophenylthio)-1-ethyl-4-isopropyl-1H-imidazole (17z), followed by addition of 5N-HCl (10 ml) at room temperature with stirring and the mixture was reacted on an oil bath at 130° C. for 3 hours during which time the mixture was concentrated. The reaction mixture was cooled, and a saturated aqueous sodium bicarbonate solution was added to be weakly alkali. The mixture was extracted with ethyl acetate, the ethyl acetate layer was washed with water and dried over magnesium sulfate, and the solvent was distilled off under reduced pressure. The residual oil was crystallized from n-hexane, and filtered to give 160 mg of Compound I-36 (yield 68%). mp 102–104° C.

$^1$H-NMR (CDCl$_3$—TMS)δ ppm: 1.19 (d, 6.8 Hz, 6H), 1.25 (t, J=7.2 Hz, 3H), 3.08 (sept), 4.02 (q, J=7.2 Hz, 2H), 4.44–4.60 (br, 1H), 4.70–4.80 (br, 2H), 6.46–6.64 (m, 3H)

EXAMPLE 37

Synthesis of [1-Ethyl-5-(3-fluorophenylthio)-4-isopropyl-1H-imidazol-2-yl]methanol (Compound I-37)

2-Benzyloxymethyl-1-ethyl-5-(3-fluorophenylthio)-4-isopropyl-1H-imidazole (17aa) was obtained by the same synthetic process as that for Compound 17z in Example 36. Yields of (17aa) and its position isomer (17aa') were 38% and 5%, respectively.

17aa' oil $^1$H-NMR (CDCl$_3$—TMS)δ ppm: 1.34 (d, J=7.4 Hz, 6H), 1.35 (t, J=7.4 Hz, 3H), 3.06 (sept, 1H), 4.05 (q, J=7.4 Hz, 2H), 4.55 (s, 2H), 4.65 (s, 2H), 6.70–6.90 (m, 3H), 7.08–7.20 (m, 1H), 7.25–7.40 (b, 5H)

17aa oil $^1$H-NMR (CDCl$_3$—TMS)δ ppm: 1.17 (d, J=7.2 Hz, 6H), 1.25 (t, J=7.0 Hz, 3H), 3.13 (sept, 1H), 3.97 (q, J=7.2 Hz, 2H), 4.56 (s, 2H), 4.67 (s, 2H), 6.60–6.86 (m, 3H), 7.13–7.24 (m, 1H), 7.28–7.38 (b, 5H).

Compound I-37 was obtained from 2-benzyloxymethyl-1-ethyl-5-(3-fluorophenylthio)-4-isopropyl-1H-imidazole (17aa) by the same synthetic process as that for Compound I-36 in Example 36 (yield 61%). mp 88–90° C.

$^1$H-NMR (CDCl$_3$—TMS)δ ppm: 1.18 (d, J=7.0 Hz, 6H), 1.23 (t, J=7.4 Hz, 3H), 3.11 (sept, 1H), 4.04 (q, J=7.4 Hz, 2H), 4.70–5.30 (b, 1H), 4.75 (s, 2H), 6.61–6.85 (m, 3H), 7.13–7.24 (m, 1H)

EXAMPLE 38

Synthesis of [4-(3-Chlorophenylthio)-5-isopropyl-1-methyl-1H-imidazol-2-yl]methanol (Compound I-38)

In 218 g of dry dimethylformamide was dissolved 21.8 g (58.5 mmol) of 2-benzyloxymethyl-5-(3-chlorophenylthio)-4-isopropyl-iH-imidazole (16e), followed by addition of 12.2 g (88.3 mmol) of anhydrous potassium carbonate and 11.6 g (81.7 mmol) of methyl iodide, the mixture was stirred at room temperature for 7 hours. To the reaction mixture was added ice-water, and the mixture was extracted with diethyl ether. The extract was washed with water and dried over sodium sulfate. The solvent was concentrated under reduced pressure and the residue was purified by silica gel chromatography (ethyl acetate:methylene chloride=1:8). From the first eluted fraction, 620 mg (yield 3%) of 2-benzyloxymethyl-4-(3-chlorophenylthio)-5-isopropyl-1-methyl-1H-imidazole (17ab') was obtained as oil. From the latter eluted fraction, 17.6 g (yield 78%) of 2-benzyloxymethyl-5-(3-chlorophenylthio)-4-isopropyl-1-methyl-1H-imidazole (17ab) was obtained as oil.

17ab' $^1$H-NMR (CDCl$_3$—TMS)δ ppm: 1.30 (d, J=7.2 Hz, 6H), 3.20 (sept, 1H), 3.65, (s, 3H), 4.55 (s, 2H), 4.65 (s, 2H), 6.96–7.34 (m, 9H)

17ab $^1$H-NMR (CDCl$_3$—TMS)δ ppm: 1.25 (d, J=7.0 Hz, 6H), 3.15 (sept, 1H), 3.51, (s, 3H), 4.54 (s, 2H), 4.68 (s, 2H), 6.78–7.35 (m, 9H)

In 5.8 ml of concented hydrochloric acid was dissolved 580 mg (1.5 mmol) of 2-benzyloxymethyl-4-(3- chlorophenylthio)-5-isopropyl-1-methyl-1H-imidazole (17ab'), and the mixture was refluxed under heating at 110° C. for 6 hours. The reaction mixture was neutralized with a saturated aqueous solution of sodium hydrogen carbonate, and extracted with methylene chloride. The organic layer was washed with water and dried over sodium sulfate, and the solvent was distilled off under reduced pressure. The crude product was recrystallized from ethyl acetate-isopropyl ether to give 289 mg of the objective Compound I-38 (yield 65%). mp 105–106° C.

$^1$H-NMR (CDCl$_3$—TMS)δ ppm: 1.32 (d, J=7.2 Hz, 6H), 3.23 (sept, 1H), 3.56, (br, 1H), 3.69 (s, 3H), 4.68 (s, 2H), 6.95–7.16 (m, 4H) IR (nujol)3146 cm$^{-1}$ Elementary analysis (C$_{14}$H$_{17}$ClN$_2$OS) Calc. (%):C, 56.65: H, 5.77: N, 9.44: S, 10.80. Cl, 11.94 Found (%):C, 56.75: H, 5.77: N, 9.39: S, 10.80: Cl, 11.93

EXAMPLE 39

Synthesis of [4-(3,5-Dichlorophenylthio)-5-isopropyl-1-methyl-1H-imidazol-2-yl]methanol (Compound I-39)

Compound I-39 was obtained from (17b')by the same synthetic process as that for Compound I-8 in Reference Example 2. mp 167–168° C.

$^1$H-NMR (CDCl$_3$—TMS)δ ppm: 1.31 (d, J=7.2 Hz, 6H), 3.20 (sept, 1H), 3.69, (s, 1H), 4.64 (s, 2H), 6.91 (d, J=1.8 Hz, 2H), 7.05 (t, J=1.8 Hz, 1H) Elementary analysis (C$_{14}$H$_{16}$Cl$_2$N$_2$OS) Calc. (%):C, 50.76: H, 4.87: N, 8.46: S, 9.68: Cl, 21.40 Found (%):C, 50.73: H, 4.86: N, 8.52: S, 9.76: Cl, 21.35

REFERENCE EXAMPLE 3

Synthesis of 2-Benzyloxymethyl-5-(3,5-dichlorophenylthio)-4-isopropyl-1-methyl-1H-imidazole (17a)

In 50 ml of methylene chloride was added 15.0 g (35.8 mmol)of glycine ethyl ester hydrochloric acid, followed by addition of 9.2 g (75.3 mmol)of 4-dimethylaminopyridine under ice-cooling. After stirring for 10 minutes, 6.5 ml (39.4 mmol)of benzyloxyacetylchloride was added dropwise under ice-cooling over 30 minutes. The temperature was raised up to room temperature, and the mixture was stirred for 12 hours. To the mixture, 20 ml of methylene chloride was added, and filtered. To the filtrate, 5% hydrochloric acid was added, and the mixture was extracted with methylene chloride. The extract was washed with saturated brine, dried over anhydrous sodium sulfate, and filtered. The filtrate was concentrated and 9.0 g of N-benzyloxyacetylglycine ethyl ester was obtained (yield 100%).

$^1$H-NMR (CDCl$_3$—TMS)δ ppm: 1.29 (t, J=7.0 Hz, 3H), 4.03 (s, 2H), 4.07 (d, J=5.4 Hz, 2H), 4.23 (q, J=7.0 Hz, 2H), 4.61 (s, 2H), 7.09 (br, 1H), 7.36 (s, 5H) Elementary analysis (C$_{13}$H$_{17}$NO$_4$) Calc. (%):C, 62.14: H, 6.82: N, 5.57 Found (%):C, 62.10: H, 6.80: N, 5.51

In 10 ml of dry tetrahydrofuran was dissolved 21.0 g (4.0 mmol)of N-benzyloxyacetylglycine ethyl ester, followed by addition of 175.0 mg (4.4 mmol)of sodium hydride (60% oil suspension)under ice-cooling. After stirring for 10 minutes, 473.0 μl (7.6 mmol)of methyl iodide was added dropwise under ice-cooling over 30 minutes. The temperature was raised up to room temperature and the mixture was stirred for 12 hours. Added was 10 ml of tetrahydrofuran, and filtered. To the filtrate was added 5% hydrochloric acid, and extracted with ethyl acetate. The extract was washed with saturated brine, dried over anhydrous sodium sulfate, and filtered. The filtrate was concentrated. The crude, product was purified by silica gel chromatography (ethyl acetate/hexane 1:1), and 30.0 mg of N-benzyloxyacetyl-N-methylglycine ethyl ester (18)was obtained (yield 40.7%).

$^1$H-NMR (CDCl$_3$—TMS)δ ppm: 1.20, 1.28. (t×2, J=7.0 Hz, 3H), 3.01, 3.07 (s×2, 3H), 4.13, 4.16 (s×2, 2H), 4.08, 4.20 (q×2, J=7.0 Hz, 2H), 4.16, 4.25 (s×2, 2H), 4.54, 4.64 (s×2, 2H), 7.27–7.40 (m×2, 5H) Elementary analysis (C$_{14}$H$_{19}$NO$_4$.0.1.H$_2$O) Calc. (%):C, 62.95: H, 7.25: N, 5.24 Found (%):C, 63.01: H, 7.24: N, 5.25

In 4 ml of dry tetrahydrofuran was dissolved 272.6 μl (1.9 mmol)of diisopropylamine, followed by addition of 1.0 ml (1.7 mmol)of n-butyllithium (1.7 M hexane solution)at 0° C. over 10 minutes. After stirring at 0° C. for 30 minutes, the mixture was cooled on a dry-ice bath to −78° C. and 430.0 mg (1.6 mmol)of N-benzyloxyacetyl-N-methylglycine ethyl ester (18)was added over 10 minutes. After stirring at −78° C. for 1 hour, the mixture was once warmed up to −40° C., and then cooled to −78° C. again. A tetrahydrofuran solution (2.0 ml) of 635.1 mg (1.8 mmol)of 3,5-dichlorophenyldisulfide was added dropwise over 10 minutes. After stirring for 30 minutes, the temperature was raised up to room temperature, and 5% hydrochloric acid was added. The mixture was extracted with ethyl acetate. The extract was washed with saturated brine, dried over anhydrous sodium sulfate, filtered and the filtrate was concentrated. The crude product was purified by silica gel chromatography (ethyl acetate:hexane=1:2), and 100.0 mg of ethyl 2-(N-benzyloxyacetyl-N-methyl)amino-2-(3,5-dichlorophenylthio)-acetate (19)was obtained (yield 13.6%).

$^1$H-NMR (CDCl$_3$—TMS)δ ppm: 1.31 (t, J=7.0 Hz, 3H), 3.04 (s, 3H), 4.13 (d, J=2.4 Hz, 2H), 4.26 (q, J=7.0 Hz, 2H), 4.49 (q, J=7.8 Hz, 2H), 6.90 (s, 1H), 7.21–7.40 (m, 8H)

In 10 ml of ethanol was dissolved 890.0 mg (2.0 mmol)of ethyl 2-(N-benzyloxyacetyl-N-methyl)amino-2-(3,5-dichlorophenylthio)acetate (19), followed by addition of 124.7 mg (2.1 mmol)of 86% potassium hydroxide under ice-cooling. The temperature was raised up to room temperature, and the mixture was stirred for 1 hour, the crystals precipitated were filtered. To the crystals was added 5% hydrochloric acid, and the mixture was extracted with ethyl acetate. The extract was washed with saturated brine, dried over anhydrous sodium sulfate, filtered, and concentrated to provide 640.0 mg of 2-(N-benzyloxyacetyl-N-methyl)amino-2-(3,5-dichlorophenylthio)acetic acid (yield 78.5%).

$^1$H-NMR (CDCl$_3$—TMS)δ ppm: 3.05 (s, 3H), 4.14 (d, J=2.0 Hz, 2H), 4.48 (d, J=5.4 Hz, 2H), 6.85 (s, 1H), 7.00 (br, 1H), 7.25–7.40 (m, 8H)

In 5 ml of dry toluene was dissolved 500.0 mg (1.2 mmol) of 2-(N-benzyloxyacetyl-N-methyl)amino-2-(3,5-dichlorophenylthio)acetic acid, followed by addition of 210.6 μl (2.4 mmol)of oxalyl chloride at room temperature, and the mixture was stirred for 1 hour. Toluene was distilled off under reduced pressure. In 5 ml of dry tetrahydrofuran was dissolved 216.2 mg (2.4 mmol)of copper (I)cyanide, followed by addition of 2.4 ml (4.8 mmol)of isopropylmagnesium chloride (2.0 M tetrahydrofuran solution)with cooling to −78° C. The mixture was once warmed up to 0° C., cooled to −78° C. again, and the above tetrahydrofuran solution (5 ml)of the acid chloride was added. After stirring for 30 minutes, 10 ml of methanol was added at −78° C., and the temperature was raised up to room temperature. Added were 3 ml of water and 5 ml of diethyl ether, and the mixture was filtered through Celite. The filtrate was extracted with diethyl ether. The extract was washed with saturated brine, dried over anhydrous sodium sulfate, filtered, and concentrated. The crude product was purified by silica gel chromatography (ethyl acetate:hexane=1:5)to give 2-benzyloxy-N-[1-(3,5-dichlorophenylthio)-3-methyl-2-oxobutyl]-N-methylacetamide (20).

$^1$H-NMR (CDCl$_3$—TMS)δ ppm: 1.15 (d, J=3.8 Hz, 3H), 1.18 (d, J=4.0 Hz, 3H), 3.02 (s, 3H), 4.15 (d, J=3.4 Hz, 2H), 4.51 (d, J=6.0 Hz, 2H), 7.02 (s, 1H), 7.22–7.40 (m, 8H)

In acetic acid was dissolved 2-benzyloxy-N-[1-(3,5-dichlorophenylthio)-3-methyl-2-oxobutyl]-N-methylacetamide (20), followed by addition of ammonium acetate, and the mixture was refluxed under heating. After 1 hour, the reaction mixture was concentrated under reduced pressure, neutralized with sodium hydroxide, and then, extracted with ethyl acetate. The extract was washed with saturated brine, dried over anhydrous sodium sulfate, and filtered. The filtrate was concentrated to give 2-benzyloxymethyl-5-(3,5-dichlorophenylthio)-4-isopropyl-1H-methylimidazole (17a).

$^1$H-NMR (CDCl$_3$—TMS)δ ppm: 1.25 (d, J=7.0 Hz, 6H), 3.51 (s, 3H), 4.54 (s, 2H), 4.69 (s, 2H), 6.79 (s, 2H), 7.10 (s, 1H), 7.22–7.40 (m, 5H)

REFERENCE EXAMPLE 4

Synthesis of 2-Benzyloxy-N-[1-(3,5-dichlorophenylthio)-3-methyl-2-oxobutyl]-N-methylacetamide (20)

To 300 ml of dry methanol was added 43.1 mg (0.5 mol)of 3-methyl-2-butanone, and the mixture was stirred at 5° C. Added was 27.3 ml (0.5 mol)of bromine at 10° C. over 30 minutes. After stirring at 10° C. for 1 hour, 150 ml of water was added, and the mixture was warmed up to room temperature and stirred for 3 hours. After addition of 300 ml of water, the mixture was extracted with 500 ml of diethyl ether 3 times. The extract was washed with a saturated aqueous solution of sodium hydrogen carbonate, and then with saturated brine, and calcium chloride was added to the diethyl ether layer. The mixture was stirred for 1 hour to dehydrate. The diethyl ether layer was filtered, concentrated at lower than 30° C., and the condensate was distilled under reduced pressure to provide 67.49 g of 1-bromo-3-methyl-2-butanone (b.p. 67–75° C./28 mmHg, yield 82%).

$^1$H-NMR (CDCl$_3$—TMS)δ ppm: 1.18 (d, J=6.0 Hz, 6H), 2.99 (m, 1H), 4.00 (s, 2H)

To a stirred mixture of 42.4 ml of 25% aqueous solution of methylamine and 24.2 ml of tetrahydrofuran was added 10.0 g (60.6 mmol)of 1-bromo-3-methyl-2-butanone was added at 10° C. over 30 minutes. After stirring at 10° C. for 30 minutes, 18.0 ml of diethyl ether and 12.1 g of potassium carbonate were added, and the mixture was stirred at room temperature for 10 minutes. The diethyl ether layer was separated, washed with saturated brine, dried over anhydrous potassium carbonate, and filtered. The filtrate was concentrated to give 6.09 g of 3-methyl-1-methylamino-2-butanone (yield 87%).

A mixture of 6.1 g (52.9 mmol)of 3-methyl-1-methylamino-2-butanone, 70.0 ml of ethyl acetate and 41.0 ml of water was stirred at 0° C. Added was 7.1 g (84.6 mmol)of sodium hydrogen carbonate, and the mixture was stirred for 10 minutes. There was added 8.5 ml (54.0 mmol)of benzyloxyacetylchloride over 30 minutes. After stirring at room temperature for 10 hours, the ethyl acetate layer was separated, washed with saturated brine, dried over anhydrous sodium sulfate, filtered, and concentrated. The crude product was purified by silica gel chromatography (hexane/ethyl acetate 1:1)to give 5.8 g of 2-benzyloxy-N-methyl-N-(3-methyl-2-oxobutyl)-acetamide (18a')(yield 42%).

$^1$H-NMR (CDCl$_3$—TMS)δ ppm: 1.04, 1.15 (d×2, J=6.6 Hz, 6H), 2.94, 3.01 (s×2, 3H), 2.52, 2.66 (m×2, 1H), 4.06, 4.25 (s×2, 2H), 4.25, 4.30 (s×2, 2H), 4.49, 4.64 (s×2, 2H), 7.27–7.45 (m, 5H)

In 2 ml of dry tetrahydrofuran was dissolved 100 mg (0.4 mmol )of 2-benzyloxy-N-methyl-N-(3-methyl-2-oxobutyl) acetamide (18a'), and there was added 223 μl (0.4 mmol)of n-butyllithium (1.7 M hexane solution)with stirring at −78° C. over 10 minutes. After stirring at −78° C. for 1 hour, and a tetrahydrofuran solution (1 ml)of 135 mg (0.4 mmol)of 3,5-dichlorophenylsulfide was added thereto over 10 minutes. After 30 minutes, the temperature was raised up to room temperature, a saturated aqueous ammonium chloride solution was added, and the mixture was extracted with ethyl acetate ester. The extract was washed with saturated brine, dried over anhydrous sodium sulfate, filtered, and concentrated. The crude product was purified by silica gel chromatography (hexane/ethyl acetate 5:1)to give 79 mg of 2-benzyloxy-N-[1-(3,5-dichlorophenylthio)-3-methyl-2-oxobutyl]-N-methylacetamide (20)(yield 47%).

$^1$H-NMR (CDCl$_3$—TMS)δ ppm: 1.15 (d, J=3.8 Hz, 3H), 1.18 (d, J=4.0 Hz, 3H), 3.02 (s, 3H), 4.15 (d, J=3.4 Hz, 2H), 4.51 (d, J=6.0 Hz, 2H), 7.02 (s, 1H), 7.22–7.40 (m, 8H)

REFERENCE EXAMPLE 5

Synthesis of 2-Benzyloxymethyl-5-(3,5-dichlorophenylthio)-1-ethyl-4-isopropyl-1H-imidazole (17o')

1-Ethylamino-3-methyl-2-butanone was obtained by the same synthetic process as that for (18a')in Reference Example 4.

$^1$H-NMR (CDCl$_3$—TMS)δ ppm: 1.12 (d, J=7.4 Hz, 6H), 1.12 (t, J=7.2 Hz, 3H), 2.61 (q, J=7.2 Hz, 2H), 3.57 (s, 2H), 3.57 (m, 1H), 3.75 (m, 1H)

2-Benzyloxy-N-ethyl-N-(3-methyl-2-oxobutyl)-acetamide (18b')was obtained by the same synthetic process as that for 2-benzyloxy-N-methyl-N-(3-methyl-2-oxobutyl)-acetamide in Reference Example 4.

$^1$H-NMR (CDCl$_3$—TMS)δ ppm: 1.05, 1.16 (d×2, J=7.2 Hz, 6H), 1.11, 1.15 (t×2, J=7.5 Hz, 3H), 2.55, 2.71 (m×2, 1H), 3.37 (q×2, J=7.5 Hz, 2H), 4.02, 4.19 (s×2, 2H), 4.25, 4.28 (s×2, 2H), 4.49, 4.64 (s×2, 2H), 7.27–7.41 (m, 5H)

2-Benzyloxy-N-[1-(3,5-dichlorophenylthio)-3-methyl-2-oxobutyl]-N-ethylacetamide (20b)was obtained by the same synthetic process as that for (20)in Reference Example 4.

$^1$H-NMR (CDCl$_3$—TMS)δ ppm: 1.09 (t, J=7.4 Hz, 3H), 1.15 (d, J=7.0 Hz, 3H), 1.20 (d, J=7.0 Hz, 3H), 2.99 (m, 1H), 3.35 (m, 1H), 3.60 (m, 1H), 4.19 (d, J=6.6 Hz, 2H), 4.57 (d, J=9.4 Hz, 2H), 6.82 (s, 1H), 7.24 (s, 1H), 7.27 (s, 2H), 7.34 (s, 5H)

2-Benzyloxymethyl-5-(3,5-dichlorophenylthio)-1-ethyl-4-isopropylimidazole (17o')was obtained by the same synthetic process as that for (17a)in Reference Example 3.

$^1$H-NMR (CDCl$_3$—TMS)δ ppm: 1.18 (t, J=7.0 Hz, 3H), 1.25 (d, J=7.0 Hz, 3H), 3.10 (m, 1H), 3.97 (q, J=7.4 Hz, 2H), 4.56 (s, 2H), 4.68 (s, 2H), 6.80 (s, 2H), 7.10 (s, 1H), 7.26–7.40 (m, 5H)

EXAMPLE 40

Synthesis of [5-(3,5-Dichlorophenylthio)-4-isopropyl-1-methyl-1H-imidazol-2-yl]methyl Acetate (Compound I-40)

In dry methylene chloride (10 ml)was dissolved 220 mg (0.700 mmol)of [5-(3,5-dichlorophenylthio)-4-isopropyl-1- methyl-iH-imidazol-2-yl]methanol (Compound I-8), followed by addition of 201 mg (2.00 mmol)of triethylamine. Then, 78.0 mg (1.00 mmol)of acetyl chloride was added under ice-cooling, and the mixture was stirred at the same temperature for 30 minutes. A saturated aqueous sodium hydrogen carbonate solution was added for neutralization, and the mixture was extracted with methylene chloride. The organic layer was washed with water and dried over sodium sulfate. The solvent was concentrated under reduced pressure, and the residue was purified by silica gel chromatography (ethyl acetate:n-hexane=1:1)to give 170 mg of [5-(3,5-dichlorophenylthio)-4-isopropyl-1-methyl-1H-imidazol-2-yl]methyl acetate (Compound I-40)(yield 69%). mp 92–93° C.

$^1$H-NMR (CDCl$_3$—TMS)δ ppm: 1.26 (d, J=6.8 Hz, 6H), 2.12 (s, 3H), 3.13 (sept, 1H), 3.54 (s, 3H), 5.21 (s, 2H), 6.80 (m, 2H)

EXAMPLE 41

Synthesis of 2-Carbamoyloxymethyl-5-(3,5-dichlorophenylthio)-4-isopropyl-1-methyl-1H-imidazole (Compound I-41)

In dry tetrahydrofuran (72 ml)was dissolved 23.9 g (72.2 mmol)of [5-(3,5-dichlorophenylthio)-4-isopropyl-1-methyl-1H-imidazol-2-yl]methanol (Compound I-8), and the mixture was cooled to −40 to −30° C. To the mixture, 16.3 g (86.6 mmol) of trichloroacetylisocyanate was added dropwise with stirring.

After completion of the addition, the reaction mixture was stirred at −30 to −10° C. for 30 minutes, and at −10 to 0° C. for 30 minutes. Into the reaction mixture, ice was added, and the mixture was stirred at room temperature. The solvent was distilled off under reduced pressure, and the residue was extracted with methylene chloride. The organic layer was washed with a saturated aqueous sodium hydrogen carbonate solution and then with brine, and dried over magnesium sulfate. The solvent was concentrated under reduced pressure. The oily residue 2-(N-trichloroacetylcarbamoyl)oxymethyl-5-(3,5-dichlorophenylthio)-4-isopropyl-1-methyl-1H-imidazole was dissolved in methanol (200 ml), followed by addition of 20 ml of triethylamine and 20 ml of water, and the mixture was refluxed under heating for 30 minutes. The reaction mixture was concentrated under reduced pressure, and the residue was extracted with methylene chloride. The organic layer was washed with an aqueous saturated sodium hydrogen carbonate solution and then brine, and dried over magnesium sulfate. The solvent was concentrated under reduced pressure, and the residue was crystalized from 100 ml of diethyl ether. Filtration afforded 22.7 g of 2-carbamoyloxymethyl-5-(3,5-dichlorophenylthio)-4-isopropyl-1-methyl-1H-imidazole (Compound I-41)(yield 87%). mp 146–148° C.

$^1$H-NMR (CDCl$_3$—TMS)δ ppm: 1.26 (d, J=7.0 Hz, 6H) 3.13 (sept, 1H), 3.56 (s, 3H), 4.75 (br, 2H), 5.23 (s, 2H), 6.80 (d, J=1.6 Hz, 2H), 7.13 (t, J=1.6 Hz, 1H) Elementary analysis (C$_{15}$H$_{17}$Cl$_2$N$_3$O$_2$S) Calc. (%):C, 48.14: H, 4.58: N, 11.23: S, 8.57: Cl, 18.57 Found (%):C, 48.23: H, 4.61: N, 11.21: S, 8.57: Cl, 18.21

EXAMPLE 42

Synthesis of 2-Carbamoyloxymethyl-5-(3-chlorophenylthio)-4-isopropyl-1-methyl-1H-imidazole (Compound I-42)

Compound I-42 was obtained from Compound I-13 by the same synthetic process as that for Compound I-41 in Example 41 by way of the intermediate 2-(N-trichloroacetylcarbamoyl) oxymethyl-5-(3-chlorophenylthio)-4-isopropyl-1-methyl-1H-imidazole.

NMR of the intermediate was measured.

$^1$H-NMR (CDCl$_3$—TMS)δ ppm: 1.27 (d, J=7.0 Hz, 6H), 3.19 (sept, 1H), 3.63 (s, 3H), 5.40 (s, 2H), 6.84 (dt, J=7.4 Hz, 2.0 Hz, 1H), 6.93 (t, J=2.0 Hz, 1H), 7.10–7.23 (m, 2H)

Compound I -42 mp 117~118° C.

$^1$H-NMR (CDCl$_3$—TMS)δ ppm: 1.26 (d, J=7.0 Hz, 6H), 3.16 (sept, 1H), 3.56 (s, 3H), 4.80 (br, 2H), 5.22 (s, 2H), 6.79–6.83 (m, 1H), 6.93–6.94 (m, 1H), 7.09–7.19 (m, 2H)

EXAMPLE 43

Synthesis of 5-(3,5-Dichlorophenylthio)-4-isopropyl-1-methyl-2-(N-methylcarbamoyl)oxymethyl-1H-imidazole (Compound I-43)

In dry tetrahydrofuran (6 ml)was dissolved 0.300 g (0.91 mmol)of [5-(3,5-dichlorophenylthio)-4-isopropyl-1-methyl-1H-imidazol-2-yl]methanol (Compound I-8)and 0.48 ml (8.15 mmol) of methylisocyanate. To this solution was added 0.04 ml of bis(tributyltin)oxide, and the mixture was stirred at room temperature for 2.5 hours. The reaction mixture was concentrated under reduced pressure. The residue was fractionated by silica gel chromatography (acetone:methylene chloride=1:4), and recrystallized from isopropyl ether to obtain 0.345 g of (Compound I-43)(yield 98%). mp 112–113° C.

$^1$H-NMR (CDCl$_3$—TMS)δ ppm: 1.26 (d, J=7.0 Hz, 6H), 2.82 (d, J=4.8 Hz, 3H), 3.13 (sept, 1H), 3.56 (s, 3H), 4.78 (br, 1H), 5.22 (s, 2H), 6.79 (d, J=2.0 Hz, 2H), 7.12 (t, J=2.0 Hz, 1H) Elementary analysis (C$_{16}$H$_{19}$Cl$_2$N$_3$O$_2$S) Calc. (%):C, 49.49: H, 4.93: N, 10.82: S, 8.26: Cl, 18.26 Found (%):C, 49.47: H, 4.94: N, 10.87: S, 8.20: Cl, 18.35

EXAMPLE 44

Synthesis of 5-(3,5-Dichlorophenylthio)-4-isopropyl-1-methyl-2-(N-methylthiocarbamoyl)oxymethyl-1H-imidazole (Compound I-44)

To a dry tetrahydrofuran-dimethylformamide (1:1 v/v, 1 ml)solution of 50 mg (0.15 mmol)of [5-(3,5-dichlorophenylthio)-4-isopropyl-1-methyl-1H-imidazol-2-yl]-methanol (Compound I-8)was added 6.6 mg (0.17 mmol)of 60% sodium hydride under nitrogen atomosphere, and the mixture was stirred at room temperature for 30 minutes. Then, 22 mg (0.3 mmol)of methylisothiocyanate was added under ice-cooling. The mixture was stirred at the same temperature for 30 minutes, and at room temperature for 30 minutes. To the reaction mixture, an aqueous ammonium chloride solution was added to terminate the reaction. The mixture was extracted with diethyl ether. The organic layer was washed with saturated brine and dried over magnesium sulfate. The solvent was concentrated under reduced pressure, and the residue was purified by silica gel chromatography (ethyl acetate:n-hexane=1:1)to give 37 mg of 5-(3,5-dichlorophenylthio)-4-isopropyl-1-methyl-2-(N-methylthiocarbamoyl)oxymethyl-1H-imidazole (Compound I-44)(yield 60%). mp 119–121° C.

$^1$H-NMR (CDCl$_3$—TMS)δ ppm: 1.25 (d, J=6.8 Hz, 6H), 3.11 (d, J=4.8 Hz, 3H), 3.12 (sept, 1H), 3.55 (s, 3H), 5.59 (s, 2H), 6.70 (br, 1H), 6.80 (d, J=1.8 Hz, 2H), 7.13 (t, J=1.8 Hz, 1H) Elementary analysis (C$_{16}$H$_{19}$Cl$_2$N$_3$OS$_2$) Calc. (%):C, 47.52: H, 4.74: N, 10.39: S, 15.86: Cl, 17.53 Found (%):C, 47.27: H, 4.80: N, 10.33: S, 15.73: Cl, 17.84

EXAMPLE 45

Synthesis of 1-Benzyl-2-carbamoyloxymethyl-5-(3,5-dichlorophenylthio)-4-isopropyl-1H-imidazole (Compound I-45)

In dry tetrahydrofuran was dissolved 204 mg (0.50 mmol) of [5-(3,5-dichlorophenylthio)-4-isopropyl-1-methyl-1H-imidazol-2-yl]methanol (Compound I-8), and to the solution, 72 mg (0.60 mmol)of chloroacetylisocyanate was added dropwise at room temperature with stirring. The mixture was stirred at the same temperature for 1 hour. The reaction mixture was neutralized with a saturated aqueous sodium hydrogen carbonate solution, and extracted with ethyl acetate. The organic layer was washed with water, and then, dried over sodium sulfate. The solvent was concentrated under reduced pressure, and thus-obtained oil 1-benzyl-2-(N-chloroacetylcarbamoyloxymethyl)-5-(3,5-dichlorophenylthio)-4-isopropyl-1H-imidazole was used in the next reaction without purification.

$^1$H-NMR (CDCl$_3$—TMS)δ ppm: 1.30 (d, J=6.9 Hz, 6H), 3.16 (sept, 1H), 4.32 (s, 2H), 5.25 (s, 2H), 5.27 (s, 2H), 6.71 (d, J=3 Hz, 2H), 6.85–6.87 (m, 2H), 7.04 (d, J=1.8 Hz, 1H), 7.2–7.3 (m, 3H), 7.65 (br, 1H)

The above intermediate was dissolved in methanol (3 ml), followed by addition of 0.1 ml of water, and 5 mg of zinc powder was added at room temperature with stirring. The mixture was stirred at room temperature for 2 hours. The reaction mixture was concentrated under reduced pressure, and a saturated aqueous solution of sodium hydrogen carbonate was added to the residue to neutralize. The insoluble material was filtered off through Celite, and the filtrate was extracted with methylene chloride. The extract was washed with water, dried over sodium sulfate, and concentrated under reduced pressure. The residue was crystallized from diethyl ether and filtrated to give 115 mg of (Compound I-45)(yield 51% from (12a)). mp 60–65° C. (bubbling degradation).

$^1$H-NMR (CDCl$_3$—TMS)δ ppm: 1.29 (d, J=7.2 Hz, 6H), 3.15 (sept, 1H), 5.20 (s, 2H), 5.23 (s, 2H), 6.66 (s, 2H), 6.89–6.92 (m, 2H), 7.00 (s, 1H), 7.10–7.22 (m, 3H) Elementary analysis (C$_{21}$H$_{21}$Cl$_2$N$_3$O$_2$S.0.15.H$_2$O) Calc. (%):C, 55.52: H, 4.99: N, 9.25: S, 7.05: Cl, 15.61 Found (%):C, 55.74: H, 5.05: N, 8.77: S, 6.84: Cl, 15.50

EXAMPLE 46

Synthesis of 1-Benzyl-2-carbamoyloxymethyl-5-(3-chlorophenylthio)-4-isopropyl-1H-imidazole (Compound I-46)

Compound I-46 was obtained by the same synthetic process as that for Compound I-45 in Example 45. The NMR data was provided only for the intermediate.

The intermediate $^1$H-NMR (CDCl$_3$—TMS)δ ppm: 1.31 (d, J=6.6 Hz, 6H), 3.24 (sept, 1H), 4.32 (s, 2H), 5.24 (s, 3H), 6.80–7.27 (m, 9H), 7.62 (br, 1H)

Compound I-46 mp 96–98° C.

$^1$H-NMR (CDCl$_3$—TMS)δ ppm: 1.29 (d, J=7.2 Hz, 6H), 3.20 (sept, 1H), 4.50 (br, 2H), 5.15 (s, 2H), 5.22 (s, 2H), 6.76–7.26 (m, 9H) Elementary analysis (C$_{21}$H$_{22}$ClN$_3$O$_2$S.0.6.H$_2$O) Calc. (%):C, 59.09: H, 5.49: N, 9.85: S, 7.51: Cl, 8.32 Found (%):C, 59.33: H, 5.44: N, 9.68: S, 7.17: Cl, 7.87

EXAMPLE 47

Synthesis of 1-Benzyl-2-carbamoyloxymethyl-4-isopropyl-5-(3-nitrophenylthio)-1H-imidazole (Compound I-47)

Compound I-47 was obtained by the same synthetic process as that for Compound I-45 in Example 45. The NMR data was provided only for the intermediate.

The intermediate $^1$H-NMR (CDCl$_3$—TMS)δ ppm: 1.32 (d, J=6.9 Hz, 6H), 3.22 (sept, 1H), 4.31 (s, 2H), 5.28 (s, 2H), 6.83–6.86 (m, 2H), 7.14–7.27 (m, 5H), 7.6 (s, 1H), 7.75 (br, 1H), 7.90 (dd, J=11.4 Hz, 1.2 Hz, 1H)

Compound I-47 mp 58° C.

$^1$H-NMR (CDCl$_3$—TMS)δ ppm: 1.29 (d, J=7.2 Hz, 6H), 3.17 (sept, 1H), 4.57 (br, 2H), 5.21 (s, 2H), 5.25 (s, 2H), 6.87–6.90 (m, 2H), 7.07–7.16 (m, 4H), 7.26 (t, J=7.5 Hz, 1H), 7.55 (t, J=1.8 Hz, 1H), 7.71 (dd, J=11 Hz, 0.9 Hz, 1H) Elementary analysis (C$_{21}$H$_{22}$N$_4$O$_4$S.0.6.H$_2$O.0.5.Et$_2$O) Calc. (%):C, 58.00: H, 6.02: N, 11.77: S, 6.73 Found (%):C, 57.91: H, 5.72: N, 11.73: S, 6.71

EXAMPLE 48

Synthesis of 1-Allyl-2-carbamoyloxymethyl-4-isopropyl-5-(3-nitrophenylthio)-1H-imidazole (Compound I-48)

Compound I-48 was obtained by the same synthetic process as that for Compound I-45 in Example 45. The NMR data was provided only for the intermediate.

The intermediate $^1$H-NMR (CDCl$_3$—TMS)δ ppm: 1.26 (d, J=9.9 Hz, 6H), 3.15 (sept, 1H), 4.42 (s, 2H), 4.67–4.69 (m, 2H), 4.84 (dt, J=20.1 Hz, 1.5 Hz, 1H), 5.07 (d, J=11.7 Hz, 1H), 5.29 (s, 2H), 5.62–5.80 (m, 1H), 7.42 (t, J=7.8 Hz, 1H), 7.78 (t, J=2.1 Hz, 1H), 7.99 (dd, J=10.5 Hz, 0.9 Hz, 1H), 8.06 (br, 1H)

Compound I-48 mp 124–125° C.

$^1$H-NMR (CDCl$_3$—TMS)δ ppm: 1.27 (d, J=6.9 Hz, 6H), 3.15 (sept, 1H), 4.65–4.66 (m, 2H), 4.88 (dd, J=17 Hz, 0.6 Hz, 1H), 5.05 (dd, J=11.1 Hz, 0.9 Hz, 1H), 5.19 (s, 2H), 5.64–5.78 (m, 1H), 7.41 (t, J=7.8 Hz, 1H), 7.81 (t, J=1.8 Hz, 1H), 7.98 (dd, J=11.1 Hz, 0.9 Hz, 1H) Elementary analysis (C$_{17}$H$_{20}$N$_4$O$_4$S.H$_2$O.0.5.Et$_2$O) Calc. (%):C, 52.87: H, 6.32: N, 12.99: S, 7.43 Found (%):C, 52.91: H, 6.00: N, 12.65: S, 7.24

EXAMPLE 49

Synthesis of 2-Carbamoyloxymethyl-1-ethyl-4-isopropyl-5-(3-nitrophenylthio)-1H-imidazole (Compound I-49)

Compound I-49 was obtained by the same synthetic process as that for Compound I-45 in Example 45. The NMR data was provided only for the intermediate.

The intermediate $^1$H-NMR (CDCl$_3$—TMS)δ ppm: 1.21 (t, J=7.5 Hz, 3H), 1.24 (d, J=7.2 Hz, 6H), 3.13 (sept, 1H), 4.13 (q, J=7.5 Hz, 2H), 5.33 (s, 2H), 7.25 (dt, J=8.1 Hz, 0.9 Hz, 1H), 7.43 (t, J=7.8 Hz, 1H), 7.94 (t, J=1.8 Hz, 1H), 7.99 (dd, J=2.4 Hz, 8.4 Hz, 1H), 8.20 (br, 1H)

Compound I-49 mp 131–137° C.

$^1$H-NMR (CDCl$_3$—TMS)δ ppm: 1.20 (t, J=7.5 Hz, 3H), 1.26 (d, J=6.9 Hz, 6H), 3.14 (sept, 1H), 4.03 (q, J=7.5 Hz, 2H), 4.75 (br, 2H), 5.23 (s, 2H), 7.27 (m, 1H), 7.42 (t, J=7.8 Hz, 1H), 7.83 (t, J=2.1 Hz, 1H), 7.98 (dd, J=9.6 Hz, 1.2 Hz, 1H) Elementary analysis (C$_{16}$H$_{20}$N$_4$O$_4$S) Calc. (%):C, 52.73: H, 5.53: N, 15.37: S, 8.80 Found (%):C, 52.83: H, 5.61: N, 15.07: S, 8.53

EXAMPLE 50

Synthesis of 2-Carbamoyloxymethyl-4-isopropyl-5-(3-nitrophenylthio)-1-n-propyl-1H-imidazole (Compound I-50)

Compound I-50 was obtained by the same synthetic process as that for Compound I-45 in Example 45. The NMR data was provided only for the intermediate.

The intermediate $^1$H-NMR (CDCl$_3$—TMS)δ ppm: 0.88 (t, J=7.2 Hz, 3H), 1.24 (d, J=6.9 Hz, 6H), 1.52–1.62 (m, 1H), 3.12 (sept, 1H), 3.94 (t, J=8.1 Hz, 2H), 4.44 (s, 2H), 5.32 (s, 2H), 7.24 (dt, J=8.1 Hz, 0.6 Hz, 1H), 7.43 (t, J=8.4 Hz, 1H), 7.77 (t, J=18 Hz, 1H), 7.99 (dd, J=2.1 Hz, 9.3 Hz, 1H)

Compound I-50 mp 120–124° C.

$^1$H-NMR (CDCl$_3$—TMS)δ ppm: 0.87 (t, J=9.9 Hz, 3H), 1.25 (d, J=7.2 Hz, 6H), 1.50–1.65 (m, 2H), 3.12 (sept, 1H), 3.91 (dt, J=8.1 Hz, 1.2 Hz, 2H), 4.75 (br, 2H), 5.22 (s, 2H), 7.22 (dt, J=7.8 Hz, 1.8 Hz, 1H), 7.41 (t, J=7.8 Hz, 1H), 7.80 (t, J=1.8 Hz, 1H), 7.98 (dd, J=0.9 Hz, 9.3 Hz, 1H) Elementary analysis (C$_{17}$H$_{22}$N$_4$O$_4$S) Calc. (%):C, 53.95: H, 5.86: N, 14.80: S, 8.47 Found (%):C, 53.83: H, 5.85: N, 14.70: S, 8.61

EXAMPLE 51

Synthesis of 2-Carbamoyloxymethyl-5-(3,5-dichlorophenylthio)-4-isopropyl-1-n-propyl-1H-imidazole (Compound I-51)

Compound I-51 was obtained by the same synthetic process as that for Compound I-45 in Example 45. mp 110–112° C.

$^1$H-NMR (CDCl$_3$—TMS)δ ppm: 0.88 (t, J=7.4 Hz, 3H), 1.25 (d, J=7.0 Hz, 6H), 1.50–1.65 (m, 2H), 3.09 (sept, 1H), 3.85–3.93 (m, 2H), 4.71 (br, 2H), 5.22 (s, 2H), 6.79 (d, J=2 Hz, 2H), 7.12 (t, J=1.6 Hz, 1H) Elementary analysis (C$_{17}$H$_{21}$Cl$_2$N$_3$O$_2$S.0.6.H$_2$O) Calc. (%):C, 49.42: H, 5.42: N, 10.17 Found (%):C, 49.14: H, 5.25: N, 10.07

EXAMPLE 52

Synthesis of 2-Carbamoyloxymethyl-5-(3,5-dichlorophenylthio)-1-ethyl-4-isopropyl-1H-imidazole (Compound I-52)

Compound I-52 was obtained by the same synthetic process as that for Compound I-45 in Example 45. mp 148–149° C.

$^1$H-NMR (CDCl$_3$—TMS)δ ppm: 1.21 (t, J=7.2 Hz, 3H), 1.26 (d, J=7.2 Hz, 6H), 3.11 (sept, 1H), 4.00 (q, J=7.2 Hz, 2H), 4.76 (br, 2H), 5.22 (s, 2H), 6.81 (d, J=1.8 Hz, 2H), 7.12 (t, J=1.8 Hz, 1H) Elementary analysis (C$_{16}$H$_{19}$Cl$_2$N$_3$O$_2$S) Calc. (%):C, 48.37: H, 5.07: N, 10.58: S, 8.07: Cl, 17.85 Found (%):C, 48.32: H, 4.94: N, 10.45: S, 8.28: Cl, 17.88

EXAMPLE 53

Synthesis of 2-Carbamoyloxymethyl-5-(3-chlorophenylthio)-1-ethyl-4-isopropyl-1H-imidazole (Compound I-53)

Compound I-53 was obtained by the same synthetic process as that for Compound I-45 in Example 45. mp 98–100° C.

$^1$H-NMR (CDCl$_3$—TMS)δ ppm: 1.19 (t, J=7.4 Hz, 3H), 1.25. (d, J=6.6 Hz, 6H), 3.15 (sept, 1H), 4.00 (q, J=7.4 Hz, 2H), 4.77 (br, 2H), 5.21 (s, 2H), 6.80–7.16 (m, 4H)

EXAMPLE 54

Synthesis of 2-Carbamoyloxymethyl-5-(3-chlorophenylthio)-4-isopropyl-1-n-propyl-1H-imidazole (Compound I-54)

Compound I-54 was obtained by the same synthetic process as that for Compound I-45 in Example 45. mp 110–112° C.

$^1$H-NMR (CDCl$_3$—TMS)δ ppm: 0.88 (t, J=7.5 Hz, 3H), 1.27 (d, J=6.6 Hz, 6H), 1.56–1.64 (m, 2H), 3.15 (sept, 1H), 3.86–3.93 (m, 2H), 4.76 (br, 2H), 5.23 (s, 2H), 6.81–7.20 (m, 4H) Elementary analysis (C$_{17}$H$_{22}$ClN$_3$O$_2$S.0.2.H$_2$O) Calc. (%):C, 54.96: H, 6.08: N, 11.31: S, 8.63: Cl, 9.54 Found (%):C, 54.89: H, 5.97: N, 11.28: S, 8.43: Cl, 10.06

EXAMPLE 55

Synthesis of 2-Carbamoyloxymethyl-5-(3,5-dichlorophenylthio)-4-isopropyl-1-(1,1,1-trifluoroethyl)-1H-imidazole (Compound I-55)

Compound I-55 was obtained by the same synthetic process as that for Compound I-45 in Example 45. The NMR data was provided only for the intermediate.

The intermediate $^1$H-NMR (CDCl$_3$—TMS)δ ppm: 1.25 (d, J=7.2 Hz, 6H), 3.08 (sept, 1H), 4.38 (s, 2H), 4.83 (q, J=7.5 Hz, 2H), 5.31 (s, 2H), 6.75 (d, J=1.8 Hz, 2H), 7.15 (t, J=1.8 Hz, 1H), 8.21 (b, 1H)

Compound I-55 mp 157–159° C.

$^1$H-NMR (CDCl$_3$—TMS)δ ppm: 1.26 (d, J=6.8 Hz, 6H), 3.11 (sept, 1H), 4.74 (b, 2H), 4.84 (q, J=7.6 Hz, 2H), 5.21 (s, 2H), 6.75 (d, J=1.4 Hz, 2H), 7.15 (t, J=1.4 Hz, 1H), 8.21 (b, 1H) Elementary analysis (C$_{16}$H$_{16}$Cl$_2$F$_3$N$_3$O$_2$S) Calc. (%):C, 43.45: H, 3.65: N, 9.50: Cl, 16.03: F, 12.89: S, 7.25 Found (%):C, 43.41: H, 3.70: N, 9.37: Cl, 15.88: F, 12.87: S, 7.24

EXAMPLE 56

Synthesis of 2-Carbamoyloxymethyl-5-(3,5-dichlorophenylthio)-1-fluoromethyl-4-isopropyl-1H-imidazole (Compound I-56)

Compound I-56 was obtained by the same synthetic process as that for Compound I-45 in Example 45. The NMR data was provided only for the intermediate.

The intermediate $^1$H-NMR (CDCl$_3$—TMS)δ ppm: 1.25 (d, J=7.0 Hz, 6H), 3.15 (sept, 1H), 4.42 (s, 2H), 6.05 (d, J=52 Hz, 2H), 6.84 (d, J=1.8 Hz, 2H), 7.16 (t, J=1.8 Hz, 1H), 8.11 (br, H)

Compound I-56 mp 166–169° C.

$^1$H-NMR (CDCl$_3$—TMS)δ ppm: 1.26 (d, J=7.2 Hz, 6H), 3.16 (sept, 1H), 5.29 (s, 2H), 6.04 (d, J=52 Hz, 2H), 6.85 (d, J=1.8 Hz, 2H), 7.14 (t, J=1.8 Hz, 1H) Elementary analysis (C$_{15}$H$_{16}$Cl$_2$FN$_3$O$_2$S) Calc. (%)C, 45.93: H, 4.11: N, 10.71: Cl, 18.08: F, 4.84: S, 8.17 Found (%):C, 45.62: H, 4.11: N, 10.71: Cl, 18.36: F, 5.08: S, 8.16

EXAMPLE 57

Synthesis of 2-Carbamoyloxymethyl-1-ethyl-5-(3-fluorophenylthio)-4-isopropylethyl-1H-imidazole (Compound I-57)

Compound I-57 was obtained by the same synthetic process as that for Compound I-45 in Example 45, mp 110–112° C.

$^1$H-NMR (CDCl$_3$—TMS)δ ppm: 1.15 (t, J=7.2 Hz, 3H), 1.25 (d, J=7.0 Hz, 6H), 3.08–3.22 (m, 1H), 4.03 (q, J=7.2 Hz, 2H), 4.60–4.80 (b, 2H), 5.21 (s, 2H), 6.60–6.86 (m, 3H), 7.15–7.25 (m, 1H)

EXAMPLE 58

Synthesis of 2-Carbamoyloxymethyl-5-(3,5-difluorophenylthio)-1-ethyl-4-isopropyl-1H-imidazole (Compound I-58)

Compound I-58 was obtained by the same synthetic process as that for Compound I-45 in Example 45. mp 128–130° C.

¹H-NMR (CDCl₃—TMS)δ ppm: 1.21 (t, J=7.2 Hz, 3H), 1.25 (d, J=7.0. Hz, 6H), 3.11 (sept, 1H), 3.98 (q, J=7.2 Hz, 2H), 4.60–4.84 (bg, 2H), 5.30 (s, 2H), 6.60–6.64 (m, 3H)

EXAMPLE 59

Synthesis of 2-Carbamoyloxymethyl-4-(3-chlorophenylthio)-5-isopropyl-1-methylimidazole (Compound I-59)

In 5 ml of dry tetrahydrofuran was dissolved 200 mg (0.67 mmol)of [4-(3-chlorophenylthio)-5-isopropyl-1-methyl-1H-imidazol-2-yl]methanol (Compound I-38), and 190 mg (1.0 mmol) of trichloroacetylisocyanate was added to the mixture with cooling at −40° C. After 10 minutes, the mixture was warmed to 0° C., and stirred at the same temperature for 10 minutes To the reaction mixture, ice-water was added, and then, the mixture was neutralized with a saturated aqueous sodium hydrogen carbonate solution, and extracted with ethyl acetate. The organic layer was washed with water and dried over sodium sulfate. The solvent was concentrated under reduced pressure, and to the residue was added 5 ml of methanol, 0.5 ml of water and 0.5 ml of triethylamine. The mixture was stirred at 50° C. for 30 minutes. To the reaction mixture was added water, extracted with methylene chloride, the extract was washed with water and dried over sodium sulfate. The solvent was concentrated under reduced pressure, and the residue was purified by silica gel chromatography (ethyl acetate). The product was recrystallized from ethyl acetate/isopropyl ether to give 180 mg of the target compound (Compound I-59)(yield 79%). mp 145–146° C.

¹H-NMR (CDCl₃—TMS)δ ppm: 1.33 (d, J=7.2 Hz, 6H), 3.24 (sept, 1H), 3.68 (s, 3H), 4.81 (br, 2H), 5.19 (s, 2H), 6.97–7.15 (m, 4H) IR (nujol)3382, 3160, 1741, 1715 cm⁻¹ Elementary analysis (C₁₅H₁₈ClN₃O₂S) Calc. (%):C, 53.01: H, 5.34: N, 12.36: S, 9.43: Cl, 10.43 Found (%):C, 53.13: H, 5.42: N, 12.28: S, 9.41: Cl, 10.40

EXAMPLE 60

Synthesis of 2-{[5-(3,5-Dichlorophenylthio)-4-isopropyl-1-methylimidazol-2-yl]methoxy}ethyl Acetate (Compound I-60)

In dry dimethylformamide (10 ml)was dissolved 500 mg (1.50 mmol)of [5-(3',5'-dichlorophenylthio)-4-isopropyl-1-methyl-1H-imidazol-2-yl]methanol (Compound I-8), followed by addition of 180 mg (4.50 mmol)of 60% sodium hydride at room temperature, and the mixture was stirred for 5 minutes. To this solution was added 452 mg (2.70 mmol)of 2-bromomethyl-1,3-dioxolan, and the mixture was heated at 50° C. for 2 hours. The reaction mixture was poured into ice-water and extracted with diethyl ether. The organic layer was washed with water, dried over sodium sulfate, and evaporated under reduced pressure. The residue was fractionated by silica gel chromatography (ethyl acetate)to give 156 mg of 5-(3,5-dichlorophenylthio)-2-(1,3-dioxolan-2-yloxymethyl)-4-isopropyl-1-methyl-1H-imidazole (23a)as oil (yield 25%).

¹H-NMR (CDCl₃—TMS)δ ppm: 1.24 (d, J=6.8 Hz, 6H), 3.11 (sept, 1H), 3.57 (s, 3H), 3.83–3.98 (m, 4H), 4.24 (d, J=4.0 Hz, 2H), 4.74 (s, 2H), 5.05 (t, J=4.0 Hz, 1H), 6.78 (m, 2H), 7.10 (m, 1H)

In a mixture of methanol (1 ml)and 6N-hydrochloric acid (1 ml)was dissolved 156 mg (0.37 mmol)of 5-(3,5-dichlorophenylthio)-2-(1,3-dioxolan-2-yloxymethyl)-4-isopropyl-1-methylimidazole (23a), and the mixture was stirred at room temperature for 3 hours. To the reaction mixture was added a saturated aqueous sodium hydrogen carbonate solution to neutralize, and extracted with methylene chloride. The organic layer was washed with water and dried over sodium sulfate. The solvent was distilled off under reduced pressure, and the residue was fractionated by silica gel chromatography (ethyl acetate)to obtain 39 mg of {[5-(3,5-dichlorophenylthio)-4-isopropyl-1-methyl-1H-imidazol-2-yl]methoxy}acetaldehyde (24a)as oil (yield 28%).

¹H-NMR (CDCl₃—TMS)δ ppm: 1.24 (d, J=7.0 Hz, 6H), 3.12 (sept, 1H), 3.63 (s, 3H), 4.23 (s, 2H), 4.75 (s, 2H), 6.81 (m, 2H), 7.13 (m, 1H), 9.64 (s, 1H)

In ethanol (6 ml)was dissolved 220 mg (0.59 mmol)of [5-(3,5-dichlorophenylthio)-4-isopropyl-1-methyl-1H-imidazol-2-ylmethoxy]acetaldehyde (24a), followed by addition of 45 mg (1.2 mmol)of sodium borohydride, and the mixture was stirred for 15 minutes. The reaction mixture was weakly acidified with acetic acid. A saturated aqueous sodium hydrogen carbonate solution was added to neutralize again, and the mixture was extracted with methylene chloride. The extract was washed with water and dried over sodium sulfate. The solvent was distilled off under reduced pressure, and the residue was fractionated by silica gel chromatography (ethyl acetate). The product was recrystallized from n-hexane to give 144 mg of 2-{[5-(3,5-dichlorophenylthio)-4-isopropyl-1-methyl-1H-imidazol-2-yl]methoxy}ethanol (25a)(yield 65%). mp 89–90° C.

¹H-NMR (CDCl₃—TMS)δ ppm: 1.25 (d, J=7.0 Hz, 6H), 3.12 (sept, 1H), 3.28 (br, 1H), 3.54 (s, 3H), 3.65–3.78 (m, 4H), 4.72 (s, 2H), 6.79 (m, 2H), 7.12 (m, 1H) Elementary analysis (C₁₆H₂₀Cl₂N₂O₂S) Calc. (%):C, 51.20. H, 5.37: N, 7.46: S, 8.54: Cl, 18.89 Found (%):C, 51.00: H, 5.41: N, 7.43: S, 8.46: Cl, 19.15

To dry methylene chloride solution (5 ml)of 200 mg (0.5 mmol)of 2-{[5-(3,5-dichlorophenylthio)-4-isopropyl-1-methyl-1H-imidazol-2-yl]methoxy}ethanol (25a), 161 mg (1.60 mmol)of triethylamine was added under ice-cooling, 63 mg (0.8 mmol)of acetyl chloride was added, and the mixture was stirred at the same temperature for 15 minutes. To the reaction mixture, a saturated aqueous solution of sodium hydrogen carbonate was added, neutralized, and extracted with methylene chloride. The extract was washed with water and dried over sodium sulfate. The solvent was distilled off under reduced pressure, and the residue was purified by silica gel chromatography (ethyl acetate:n-hexane=1:1)to obtain 200 mg of 2-[5-(3,5-dichlorophenylthio)-4-isopropyl-1-methylimidazol-2-ylmethoxy]ethyl acetate (Compound I-60)as oil (yield 90%).

¹H-NMR (CDCl₃—TMS)δ ppm: 1.25 (d, J=7.0 Hz, 6H), 2.05 (s, 3H), 3.12 (sept, 1H), 3.57 (s, 3H), 3.68 (t, J=4.6 Hz, 2H), 4.22 (t, J=4.6 Hz, 2H), 4.70 (s, 2H), 6.78 (m, 2H), 7.12 (m, 1H)

EXAMPLE 61

Synthesis of (2-Carbamoyloxy)ethoxymethyl-5-(3,5-dichlorophenylthio)-4-isopropyl-1-methyl-1H-imidazole (Compound I-61)

Dry tetrahydrofuran solution (5 ml)of 200 mg (0.50 mmol) of 2-{[5-(3,5-dichlorophenylthio)-4-isopropyl-1-methyl-1H-imidazol-2-yl]methoxy}ethanol (25a)was cooled to −40° C., and 150 mg (0.8 mmol)of trichloroacetyl-isocyanate was added. The mixture was stirred at the same temperature for 10 minutes. Then, the mixture was warmed to 0° C. and stirred at the same temperature for 10 minutes.

To the reaction mixture, ice-water was added, extracted with ethyl acetate, the organic layer was washed with water and dried over sodium sulfate. The solvent was concentrated under reduced pressure, and to the residue was added 4 ml of methanol, 0.5 ml of water and 0.5 ml of triethylamine, and the mixture was stirred at 50° C. for 30 minutes. The reaction mixture was cooled to room temperature, water was added, extracted with methylene chloride. The extract was washed with water and dried over sodium sulfate. The solvent was distilled off under reduced pressure, and the residue was purified by silica gel chromatography (ethyl acetate). The product was recrystallized from n-hexane to give 197 mg of the target compound (Compound I-61)(yield 88%). mp 102–103° C.

$^1$H-NMR (CDCl$_3$—TMS)δ ppm: 1.25 (d, J=7.0 Hz, 6H), 3.12 (sept, 1H), 3.56 (s, 3H), 3.69 (t, J=4.8 Hz, 2H), 4.24 (t, J=4.8 Hz, 2H), 4.66 (br, 2H), 4.70 (s, 2H), 6.79 (m, 2H), 7.11 (m, 1H) IR (nujol)3360, 3160, 1696, 1079 cm$^{-1}$ Elementary analysis (C$_{17}$H$_{21}$Cl$_2$N$_3$O$_3$S) Calc. (%):C, 48.81: H, 5.06: N, 10.04: S, 7.66: Cl, 16.95 Found (%):C, 48.73: H, 5.09: N, 9.93: S, 7.68: Cl, 16.66

EXAMPLE 62

Synthesis of 2-{[5-(3,5-Dichlorophenylthio)-1-ethyl-4-isopropyl-1H-imidazol-2-yl]methoxy}ethyl Acetate (Compound I-62)

5-(3,5-Dichlorophenylthio)-2-(1,3-dioxolan-2-yloxymethyl)-1-ethyl-4-isopropyl-iH-imidazole (23b)was obtained by the same synthetic process as that for (23a)in Example 60. Oil.

$^1$H-NMR (CDCl$_3$—TMS)δ ppm: 1.24 (d, J=6.8 Hz, 6H), 1.24 (t, J=7.2 Hz, 3H), 3.09 (sept, 1H), 3.57 (d, J=3.8 Hz, 2H), 3.88–4.10 (m, 6H), 4.73 (s, 2H), 5.06 (t, J=3.8 Hz, 1H), 6.79 (m, 2H), 7.11 (m, 1H)

{[5-(3,5-Dichlorophenylthio)-4-isopropyl-1-methyl-1H-imidazol-2-yl]methoxy}acetaldehyde (24b)was obtained from (23b). Oil.

$^1$H-NMR (CDCl$_3$—TMS)δ ppm: 1.24 (d, J=7.0 Hz, 6H), 1.26 (t, J=7.0 Hz, 3H), 3.09 (sept, 1H), 4.07 (q, J=7.0 Hz, 2H), 4.23 (s, 2H), 4.74 (s, 2H), 6.81 (m, 2H), 7.16 (m, 1H), 9.65 (s, 1H)

2-{[5-(3,5-Dichlorophenylthio)-4-isopropyl-1-methyl-1H-imidazol-2-yl]methoxy}ethanol (25b)was obtained from {[5-(3,5-dichlorophenylthio)-4-isopropyl-1-methyl-1H-imidazol-2-yl]methoxy}acetaldehyde (24b). mp 93–94° C.

$^1$H-NMR (CDCl$_3$—TMS)δ ppm: 1.22 (t, J=7.4 Hz, 3H), 1.25 (d, J=7.0 Hz, 6H), 3.10 (sept, 1H), 3.52 (br, 1H), 3.71–3.79 (m, 4H), 3.97 (q, J=7.4 Hz, 2H), 4.71 (s, 2H), 6.80 (m, 2H), 7.12 (m, 1H) IR (nujol)3274, 1560 cm$^{-1}$ Elementary analysis (C$_{17}$H$_{22}$Cl$_2$N$_2$O$_2$S) Calc. (%):C, 52.44: H, 5.70: N, 7.19: S, 8.24: Cl, 18.21 Found (%):C, 51.98: H, 5.76: N, 7.14: S, 8.10: Cl, 18.08

Compound I-62 was obtained from 2-{[5-(3,5-dichlorophenylthio)-4-isopropyl-1-methyl-1H-imidazol-2-yl]methoxy}ethanol (25b)by the same synthetic process as that for Compound I-60 in Example 60. Oil.

$^1$H-NMR (CDCl$_3$—TMS)δ ppm: 1.24 (t, J=7.2 Hz, 3H), 1.25 (d, J=6.8 Hz, 6H), 2.05 (s, 3H), 3.09 (sept, 1H), 3.70 (t, J=4.6 Hz, 2H), 4.01 (q, J=7.2 Hz, 2H), 4.23 (t, J=4.6 Hz, 2H), 4.69 (s, 2H), 6.80 (m, 2H), 7.11 (m, 1H) IR (nujol) 1741, 1563, 1231 cm$^{-1}$

EXAMPLE 63

Synthesis of 2-(2-Carbamoyloxyethoxy)methyl-5-(3,5-dichlorophenylthio)-1-ethyl-4-isopropyl-1H-imidazole (Compound I-63)

Compound I-63 was obtained by the same synthetic process as that for Compound I-61 in Example 61.

$^1$H-NMR (CDCl$_3$—TMS)δ ppm: 1.24 (t, J=7.0 Hz, 3H), 1.25 (d, J=7.0 Hz, 6H), 3.09 (sept, 1H), 3.69–3.73 (m, 2H), 4.00 (q, J=7.0 Hz, 2H), 4.22–4.26 (m, 2H), 4.69 (s, 2H), 4.79 (br, 2H), 6.80 (m, 2H), 7.12 (m, 1H) IR (nujol)3348, 3184, 1725, 1563, 1324 cm$^{-1}$

EXAMPLE 64

Synthesis of 2-[4-(3,5-Dichlorophenylthio)-5-isopropyl-1-methyl-1H-imidazol-2-yl]methoxy}ethyl Acetate (Compound I-64)

4-(3,5-Dichlorophenylthio)-2-(1,3-dioxolan-2-yloxymethyl)-5-isopropyl-1-methyl-1H-imidazole (23a') was obtained from [4-(3,5-dichlorophenylthio)-5-isopropyl-1-methyl-1H-imidazol-2-yl]methanol by the same synthetic process as that for (23a)in Example 60 as oil.

$^1$H-NMR (CDCl$_3$—TMS)δ ppm: 1.32 (d, J=7.2 Hz, 6H), 3.21 (sept, 1H), 3.56 (d, J=4.0 Hz, 2H), 3.71 (s, 3H), 3.80–4.00 (m, 4H), 4.70 (s, 2H), 5.05 (t, J=4.0 Hz, 1H), 6.91 (m, 2H), 7.04 (m, 1H)

{[4-(3,5-dichlorophenylthio)-5-isopropyl-1-methyl-1H-imidazol-2-yl]methoxy}acetoaldehyde (24a')was obtained as oil from 4-(3,5-dichlorophenylthio)-2-(1,3-dioxolan-2-yloxymethyl)-5-isopropyl-1-methyl-1H-imidazole (23a')by the same synthetic process as that for (24)in Example 60.

$^1$H-NMR (CDCl$_3$—TMS)δ ppm: 1.34 (d, J=7.2 Hz, 6H), 3.22 (sept, 1H), 3.78 (s, 3H), 4.25 (s, 2H), 4.70 (s, 2H), 6.89 (m, 2H), 7.05 (m, 1H), 9.62 (s, 1H)

2-{[4-(3,5-dichlorophenylthio)-5-isopropyl-1-methyl-1H-imidazol-2-yl]methoxy}ethanol (25a')was obtained by the same synthetic process as that for (25a)in Example 60. mp 67–68° C.

$^1$H-NMR (CDCl$_3$—TMS)δ ppm: 1.33 (d, J=7.2 Hz, 6H), 2.30 (br, 1H), 3.21 (sept, 1H), 3.59–3.78 (m, 4H), 3.70 (s, 3H), 4.66 (s, 2H), 6.91 (m, 2H), 7.05 (m, 1H) Elementary analysis (C$_{16}$H$_{20}$Cl$_2$N$_2$O$_2$S) Calc. (%):C, 51.20: H, 5.37: N, 7.46: S, 8.54: Cl, 18.89 Found (%):C, 51.18: H, 5.38: N, 7.55: S, 8.75: Cl, 18.80

Compound I-64 was obtained by the same synthetic process as that for Compound I-60 in Example 60 as oil.

$^1$H-NMR (CDCl$_3$—TMS)δ ppm: 1.33 (d, J=7.2 Hz, 6H), 2.08 (s, 3H), 3.21 (sept, 1H), 3.69 (t, J=4.6 Hz, 2H), 3.70 (s, 3H), 4.21 (t, J=4.6 Hz, 2H), 4.65 (s, 2H), 6.91 (m, 2H), 7.05 (m, 1H) IR (nujol)1738, 1563, 1232 cm$^{-1}$

EXAMPLE 65

Synthesis of (2-Carbamoyloxy)ethoxymethyl-4-(3,5-dichlorophenylthio)-5-isopropyl-1-methyl-1H-imidazole (Compound I-65)

Compound I-65 was obtained as oil from the alcohol compound (25a')that was synthesized in Example 64 by the same synthetic process as that for Compound I-61 in Example 61.

$^1$H-NMR (CDCl$_3$—TMS)δ ppm: 1.33 (d, J=7.2 Hz, 6H), 3.21 (sept, 1H), 3.67–3.72 (m, 2H), 3.70 (s, 3H), 4.21–4.25 (m, 2H), 4.66 (s, 2H), 4.73 (br, 2H), 6.91 (m, 2H), 7.05 (m, 1H)

EXAMPLE 66

Synthesis of 2-Aminomethyl-5-(3,5-dichlorophenylthio)-4-isopropyl-1-methylimidazole Oxalate (Compound I-66)

To dry dimethylformamide (50 ml)solution of 22.5 g (67.9 mmol)of [5-(3,5-dichlorophenylthio)-4-isopropyl-1- methyl-1H-imidazol-2-yl]methanol (Compound I-8)was added 25.0 ml of thionyl chloride, and the mixture was stirred at room temperature for 1 hour. The reaction mixture was concentrated under reduced pressure, and to the residue, ethyl acetate was added and extracted. The extract was neutralized with a saturated aqueous sodium hydrogen carbonate solution and dried over magnesium sulfate. The solvent was distilled off under reduced pressure to give 23.7 g of 2-chloromethyl-5-(3,5-dichlorophenylthio)-4-isopropyl-1-methylimidazole (28a)(yield about 100%). mp 110–111° C.

$^1$H-NMR (CDCl$_3$—TMS)δ ppm: 1.25 (d, J=7.0 Hz, 6H), 3.12 (sept, 1H), 3.59 (s, 3H), 4.73 (s, 2H), 6.79 (d, J=1.8 Hz, 2H), 7.13 (t, J=1.8 Hz, 1H) Elementary analysis (C$_{14}$H$_{15}$Cl$_3$N$_2$S) Calc. (%):C, 48.08: H, 4.32: N, 8.01 Found (%):C, 47.98: H, 4.39: N, 8.12

To dry dimethylformamide solution (70 ml)of 23.7 g of 2-chloromethyl-5-(3,5-dichlorophenylthio)-4-isopropyl-1-methyl-1H-imidazol (28a)was added 5.30 g of sodium azide, and the mixture was stirred with heating at 80° C. for 16 hours. The reaction mixture was added to ice-water, and extracted with diethyl ether. The organic layer was washed with water and dried over magnesium sulfate. The solvent was distilled off under reduced pressure, and 24.2 g of 2-azidomethyl-5-(3,5-dichlorophenylthio)-4-isopropyl-1-methyl-1H-imidazole (29a) was obtained (yield about 100%). mp 84–85° C.

$^1$H-NMR (CDCl$_3$—TMS)δ ppm: 1.26 (d, J=6.6 Hz, 6H), 3.13 (sept, 1H), 3.55 (s, 3H), 4.35 (s, 2H), 6.79 (d, J=2.0 Hz, 2H), 7.13 (t, J=2.0 Hz, 1H) Elementary analysis (C$_{14}$H$_{15}$Cl$_2$N$_5$S) Calc. (%):C, 47.20: H, 4.24: N, 19.66: S, 9.00: Cl, 19.90 Found (%):C, 47.24: H, 4.31: N, 19.60: S, 8.93: Cl, 20.12

To dry tetrahydrofuran solution (60 ml)of 24.2 g of 2-azidomethyl-5-(3,5-dichlorophenylthio)-4-isopropyl-1-methyl-1H-imidazole (29a)was added 19.6 g of tripenylphosphine under ice-cooling, and the mixture was stirred at room temperature for 4 hours. After the reaction completion was confirmed (the disappearance of 29a)by TLC (silica gel, methylene chloride-ethyl acetate=10:1), 50 ml of water was added, and the mixture was stirred at room temperature for 1.5 hours, and left overnight. Tetrahydrofuran was distilled off under reduced pressure, and to the residue, 400 ml of 3N-hydrochloric acid was added. When the mixture was washed with diethyl ether, crystals were precipitated from the hydrochloric acid layer. The crystals were collected by filtration, and neutralized with a saturated aqueous sodium hydrogen carbonate solution. The mixture was extracted with diethyl ether. The aqueous layer was also neutralized with a saturated aqueous sodium hydrogen carbonate solution, and was extracted with diethyl ether. These ether extracts were combined and dried over magnesium sulfate. The solvent was distilled off under reduced pressure, and 20.6 g of 2-aminomethyl-5-(3,5-dichlorophenylthio)-4-isopropyl-1-methyl-1H-imidazole (30a)was obtained (yield 92%)mp 86–87° C.

$^1$H-NMR (CDCl$_3$—TMS)δ ppm: 1.24 (d, J=6.9 Hz, 6H), 3.11 (sept, 1H), 3.52 (s, 3H), 4.01 (s, 2H), 6.80 (d, J=1.8 Hz, 2H), 7.11 (t, J=1.8 Hz, 1H) Elementary analysis (C$_{14}$H$_{17}$Cl$_2$N$_3$S) Calc. (%):C, 50.91: H, 5.19: N, 12.72: S, 9.71: Cl, 21.47 Found (%):C, 50.88: H, 5.24: N, 12.53: S, 9.49: Cl, 21.51

In ethyl acetate was dissolved 20.6 g of 2-aminomethyl-5-(3,5-dichlorophenylthio)-4-isopropyl-1-methyl-1H-imidazole (30a), followed by addition of ethyl acetate solution of 16.9 g of oxalic acid, and the mixture was heated. The reaction mixture was cooled, and the crystals were filtered. The crystals were recrystallized from ethanol to give 19.3 g of the target compound (Compound I-66)(yield 60%). mp 162–163° C.

Elementary analysis (C$_{14}$H$_{17}$Cl$_2$N$_3$S.1.5. (COOH)$_2$.0.5.H$_2$O) Calc. (%):C, 43.05: H, 4.46: N, 8.86: S, 6.76: Cl, 14.95 Found (%):C, 42.96: H, 4.47: N, 9.06: S, 6.74: Cl, 14.86

From 2-aminomethyl-5-(3,5-dichlorophenylthio)-4-isopropyl-1-methyl-1H-imidazole (30a), the corresponding hydrochloride was prepared by the same process as that for this Example. mp 123–125° C.

Elementary analysis (C$_{14}$H$_{17}$Cl$_2$N$_3$S.2.HCl.0.25.H$_2$O) Calc. (%):C, 41.24: H, 4.82: N, 10.31: S, 7.86: Cl, 34.78 Found (%):C, 41.10: H, 4.74: N, 10.27: S, 7.93: Cl, 35.05

EXAMPLE 67

Synthesis of 2-Aminomethyl-4-isopropyl-1-methyl-5-(3-nitrophenylthio)-1H-imidazole (Compound I-67)

2-Chloromethyl-4-isopropyl-1-methyl-5-(3-nitrophenylthio)-1H-imidazole (28b)was obtained from 2-[(4-isopropyl-1-methyl-3-nitrophenylthio)-1H-imidazol-2-yl]methanol by the same synthetic process as that for (28a)in Example 66. mp 106– 107° C.

$^1$H-NMR (CDCl$_3$—TMS)δ ppm: 1.25 (d, J=7.0 Hz, 6H), 3.14 (sept, 1H), 3.60 (s, 3H), 4.73 (s, 2H), 7.19 (d, J=7.0 Hz, 1H), 7.43 (t, J=7.8 Hz, 1H), 7.85 (t, J=2.0 Hz, 1H), 8.00 (d, J=7.8 Hz, 1H) Elementary analysis (C$_{14}$H$_{16}$ClN$_3$O$_2$S) Calc. (%):C, 51.61: H, 4.95: N, 12.90: S, 9.84: Cl, 10.88 Found (%):C, 51.61: H, 5.00: N, 12.75: S, 9.88: Cl, 10.89

2-Azidomethyl-4-isopropyl-1-methyl-5-(3-nitrophenylthio)-1H-imidazole (29b)was obtained from 2-chloromethyl-4-isopropyl-1-methyl-5-(3-nitrophenylthio)-1H-imidazole (28b)by the same synthetic process as that for (29a)in Example 66. mp 100–101° C.

$^1$H-NMR (CDCl$_3$—TMS)δ ppm: 1.26 (d, J=7.0 Hz, 6H), 3.15 (sept, 1H), 3.56 (s, 3H), 4.54 (s, 2H), 7.19 (d, J=8.0 Hz, 1H), 7.43 (t, J=8.0 Hz, 1H), 7.84 (t, J=2.2 Hz, 1H), 8.00 (d, J=8.0 Hz, 1H) Elementary analysis (C$_{14}$H$_{16}$N$_6$O$_2$S) Calc. (%):C, 50.59: H, 4.85: N, 25.28: S, 9.65 Found (%):C, 50.63: H, 4.88: N, 24.94: S, 9.64

The title Compound I-67 was obtained by the same synthetic process as that for Compound I-66 in Example 66. mp 77–78° C.

$^1$H-NMR (CDCl$_3$—TMS)δ ppm: 1.25 (d, J=7.0 Hz, 6H), 3.14 (sept, 1H), 3.53 (s, 3H), 4.00 (s, 2H), 7.22 (d, J=8.2 Hz, 1H), 7.83 (t, J=2.4 Hz, 1H), 7.97 (d, J=8.2 Hz, 1H) Elementary analysis (C$_{14}$H$_{18}$N$_4$O$_2$S) Calc. (%):C, 54.88: H, 5.92: N, 18.29: S, 10.47 Found (%):C, 54.70: H, 5.92: N, 18.11: S, 10.38

EXAMPLE 68

Synthesis of 2-Aminomethyl-1-n-butyl-5-(3,5-dichlorophenylthio)-4-isopropyl-1H-imidazole (Compound I-68)

Compound I-68 was obtained from [5-(3,5-dichlorophenylthio)-1-n-butyl-4-isopropyl-1H-imidazol-2-yl]methanol (12)by the same synthetic process as that for Compound I-66 in Example 66. Oil.

$^1$H-NMR (CDCl$_3$—TMS)δ ppm: 0.86 (t, J=7.2 Hz, 3H), 1.23–1.34 (m, 2H), 1.24 (d, J=7.2 Hz, 6H), 1.47–1.58 (m, 2H), 3.09 (sept, 1H), 3.87 (t, J=7.6 Hz, 2H), 3.96 (s, 3H), 6.80 (d, J=1.8 Hz, 2H), 7.10 (t, J=1.8 Hz, 1H)

EXAMPLE 69

Synthesis of 2-Aminomethyl-5-(3-chlorophenylthio)-4-isopropyl-1-methyl-1H-imidazole Hydrochloride (Compound I-69)

2-aminomethyl-5-(3-chlorophenylthio)-4-isopropyl-1-methyl-1H-imidazole (30c)was obtained from 2-(3-chlorophenylthio-4-isopropyl-1-methyl)imidazolyl-1H-methanol (12)by the same synthetic process as that for Compound I-66 in Example 66. Oil.

$^1$H-NMR (CDCl$_3$—TMS)δ ppm: 1.25 (d, J=6.8 Hz, 6H), 1.78 (s, 2H), 3.14 (sept, 1H), 3.51 (s, 3H), 3.99 (s, 2H), 6.81 (dt, J=7.2 Hz, 1.8 Hz, 1H), 6.93 (t, J=1.8 Hz, 1H), 7.07–7.20 (m, 2H)

Compound I-69 was obtained from 2-aminomethyl-5-(3-chlorophenylthio)-4-isopropyl-1-methylimidazole (30c)by the same synthetic process as that for Compound I-66 in Example 66. mp 99–101° C.

Elementary analysis (C$_{14}$H$_{18}$ClN$_3$S.2.HCl.0.67.H$_2$O) Calc. (%):C, 44.16: H, 5.65: N, 11.04: S, 8.42: Cl, 27.93 Found (%):C, 44.19: H, 5.67: N, 11.09: S, 8.53: Cl, 27.67

EXAMPLE 70

Synthesis of 2-Aminomethyl-1-benzyl-5-(3,5-dichlorophenylthio)-4-isopropylimidazole (Compound I-70)

1-Benzyl-2-chloromethyl-5-(3,5-dichlorophenylthio)-4-isopropyl-1H-imidazole (28e)was synthesized from [1-benzyl-5-(3,5-dichlorophenylthio)-4-isopropyl-1H-imidazol-2-yl]methanol by the same synthetic process as that for (28a)in Example 66, and without purification of this compound, 2-azidomethyl- 1-benzyl-5-(3,5-dichlorophenylthio)-4-isopropylimidazole (29e)was obtained by the same synthetic process as that for (29a)in Example 66. Oil.

$^1$H-NMR (CDCl$_3$—TMS)δ ppm: 1.29 (d, J=10.5 Hz, 6H), 3.16 (sept, 1H), 4.44 (s, 2H), 5.20 (s, 2H), 6.67 (d, J=2.4 Hz, 2H), 6.85–6.95 (m, 2H), 7.02 (t, J=2.4 Hz, 1H), 7.1–7.3 (m, 3H) IR (nujol)2100 cm$^{-1}$ Compound I-70 was obtained from 2-azidomethyl-1-benzyl-5-(3,5-dichlorophenylthio)-4-isopropyl-1H-imidazole (29e)by the same synthetic process as that for Compound I-66 in Example 66. Oil.

$^1$H-NMR (CDCl$_3$—TMS)δ ppm: 1.28 (d, J=6.9 Hz, 6H), 1.93 (b, 2H), 3.15 (sept, 1H), 3.93 (s, 2H), 5.19 (s, 2H), 6.69 (s, 2H), 6.93 (d, J=7.8 Hz, 2H), 7.0 (s, 1H), 7.15–7.30 (m, 3H)

EXAMPLE 71

Synthesis of 2-Aminomethyl-5-(3,5-dichlorophenylthio)-1-ethyl-4-isopropyl-1H-imidazole (Compound I-71)

Compound I-71 was obtained by the same synthetic process as that for Compound I-66 in Example 66. mp 63–67° C.

$^1$H-NMR (CDCl$_3$—TMS)δ ppm: 1.20 (t, J=7.0 Hz, 3H), 1.24 (d, J=7.0 Hz, 6H), 1.85 (s, 2H), 3.09 (sept, 1H), 3.96 (q, J=7.0 Hz, 2H), 3.99 (s, 2H), 6.81 (d, J=1.0 Hz, 2H), 7.10 (t, J=1.4 Hz, 1H)

EXAMPLE 72

Synthesis of 2-Aminomethyl-5-(3,5-dichlorophenylthio)-1,4-diisopropylimidazole (Compound I-72)

Compound I-72 was obtained by the same synthetic process as that for Compound I-66 in Example 66. mp 99–100° C.

$^1$H-NMR (CDCl$_3$—TMS)δ ppm: 1.22 (d, J=6.8 Hz, 6H), 1.43 (d, J=7.6 Hz, 6H), 3.07 (sept, 1H), 4.02 (s, 2H), 4.61–4.75 (m, 1H), 6.80 (d, J=1.4 Hz, 2H), 7.10 (t, J=1.2 Hz, 1H)

EXAMPLE 73

Synthesis of 2-Aminomethyl-5-(3-chlorophenylthio)-1-ethyl-4-isopropylimidazole (Compound I-73)

Compound I-73 was obtained by the same synthetic process as that for Compound I-66 in Example 66. Oil.

$^1$H-NMR (CDCl$_3$—TMS)δ ppm: 1.19 (t, J=7.4 Hz, 3H), 1.24 (d, J=7.6 Hz, 6H), 2.1 (b, 2H), 3.13 (sept, 1H), 3.97 (q, J=7.4 Hz, 2H), 3.99 (s, 2H), 6.80–7.19 (m, 4H)

EXAMPLE 74

Synthesis of 2-Aminomethyl-4-isopropyl-1-methyl-5-phenylthioimidazole (Compound I-74)

2-Chloromethyl-4-isopropyl-1-methyl-5-phenylthio-1H-imidazole (28i)was obtained from [(4-isopropyl-1-methyl-5-phenylthio-1H-imidazol-2-yl)methanol by the same synthetic process as that for (28a)in Example 66. Oil.

$^1$H-NMR (CDCl$_3$—TMS)δ ppm: 1.25 (d, J=7.2 Hz, 6H), 3.14 (sept, 1H), 3.53 (s, 3H), 4.50 (s, 2H), 6.91–7.28 (m, 5H)

2-Azidomethyl-4-isopropyl-1-methyl-5-phenylthio-1H-imidazole (29i)was obtained from 2-chloromethyl-4-isopropyl-1-methyl-5-phenylthio-1H-imidazole (28i)by the same synthetic process as that for (29a)in Example 66. Oil.

$^1$H-NMR (CDCl$_3$—TMS)δ ppm: 1.25 (d, J=7.0 Hz, 6H), 3.19 (sept, 1H), 3.53 (s, 3H), 4.50 (s, 2H), 6.91–7.27 (m, 5H) IR (nujol)2096 cm$^{-1}$ Compound I-74 was obtained by the sane synthetic process as that for Compound I-66 in Example 66. Oil.

$^1$H-NMR (CDCl$_3$—TMS)δ ppm: 1.25 (d, J=7.0 Hz, 6H), 1.52 (br, 2H), 3.18 (sept, 1H), 3.51 (s, 3H), 3.96 (s, 2H), 6.93–7.28 (m, 5H)

EXAMPLE 75

Synthesis of 2-Aminomethyl-1-ethyl-4-isopropyl-5-phenylthio-1H-imidazole (Compound I-75)

2-Chloromethyl-1-ethyl-4-isopropyl-5-phenylthioimidazole (28j)was obtained from [(1-ethyl-4-isopropyl-5-phenylthio)-1H-imidazol-2-yl]methanol by the same synthetic process as that for (28a)in Example 66. Oil.

$^1$H-NMR (CDCl$_3$—TMS)δ ppm: 1.24 (d, J=7.0 Hz, 6H), 1.25 (t, J=7.0 Hz, 3H), 3.17 (sept, 1H), 4.04 (q, J=7.0 Hz, 2H), 4.71 (s, 2H), 6.93–7.27 (m, 5H)

2-Azidomethyl-1-ethyl-4-isopropyl-5-phenylthio-1H-imidazole (29j)was obtained from 2-chloromethyl-1-ethyl-4-isopropyl-5-phenylthio-3H-imidazole (28j)by the same synthetic process as that for (29a)in Example 66. Oil.

$^1$H-NMR (CDCl$_3$—TMS)δ ppm: 1.21 (t, J=7.2 Hz, 3H), 1.25 (d, J=6.8 Hz, 6H), 3.17 (sept, 1H), 3.98 (q, J=7.2 Hz, 2H), 4.49 (s, 2H), 6.92–7.27 (m, 5H)IR (nujol)2094 cm$^{-1}$ Compound I-75 was obtained by the same synthetic process as that for Compound I-66 in Example 66. Oil.

$^1$H-NMR (CDCl$_3$—TMS)δ ppm: 1.17 (t, J=7.2 Hz, 3H), 1.24 (d, J=7.0 Hz, 6H), 1.65 (s, 2H), 3.16 (sept, 1H), 3.96 (s, 2H), 3.97 (q, J=7.2 Hz, 2H), 6.94–7.25 (m, 5H)

EXAMPLE 76

Synthesis of 2-Aminomethyl-5-(3,5-dichlorophenylthio)-4-isopropyl-1-(2,2,2-trifluoroethyl)-1H-imidazole (Compound I-76)

2-Chloromethyl-5-(3,5-dichlorophenylthio)-4-isopropyl-1-(2,2,2-trifluoroethyl)-1H-imidazole (28k)was synthesized from [5-(3,5-dichlorophenylthio)-4-isopropyl-1-(2,2,2-trifluoroethyl)-1H-imidazol-2-yl]methanol (Compound I-33)by the same synthetic process as that for (28a)in Example 66, and without purification of this compound, 2-azidomethyl-5-(3,5-dichlorophenylthio)-4-isopropyl-1-(2,2,2-trifluoroethyl)-1H-imidazole (29k)was obtained by the same synthetic process as that for (29a)in Example 66. Oil.

$^1$H-NMR (CDCl$_3$—TMS)δ ppm: 1.26 (d, J=7.8 Hz, 6H), 3.10 (sept, 1H), 4.60 (s, 2H), 4.66 (q, J=8.6 Hz, 2H), 6.76~6.78 (m, 2H), 7.14~7.16 (m, 1H)

Compound I-76 was obtained from 2-azidomethyl-5-(3,5-dichlorophenylthio)-4-isopropyl-1-(2,2,2-trifluoroethyl)-1H-imidazole (29k)by the same synthetic process as that for Compound I-66 in Example 66. Oil.

$^1$H-NMR (CDCl$_3$—TMS)δ ppm: 1.25 (d, J=7.2 Hz, 6H), 3.09 (sept, 1H), 4.10 (s, 2H), 4.85 (q, J=8.7 Hz, 2H), 6.78 (d, J=1.8 Hz, 2H), 7.13 (t, J=1.8 Hz, 1H)

EXAMPLE 77

Synthesis of 2-Aminomethyl-5-(3,5-dichlorophenylthio)-1-fluoromethyl-4-isopropylimidazole (Compound I-77)

2-Azidomethyl-5-(3,5-dichlorophenylthio)-1-fluoromethyl-4-isopropyl-1H-imidazole (29l)was obtained by the same synthetic process as that for (29k)in Example 76. Oil.

$^1$H-NMR (CDCl$_3$—TMS)δ ppm: 1.25 (d, J=7.2 Hz, 6H), 3.13 (sept, 1H), 4.60 (s, 2H), 5.97 (d, J=51.9 Hz, 2H), 6.84 (d, J=1.5 Hz, 2H), 7.15 (t, J=1.5 Hz, 1H)IR (nujol)2090 cm$^{-1}$ Compound I-77 was obtained from 2-azidomethyl-5-(3,5-dichlorophenylthio)-1-fluoromethyl-4-isopropyl-1H-imidazole (29l)by the same synthetic process as that for Compound I-66 in Example 66. Oil.

$^1$H-NMR (CDCl$_3$—TMS)δ ppm: 1.26 (d, J=6.9 Hz, 6H), 1.61 (b, 2H), 3.13 (sept, 1H), 4.10 (s, 2H), 6.05 (q, J=52.5 Hz, 2H), 6.86 (d, J=1.2 Hz, 2H), 7.13 (m, 1H)

EXAMPLE 78

Synthesis of 5-(3,5-Dichlorophenylthio)-2-dimethylaminomethyl-4-isopropyl-1-methyl-1H-imidazole (Compound I-78)

A mixture of 0.15 g (0.43 mmol)of 2-chloromethyl-5-(3,5-dichlorophenylthio)-4-isopropyl-1-methyl-1H-imidazole (28a), 1 ml of acetonitrile and 1.5 ml of a 50% methylamine aqueous solution was stirred at room temperature for 1 hour. The reaction mixture was concentrated under reduced pressure, and the residue was extracted with diethyl ether. The extract was washed with water and with saturated brine and dried over potassium carbonate. The solvent was distilled off under reduced pressure, and the residue was fractionated by silica gel chromatography (ethyl acetate:methylene chloride=1:4)to obtain 0.148 g of (Compound I-78)(yield 95%). Oil.

$^1$H-NMR (CDCl$_3$—TMS)δ ppm: 1.24 (d, J=6.8 Hz, 6H), 3.10 (sept, 1H), 3.56 (s, 2H), 3.59 (s, 2H), 6.75 (d, J=1.6 Hz, 2H), 7.10 (t, J=1.6 Hz, 1H)

EXAMPLE 79

Synthesis of 2-{[5-(3,5-Dichlorophenylthio)-4-isopropyl-1-methyl-1H-imidazol-2-yl]methylamino}ethanol (Compound I-79)

Compound I-79 was obtained by the same synthetic process as that for Compound I-78 in Example 78. mp 125–126° C.

$^1$H-NMR (CDCl$_3$—TMS)δ ppm: 1.24 (d, J=7.0 Hz, 6H), 2.50 (br, 2H), 2.91 (t, J=5.2 Hz, 2H), 3.11 (sept, 1H), 3.49 (s, 3H), 3.65 (t, J=5.2 Hz, 2H), 3.95 (s, 2H), 6.79 (d, J=1.8 Hz, 2H), 7.27 (t, J=1.8 Hz, 1H) Elementary analysis (C$_{16}$H$_{21}$Cl$_2$N$_3$OS) Calc. (%):C, 51.34: H, 5.65: N, 11.23: S, 8.57: Cl, 18.94 Found (%):C, 51.00: H, 5.67: N, 11.03: S, 8.44: Cl, 19.01

EXAMPLE 80

Synthesis of [5-(3,5-Dichlorophenylthio)-4-isopropyl-1-methyl-1H-imidazol-2-yl]acetic Acid (Compound I-80)

In 13.6 ml of dry dimethylformamide was dissolved 4.75 g (13.6 mmol)of 2-chloromethyl-5-(3,5-dichlorophenylthio)-4-isopropyl-1-methyl-1H-imidazole (28a)and 1.0 g of potassium cyanide (97.5%), and the mixture was stirred with heating at 70 to 75° C. for 24 hours. The reaction mixture was concentrated under reduced pressure, and to the residue, water was added. The mixture was extracted with diethyl ether, and the organic layer was washed with water 3 times and dried over magnesium sulfate. The solvent was distilled off under reduced pressure, and the residue was fractionated by silica gel chromatography (ethyl acetate:methylene chloride=1:9 to 4)to obtain 2.43 g of [5-(3,5-dichlorophenylthio)-4-isopropyl-1-methyl-1H-imidazol-2-yl]acetonitrile (Compound I-80a)(yield 53%). mp 103–105° C.

$^1$H-NMR (CDCl$_3$—TMS)δ ppm: 1.24 (d, J=7.0 Hz, 6H), 3.12 (sept, 1H), 3.59 (s, 3H), 3.97 (s, 2H), 6.81 (d, J=1.8 Hz, 2H), 7.14 (t, J=1.8 Hz, 1H) Elementary analysis (C$_{15}$H$_{15}$Cl$_2$N$_3$S) Calc. (%):C, 52.95: H, 4.44: N, 12.35: S, 9.42: Cl, 20.84 Found (%):C, 52.90: H, 4.48: N, 12.28: S, 9.49: Cl, 20.78

Methanol (12 ml)suspension of 1.0 g (2.9 mmol)of [5-(3,5-dichlorophenylthio)-4-isopropyl-1-methyl-1H-imidazol-2-yl]acetonitrile (Compound I-80a)was saturated with dry hydrogen chloride gas under ice-cooling with stirring, and the mixture was bubbled with hydrogen chloride gas at room temperature for 30 minutes. The reaction mixture was heated at 60° C., into which hydrogen chloride gas was blown for 30 minutes, and the reaction mixture was left overnight. The solvent was distilled off under reduced pressure, and to the residue, a saturated aqueous sodium hydrogen carbonate solution was added to neutralize. The mixture was extracted with diethyl ether. The organic layer was washed with brine and dried over magnesium sulfate, and the solvent was distilled off under reduced pressure. The residue was crystallized from isopropyl ether, and 0.68 g of methyl [5-(3,5-dichlorophenylthio)-4-isopropyl-1-methyl-1H-imidazol-2-yl]acetate (33)was obtained. The mother liquor of crystallization was purified by silica gel chromatography (ethyl acetate:methylene chloride=1:4), to give 0.26 g of (33). The total yield was 0.94 g (yield 87%), recrystallized from n-hexane, mp 110–111° C.

$^1$H-NMR (CDCl$_3$—TMS)δ ppm: 1.24 (d, J=7.2 Hz, 6H), 3.11 (sept, 1H), 3.47 (s, 3H), 3.75 (s, 3H), 3.92 (s, 2H), 6.78 (d, J=1.8 Hz, 2H), 7.11 (t, J=1.8 Hz, 1H) Elementary analysis (C$_{16}$H$_{18}$Cl$_2$N$_2$O$_2$S) Calc. (%):C, 51.48: H, 4.86: N, 7.50: S, 8.59: Cl, 18.99 Found (%):C, 51.42: H, 4.85: N, 7.56: S, 8.61: Cl, 18.80

A mixture of methanol (1 ml), 0.10 g of methyl [5-(3,5-dichlorophenylthio)-4-isopropyl-1-methyl-1H-imidazol-2-yl]acetate (33)and 1N-sodium hydroxide (0.32 ml)was stirred at room temperature for 1.5 hours. To the reaction mixture was added 0.32 ml of 1N-hydrochloric acid to yield crystals, which were filtered, washed with water and then with chilled methanol to obtain 87 mg of the target compound (Compound I-80)(yield 90%). mp 118° C. (degradation).

$^1$H-NMR (CDCl$_3$—TMS)δ ppm: 1.25 (d, J=7.2 Hz, 6H), 3.15 (sept, 1H), 3.50 (s, 3H), 3.88 (s, 2H), 5.70 (b, 1H), 6.83 (d, J=1.8 Hz, 2H), 7.26 (t, J=1.8 Hz, 1H) Elementary analysis (C$_{15}$H$_{16}$Cl$_2$N$_2$O$_2$S) Calc. (%):C, 50.15: H, 4.49: N, 7.80: S, 8.93: Cl, 19.74 Found (%):C, 50.17: H, 4.53: N, 7.87: S, 9.06: Cl, 19.61

EXAMPLE 81

Synthesis of 2-(2-Carbamoyloxy)ethyl-5-(3,5-dichlorophenylthio)-4-isopropyl-1-methyl-1H-imidazole (Compound I-81)

To a suspension of 0.08 g (2.1 mmol)of lithium aluminium hydride in dry diethyl ether was added dropwise in nitrogen gas a solution of 0.766 g (2.05 mmol)of methyl [5-(3,5-dichlorophenylthio)-4-isopropyl-1-methyl-1H-imidazol-2-yl]acetate (33)in diethyl ether (10 ml)under ice-cooling over 10 minutes with stirring. The reaction mixture was stirred at the same temperature for 0.5 hours and at room temperature for 1 hour, and then, there was added ice-water. The ether layer was separated by decantation, and the aqueous layer was extracted with diethyl ether. The ether extracts were combined, dried over magnesium sulfate, and the solvent was distilled off under reduced pressure. The residue was recrystallized from isopropyl ether, and filtered to give 0.58 g of 2-[5-(3,5-dichlorophenylthio)-4-isopropyl-1-methyl-1H-imidazol-2-yl]ethanol (Compound I-81a) (yield 82%).

$^1$H-NMR (CDCl$_3$—TMS)δ ppm: 1.22 (d, J=7.0 Hz, 6H), 2.88 (t, J=5.8 Hz, 2H), 3.08 (sept, 1H), 3.42 (s, 3H), 4.09 (t, J=5.8 Hz, 2H), 4.70 (b, 1H), 6.81 (d, J=1.8 Hz, 2H), 7.12 (t, J=1.8 Hz, 1H) Elementary analysis (C$_{15}$H$_{18}$Cl$_2$N$_2$OS) Calc. (%):C, 52.18: H, 5.25: N, 8.11: S, 9.29: Cl, 20.53 Found (%):C, 52.08: H, 5.28: N, 8.10: S, 9.34: Cl, 20.31

Compound I-81 was obtained from 2-[5-(3,5-dichlorophenylthio)-4-isopropyl-1-methyl-1H-imidazol-2-yl]ethanol (Compound I-81a)by the same synthetic process as that for Compound I-41 in Example 41. mp 177–178° C.

$^1$H-NMR (CDCl$_3$—TMS)δ ppm: 1.23 (d, J=6.8 Hz, 6H), 3.10 (sept, 1H), 3.12 (t, J=6.8 Hz, 2H), 3.48 (s, 3H), 4.43 (t, J=6.8 Hz, 2H), 4.65 (b, 2H), 6.80 (d, J=1.8 Hz, 2H), 7.26 (t, J=1.8 Hz, 1H) Elementary analysis (C$_{16}$H$_{19}$Cl$_2$N$_3$O$_2$S) Calc. (%):C, 49.49: H, 4.93: N, 10.82: S, 8.26: Cl, 18.26 Found (%):C, 49.28: H, 4.92: N, 10.84: S, 8.33: Cl, 18.05

EXAMPLE 82

Synthesis of 2-(2-Aminoethyl)-5-(3,5-dichlorophenylthio)-4-isopropyl-1-methyl-1H-imidazole (Compound I-82)

2-(2-Chloroethyl)-5-(3,5-dichlorophenylthio)-4-isopropyl-1-methyl-1H-imidazole (37)was obtained from (Compound I-8)by the same synthetic process as that for (28a)in Example 66. mp 101–102° C.

$^1$H-NMR (CDCl$_3$—TMS)δ ppm: 1.23 (d, J=7.0 Hz, 6H), 3.11 (sept, 1H), 3.23 (t, J=7.0 Hz, 2H), 3.50 (s, 3H), 3.92 (t, J=7.0 Hz, 2H), 6.77 (d, J=1.8 Hz, 2H), 7.10 (t, J=1.8 Hz, 1H) Elementary analysis (C$_{15}$H$_{17}$Cl$_3$N$_2$S) Calc. (%):C, 49.53: H, 4.71: N, 7.70: S, 8.82: Cl, 29.24 Found (%):C, 49.40: H, 4.74: N, 7.74: S, 8.86: Cl, 28.94

2-(2-Azidoethyl)-5-(3,5-dichlorophenylthio)-4-isopropyl-1-methyl-1H-imidazole (38)was obtained from (37)by the same synthetic process as that for (29a)in Example 66.

$^1$H-NMR (CDCl$_3$—TMS)δ ppm: 1.24 (d, J=7.0 Hz, 6H), 3.01 (t, J=6.8 Hz, 2H), 3.11 (sept, 1H), 3.48 (s, 3H), 3.76 (t, J=6.8 Hz, 2H), 6.80 (d, J=1.8 Hz, 2H), 7.11 (t, J=1.8 Hz, 1H)

5-(3,5-Dichlorophenylthio)-4-isopropyl-1-methyl-2-vinyl-1H-imidazole (37')was obtained as a by-product. mp 124–125° C.

$^1$H-NMR (CDCl$_3$—TMS)δ ppm: 1.27 (d, J=6.8 Hz, 6H), 3.13 (sept, 1H), 3.53 (s, 3H), 5.55 (dd, J=11.2 Hz, 1.5 Hz, 1H), 6.28 (dd, J=17.2 Hz, 1.5 Hz, 1H), 6.65 (dd, J=17.2 Hz, 11.2 Hz, 1H), 6.81 (d, J=1.8 Hz, 2H), 7.11 (t, J=1.8 Hz, 1H)

Compound I-82 was obtained from (38)by the same synthetic process as that for Compound I-66 in Example 66. Oil.

$^1$H-NMR (CDCl$_3$—TMS)δ ppm: 1.24 (d, J=7.0 Hz, 6H), 1.60 (b, 2H), 2.88 (t, J=7.0 Hz, 2H), 3.10 (sept, 1H), 3.14 (t, J=6.8 Hz, 2H), 6.79 (d, J=1.8 Hz, 2H), 7.10 (t, J=1.8 Hz, 1H) oxalate of Compound I-82. mp 160–161° C. Elementary analysis (C$_{15}$H$_{19}$Cl$_2$N$_2$S.C$_2$H$_2$O$_4$) Calc. (%):C, 47.01: H, 4.87: N, 9.67: S, 7.38: Cl, 16.32 Found (%):C, 47.08: H, 4.88: N, 9.81: S, 7.45: Cl, 16.04

EXAMPLE 83

Synthesis of 2-(N-Acetylaminomethyl-5-(3,5-dichlorophenylthio)-4-isopropyl-1-methyl-1H-imidazole (Compound I-83)

In pyridine (1 ml)was dissolved 220 mg (0.67 mmol)of 2-aminomethyl-5-(3,5-dichlorophenylthio)-4-isopropyl-1-methyl-1H-imidazole (30a), followed by dropwise addition of 82 mg (0.80 mmol)of acetic anhydride at room temperature with stirring, and the reaction mixture was left overnight. The reaction mixture was concentrated under reduced pressure, and the residue was extracted with ethyl acetate. The extract was washed with a saturated aqueous sodium hydrogen carbonate solution and then with water, and dried over sodium sulfate. The solvent was distilled off under reduced pressure, and this crude product was washed with n-hexane, and filtered to give 210 mg of Compound I-83 (yield 84%). mp 139–141° C.

$^1$H-NMR (CDCl$_3$—TMS)δ ppm: 1.24 (d, J=7.2 Hz, 6H), 2.07 (s, 3H), 3.12 (sept, 1H), 3.52 (s, 3H), 4.55 (d, J=3.4 Hz, 2H), 6.60 (b, 1H), 6.80 (d, J=2.0 Hz, 2H), 7.13 (t, J=2.0 Hz, 1H) Elementary analysis (C$_{16}$H$_{19}$Cl$_2$N$_3$OS) Calc. (%):C, 50.05: H, 5.50: N, 10.74: S, 8.28: Cl, 18.15 Found (%):C, 50.40: H, 5.02: N, 10.86: S, 8.38: Cl, 17.77

EXAMPLE 84

Synthesis of 5-(3,5-Dichlorophenylthio)-4-isopropyl-1-methyl-2-methylamidinomethyl-1H-imidazole (Compound I-84)

To a solution of 101 mg (0.30 mmol)of 2-aminomethyl-5-(3,5-dichlorophenylthio)-4-isopropyl-1-methyl-1H-imidazole (30a)in methanol (2 ml)was added 18.5 mg (0.15 mmol)of ethyl N-methylacetoimidate hydrochloride at room temperature with stirring, and the mixture was stirred at room temperature for 3 hours, and left overnight. To the reaction mixture was added a saturated aqueous sodium hydrogen carbonate solution to neutralize, and the reaction mixture was concentrated under reduced pressure. Methanol (10 ml)was added to the residue, and the mixture was concentrated under reduced pressure. This procedure was repeated 3 times, and to the residue, methanol was added. The insoluble material was filtered, and the filtrate was purified by silica gel chromatography (0.5% ammonia/methanol)to obtain 35 mg of (Compound I-84)(yield 63%). mp 176–178° C.

$^1$H-NMR (CDCl$_3$—TMS)δ ppm: 1.85 (d, J=7.2 Hz, 6H), 2.10 (s, 3H), 3.55 (s, 3H), 4.52 (s, 2H), 6.78 (d, J==1.8 Hz, 2H), 7.12 (t, J=1.8 Hz, 1H) Elementary analysis (C$_{16}$H$_{20}$Cl$_2$N$_4$S) Calc. (%):C, 49.34: H, 5.70: N, 14.39: S, 8.23: Cl, 18.27 Found (%):C, 48.90: H, 5.13: N, 14.02: S, 8.21: Cl, 18.28

EXAMPLE 85

Synthesis of 5-(3,5-Dichlorophenylthio)-4-isopropyl-1-methyl-2-methylaminomethyl-1H-imidazole (Compound I-85)

To a solution of 206 mg (0.76 mmol)of 2-aminomethyl-5-(3,5-dichlorophenylthio)-4-isopropyl-1-methyl-1H-imidazole (30a)and 100 mg (1.14 mmol)of triethylamine in methylene chloride (3 ml)was added dropwise 190 mg (0.91 mmol)of trifluoroacetatic anhydride with stirring under ice-cooling, and the mixture was stirred at room temperature. After disappearance of the starting materials on TLC, water was added to the reaction mixture and extracted with diethyl ether. The organic layer was washed with 1N-hydrochloric acid, a saturated aqueous sodium hydrogen carbonate solution and water, and dried over magnesium sulfate. The solvent was concentrated under reduced pressure, and the residue was purified by silica gel chromatography (ethyl acetate:methylene chloride=1:4)to obtain 315 mg of 5-(3,5-dichlorophenylthio)-4-isopropyl-1-methyl-2-trifluoroacetylaminomethyl-1H-imidazole (40c)(yield 97%). Recrystallized from isopropyl ether. mp 157–158° C.

$^1$H-NMR (CDCl$_3$—TMS)δ ppm: 1.24 (d, J=7.0 Hz, 6H), 3.12 (sept, 1H), 3.50 (s, 3H), 4.62 (d, J=5.0 Hz, 2H), 6.78 (d, J=1.6 Hz, 2H), 7.14 (t, J=1.6 Hz, 1H), 7.85 (b, 1H) Elementary analysis (C$_{16}$H$_{16}$Cl$_2$F$_3$N$_3$OS) Calc. (%):C, 45.08: H, 3.78: N, 9.86: S, 7.52: Cl, 16.63: F, 13.37 Found (%):C, 44.90: H, 3.87: N, 9.87: S, 7.64: Cl, 16.38: F, 13.16

To a solution of 286 mg (0.67 mmol)of 5-(3,5-dichlorophenylthio)-4-isopropyl-1-methyl-2-trifluoroacetylaminomethyl-1H-imidazole (40c)in dry dimethylformamide (2 ml) was added 32 mg (0.80 mmol)of 60% sodium hydride under a stream of nitrogen, and the mixture was stirred under ice-cooling for 10 minutes. Then, 115 mg (0.80 mmol)of methyl iodide was added, and the mixture was stirred at room temperature for 3 hours. To the reaction mixture, an aqueous solution of ammonium chloride was added, and the reaction was completed. The mixture was extracted with ethyl acetate, and the extract was washed with brine 3 times and dried over magnesium sulfate. The solvent was distilled off under reduced pressure, and the residue was purified by silica gel chromatography (ethyl acetate:methylene chloride=1:4)to obtain 232 mg of 5-(3,5-dichlorophenylthio)-4-isopropyl-1-methyl-2-(N-trifluoroacetyl-N-methyl)aminomethyl-1H-imidazole (40d) (yield 79%). Oil.

$^1$H-NMR (CDCl$_3$—TMS)δ ppm: 1.25 (d, J=6.8 Hz, 6H), 3.12 (sept, 1H), 3.20 (m, 3H), 3.51 (s, 3H), 4.83 (s, 2H), 6.74 (d, J=1.8 Hz, 2H), 7.13 (t, J=1.8 Hz, 1H)

A mixture 225 mg (0.51 mmol)of 5-(3,5-dichlorophenylthio)-4-isopropyl-1-methyl-2-(N-trifluoroacetyl-N-methyl)aminomethyl-1H-imidazole (40d), 2 ml of methanol and 1 ml of N-sodium hydroxide was stirred at room temperature for 30 minutes. The reaction mixture was concentrated under reduced pressure to remove methanol. The residue was extracted with diethyl ether, and the organic layer was washed with brine and dried over potassium carbonate. The solvent was distilled off under reduced pressure, and 175 mg of Compound I-85 was obtained as oil (yield 100%).

$^1$H-NMR (CDCl$_3$—TMS)δ ppm: 1.24 (d, J=7.0 Hz, 6H), 2.49 (s, 3H), 3.11 (sept, 1H), 3.54 (m, 3H), 3.87 (s, 2H), 6.78 (d, J=1.8 Hz, 2H), 7.10 (t, J=1.8 Hz, 1H)

EXAMPLE 86

Synthesis of 2-Diaminomethylenemethylaminomethyl-5-(3,5-dichlorophenylthio)-4-isopropyl-1-methylimidazole (Compound I-86)

A solution of 100 mg (0.292 mmol)of 2-aminomethyl-5-(3,5-dichlorophenylthio)-4-isopropyl-1-methylimidazole (30a), 97 mg (0.35 mmol)of N,N-di(t-butoxycarbonyl) thiourea and 67 mg (0.35 mmol)of EDC in dry dimethylformamide (0.3 ml)was stirred at room temperature overnight. To the reaction mixture was added water, extracted with diethyl ether, and the extract was washed with brine and dried over magnesium sulfate. The solvent was distilled off under reduced pressure, and the residue was purified by silica gel chromatography (ethyl acetate:n-hexane=1:2)to obtain 165 mg of an addition product 2-[(N,N'-di-t-butoxycarbonyl)-guanidinomethyl]-5-(3,5-dichlorophenylthio)-4-isopropyl-1-methyl-1H-imidazole (40f)(yield 100%). Oil.

$^1$H-NMR (CDCl$_3$—TMS)δ ppm: 1.26 (d, J=6.8 Hz, 6H), 1.50 and 1.51 (s×2 18H), 3.11 (sept, 1H), 3.53 (s, 3H), 4.72 (d, J=5.2 Hz, 2H), 6.78 (d, J=1.8 Hz, 2H), 7.11 (t, J=1.8 Hz, 1H), 11.43 (b, 1H)

A solution of 150 mg of 2-[(N,N'-di-t-butoxycarbonyl) guanidinomethyl]-5-(3,5-dichlorophenylthio)-4-isopropyl-1-methyl-1H-imidazole (40f)in trifluoroacetic acid (1.5 ml)was stirred at room temperature for 1 hour. The reaction mixture was concentrated under reduced pressure, the residue was dissolved to ethyl acetate, washed with N-sodium hydroxide 3 times, and the organic layer was dried over potassium carbonate. The solvent was distilled off under reduced pressure, and 66 mg of the target compound (Compound I-86) was obtained as oil (yield 68%).

$^1$H-NMR (CDCl$_3$—TMS)δ ppm: 1.17 (d, J=7.0 Hz, 6H), 3.08 (sept, 1H), 3.53 (s, 3H), 4.37 (s, 2H), 6.35 (b, 2H), 6.78 (d, J=1.8 Hz, 2H), 7.12 (t, J=1.8 Hz, 1H)

EXAMPLE 87

Synthesis of 5-(3,5-Dichlorophenylthio)-4-isopropyl-2-methanesulfonylaminomethyl-1-methyl-1H-imidazole (Compound I-87)

Compound I-87 was obtained by the same synthetic process as that for Compound I-86 in Example 86, using 30a as a starting material. mp 116–118° C.

$^1$H-NMR (CDCl$_3$—TMS)δ ppm: 1.22 (d, J=7.0 Hz, 6H), 3.11 (sept, 1H), 3.54 (s, 3H), 4.45 (d, J=5.8 Hz, 2H), 5.38 (b, 1H), 6.80 (d, J=1.8 Hz, 2H), 7.14 (t, J=1.8 Hz, 1H) Elementary analysis (C$_{15}$H$_{19}$Cl$_2$N$_3$O$_2$S$_2$) Calc. (%):C, 44.12: H, 4.69: N, 10.29: S, 15.72: Cl, 17.36 Found (%):C, 44.08: H, 4.68: N, 10.24: S, 15.60: Cl, 17.29

EXAMPLE 88

Synthesis of 5-(3,5-Dichlorophenylthio)-4-isopropyl-1-methyl-2-p-toluenesulfonylaminomethyl-1H-imidazole (Compound I-88)

Compound I-88 was obtained by the same synthetic process as that for Compound I-86 in Example 86, using 30a as a starting material. mp 85–87° C.

¹H-NMR (CDCl₃—TMS)δ ppm: 1.14 (d, J=7.0 Hz, 6H), 2.44 (s, 3H), 3.04 (sept, 1H), 3.50 (s, 3H), 4.14 (d, J=5.4 Hz, 2H), 6.03 (b, 1H), 6.77 (d, J=1.6 Hz, 2H), 7.13 (t, J=1.6 Hz, 1H), 7.29 (d, J=8.2 Hz, 2H), 7.72 (d, J=8.2, 2H) Elementary analysis (C₂₁H₂₃Cl₂N₃O₂S₂) Calc. (%):C, 52.20: H, 5.02: N, 8.36: S, 12.76: Cl, 14.11 Found (%):C, 52.20: H, 5.03: N, 8.37: S, 12.43: Cl, 13.91

EXAMPLE 89

Synthesis of 5-(3,5-Dichlorophenylthio)-4-isopropyl-1-methyl-2-(N-methylthiocarbamoyl)aminomethyl-1H-imidazole (Compound I-89)

Compound I-89 was obtained by the same synthetic process as that for Compound I-44 in Example 44, using 30a as a starting material. mp 188–190° C.

¹H-NMR (CDCl₃—TMS)δ ppm: 1.21 (d, J=7.0 Hz, 6H), 3.04 (d, J=4.8 Hz, 3H), 3.13 (sept, 1H), 3.58 (s, 3H), 4.85 (d, 2H), 6.82 (d, J=1.6 Hz, 2H), 7.14 (t, J=1.6 Hz, 1H) Elementary analysis (C₁₆H₂₀Cl₂N₄S₂) Calc. (%):C, 47.64: H, 5.00: N, 13.89: S, 15.90: Cl, 17.58 Found (%):C, 47.66: H, 5.05: N, 13.77: S, 15.88: Cl, 17.55

EXAMPLE 90

Synthesis of 5-(3,5-Difluorophenylthio)-4-isopropyl-1-methyl-2-ureidomethyl-1H-imidazole (Compound I-90)

Compound I-90 was obtained by the same synthetic process as that for Compound I-41 in Example 41, using Compound I-85 as a starting material. Physical properties of the intermediate, mp 163–165° C.

¹H-NMR (CDCl₃—TMS)δ ppm: 1.28 (d, J=7.2 Hz, 6H), 3.13 (sept, 1H), 3.59 (s, 3H), 4.72 (d, J=5.8 Hz, 2H), 6.82 (d, J=1.8 Hz, 2H), 7.15 (t, J=1.8 Hz, 1H), 8.53 (b, 1H), 8.65 (b, 1H)
Physical properties of Compound I-90, mp 192–194° C.

¹H-NMR (CDCl₃—TMS)δ ppm: 1.21 (d, J=7.2 Hz, 6H), 3.11 (sept, 1H), 3.53 (s, 3H), 4.50 (d, J=5.8 Hz, 2H), 4.85 (b, 2H), 6.32 (b, 1H), 6.80 (d, J=1.8 Hz, 2H), 7.26 (t, J=1.8 Hz, 1H) Elementary analysis (C₁₅H₁₈Cl₂N₄OS) Calc. (%):C, 48.26: H, 4.86: N, 15.01: S, 8.59: Cl, 18.99 Found (%):C, 48.21: H, 4.91: N, 14.85: S, 8.51: Cl, 18.85

EXAMPLE 91

Synthesis of 5-(3,5-Dichlorophenylthio)-4-isopropyl-1-methyl-2-methoxycarbonylaminomethyl-1H-imidazole (Compound I-91)

Compound I-91 was obtained by the same synthetic process as that for Compound I-84 in Example 84, using 30a as a starting material. mp 138–139° C.

¹H-NMR (CDCl₃—TMS)δ ppm: 1.23 (d, J=7.0 Hz, 6H), 3.10 (sept, 1H), 3.54 (s, 3H), 3.71 (s, 3H), 4.50 (d, J=5.6 Hz, 2H), 5.75 (b, 1H), 6.79 (d, J=1.8 Hz, 2H), 7.12 (t, J=1.8 Hz, 1H) Elementary analysis (C₁₆H₁₉Cl₂N₃O₂S) Calc. (%):C, 49.49: H, 4.93: N, 10.82: S, 8.26: Cl, 18.26 Found (%):C, 49.18: H, 4.92: N, 10.53: S, 8.27: Cl, 18.64

EXAMPLE 92

Synthesis of 2-Carbamoyloxymethyl-5-(3,5-dichlorophenylthio)-4-isopropyl-1-(pyridin-3-yl)methyl-1H-imidazole (Compound I-92)

Compound 5-(3,5-dichlorophenylthio)-4-isopropyl-2-(p-methoxybenzyloxymethyl)-1-(pyridin-3-yl)methyl-1H-imidazole (17ab)was obtained from (16b)by the same synthetic process as that for (17b)in Reference Example 2. Oil.

¹H-NMR (CDCl₃—TMS)δ ppm: 1.27 (d, J=7.0 Hz, 6H), 3.10 (sept, 1H), 3.79 (s, 3H), 4.48 (s, 2H), 4.64 (s, 2H), 5.16 (s, 2H), 6.61 (d, J=1.2 Hz, 2H), 6.84 (d, J=8.6 Hz, 2H), 7.02~7.07(m, 2H), 7.16~7.26 (m, 5H), 8.34 (b, 2H)

Compound [5-(3,5-dichlorophenylthio)-4-isopropyl-1-(pyridin-3-yl)methyl-1H-imidazol-2-yl]methanol (12ad) was obtained from (17ad)by the same synthetic process as that for Compound I-8 in Reference Example 2. mp 136–139° C.

¹H-NMR (CDCl₃—TMS)δ ppm: 1.23 (d, J=6.9 Hz, 6H), 3.15 (sept, 1H), 3.81 (s, 3H), 4.39 (s, 3H), 4.80 (s, 2H), 5.27 (s, 2H), 6.20 (s, 2H), 6.88 (d, J=8.7 Hz,), 7.02 (s, 1H), 7.10~7.24 (m, 1H), 7.35~7.38 (m, 1H), 8.40~8.42 (m, 1H) Elementary analysis (C₁₉H₁₉Cl₂N₃OS) Calc. (%):C, 55.89: H, 4.69: N, 10.29: S, 7.85: Cl, 17.36 Found (%):C, 55.78: H, 4.79: N, 10.20: S, 7.88: Cl, 17.60

2-(N-chloroacetylcarbamoyloxy)methyl-5-(3,5-dichlorophenylthio)-4-isopropyl-1-(pyridin-3-yl)methyl-1H-imidazole (22ad)was obtained from (12ad)by the same synthetic process as that for (22)in Example 45. Oil.

¹H-NMR (CDCl₃—TMS)δ ppm: 1.31 (d, J=8.1 Hz, 6H), 3.17 (sept, 1H), 4.35 (s, 2H), 5.03 (s, 2H), 5.33 (s, 2H), 6.68 (s, 2H), 7.08 (s, 1H), 7.25~7.29 (m, 2H), 8.34~8.35 (m, 1H), 8.46~8.48 (m, 1H)

Compound I-92 was obtained by the same synthetic process as that for Compound I-45 in Example 45. mp 152–155° C.

¹H-NMR (CDCl₃—TMS)δ ppm: 1.28 (d, J=7 Hz, 6H), 3.15 (sept, 1H), 4.63 (b, 2H), 5.23 (s, 2H), 5.24 (s, 2H), 6.64 (d, J=1.6 Hz, 2H), 7.04 (d, J=16 Hz, 1H), 7.04~7.26 (m, 4H), 8.30 (d, J=0.8 Hz, 1H), 8.41, 8.42 (dd, J=4.6 Hz, 1.2 Hz, 1H) Elementary analysis (C₂₀H₂₀Cl₂N₄O₂S) Calc. (%):C, 53.22: H, 4.47: N, 12.41: S, 7.00: Cl, 15.71 Found (%):C, 52.96: H, 4.52: N, 12.13: S, 7.00: Cl, 15.80

EXAMPLE 93

Synthesis of 2-Carbamoyloxymethyl-5-(3,5-dichlorophenylthio)-4-isopropyl-1-(pyridin-2-yl)methyl-1H-imidazole (Compound I-93)

2-Benzyloxymethyl-5-(3,5-dichlorophenylthio)-4-isopropyl-1-(pyridin-2-yl)methyl-1H-imidazole (17ae)was obtained from (16a)by the same synthetic process as that for (17a)in Reference Example 1. Oil.

¹H-NMR (CDCl₃—TMS)δ ppm: 1.28 (d, J=7 Hz, 6H), 3.12 (sept, 1H), 4.53 (s, 2H), 4.77 (s, 2H), 5.32 (s, 2H), 6.31 (d, J=1.8 Hz, 2H), 6.73 (d, J=7.8 Hz, 1H), 6.94 (t, J=1.8 Hz, 1H), 6.95~7.03 (m, 2H), 7.27~7.36 (m, 6H), 8.40~8.43 (m, 1H)

[5-(3,5-Dichlorophenylthio)-4-isopropyl-1-(pyridin-2-yl)methyl-1H-imidazol-2-yl]methanol (12ae)was obtained from (17ae)by the same synthetic process as that for (12a)in Reference Example 1. mp 145–146° C.

¹H-NMR (CDCl₃—TMS)δ ppm: 1.22 (d, J=7.0 Hz, 6H), 3.07 (sept, 1H), 4.91 (d, J=5.8 Hz, 2H), 5.34 (t, J=5.8 Hz, 1H), 6.41 (d, J=2 Hz, 2H), 6.91 (t, J=2 Hz, 1H), 7.05~7.13 (m, 2H), 7.32~7.37 (m, 1H), 8.43~8.47 (m, 1H) Elementary analysis (C₁₉H₁₉Cl₂N₃OS) Calc. (%):C, 55.89: H, 4.69: N, 10.29: S, 7.85: Cl, 17.36 Found (%):C, 55.83: H, 4.82: N, 10.11: S, 7.78: Cl, 17.08

The title Compound I-93 was obtained from (12ae)by the same synthetic process as that for Compound I-45 in Example 45. mp 127–130° C.

¹H—NMR (CDCl₃—TMS)δ ppm: 1.28 (d, J=6.9 Hz, 6H), 3.13 (sept, 1H), 4.62 (b, 2H), 5.32 (s, 2H), 5.36 (s, 2H), 6.62 (s, 2H), 6.78 (d, J=7.8 Hz, 1H), 6.95 (s, 1H), 7.02~7.07 (m, 1H), 7.38~7.44 (m, 1H), 8.43~8.46 (m, 1H) Elementary analysis (C₂₀H₂₀Cl₂N₄O₂S) Calc. (%):C, 53.22: H, 4.47: N, 12.41: S, 7.00: Cl, 15.71 Found (%):C, 53.23: H, 4.51: N, 12.36: S, 6.98: Cl, 15.45

EXAMPLE 93'

Synthesis of 2-carbamoyloxymethyl-5-(3,5-dichlorophenylthio)-4-isopropyl-1-(pyridin-4-yl)methyl-1H-imidazole (Compound I-93')

2-Benzyloxymethyl-5-(3,5-dichlorophenylthio)-4-isopropyl-1-(pyridin-4-yl)methyl-1H-imidazole (17af)was obtained from (16a)by the same synthetic process as that for (17a)in Reference Example 1.

[5-(3,5-Dichlorophenylthio)-4-isopropyl-1-(pyridin-4-yl)methyl-1H-imidazol-2-yl]methanol (12af)was obtained from (17af)by the same synthetic process as that for (12a)in Reference Example 1. mp 137–139° C.

¹H—NMR (CDCl₃—TMS)δ ppm: 1.27 (d, J=7.0 Hz, 6H), 3.12 (sept, 1H), 4.75 (s, 2H), 5.26 (s, 2H), 6.66 (d, J=2 Hz, 2H), 6.87 (dd, J=1.6 Hz, 6Hz, H), 7.05 (t, J=2.4 Hz, H), 8.44 (dd, J=1.6 Hz, 6Hz, H) Elementary analysis (C₁₉H₁₉Cl₂N₃OS) Calc. (%):C, 55.89: H, 4.69: N, 10.29: S, 7.85: Cl, 17.36 Found (%):C, 55.92: H, 4.74: N, 10.24: S, 7.64: Cl, 17.09

The 2HCl salt of (12af): mp 223–235° C. (dec).

2-(N (chloroacetyl)carbamoyloxy)methyl-5-(3,5-dichlorophenylthio)-4-isopropyl-1-(pyridin-4-yl)methyl-1H-imidazole (22af)was obtained from (12af)by the same synthetic process as that for (22)in Example 45. Oil.

¹H—NMR (CDCl₃—TMS)δ ppm: 1.32 (d, J=7.0 Hz, 6H), 3.17 (sept, 1H), 4.30 (s, 2H), 5.28 (s, 2H), 5.31 (s, 2H), 6.71 (d, J=1.4 Hz, 2H), 6.82 (d, J=5.8 Hz, 2H), 7.05 (t, J=1.4 Hz, 1H), 8.20 (b, 1H), 8.49 (d, J=5.4 Hz, 2H)

The title Compound I-93' was obtained from (12af)by the same synthetic process as that for Compound I-45 in Example 45. mp 88° C. (dec)

¹H—NMR (CDCl₃—TMS)δ ppm: 1.32 (d, J=6.9 Hz, 6H), 3.17 (sept, 1H), 4.53 (b, 2H), 5.21 (s, 2H), 5.27 (s, 2H), 6.69 (d, J=1.6 Hz, 2H), 6.82 (d, J=5.2 Hz, 2H), 7.06 (t, J=1.6 Hz, 1H), 8.46 (b, 2H), Elementary analysis (C₂₀H₂₀Cl₂N₄O₂S.0.5H₂O) Calc. (%):C, 52.16: H, 4.61: N, 12.17: S, 6.96: Cl, 15.42 Found (%):C, 52.45: H, 4.72: N, 11.73: S, 7.08: Cl, 14.81

The 2HCl salt of Compound I-93': mp 214–222° C. (dec).

EXAMPLE 94

Synthesis of 2-aminomethyl-5-(3,5-dichlorophenylthio)-4-isopropyl-1-(pyridin-3-yl)methyl-1H-imidazole (Compound I-94)

2-Azidomethyl-5-(3,5-dichlorophenylthio)-4-isopropyl-1-(pyridin-3-yl)methyl-1H-imidazole (29ad)was obtained from (12ae)by the same synthetic process as that for (29a)in Example 66. Oil.

¹H—NMR (CDCl₃—TMS)δ ppm: 1.28 (d, J=6.8 Hz, 6H), 3.15 (sept, 1H), 4.50 (s, 2H), 5.20 (s, 2H), 6.65 (d, J=1.8 Hz, 2H), 7.06 (t, J=1.8 Hz, 1H), 7.06~7.27 (m, 2H), 8.36 (b, 1H), 8.45 (b, 1H) IR (film)2100 cm⁻¹

Compound I-94 was obtained from (29ad)by the same synthetic process as that for (30a)in Example 66. mp 99–103° C.

¹H—NMR (CDCl₃—TMS)δ ppm: 1.28 (d, J=6.6 Hz, 6H), 3.14 (sept, 1H), 3.99 (s, 2H), 5.26 (s, 2H), 6.67 (s, 2H), 7.04 (s, 1H), 7.11~7.20 (m, 1H), 7.25~7.35 (m, 1H), 8.37 (d, J=0.9 Hz, 1H), 8.43 (d, J=6.6 Hz, 1H) Elementary analysis (C₁₉H₂₀Cl₂N₄OS.0.2.H₂O) Calc. (%):C, 55.53: H, 5.00: N, 13.63: S, 7.80 Found (%):C, 55.46: H, 4.96: N, 13.57: S, 7.60

EXAMPLE 95

Synthesis of 2-aminomethyl-5-(3,5-dichlorophenylthio)-4-isopropyl-1-(pyridin-2-yl)methyl-1H-imidazole (Compound I-95)

2-Azidomethyl-5-(3,5-dichlorophenylthio)-4-isopropyl-1-(pyridin-2-yl)methyl-1H-imidazole (29ae)was obtained from (12ae)by the same synthetic process as that for (29a)in Example 66. Oil.

¹H—NMR (CDCl₃—TMS)δ ppm: 1.28 (d, J=6.9 Hz, 6H), 3.15 (sept, 1H), 4.69 (s, 2H), 5.29 (s, 2H), 6.60 (s, 2H), 6.83 (d, J=7.8 Hz, 1H), 6.95 (s, 1H), 7.06~7.10 (m, 1H), 7.39~7.45 (m, 1H), 8.46~8.49 (m, 1H) IR (film)2100 cm⁻¹

Compound I-95 was obtained from (29ae)by the same synthetic process as that for (30a)in Example 66. Oil.

¹H—NMR (CDCl₃—TMS)δ ppm: 1.26 (d, J=6.9 Hz, 6H), 3.12 (sept, 1H), 4.01 (s, 2H), 5.05 (s, 2H), 6.60 (s, 2H), 6.85 (d, J=7.8 Hz, 1H), 6.95 (s, 1H), 7.02~7.10 (m, 1H), 7.22~7.28 (m, 1H), 7.38~7.43 (m, 1H)

EXAMPLE 95'

Synthesis of 2-aminomethyl-5-(3,5-dichlorophenylthio)-4-isopropyl-1-(pyridin-4-yl)methyl-1H-imidazole (Compound I-95')

2-Azidomethyl-5-(3,5-dichlorophenylthio)-4-isopropyl-1-(pyridin-4-yl)methyl-1H-imidazole (29af)was obtained from (12af)by the same synthetic process as that for (29a)in Example 66. Oil.

¹H—NMR (CDCl₃—TMS)δ ppm: 1.31 (d, J=6.8 Hz, 6H), 3.18 (sept, 1H), 4.47 (s, 2H), 5.20 (s, 2H), 6.69 (d, J=1.8 Hz, 2H), 6.82 (d, J=5.6 Hz, 2H), 7.06 (t, J=1.8 Hz, 1H), 8.47 (b, 2H)IR (film)2080 cm⁻¹

Compound I-95' was obtained from (29af)by the same synthetic process as that for (30a)in Example 66. Oil.

¹H—NMR (CDCl₃—TMS)δ ppm: 1.30 (d, J=8.2 Hz, 6H), 3.16 (sept, 1H), 3.95 (s, 2H), 5.25 (s, 2H), 6.71 (d, J=1.2 Hz, 2H), 6.83 (d, J=4.8 Hz, 2H), 7.04 (t, J=1.2 Hz, 1H), 8.42~8.48 (m, 1H)

The 3HCl salt of Compound I-95':m.p. 252–260° C. (dec). Elementary analysis (C₁₉H₂₀Cl₂N₄S.3HCl.1.3 H₂O) Calc. (%):C, 42.25: H, 4.78: N, 10.37: S, 5.94: Cl, 32.82 Found (%):C, 42.07: H, 4.67: N, 10.55: S, 5.92: Cl, 32.51

EXAMPLE 96

Synthesis of methyl 2-[1,2-dimethyl-5-(3,5-dimethylphenylthio)-1H-imidazol-4-yl]propionate (Compound I-96)

Heated was a solution of 7.0 g (3.2 mmol)of 5-(3,5-dimethylphenylthio)-2-methyl-1H-imidazole (5b)in 37% aqueous formaline (20 ml)at 120° C. for 15 hours in a sealed tube. The reaction mixture was dissolved in methanol/methylene chloride, and the aqueous layer was separated off. The organic layer was dried over sodium sulfate, and the solvent was distilled off under reduced pressure. The residue was purified by silica gel chromatography (methanol:ethyl acetate=2:98), and the crude product was washed with isopropyl ether to obtain 1.7 g of [5-(3,5- dimethylphenylthio)-2-methyl-1H-imidazol-4-yl]methanol (41d)(yield 21%). mp 199–201° C.

$^1$H—NMR (DMSO-d6—TMS)δ ppm: 2.17 (s, 6H), 2.27 (s, 3H), 4.41 (m, 2H), 5.09 (b, 1H), 6.74 (m, 3H), 12.16 (b, 1H)

In dry methylene chloride (85 ml)was dissolved 1.7 g (6.8 mmol)of [5-(3,5-dimethylphenylthio)-2-methyl-1H-imidazol-4-yl]methanol (41d), followed by addition of 2.10 g (20.8 mmol)of trimethylamine. To this solution, acetyl chloride was added dropwise with stirring under ice-cooling. At the same temperature, the mixture was stirred for 30 minutes, then, 8.3 ml of 6N hydrochloric acid was added, and the mixture was stirred at room temperature for 1 hour. To the reaction mixture was added a saturated aqueous sodium hydrogen carbonate solution to neutralize, and extracted with methylene chloride. The extract was washed with water and dried over sodium sulfate. The solvent was distilled off under reduced pressure, and the residue was purified by silica gel chromatography (ethyl acetate)to obtain 1.55 g of [5-(3,5-dimethylphenylthio)-2-methyl-1H-imidazol-4-yl]methyl acetate (41b)as oil (yield 78%).

$^1$H—NMR (CDCl$_3$—TMS)δ ppm: 2.05 (s, 6H), 2.21 (s, 3H), 2.39 (S, 3H), 5.11 (s, 2H), 6.75 (s, 3H), 9.81 (b, 1H)

In 26 ml of dry dimethylformamide was dissolved 1.33 g (4.6 mmol)of [5-(3,5-dimethylphenylthio)-2-methyl-1H-imidazol-4-yl]methyl acetate (41b), followed by addition of 1.28 g (9.3 mmol)of anhydrous potassium carbonate and 715 mg (5.0 mmol)of methyl iodide, and the mixture was stirred at room temperature for 2 hours. To the reaction mixture, ice-water was added, extracted with diethyl ether, and the organic layer was washed with water and dried over sodium sulfate. The solvent was distilled off under reduced pressure, and this crude product was fractionated by silica gel chromatography (ethyl acetate)to obtain 510 mg of [5-(1,2-dimethyl-3,5-dimethylphenylthio)imidazol-4-yl]methyl acetate (42a)as oil (yield 37%).

$^1$H—NMR (CDCl$_3$—TMS)δ ppm: 2.05 (s, 6H), 2.23 (s, 3H), 2.46 (s, 3H), 3.46 (s, 3H), 5.13 (s, 2H), 6.65 (s, 2H), 6.65 (s, 2H), 6.78 (s, 1H)

In methanol (0.5 ml)was dissolved 500 mg (1.6 mmol)of [5-(1,2-dimethyl-3,5-dimethylphenylthio)-1H-imidazol-4-yl]methyl acetate (42a), followed by addition of 4.9 ml of 1M sodium methylate solution at room temperature, and the mixture was stirred for 30 minutes. To the reaction mixture, water was added, extracted with methylene chloride, the organic layer was washed with water and dried over sodium sulfate. The solvent was concentrated under reduced pressure, and the residue was recrystallized from ethyl acetate/isopropyl ether to obtain 398 mg of [1,2-dimethyl-5-(3,5-dimethylphenylthio)-1H-imidazol-4-yl]methanol (42b)(yield 93%), mp 198–199° C.

$^1$H—NMR (CDCl$_3$—TMS)δ ppm: 2.23 (s, 6H), 2.40 (b, 1H), 2.46 (s, 3H), 3.45 (s, 3H), 4.47 (s, 2H), 6.64 (s, 2H), 6.78 (s, 1H)

To 19 ml of thionyl chloride was added 370 mg (1.4 mmol) of [1,2-dimethyl-5-(3,5-dimethylphenylthio)-1H-imidazol-4-yl]methanol (42b), and the mixture was heated at 70° C. for 3 hours. The reaction mixture was concentrated under reduced pressure. Ice-water and then a saturated aqueous sodium hydrogen carbonate solution were added to the reaction mixture to neutralize, and extracted with diethyl ether. The organic layer was washed with water and dried over sodium sulfate, and the solvent was concentrated under reduced pressure. The residue was purified by silica gel chromatography (ethyl acetate)to give 288 mg of 4-chloromethyl-1,2-dimethyl-5-(3,5-dimethylphenylthio) imidazole (42c)as oil (yield 73%).

$^1$H—NMR (CDCl$_3$—TMS)δ ppm: 2.25 (s, 6H), 2.48 (s, 3H), 3.46 (s, 3H), 4.71 (s, 2H), 6.71 (s, 2H), 6.81 (s, 1H)

In 5.6 ml of dry dimethylformamide was dissolved 280 mg (1.0 mmol)of 4-chloromethyl-1,2-dimethyl-5-(3,5-dimethylphenylthio)-1H-imidazole (42c). Added was 98 mg (1.5 mmol)of potassium cyanide, and the mixture was heated at 50° C. for 5 hours. To the reaction mixture, ice-water was added, extracted with diethyl ether, the extract was washed with water and dried over sodium sulfate. The solvent was distilled off under reduced pressure, and the residue was purified by silica gel chromatography (ethyl acetate)to obtain 114 mg of [1,2-dimethyl-5-(3,5-dimethylphenylthio)-1H-imidazol-4-yl]acetonitrile (42d) (yield 42%). mp 81–82° C.

$^1$H—NMR (CDCl$_3$—TMS)δ ppm: 2.24 (s, 6H), 2.47 (s, 3H), 3.47 (s, 3H), 3.76 (s, 2H), 6.60 (s, 2H), 6.80 (s, 1H)

In dry tetrahydrofuran (5 ml)was dissolved 49 mg (0.48 mmol)of diisopropylamine, and the solution was cooled to 0° C. To this, 0.3 ml of 1.62 M hexane solution of n-butyllithium was added under a stream of nitrogen, and the mixture was stirred for 10 minutes. The mixture was cooled to −78° C., and 85 mg (0.31 mmol)of [1,2-dimethyl-5-(3, 5-dimethylphenylthio)imidazol-4-yl]acetonitrile (42d)was added, and the mixture was stirred for 15 minutes. Then, 86 mg (0.48 mmol)of hexamethylphosphoric triamide and 68 mg (0.48 mmol)of methyl iodide were added dropwise, and the mixture was stirred at −78° C. for 30 minutes. The reaction mixture was poured into ice-water, extracted with diethyl ether, and the extract was washed with water and dried over sodium sulfate. The solvent was distilled off under reduced pressure, the residue was purified by silica gel chromatography (ethyl acetate)to give 51 mg of 2-[1,2-dimethyl-5-(3,5-dimethylphenylthio)-1H-imidazol-4-yl] propiononitrile (43a)as oil (yield 57%).

$^1$H—NMR (CDCl$_3$—TMS)δ ppm: 1.63 (d, J=7.2 Hz, 3H), 2.24 (s, 6H), 2.48 (s, 3H), 3.46 (s, 3H), 4.15 (q, J=7.2 Hz, 1H), 6.60 (s, 2H), 6.80 (s, 1H)

In 5 ml of methanol/diethyl ether (1/3 v/v %)saturated with hydrogen chloride was dissolved 60 mg (0.21 mmol)of 2-[1,2-dimethyl-5-(3,5-dimethylphenylthio)-1H-imidazol-4-yl]propiononitrile (43a), and the mixture was left at 4° C. for 23 hours. To the reaction mixture, 2 ml of methanol and 0.3 ml of water were added, and the mixture was stirred at room temperature for 4 hours. The reaction mixture was added to a saturated aqueous sodium hydrogen carbonate solution and extracted with methylene chloride. The organic layer was washed with water and dried over sodium sulfate. The solvent was concentrated under reduced pressure, and the residue was purified by silica gel chromatography (ethyl acetate)to obtain 57 mg of Compound I-96 as oil (yield 85%).

$^1$H—NMR (CDCl$_3$—TMS)δ ppm: 1.51 (d, J=7.4 Hz, 3H), 2.23 (s, 6H), 2.45 (s, 3H), 3.43 (s, 3H), 3.59 (s, 3H), 4.01 (q, J=7.4Hz, 1H), 6.63 (s, 2H), 6.77 (s, 1H)

EXAMPLE 97

Synthesis of 2-[5-(3-chlorophenylthio)-1,2-dimethyl-1H-imidazol- 4-yl]propiononitrile
(Compound I-97)

[5-(3-Chlorophenylthio)-1,2-dimethyl-1H-imidazol-4-yl] acetonitrile (42f)was obtained from [5-(3-chlorophenylthio)-1,2-dimethyl-1H-imidazol-4-yl] methanol (42e)by the same synthetic process as that for Compound 42d in Example 96. mp 90–91° C.

$^1$H—NMR (CDCl$_3$—TMS)δ ppm: 2.48 (s, 3H), 3.47 (s, 3H), 3.76 (s, 2H), 6.82~7.27 (m, 4H)

Compound I-97 was obtained by the same synthetic process as that for Compound I-96 in Example 96.

$^1$H—NMR (CDCl$_3$—TMS)δ ppm: 1.64 (d, J=6.8 Hz, 3H), 2.49 (s, 3H), 3.47 (s, 3H), 4.13. (q, J=6.8 Hz, 1H), 6.81~7.27 (m, 4H)

EXAMPLE 98

Synthesis of 2-[2-carbamoyloxymethyl-5-(3-chlorophenylthio)-1-methyl-1H-imidazol-4-yl] propiononitrile (Compound I-98)

1-Benzyloxymethyl-2-imidazolecarboaldehyde (44)was obtained as oil from 1-benzyloxymethyl-1H-imidazole by the same synthetic process as that for Compound I-6 in Example 6. Yield 95%.

$^1$H—NMR (CDCl$_3$—TMS)δ ppm: 4.55 (s, 2H), 5.87 (s, 2H), 7.26~7.37 (m, 7H), 9.86 (s, 1H)

By the same synthetic process as that for Compound I-8 in Example 8, (1-benzyloxymethylimidazol-2-yl)methanol was obtained as oil from 1-benzyloxymethyl-1H-imidazole-2-carbaldehyde (44)by purification by silica gel chromatography (ethyl acetate:methanol=19.1). yield 53%.

$^1$H—NMR (CDCl$_3$—TMS)δ ppm: 4.49 (s, 2H), 4.71 (s, 2H), 5.10 (b, 1H), 5.44 (s, 2H), 6.92 (m, 1H), 6.99 (m, 1H), 7.33 (m, 5H)

In a solution of 29.5 g (135 mmol)of (1-benzyloxymethyl-1H-imidazol-2-yl)methanol in dry methylene chloride (295 ml) was added 11.1 g (163 mmol)of imidazole, and there was added dropwise 24.4 g (162 mmol)of t-butyldimethylsilylchloride with ice-cooling. After completion of the dropwise addition, the reaction mixture was stirred at room temperature for 30 minutes. To the reaction mixture, ice-water was added, extracted with methylene chloride, and the extract was washed with water and dried over sodium sulfate. The solvent was distilled off under reduced pressure, and 43.0 g of 1-benzyloxymethyl-2-t-butyldimethylsilyloxymethylimidazole (44')was obtained as oil (yield 96%).

$^1$H—NMR (CDCl$_3$—TMS)δ ppm: 0.05 (s, 6H), 0.81 (s, 9H), 4.43 (s, 2H), 4.76 (s, 2H), 5.42 (s, 2H), 6.92~7.30 (m, 7H)

A dry tetrahydrofuran solution of 29.5 g (88.7 mmol)of 1-benzyloxymethyl-2-t-butyldimethylsilyloxymethyl-1H-imidazole (44')was cooled to −78° C., and 76 ml of 1.66 M hexane solution of n-butyllithium was added dropwise under a stream of nitrogen. The mixture was stirred at the same temperature for 5 minutes, then, 28 g (97.5 mmol)of di-3-chlorophenyldisulfide was added little by little, and after completion of the addition, further the mixture was stirred for 15 minutes. The reaction mixture was poured into ice-water, extracted with diethyl ether, and the organic layer was washed with water and dried over sodium sulfate. The solvent was distilled off under reduced pressure, the residue was purified by silica gel chromatography (ethyl acetate:n-hexane=1:2)to give 21.5 g of 1-benzyloxymethyl-2-t-butyldimethylsilyloxymethyl-5-(3-chlorophenylthio) imidazole (45)as oil (yield 51%).

$^1$H—NMR (CDCl$_3$—TMS)δ ppm: 0.09 (s, 6H), 0.87 (s, 9H), 4.39 (s, 2H), 4.86 (s, 2H), 5.51 (s, 2H), 6.90~7.36 (m, 10H)

To a solution of 1-benzyloxymethyl-2-t-butyldimethylsilyloxymethyl-5-(3-chlorophenylthio) imidazole (45)in nitromethane (108 ml)was added 14.7 g of (137 mmol)of anisole, and then, 18.1 g (136 mmol)of anhydrous aluminium chloride was gradually added at lower than 30° C. After completion of the addition, the mixture was stirred at room temperature for 15 minutes. The reaction mixture was cooled, and there were added water and a saturated aqueous sodium hydrogen carbonate solution to be alkaline. Ethyl acetate was added to the mixture, and the mixture was filtered on Hiflow Super Cell to separate. The organic layer was washed with water, dried over sodium sulfate, and the solvent was concentrated under reduced pressure. The residue was purified by silica gel chromatography (7% methanol-methylene chloride) to give 9.5 g of [5-(3-chlorophenylthio)-1H-imidazol-2-yl]methanol as oil (yield 87%).

$^1$H—NMR (CDCl$_3$—TMS)δ ppm: 4.00 (b, 2H), 4.64 (s, 2H), 7.03~7.28 (m, 5H)

By the same synthetic process as that for the above 1-benzyloxymethyl-2-t-butyldimethylsilyloxymethylimidazole (44'), 2-t-butyldimethylsilyloxymethyl-5-(3-chlorophenylthio)-imidazole was obtained from [5-(3-chlorophenylthio)-1H-imidazol-2-yl]methanol (yield 60%). mp 107–108° C.

$^1$H—NMR (CDCl$_3$—TMS)δ ppm: 0.03 (s, 6H), 0.82 (s, 9H), 4.74 (s, 2H), 7.00 (m, 4H), 7.20 (s, 1H), 9.50 (b, 1H)

An aqueous solution of 2.0 g (5.6 mmol)of 2-t-butyldimethylsilyloxymethyl-5-(3-chlorophenylthio)-1H-imidazole (45')in 37% formaline (10 ml)was heated at 120° C. for 10 hours in a sealed tube. The reaction mixture was washed out with methanol from the tube, dried over sodium sulfate, and the solvent was distilled off under reduced pressure. The residue was purified by silica gel chromatography (ethyl acetate:n-hexane=1:1), the crude product was washed with n-hexane, and filtered to give 716 mg of [2-t-butyldimethylsilyloxymethyl-5-(3-chlorophenylthio)-1H-imidazol-4-yl]methanol (46)(yield 33%). mp 136–137° C.

$^1$H—NMR (CDCl$_3$—TMS)δ ppm: 0.08 (s, 6H), 0.89 (s, 9H), 4.46 (d, J=5.0 Hz, 2H), 4.62 (s, 2H), 5.23 (t, J=5.0 Hz, 1H), 7.05~7.30 (m, 4H), 12.59 (b, 1H)

To a solution of 700 mg (1.8 mmol)of [2-t-butyldimethylsilyloxymethyl-5-(3-chlorophenylthio)-1H-imidazol- 4-yl]methanol (46)in methylene chloride (14 ml), was added 1.29 g (12.8 mmol)of triethylamine, and then, 1.00 g (12.8 mmol)of acetyl chloride was added dropwise under ice-cooling with stirring. The reaction mixture was stirred at room temperature for 15 minutes, and added to a cooled saturated aqueous sodium hydrogen carbonate solution to neutralize and extracted with methylene chloride. The organic layer was washed with water and dried over sodium sulfate. The solvent was distilled off under reduced pressure. The residue was dissolved in 5 ml of methanol, to which was added 5 ml of 50% aqueous acetic acid, and the mixture was stirred at room temperature for 1 hour. To the reaction mixture was added a saturated aqueous sodium hydrogen carbonate solution to neutralize, and extracted with methylene chloride. The organic layer was washed with water and dried over sodium sulfate. The solvent was concentrated under reduced pressure, and the residue was purified by silica gel chromatography (ethyl acetate:n-hexane=1:2)to give 602 mg of [2-t-butyldimethylsilyloxymethyl-5-(3-chlorophenylthio)-1H-imidazol-4-yl]methyl acetate as oil (yield 78%).

$^1$H—NMR (CDCl$_3$—TMS)δ ppm: 0.13 (s, 6H), 0.95 (s, 9H), 2.08 (s, 3H), 4.80 (s, 2H), 5.16 (s, 2H), 7.10 (m, 4H), 9.83 (b, 1H)

In 12 ml of dry dimethylformamide was dissolved 600 mg (1.4 mmol)of [2-t-butyldimethylsilyloxymethyl-5-(3-chlorophenylthio)-1H-imidazol-4-yl]methyl acetate, followed by addition of anhydrous potassium carbonate (2.8 mmol). Then, 240 mg (1.7 mmol) of methyl iodide was added, and the reaction mixture was stirred at room temperature for 1 hour. To the reaction mixture, ice-water was added, extracted with diethyl ether, the organic layer was washed with water and dried over sodium sulfate. The solvent was distilled off under reduced pressure, and the residue was purified by silica gel chromatography (ethyl acetate:n-hexane=1:2) to obtain 288 mg of [2-t-butyldimethylsilyloxymethyl-5-(3-chlorophenylthio)-1-methyl-1H-imidazol-4-yl]methyl acetate (47) as oil (yield 46%).

$^1$H—NMR (CDCl$_3$—TMS)δ ppm: 0.08 (s, 6H), 0.87 (s, 9H), 2.02 (s, 3H), 3.60 (s, 3H), 4.82 (s, 2H), 5.13 (s, 2H), 6.90~7.18 (m, 4H)

[2-t-Butyldimethylsilyloxymethyl-5-(3-chlorophenylthio)-1-methyl-1H-imidazol-4-yl]methanol was obtained from (47) by the same synthetic process as that for (42b) in Example 96. mp 111–112° C.

$^1$H—NMR (CDCl$_3$—TMS)δ ppm: 0.72 (s, 6H), 0.87 (s, 9H), 3.30 (b, 1H), 3.59 (s, 3H), 4.68 (b, 2H), 4.80 (s, 2H), 6.88~7.17 (m, 4H)

By the same synthetic process as that for (42c) in Example 96, 2-t-butyldimethylsilyloxymethyl-4-chloromethyl-5-(3-chlorophenylthio)-1-methyl-1H-imidazole was obtained from [2-t-butyldimethylsilyloxymethyl-5-(3-chlorophenylthio)-1-methyl-1H-imidazol-4-yl]methanol. Oil.

$^1$H—NMR (CDCl$_3$—TMS)δ ppm: 0.07 (s, 6H), 0.87 (s, 9H), 3.30 (b, 1H), 3.58 (s, 3H), 4.67 (s, 2H), 4.81 (s, 2H), 6.90~7.22 (m, 4H)

By the same synthetic process as that for (42d) in Example 96, [2-t-butyldimethylsilyloxymethyl-5-(3-chlorophenylthio)-1-methyl-1H-imidazol-4-yl]acetonitrile (48) was obtained from 2-t-butyldimethylsilyloxymethyl-4-chloromethyl-5-(3-chlorophenylthio)-1-methylimidazole. Oil.

$^1$H—NMR (CDCl$_3$—TMS)δ ppm: 0.09 (s, 6H), 0.88 (s, 9H), 3.60 (s, 3H), 3.77 (s, 2H), 4.81 (s, 2H), 6.80~7.22 (m, 4H)

In dry tetrahydrofuran (5 ml) was dissolved 87 mg (0.86 mmol) of diisopropylamine, and the solution was cooled to 0° C. There was added 0.5 ml of 1.71 M hexane solution of n-butyllithium under nitrogen gas, and the mixture was stirred for 10 minutes. The mixture was cooled to −78° C., followed by addition of 200 mg of [2-t-butyldimethylsilyloxymethyl-5-(3-chlorophenylthio)-1-methyl-1H-imidazol-4-yl]acetonitrile (48), and the mixture was stirred for 25 minutes. Then, 154 mg (0.86 mmol) of hexamethylphosphoric triamide and 122 mg (0.86 mmol) of methyl iodide were added dropwise, and the mixture was stirred at −78° C. for 10 minutes. The reaction mixture was poured into ice-water, extracted with diethyl ether, and the extract was washed with water and dried over sodium sulfate. The solvent was distilled off under reduced pressure, and the residue was fractionated by silica gel chromatography (ethyl acetate:n-hexane=1:2). From the first fraction, 40 mg of 2-(2-t-butyldimethylsilyloxymethyl-5-(3-chlorophenylthio)-1-methyl-1H-imidazol-4-yl)-2-methylpropiononitrile (49') was obtained as oil (yield 19%), while from the subsequent fraction, 70 mg of 2-(2-t-butyldimethylsilyloxymethyl-5-(3-chlorophenylthio)-1-methyl-1H-imidazol-4-yl)propiononitrile (50') was obtained as oil (yield 34%), 49' $^1$H—NMR (CDCl$_3$—TMS)δ ppm: 0.08 (s, 6H), 0.88 (s, 9H), 1.76 (s, 6H), 3.56 (s, 3H), 4.79 (s, 2H), 6.80~7.22 (m, 4H)

50' $^1$H—NMR (CDCl$_3$—TMS)δ ppm: 0.08 (s, 6H), 0.87 (s, 9H), 1.63 (d, J=7.4 Hz, 3H), 3.60 (s, 3H), 4.12 (q, J=7.4 Hz, 1H), 4.82 (s, 2H), 6.80~7.22 (m, 4H)

In dry tetrahydrofuran (2 ml) was dissolved 70 mg of 2-(2-t-butyldimethylsilyloxymethyl-5-(3-chlorophenylthio)-1-methyl-1H-imidazol-4-yl)propiononitrile (50'), followed by addition of 0.33 ml of 1 M tetrabutylammoniumfluoride-tetrahydrofuran solution, and the reaction mixture was stirred at room temperature for 10 minutes. To the reaction mixture, water was added, extracted with methylene chloride, the organic layer was washed with water and dried over sodium sulfate. The solvent was concentrated under reduced pressure, and the residue was purified by silica gel chromatography (ethyl acetate) to obtain 50 mg of 2-[5-(3-chlorophenylthio)-2-hydroxymethyl-1-methyl-1H-imidazol-4-yl]propiononitrile (50) as oil (yield 98%).

$^1$H—NMR (CDCl$_3$—TMS)δ ppm: 1.61 (d, J=7.4 Hz, 3H), 3.60 (s, 3H), 4.13 (q, J=7.4 Hz, 1H), 4.20 (b, 1H), 4.79 (s, 2H), 6.79~7.25 (m, 4H)

2-[5-(3-Chlorophenylthio)-2-hydroxymethyl-1-methylimidazol-4-yl]-2-methylpropiononitrile (49) was obtained from (49') by the same synthetic process as that for 2-[5-(3-chlorophenylthio)-2-hydroxymethyl-1-methylimidazol-4-yl]propiononitrile (50). Oil.

$^1$H—NMR (CDCl$_3$—TMS)δ ppm: 1.76 (s, 6H), 3.24 (m, 1H), 3.56 (s, 3H), 4.76 (d, J=5.4 Hz, 2H), 6.80~7.22 (m, 4H)

Compound I-98 was obtained from 2-[5-(3-chlorophenylthio)-2-hydroxymethyl-1-methyl-1H-imidazol-4-yl]propiononitrile (50) by the same synthetic process as that for Compound I-59 in Example 59. Oil.

$^1$H—NMR (CDCl$_3$—TMS)δ ppm: 1.63 (d, J=7.2 Hz, 3H), 3.60 (s, 3H), 4.15 (q, J=7.2 Hz, 1H), 4.82 (b, 2H), 5.23 (s, 2H), 6.80~7.25 (m, 4H)

EXAMPLE 99

Synthesis of 2-[5-(3-chlorophenylthio)-1,2-dimethyl-1H-imidazol-4-yl]propionic acid (Compound I-99)

A solution of 30 mg of 2-[5-(3-chlorophenylthio)-1,2-dimethyl-1H-imidazol-4-yl]propiononitrile (52) in 3 ml of 6N-hydrochloric acid was allowed to react at 110° C. The mixture was concentrated under reduced pressure, made alkaline with 28% ammonia water, and then, acidic with acetic acid. The aqueous solution was charged on a column of 25 g of MCI GEL (CHP20P 75–150μ), and eluted with purified water and then methanol. The methanol fraction was concentrated under reduced pressure to give 25 mg of the target compound (Compound I-99) as oil (yield 78%).

$^1$H—NMR (CDCl$_3$—TMS)δ ppm: 1.49 (d, J=7.4 Hz, 3H), 2.48 (s, 3H), 3.46 (s, 3H), 3.95 (q, J=7.4 Hz, 1H), 6.84~7.20 (m, 5H)

EXAMPLE 100

Synthesis of 5-(3,5-dichlorobenzyl)-1,2-dimethyl-4-isopropyl-1H-imidazole (Compound I-100)

In 20 ml of dry acetone was dissolved 930 mg (3.3 mmol) of 5-(3,5-dichlorobenzyl)-4-isopropyl-2-methyl-1H-imidazole (54), followed by addition of 1.4 g (10.1 mmol) of anhydrous potassium carbonate, and the mixture was stirred at room temperature. After 5 minutes, 225 μl (3.6 mmol) of methyl iodide was added at room temperature, and the mixture was heated to 80° C. After 5 hours, the mixture was cooled to room temperature, filtered, and the filtrate was concentrated under reduced pressure. The residue was diluted with water, and extracted with chloroform. The extract was washed with saturated brine, dried over anhydrous sodium sulfate, filtered, and the filtrate was concentrated under reduced pressure. The crude product was purified by silica gel chromatography (ethyl acetate)to give 218 mg of the target compound (Compound I-100)(yield 22%).

$^1$H—NMR (CDCl$_3$—TMS)δ ppm: 1.27 (d, J=4.2 Hz, 6H), 2.36 (s, 3H), 2.86 (m, 1H), 3.21 (s, 3H), 3.88 (s, 2H), 6.96 (s, 2H), 7.21 (s, 1H)

EXAMPLE 101

Synthesis of 2-aminomethyl-5-(3,5-dichlorophenylbenzyl)-4-isopropyl-1-methyl-1H-imidazole (Compound I-101)

In 30 ml of dry tetrahydrofuran was dissolved 3.31 g (8.94 mmol)of 2-benzyloxymethyl-5-iodo-4-isopropyl-1-methylimidazole (4c), followed by addition of 5.78 ml (9.83 mmol)of n-butyllithium (1.70 M hexane solution)at –70° C. over 30 minutes. Then, after 5 minutes, a solution of 1.56 g (8.91 g)of 3,5-dichlorobenzaldehyde dissolved in 10 ml of dry tetrahydrofuran was added at –70° C. over 30 minutes. After 1 hour, the mixture was left to cool to room temperature, and an aqueous solution of ammonium chloride was added thereto, and extracted with ethyl acetate. The organic layer was washed with saturated brine, dried over anhydrous sodium sulfate, filtered, and the filtrate was concentrated under reduced pressure. The crude product was purified by silica gel chromatography (ethyl acetate/methylene chloride 10:1)to give 1.25 g of [2-benzyloxymethyl-5-isopropyl-3-methyl-3H-imidazol-4-yl]-(3,5-dichlorophenyl)-methanol (56) (yield 33.3%).

1H—NMR (CD$_3$OD—TMS)δ ppm: 1.24 (d, J=8.2 Hz, 6H), 2.94 (m, 1H), 3.38 (s, 3H), 4.49 (s, 2H), 4.55 (s, 2H), 5.99 (s, 1H), 7.21~7.39 (m, 8H)

In 20 ml of methylene chloride was dissolved 1.25 g (2.98 -mmol)of [2-benzyloxymethyl-5-isopropyl-3-methyl-$^3$H-imidazol-4-yl]-(3,5-dichlorophenyl)methanol (56), followed by addition of 1.45 g (11.9 mmol)of 4-(dimethylamino)-pyridine at room temperature. After 5 minutes, 0.49 ml (3.54 mmol)of phenylchlorothionoformate was added at room temperature, and the mixture was stirred. After 2 hours, the reaction mixture was concentrated under reduced pressure, and purified by silica gel chromatography (ethyl acetate-hexane 1:1)to give 1.07 g of 2-benzyloxymethyl-5-(1-(3,5-dichlorophenyl)-1-phenoxythiocarbonyloxy)methyl-4-isopropyl-1-methyl-1H-imidazole (57)(yield 64.6%).

1H—NMR (CDCl$_3$—TMS)δ ppm: 1.24 (d, J=6.0 Hz, 6H), 2.92 (m, 1H), 3.46 (s, 3H), 4.51 (s, 2H), 4.61 (s, 2H), 6.01 (s, 1H), 6.85~7.42 (m, 13H)

In 20 ml of dry toluene was dissolved 1.07 g (1.93 mmol) of 2-benzyloxymethyl-5-[1-(3,5-dichlorophenyl)-1-phenoxythiocarbonyloxy]methyl-4-isopropyl-1-methyl-1H-imidazole (57), followed by addition of 158 mg (0.96 mmol)of α,α'-azobisisobutyronitrile and 1.14 ml (4.24 mmol)of tributyltinhydride at room temperature and the mixture was heated to 85° C. After 5 hours, the reaction mixture was concentrated under reduced pressure, and purified by silica gel chromatography (ethyl acetate-hexane 1:1)to give 470 m of 2-benzyloxymethyl-5-(3,5-dichlorobenzyl)-4-isopropyl-1-methyl-1H-imidazole (58) (yield 60.5%).

$^1$H—NMR (CDCl$_3$—TMS)δ ppm: 1.28. (d, J=6.8 Hz, 6H), 2.90 (m, 1H), 3.31 (s, 3H), 3.88 (s, 2H), 4.52 (s, 2H), 4.63 (s, 2H), 6.94 (s, 2H), 7.22 (s, 1H), 7.30 (s, 5H)

In 3 ml of ethanol was dissolved 470 mg (1.17 mmol)of 2-benzyloxymethyl-5-(3,5-dichlorobenzyl)-4-isopropyl-1-methyl-1H-imidazole (58), followed by addition of 10 ml of concentrated hydrochloric acid (36% aqueous solution), and the mixture was refluxed under heating at 110° C. After 3 hours, the reaction mixture was concentrated under reduced pressure, neutralized with aqueous sodium hydroxide, and extracted with ethyl acetate. The extract was washed with saturated brine, dried over anhydrous sodium sulfate, filtered, and the filtrate was concentrated. To the crude crystals, 5 ml of diethyl ether was added, and filtered to give 350 mg of [5-(3,5-dichlorobenzyl)-4-isopropyl-1-methyl-1H-imidazol-2-yl]methanol (59a)(yield 95.9%).

$^1$H—NMR (CD$_3$OD—TMS)δ ppm: 1.22 (d, J=7.0 Hz, 6H), 2.92 (m, 1H), 3.45 (s, 3H), 4.02 (s, 2H), 4.62 (s, 2H), 7.06 (s, 2H), 7.29 (s, 1H)

In 5 ml of thionyl chloride was dissolved 160 mg (0.51 mmol)of [5-(3,5-dichlorobenzyl)-4-isopropyl-1-methyl-1H-imidazol-2-yl]methanol (59a), and the mixture was stirred at room temperature. After 2 hours, the reaction mixture was concentrated under reduced pressure, and to the residue, 5 ml of dry dimethylformamide and 80 mg (1.23 mmol)of sodium azide were added. The mixture was stirred at room temperature for 3 hours, diluted with water, and extracted with ethyl acetate. The extract was washed with saturated brine, dried over anhydrous sodium sulfate, and filtered. The filtrate was concentrated to give 150 mg of 2-azidomethyl-5-(3,5-dichlorobenzyl)-4-isopropyl-1-methyl-1H-imidazole (60)(yield 87%).

$^1$H—NMR (CDCl$_3$—TMS)δ ppm: 1.27 (d, J=7.0 Hz, 6H), 2.89 (m, 1H), 3.35 (s, 3H), 3.92 (s, 2H), 4.46 (s, 2H), 6.94 (s, 2H), 7.23 (s, 1H)

In 8 ml of ethanol was dissolved 150 mg (0.44 mmol)of 2-azidomethyl-5-(3,5-dichlorobenzyl)-4-isopropyl-1-methyl-1H-imidazole (60), and 50 mg of 10% palladium carbon was added at –20° C. The mixture was stirred at room temperature under a stream of hydrogen. After 4 hours, the reaction mixture was filtered through Celite, and the filtrate was concentrated to give 94 mg of Compound I-101 (yield 68%).

$^1$H—NMR (CDCl$_3$—TMS)δ ppm: 1.24 (d, J=6.6 Hz, 6H), 3.37 (s, 3H), 3.89 (s, 2H), 3.95 (b, 2H), 4.02 (s, 2H), 6.95 (s, 2H), 7.21 (s, 1H)

EXAMPLE 102

Synthesis of [5-(3-chlorobenzyl)-4-isopropyl-1-methyl-1H-imidazol-2-yl]methanol (Compound I-102)

[2-(benzyloxymethyl)-5-isopropyl-3-methyl-3H-imidazol-4-yl]-(3-chlorophenyl)methanol (56')was obtained from (4c)and 3-chlorobenzaldehyde by the same synthetic process as that for (56)in Example 101.

$^1$H—NMR (CDCl$_3$—TMS)δ ppm: 1.23 (d, J=8.2 Hz, 6H), 2.96 (m, 1H), 3.34 (s, 3H), 4.47 (s, 2H), 4.53 (s, 2H), 6.02 (s, 1H), 7.12~7.43 (m, 9H)

2-Benzyloxymethyl-5-(3-chlorobenzyl)-4-isopropyl-1-methyl-1H-imidazole (58')was obtained from (56')by the same synthetic process as that for (58)in Example 101.

$^1$H—NMR (CDCl$_3$—TMS)δ ppm: 1.28 (d, J=6.8 Hz, 6H), 2.91 (m, 1H), 3.30 (s, 3H), 3.90 (s, 2H), 4.52 (s, 2H), 4.63 (s, 2H), 6.90 (m, 1H), 7.20 (m, 2H), 7.30 (m, 5H)

Compound I-102 was obtained from (58')by the same synthetic process as that for (59a)in Example 101. Oil.

$^1$H—NMR (CDCl$_3$—TMS)δ ppm: 1.22 (d, J=7.2 Hz, 6H), 2.95 (m, 1H), 3.43 (s, 3H), 4.01 (s, 2H), 4.61 (s, 2H), 7.00~7.12 (m, 2H), 7.17~7.35 (m, 2H)

EXAMPLE 103

Synthesis of 2-carbamoyloxymethyl-5-(3,5-dichlorobenzyl)- 4-isopropyl-1-methyl-1H-imidazole (Compound I-103)

In 5 ml of dry tetrahydrofuran was dissolved 167 mg (0.53 mmol)of [5-(3,5-dichlorobenzyl)-4-isopropyl-1-methyl-1H-imidazol-2-yl]methanol (59a); 50 μl (0.59 mmol)of chloroacetylisocyanate was added at room temperature, and the mixture was stirred. After 1 hour, the mixture was diluted with water, extracted with ethyl acetate, the extract was washed with saturated brine, dried over anhydrous sodium sulfate, and filtered. The filtrate was concentrated to give 210 mg of 2-N-chloroacetylcarbamoyloxy-methyl-5-(3,5-dichlorobenzyl)-4-isopropyl-1-methyl-1H-imidazole (62) (yield 99%).

$^1$H—NMR (CDCl$_3$—TMS)δ ppm: 1.26 (d, J=6.6 Hz, 6H), 2.90 (m, 1H), 3.39 (s, 3H), 3.92 (s, 2H), 4.44 (s, 2H), 5.26 (s, 2H), 6.94 (s, 2H), 7.25 (s, 1H), 8.55 (b, 1H)

In 20 ml of methanol was dissolved 210 mg (0.53 mmol)of 2-N-chloroacetylcarbamoyloxymethyl-5-(3,5-dichlorobenzyl)-4-isopropyl-1-methyl-1H-imidazole (62), 2 g (30.60 mmol)of zinc was added at room temperature, and the mixture was stirred. After 4 hours, the reaction mixture was filtered through Celite, and the filtrate was concentrated under reduced pressure. The residue was purified by silica gel chromatography (ethyl acetate)to give 85 mg of the target compound (Compound I-103)(yield 45%), $^1$H—NMR (CDCl$_3$—TMS)δ ppm: 1.27 (d, J=4.6 Hz, 6H), 2.90 (m, 1H), 3.36 (s, 3H), 3.91 (s, 2H), 4.85 (b, 2H), 5.17 (s, 2H), 6.95 (s, 2H), 7.23 (s, 1H) Elementary analysis (C$_{16}$H$_{19}$N$_3$O$_2$C$_2$) Calc. (%):C, 53.94: H, 5.38: N, 11.80: Cl, 19.90 Found (%):C, 53.94: H, 5.43: N, 11.59: Cl, 19.66

EXAMPLE 104

Synthesis of 5-(3,5-dimethylphenylsulfinyl)-4-isopropyl-1,2-dimethyl-1H-imidazole (Compound I-104)

In methylene chloride (10 ml)was dissolved 150 mg (0.55 mmol)of 5-(3,5-dimethylphenylthio)-4-isopropyl-1,2-dimethyl-1H-imidazole, followed by addition of 177 mg (0.82 mmol)of 80% metachloroperbenzoic acid under ice-cooling, and the mixture was stirred for 10 minutes. To the reaction mixture, an aqueous solution of sodium thiosulfate and then, an aqueous sodium hydrogen carbonate solution was added, and extracted with methylene chloride. The extract was washed with saturated brine, dried over anhydrous sodium sulfate, filtered, and the filtrate was concentrated under reduced pressure. The residue purified by silica gel chromatography (ethyl acetate), and recrystallized from n-hexane to give 100 mg of Compound I-104 (yield 63%). mp 100–101° C.

$^1$H—NMR (CDCl$_3$—TMS)δ ppm: 1.36 (d, J=7.0 Hz, 3H), 1.37 (d, J=7.0 Hz, 3H), 2.33 (s, 3H), 2.35 (s, 3H), 3.26 (s, 3H), 3.32 (sept, 1H), 7.06 (m, 3H) Elementary analysis (C$_{16}$H$_{22}$N$_2$OS) Calc. (%):C, 66.17: H, 7.58: N, 9.65: S, 11.04 Found (%):C, 65.32: H, 7.63: N, 9.37: S, 10.62

EXAMPLE 105

Synthesis of 5-(3,5-dimethylphenylsulfonyl)-4-isopropyl-1,2-dimethyl-1H-imidazole (Compound I-105)

In methylene chloride (6 ml)was dissolved 60 mg (0.20 mmol)of 5-(3,5-dimethylphenylthio)-4-isopropyl-1,2-dimethyl-1H-imidazole, followed by addition of 223 mg (1.00 mmol)of 80% metachloroperbenzoic acid, and the mixture was stirred at room temperature for 1 hour. To the reaction mixture, an aqueous solution of sodium thiosulfate and then an aqueous solution of sodium hydrogen carbonate were added, and the mixture was extracted with methylene chloride. The extract was washed with saturated brine and dried over anhydrous sodium sulfate, filtered, and the filtrate was concentrated under reduced pressure. The residue purified by silica gel chromatography (ethyl acetate), and recrystallized from n-hexane, to give 24 mg of Compound I-105 (yield 39%), mp 126– 128° C.

$^1$H—NMR (CDCl$_3$—TMS)δ ppm: 129 (d, J=6.8 Hz, 6H), 2.36 (s, 3H), 3.59 (s, 3H), 3.82 (sept, 1H), 7.19 (s, 1H), 7.46 (s, 2H)

EXAMPLE 106

Synthesis of [5-(3,5-dimethylphenylsulfinyl)-4-isopropyl-1-methyl-1H-imidazol-2-yl]methanol (Compound I-106)

Compound I-106 was obtained from Compound I-9 by the same synthetic process as that in Example 104. mp 125° C.

$^1$H—NMR (CDCl$_3$—TMS)δ ppm: 1.29 (d, J=6.8 Hz, 3H), 1.31 (d, J=6.8 Hz, 3H), 2.36 (s, 6H), 3.31 (sept, 1H), 3.42 (s, 3H), 4.50 (br, 1H), 4.63 (s, 2H), 7.09 (m, 3H)

EXAMPLE 107

Synthesis of [5-(3,5-dimethylphenylsulfonyl)-4-isopropyl-1-methyl-1H-imidazol-2-yl]methanol (Compound I-107)

Compound I-107 was obtained from Compound I-9 by the same synthetic process as that in Example 105. mp 180–182° C.

$^1$H—NMR (CDCl$_3$—TMS)δ ppm: 1.16 (d, J=6.8 Hz, 6H), 2.38 (s, 3H), 3.73 (s, 3H), 3.74 (sept, 1H), 4.40 (br, 1H), 4.66 (s, 2H), 7.21 (s, 1H), 7.47 (s, 2H)

EXAMPLE 108

Synthesis of [5-(3,5-dichlorophenylsulfinyl)-4-isopropyl-1-methyl-1H-imidazol-2-yl]methanol (Compound I-108)

Compound I-108 was obtained from Compound I-8 by the same synthetic process as that in Example 104. mp 128–130° C.

$^1$H—NMR (CDCl$_3$—TMS)δ ppm: 1.26 (d, J=5.0 Hz, 3H), 1.28 (d, J=5.0 Hz, 3H), 3.26 (sept, 1H), 3.46 (s, 3H), 4.65 (s, 2H), 7.37 (d, J=1.4 Hz, 2H), 7.46 (t, J=1.4 Hz, 1H) Elementary analysis (C$_{14}$H$_{16}$Cl$_2$N$_2$O$_2$S) Calc. (%):C, 48.42: H, 4.64: N, 8.07: S, 9.23: Cl, 20.42 Found (%):C, 48.27: H, 4.73: N, 7.99: S, 9.23: Cl, 20.60

EXAMPLE 109

Synthesis of [5-(3,5-dichlorophenylsulfonyl)-4-isopropyl-1-methyl-1H-imidazol-2-yl]methanol (Compound I-109)

Compound I-109 was obtained from Compound I-8 by the same synthetic process as that in Example 105. mp 202–204° C.

$^1$H—NMR (CDCl$_3$—TMS)δ ppm: 1.22 (d, J=4.4 Hz, 6H), 3.71 (sept, 1H), 4.69 (s, 2H), 7.56 (t, J=1.2 Hz, 1H), 7.72 (d, J=1.2 Hz, 2H)

EXAMPLE 110

Synthesis of 2-aminomethyl-5-(3,5-dichlorophenylsulfinyl)-4-isopropyl-1-methyl-1H-imidazole (Compound I-110)

Compound I-110 was obtained from Compound I-66 by the same synthetic process as that in Example 104. Oil.

$^1$H—NMR (CDCl$_3$—TMS)δ ppm: 1.36 (d, J=4.6 Hz, 3H), 1.37 (d, J=4.6 Hz, 3H), 3.29 (sept, 1H), 3.38 (s, 3H), 3.88 (s, 2H), 7.38 (d, J=1.2 Hz, 2H), 7.45 (t, J=1.2 Hz, 1H)

EXAMPLE 111

Synthesis of 2-aminomethyl-5-(3,5-dichlorophenylsulfonyl)-4-isopropyl-1-methyl-1H-imidazole (Compound I-111)

Compound I-111 was obtained from Compound I-66 by the same synthetic process as that in Example 105. Oil.

$^1$H—NMR (CDCl$_3$—TMS)δ ppm: 1.15 (d, J=4.4 Hz, 3H), 3.69 (sept, 1H), 3.81 (s, 3H), 4.70 (br, 2H), 7.56 (t, J=1.2 Hz, 1H), 7.71 (d, J=1.2 Hz, 2H)

EXAMPLE 112

Synthesis of 5-(3,5-dichlorophenylsulfinyl)-4-isopropyl-1-methyl-2-trifluoroacetylaminomethyl-1H-imidazole (Compound I-112)

Compound I-112 was obtained from (40c) by the same synthetic process as that in Example 104. Oil.

$^1$H—NMR (CDCl$_3$—TMS)δ ppm: 1.35 (d, J=6.8 Hz, 3H), 1.36 (d, J=6.8 Hz, 3H), 3.29 (sept, 1H), 3.38 (s, 3H), 4.49 (dd, J=5.2, 1.6 Hz, 2H), 7.37 (d, J=1.8 Hz, 2H), 7.47 (t, J=1.8 Hz, 1H)

EXAMPLE 113

Synthesis of [5-(3,5-dichlorophenylsulfinyl)-4-isopropyl-1H-imidazol-2-yl]methanol (Compound I-113)

Compound I-113 was obtained from (12)(R$^1$=H) by the same synthetic process as that in Example 104. mp 217–218° C.

$^1$H—NMR (d$_6$-DMSO—TMS)δ ppm: 1.27 (d, J=7.0 Hz, 3H), 1.32 (d, J=7.0 Hz, 3H), 3.37 (sept, 1H), 4.34 (d, J=5.8 Hz, 2H), 5.46 (t, J=5.8 Hz, 1H), 7.53 (d, J=1.6 Hz, 2H), 7.75 (t, J=1.6 Hz, 1H) Elementary analysis (C$_{13}$H$_{14}$Cl$_2$N$_2$O$_2$S) Calc. (%):C, 46.86: H, 4.23: N, 8.41: S, 9.62: Cl, 21.28 Found (%):C, 46.73: H, 4.34: N, 8.15: S, 9.39: Cl, 21.13

EXAMPLE 114

Synthesis of [5-(3,5-dichlorophenylsulfonyl)-4-isopropyl-1H-imidazol-2-yl]methanol (Compound I-114)

Compound I-114 was obtained from (12)(R$^1$=H) by the same synthetic process as that in Example 105. mp 217° C.

$^1$H—NMR (d$_6$-DMSO—TMS)δ ppm: 1.23 (d, J=6.6 Hz, 6H), 3.75 (m, 1H), 4.39 (d, J=5.6 Hz, 2H), 5.50 (t, J=5.6 Hz, 1H), 7.80 (d, J=1.6 Hz, 2H), 7.98 (t, J=1.6 Hz, 1H), 12.81 (br, 1H) Elementary analysis (C$_{13}$H$_{14}$Cl$_2$N$_2$O$_3$S) Calc. (%):C, 44.71: H, 4.04: N, 8.02: S, 9.18: Cl, 20.30 Found (%):C, 44.94: H, 4.11: N, 7.90: S, 8.91: Cl, 20.12

EXAMPLE 115

Synthesis of 2-carbamoyloxymethyl-5-(3,5-dichlorophenylsulfinyl)-4-isopropyl-1-methyl-1H-imidazole (Compound I-115)

Compound I-115 was obtained from Compound I-41 by the same synthetic process as that in Example 104. m.p. 148–149° C.

$^1$H—NMR (d$_6$-DMSO—TMS)δ ppm: 1.37 (d, J=7.2 Hz, 3H), 1.39 (d, J=7.2 Hz, 3H), 3.31 (sept, 1H), 3.44 (s, 3H), 4.70 (br, 2H), 5.13 (s, 2H), 7.38 (d, J=1.8 Hz, 2H), 7.47 (t, J=1.8 Hz, 1H) Elementary analysis (C$_{15}$H$_{17}$Cl$_2$N$_3$O$_3$S) Calc. (%):C, 46.16: H, 4.39: N, 10.77: S, 8.22: Cl, 18.17 Found (%):C, 45.94: H, 4.45: N, 10.61: S, 8.02: Cl, 18.36

EXAMPLE 116

Synthesis of 1-(p-t-butylbenzyl)-5-(3,5-dichlorophenylthio)-2-hydroxymethyl-4-isopropyl-1H-imidazole hydrochloride (Compound I-116)

In dimethylformamide was dissolved 114 mg of p-t-butylbenzylbromide and 152 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b) was added, followed by addition of 126 mg of potassium carbonate, and the mixture was warmed to 50° C. The mixture was allowed to react for 6 hours. After completion of the reaction, the mixture was diluted with water, extracted with diethyl ether, the extract was dried over anhydrous sodium sulfate, and the solvent was distilled off under reduced pressure. To thus-obtained oil, 5 ml of ethanol and 10 ml of 36% hydrochloric acid were added, and the mixture was stirred at 90° C. for 2 hours. After completion of the reaction, the solvent was distilled off under reduced pressure, the crystals were washed with diethyl ether, filtered, and 220 mg of Compound I-116 was obtained (yield 96%). mp 174–177° C.

$^1$H—NMR (CD$_3$OD—TMS)δ ppm: 1.22 (s, 9H), 1.35 (d, J=7.0 Hz, 6H), 3.30 (sept, 1H), 5.02 (s, 2H), 5.44 (s, 2H), 6.72 (d, J=1.8 Hz, 2H), 7.05~7.25 (m, 5H)

EXAMPLE 117

Synthesis of 1-(p-N-acetylaminobenzyl)-5-(3,5-dichlorophenylthio)-2-hydroxymethyl-4-isopropyl-1H-imidazole (Compound I-117)

In dimethylformamide was added 118 mg of p-nitrobenzylbromide and 114 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b) was added, followed by addition of 76 mg of potassium carbonate. At the beginning, the reaction mixture was green, and soon it disappeared. Then, the mixture was warmed to 50° C. and was allowed to react for 3 hours. After completion of the reaction, the mixture was diluted with water, extracted with diethyl ether, the extract was dried over sodium sulfate, and the solvent was distilled off under reduced pressure. To thus-obtained oil, 5 ml of ethanol and 10 ml of 36% hydrochloric acid were added, and the mixture was stirred at 90° C. for 2 hours. After completion of the reaction, the solvent was distilled off under reduced pressure. To the residue, an aqueous sodium hydrogen carbonate solution was added, extracted with ethyl acetate, the extract was dried over sodium sulfate, and the solvent was distilled off under reduced pressure. The crystals were washed with diethyl ether, filtered, and 150 mg of 5-(3,5-dichlorophenylthio)-2-hydroxymethyl-4-isopropyl-1-(p-nitrobenzyl)-1H-imidazole (103a) was obtained (yield 73%). mp 192–194° C.

$^1$H—NMR (CD$_3$OD—TMS)δ ppm: 1.25 (d, J=7.0 Hz, 6H), 3.12 (sept, 1H), 4.79 (s, 2H), 5.47 (s, 2H), 6.58 (d, J=2.0 Hz, 2H), 6.99 (d, 1H), 7.32 (d, J=9.0 Hz, 2H), 7.96 (d, J=9.0 Hz, 2H)

In ethyl acetate was dissolved 800 mg of 5-(3,5-dichlorophenylthio)-2-hydroxymethyl-4-isopropyl-1-(p-nitrobenzyl)-1H-imidazole (103a), and platinum sulfided carbon was added. After replacement with hydrogen atomsphere, the mixture was catalytically hydrogenated under atmospheric pressure at room temperatures After 1 hour, the mixture was filtered through Celite, the filtrate was distilled off under reduced pressure, and to the residue, diethyl ether was added. The precipitated crystals were filtered, and 579 mg of 1-(p-aminobenzyl)-5-(3,5-dichlorophenylthio)-2-hydroxymethyl-4-isopropyl-1H-imidazole (104a)was obtained (yield 78%). mp 130° C. (decomp.)

$^1$H—NMR (CDCl$_3$—TMS)δ ppm: 1.19 (d, J=7.0 Hz, 6H), 3.08 (sept, 1H), 4.28 (br, 2H), 4.75 (s, 2H), 5.12 (s, 2H), 6.43 (d, J=8.2 Hz, 2H), 6.60 (d, 2H), 6.80 (d, J=8.2 Hz, 2H), 7.00 (d, 1H)

In methylene chloride was dissolved 200 mg of 1-(p-aminobenzyl)-5-(3,5-dichlorophenylthio)-2-hydroxymethyl-4-isopropyl-1H-imidazole (104a), there were added 116 mg of dimethylaminopyridine and 212 μl of acetic anhydride under ice-cooling, and the mixture was allowed to warm up to room temperature and stirred for 1 hour. After completion of the reaction, the mixture was diluted with water, extracted with methylene chloride, the extract was dried over sodium sulfate, and the solvent was distilled off under reduced pressure. The residue was purified by silica gel chromatography (methylene chloride:ethyl acetate=2:1)to provide 2-acetoxymethyl-1-(p-N-acetylaminobenzyl)-5-(3,5-dichlorophenylthio)-4-isopropyl-1H-imidazole. The compound was dissolved in 10 ml of methanol, and under ice-cooling, 1 ml of 1M sodium methoxide solution was added. The mixture was allowed to warm up to room temperature and stirred for 1 hour. After completion of the reaction, the solvent was distilled off under reduced pressure, and 41.2 mg of Compound I-117 was obtained (yield 19%).

$^1$H—NMR (CDCl$_3$—TMS)δ ppm: 1.22 (d, J=7.0 Hz, 6H), 2.16 (s, 3H), 3.10 (sept, 1H), 4.72 (s, 2H), 5.19 (s, 2H), 6.62 (d, J=1.8 Hz, 2H), 6.87~7.38 (m, 5H)

EXAMPLE 118

Synthesis of 1-(m-aminobenzyl)-5-(3,5-dichlorophenylthio)-2-hydroxymethyl-4-isopropyl-1H-imidazole (Compound I-118).

To dimethylformamide was added 94 mg of m-nitrobenzyl chloride and 114 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b)was added, followed by addition of 76 mg of potassium carbonate. Then, the mixture was warmed up to 50° C. and allowed to react for 6 hours. After completion of the reaction, the mixture was diluted with water, extracted with diethyl ether, the extract was dried over sodium sulfate, and the solvent was distilled off under reduced pressure. To thus-obtained oil, 5 ml of ethanol and 10 ml of 36% hydrochloric acid were added, and the mixture was stirred at 90° C. for 2 hours. After completion of the reaction, the solvent was distilled off under reduced pressure, an aqueous sodium hydrogen carbonate solution and ethyl acetate were added. Insoluble materials in both layers were filtered to give 72 mg of 5-(3,5-dichlorophenylthio)-2-hydroxymethyl-4-isopropyl-1-(m-nitrobenzyl)-1H-imidazole hydrochloride. The ethyl acetate layer of the filtrate was dried over sodium sulfate, and the solvent was distilled off under reduced pressure. The crystals were washed with diethyl ether, filtered, and 80 mg of 5-(3,5-dichlorophenylthio)-2-hydroxymethyl-4-isopropyl-1-(m-nitrobenzyl)-1H-imidazole (103b)was obtained (yield 71%).

103b, mp 197–198° C.

$^1$H—NMR (CD$_3$OD—TMS)δ ppm: 1.25 (d, J=7.0 Hz, 6H), 3.10 (sept, 1H), 4.81 (s, 2H), 5.47 (s, 2H), 6.53 (d, J=1.8 Hz, 2H), 6.99 (d, 1H), 7.32 (d, 1H), 7.59 (d, 1H), 7.89 (d, 1H), 8.00 (s, 1H)

The hydrochloride of 103b $^1$H—NMR (CD$_3$OD—TMS)δ ppm: 1.37 (d, J=7.0 Hz, 6H), 3.36 (sept, 1H), 5.06 (s, 2H), 5.64 (s, 2H), 6.68 (d, J=1.6 Hz, 2H), 7.12 (d, J=1.6 Hz, 1H), 7.45 (d, J=8.2 Hz, 1H), 7.63 (d, 1H), 7.99 (d, 1H), 8.07 (s, 1H) Elementary analysis (C$_{20}$H$_{19}$Cl$_2$N$_3$O$_3$S.HCl.1.1H$_2$O) Calc. (%):C, 47.23; H, 4.40; N, 8.26; Cl, 20.91; S, 6.30 Found (%):C, 47.06; H, 4.42; N, 8.37; Cl, 20.98; S, 6.49

In ethyl acetate was dissolved 64 mg of 5-(3,5-dichlorophenylthio)-2-hydroxymethyl-4-isopropyl-1-(m-nitrobenzyl)-1H-imidazole (103b), and platinum sulfided carbon was added. After replacement with hydrogen atomosphere, the mixture was catalytically hydrogenated under atmospheric pressure at room temperature. After 3 hours, the mixture was filtered through Celite, the filtrate was distilled off under reduced pressure, and diethyl ether was added. Crystals precipitated were filtered, and 25 mg of Compound I-118 was obtained (yield 42%). mp 145–148° C.

$^1$H—NMR (CDCl$_3$—TMS)δ ppm: 1.22 (d, J=7.0 Hz, 6H), 3.11 (sept, 1H), 4.71 (s, 2H), 5.13. (s, 2H), 6.21 (s, 1H), 6.32~6.50 (m, 2H), 6.68 (d, J=1.8 Hz, 2H), 6.96 (m, 1H), 7.01 (d, J=1.8 Hz, 1H)

EXAMPLE 119

Synthesis of 1-(o-aminobenzyl)-5-(3,5-dichlorophenylthio)-2-hydroxymethyl-4-isopropyl-1H-imidazole (Compound I-119).

To dimethylformamide was added 237 mg of o-nitrobenzyl chloride and 228 mg of potassium iodide under ice-cooling, the mixture was allowed to warm up to room temperature and stirred for 20 minutes. Then, 400 mg of 5-(3,5-dichlorophenylthio)-4-isopropyl-2-(p-methoxybenzyloxymethyl)-1H-imidazole (101b)was added, followed by addition of 152 mg of potassium carbonate. Then, the mixture was warmed up to 50° C., and allowed to react for 6 hours. After completion of the reaction, the mixture was diluted with water, extracted with diethyl ether, the extract was dried over sodium sulfate, and the solvent was distilled off under reduced pressure. To thus-obtained oil were added 10 ml of ethanol and 20 ml of 36% hydrochloric acid, and the mixture was stirred at 90° C. for 2 hours. After completion of the reaction, the solvent was distilled off under reduced pressure, an aqueous sodium hydrogen carbonate solution was added, extracted with ethyl acetate, the extract was dried over sodium sulfate, and the solvent was distilled off under reduced pressure. The crystals were washed with diethyl ether, filtered, and 195 mg of 5-(3,5-dichlorophenylthio)-2-hydroxymethyl-4-isopropyl-1-(o-nitrobenzyl)-1H-imidazole (103c)was obtained (yield 47%). mp 160–166° C.

$^1$H—NMR (CDCl$_3$—TMS)δ ppm: 1.31 (d, J=6.6 Hz, 6H), 3.19 (sept, 1H), 4.75 (s, 2H), 5.65 (s, 2H), 6.51 (d, 1H), 6.70 (d, J=1.6 Hz, 2H), 7.00 (d, J=1.6 Hz, 1H), 7.37 (m, 2H), 8.03 (d, 1H) Elementary analysis (C$_{20}$H$_{19}$Cl$_2$N$_3$O$_3$S) Calc.

(%):C, 53.10; H, 4.23; N, 9.29; Cl, 15.67; S, 7.09 Found (%):C, 53.03; H, 4.44; N, 9.38; Cl, 15.38; S, 6.99

In ethyl acetate was dissolved 170 mg of 5-(3,5-dichlorophenylthio)-2-hydroxymethyl-4-isopropyl-1-(o-nitrobenzyl)-1H-imidazole (103c), platinum sulfided carbon was added. After replacement with hydrogen atomosphere, catalytic hydrogenation was performed at atmospheric pressure at room temperature. After 1 hour, the mixture was filtered through Celite, and the filtrate was distilled off under reduced pressure To the residue, diethyl ether was added, the precipitated crystals were collected by filtration, and 77 mg of Compound I-119 was obtained (yield 49%).

$^1$H—NMR (CDCl$_3$—TMS)δ ppm: 1.24 (d, J=6.6 Hz, 6H), 3.12 (sept, 1H), 4.63 (s, 2H), 5.20 (s, 2H), 6.50~7.25 (m, 4H), 6.66 (d, 2H), 6.96 (d, 1H)

EXAMPLE 120

Synthesis of 5-(3,5-dichlorophenylthio)-2-hydroxymethyl-4-isopropyl-1-(1-naphthylmethyl)-1H-imidazole hydrochloride (Compound I-120).

To dimethylformamide was added 89 mg of 1-(chloromethyl)naphthalene and 152 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b)was added, followed by addition of 126 mg of potassium carbonate. The mixture was warmed up to 50° C. and allowed to react for 6 hours. After completion of the reaction, the mixture was diluted with water, and extracted with diethyl ether. The extract was dried over sodium sulfate, and the solvent was distilled off under reduced pressure. To thus-obtained oil, 5 ml of ethanol and 10 ml of 36% hydrochloric acid were added, and the mixture was stirred at 90° C. for 2 hours. After completion of the reaction, the solvent was distilled off under reduced pressure. The crystals were washed with diethyl ether, filtered, and 220 mg of Compound I-120 was obtained (yield 97%). mp 135–140° C.

$^1$H—NMR (CD$_3$OD—TMS)δ ppm: 1.42 (d, J=7.2 Hz, 6H), 3.43 (sept, 1H), 4.98 (s, 2H), 5.99 (s, 2H), 6.57 (d, J=1.8Hz, 2H), 6.78 (d, 1H), 7.03 (d, J=1.8 Hz, 1H), 7.25 (t, 1H), 7.45~7.78 (m, 3H), 7.85 (d, 1H), 8.13 (d, 1H)

EXAMPLE 121

Synthesis of 5-(3,5-dichlorophenylthio)-2-hydroxymethyl-4-isopropyl-1-(2-phenylethyl)-1H-imidazole (Compound I-121).

To dry tetrahydrofuran was added 44 mg of powdery sodium hydroxide and 30 mg of tetrabutylammonium bromide under ice-cooling, and after 10 minutes, 200 mg of 5-(3,5-dichlorophenylthio)-4-isopropyl-2-(p-methoxybenzyloxymethyl)-1H-imidazole (101b)was added. After 20 minutes, to the mixture, 129 μl of 1-bromo-2-phenylethane was added. After stirred at room temperature for 3 hours, the mixture was diluted with water, extracted with diethyl ether, the extract was dried over sodium sulfate, and the solvent was distilled off under reduced pressure. To thus-obtained oil, 10 ml of ethanol and 20 ml of 36% hydrochloric acid were added, and the mixture was stirred at 90° C. for 2 hours. After completion of the reaction, the solvent was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (hexane:ethyl acetate=1:1)to give 100 mg of Compound I-121 (yield 52%).

$^1$H—NMR (CDCl$_3$—TMS)δ ppm: 1.19 (d, J=7.0 Hz, 6H), 2.88 (m, 2H), 3.05 (sept, 1H), 4.19 (m, 2H), 4.89 (s, 2H), 6.84 (d, J=1.8 Hz, 2H), 6.98~7.39 (m, 5H), 7.12 (d, J=1.8 Hz, 1H) Elementary analysis (C$_{21}$H$_{22}$Cl$_2$N$_2$OS) Calc. (%):C, 59.86; H, 5.26; N, 6.65; Cl, 16.83; S, 7.61 Found (%):C, 59.93; H, 5.52; N, 6.54; Cl, 16.00; S, 7.38

EXAMPLE 122

Synthesis of 5-(3,5-dichlorophenylthio)-2-hydroxymethyl-4-isopropyl-1-(3-phenylpropyl)-1H-imidazole (Compound I-122).

To dry tetrahydrofuran was added 40 mg of 60% sodium hydride, and under ice-cooling, 200 mg of 5-(3,5-dichlorophenylthio)-4-isopropyl-2-(p-methoxybenzyloxymethyl)-1H-imidazole (101b)was added. After 20 minutes, 136 μl of 1-bromo-3-phenylpropane was added. After stirred at room temperature for 3 hours, the mixture was diluted with water and extracted with diethyl ether. The extract was dried over sodium sulfate, and the solvent was distilled off under reduced pressure. To thus-obtained oil were added 10 ml of ethanol and 20 ml of 36% hydrochloric acid, and the mixture was stirred at 90° C. for 2 hours. After completion of the reaction, the solvent was distilled off under reduced pressure, an aqueous sodium hydrogen carbonate solution was added, and extracted with ethyl acetate. The extract was dried over sodium sulfate, and the solvent was distilled off under reduced pressure. The residue was purified by silica gel chromatography (hexane:ethyl acetate=1:1)to give 80 mg of Compound I-122 (yield 40%).

$^1$H—NMR (CDCl$_3$—TMS)δ ppm: 1.19 (d, J=6.6 Hz, 6H), 1.93 (m, 2H), 2.61 (m, 2H), 3.05 (sept, 1H), 3.92 (m, 2H), 4.68 (s, 2H), 6.75 (d, J=1.8 Hz, 2H), 7.01~7.36 (m, 6H) Elementary analysis (C$_{22}$H$_{24}$Cl$_2$N$_2$OS) Calc. (%):C, 60.69; H, 5.56; N, 6.43; Cl, 16.28; S, 7.36 Found (%):C, 60.57; H, 5.64; N, 6.41; Cl, 16.01; S, 7.43

EXAMPLE 123

Synthesis of 5-(3,5-dichlorophenylthio)-2-hydroxymethyl-4-isopropyl-1-(4-phenylbutyl)-1H-imidazole (Compound I-123).

To dimethylformamide was added 85 mg of 1-chloro-4-phenylbutane and 152 mg of potassium iodide under ice-cooling, the mixture was allowed to warm up to room temperature and stirred for 20 minutes. Then 200 mg of 5-(3,5-dichlorophenylthio)-4-isopropyl-2-(p-methoxybenzyloxymethyl)-1H-imidazole (101b)was added, followed by addition of 126 mg of potassium carbonate. Then, the mixture was warmed up to 50° C. and allowed to react for 6 hours. After completion of the reaction, the mixture was diluted with water, extracted with diethyl ether, the extract was dried over sodium sulfate, and the solvent was distilled off under reduced pressure. To thus-obtained oil were added 10 ml of ethanol and 20 ml of 36% hydrochloric acid, and the mixture was stirred at 90° C. for 2 hours. After completion of the reaction, the solvent was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (hexane: ethyl acetate=1:1)to give 86 mg of Compound I-123 (yield 42%).

¹H—NMR (CDCl₃—TMS)δ ppm: 1.15 (d, J=6.6 Hz, 6H), 1.61 (m, 4H), 2.54 (m, 2H), 3.03 (sept, 1H), 3.98 (m, 2H), 4.71 (s, 2H), 6.78 (s, 2H), 7.01~7.39 (m, 6H)

EXAMPLE 124

Synthesis of 5-(3,5-dichlorophenylthio)-2-hydroxymethyl-4-isopropyl-1-(5-phenylpentyl)-1H-imidazole (Compound I-124).

To dimethylformamide was added 92 mg of 1-chloro-5-phenylpentane and 152 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b)was added, followed by addition of 126 mg of potassium carbonate. Then the mixture was warmed up to 50° C. and allowed to react for 6 hours. After completion of the reaction, the mixture was diluted with water, extracted with diethyl ether, the extract was dried over sodium sulfate, and the solvent was distilled off under reduced pressure. To thus-obtained oil were added 10 ml of ethanol and 20 ml of 36% hydrochloric acid, and the mixture was stirred at 90° C. for 2 hours. After completion of the reaction, the solvent was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (hexane:ethyl acetate=1:1)to give 120 mg of Compound I-124 (yield 57%).

¹H—NMR (CDCl₃—TMS)δ ppm: 1.16 (d, J=7.0 Hz, 6H), 1.30 (m, 2H), 1.58 (m, 4H), 2.53 (m, 2H), 3.05 (sept, 1H), 3.96 (m, 2H), 4.74 (s, 2H), 6.80 (d, J=1.8 Hz, 2H), 7.07~7.34 (m, 6H)

EXAMPLE 125

Synthesis of 5-(3,5-dichlorophenylthio)-2-hydroxymethyl-4-isopropyl-1-(6-phenylhexyl)-1H-imidazole (Compound I-125)

To dimethylformamide was added 99 mg of 1-chloro-6-phenylhexane and 152 mg of potassium iodide under ice-cooling, the mixture was allowed to warm up to room temperature and stirred for 20 minutes. Then, 200 mg of 5-(3,5 -dichlorophenylthio)-4-isopropyl-2-(p-methoxybenzyloxymethyl)-1H-imidazole (101b)was added, followed by addition of 126 mg of potassium carbonate. Then, the mixture was warmed up to 50° C. and allowed to react for 6 hours. After completion of the reaction, the mixture was diluted with water, extracted with diethyl ether, the extract was dried over sodium sulfate, and the solvent was distilled off under reduced pressure. To thus-obtained oil were added 10 ml of ethanol and 20 ml of 36% hydrochloric acid, and the mixture was stirred at 90° C. for 2 hours. After completion of the reaction, the solvent was distilled off under reduced pressure, an aqueous sodium hydrogen carbonate solution was added, and extracted with ethyl acetate. The extract was dried over sodium sulfate, and the solvent was distilled off under reduced pressure. The residue was purified by silica gel chromatography (hexane:ethyl acetate=1:1)to give 81 mg of Compound I-125 (yield 37%).

¹H—NMR (CDCl₃—TMS)δ ppm: 1.17 (d, J=7.0 Hz, 6H), 1.26 (m, 4H), 1.53 (m, 4H), 2.52 (m, 2H), 3.05 (sept, 1H), 3.92 (m, 2H), 4.73 (s, 2H), 6.80 (d, J=1.6 Hz, 2H), 7.03~7.34 (m, 6H)

EXAMPLE 126

Synthesis of 5-(3,5-dichlorophenylthio)-2-hydroxymethyl-4-isopropyl-1-(2-thienylmethyl)-1H-imidazole hydrochloride (Compound I-126).

To dimethylformamide was added 67 mg of 2-(chloromethyl)thiophene and 152 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b)was added, followed by addition of 126 mg of potassium carbonate. Then, the mixture was warmed up to 50° C., and allowed to react for 6 hours. After completion of the reaction, the mixture was diluted with water, extracted with diethyl ether, the extract was dried over sodium sulfate, and the solvent was distilled off under reduced pressure. To thus-obtained oil were added 5 ml of ethanol and 10 ml of 36% hydrochloric acid, and the mixture was stirred at 90° C. for 2 hours. After completion of the reaction, the solvent was distilled off under reduced pressure. The crystals were washed with diethyl ether, filtered, and 170 mg of Compound I-126 was obtained (yield 83%).

¹H—NMR (CD₃OD—TMS)δ ppm: 1.32 (d, J=7.0 Hz, 6H), 3.32 (sept, 1H), 5.04 (s, 2H), 5.68 (s, 2H), 6.80 (m, 1H), 6.86 (d, 2H), 7.05 (m, 1H), 7.26 (m, 1H), 7.32 (m, 1H)

EXAMPLE 127

Synthesis of 5-(3,5-dichlorophenylthio)-2-hydroxymethyl-4-isopropyl-1-(3-thienylmethyl)-1H-imidazole hydrochloride (Compound I-127).

In dimethylformamide was added 67 mg of 3-(chloromethyl)thiophene and 152 mg of potassium iodide under ice-cooling, the mixture was allowed to warm up to room temperature and stirred for 20 minutes. Then, 200 mg of 5-(3,5-dichlorophenylthio)-4-isopropyl-2-(p-methoxybenzyloxymethyl)-1H-imidazole (101b)was added, followed by addition of 126 mg of potassium carbonate. Then the mixture was warmed up to 50° C. and allowed to react for 6 hours. After completion of the reaction, the mixture was diluted with water, extracted with diethyl ether, the extract was dried over sodium sulfate, and the solvent was distilled off under reduced pressure. To thus-obtained oil was added 5 ml of ethanol and 10 ml of 36% hydrochloric acid, and the mixture was stirred at 90° C. for 2 hours. After completion of the reaction, the solvent was distilled off under reduced pressure. The crystals were washed with diethyl ether, filtered, and 200 mg of Compound I-127 was obtained (yield 97%).

¹H—NMR (CD₃OD—TMS)δ ppm: 1.33 (d, J=7.0 Hz, 6H), 3.32 (sept, 1H), 5.01 (s, 2H), 5.49 (s, 2H), 6.82 (d, J=1.8 Hz, 2H), 7.01 (m, 1H), 7.23 (d, J=1.8 Hz, 1H), 7.25~7.40 (m, 2H)

EXAMPLE 128

Synthesis of 2-carbamoyloxymethyl-5-(3,5-dichlorophenylthio)-4-isopropyl-1-(quinolin-3-ylmethyl)-1H-imidazole (Compound I-128).

In tetrahydrofuran (10 ml)was dissolved 245 mg (2 mmol) of 2-benzyloxymethyl-5-(3,5-dichlorophenylthio)-4-isopropyl-1H-imidazole (101a). To this solution, a methylene chloride solution of quinolin-3-ylmethylbromide was added at room temperature with stirring, followed by addition of 200 mg (5 mmol)of sodium hydroxide and 39 mg (0.12 mmol)of n-tetrabutylammonium bromide. After stirring for 2 hours, the mixture was left overnight and worked up. The reaction mixture was distilled off under reduced pressure. The residue was extracted with methylene chloride, and the extract was washed with water and dried. The solvent was distilled off, and the residual oil was purified by silica gel column chromatography (methylene chloride-ethyl acetate). As the first eluate, 26 g (2.6%)of 2-benzyloxymethyl-4-(3,5-dichlorophenylthio)-5-isopropyl-1-(quinolin-3-ylmethyl)-1H-imidazole (100a)was obtained. From the subsequent eluate, 730 mg of 2-benzyloxymethyl-5-(3,5-dichlorophenylthio)-4-isopropyl-1-(quinolin-3-ylmethyl)-1H-imidazole (100b) suited to the next step of the reaction was obtained (yield 73%). mp 95–98° C.

$^1$H—NMR (CDCl$_3$)δ ppm: (100a)1.29 (d, J=6.8 Hz, 6H), 3.05~3.2 (m, 2H), 4.60 (s, 2H), 4.74 (s, 2H), 5.35 (s, 2H), 6.5 (d, J=1.6 Hz, 2H), 6.59 (t, J=1.8 Hz, 1H), 7.5~7.75 (m, 4H), 8.91 (d, J=9.8 Hz, 1H), 8.7 (d, J=2.2 Hz)

(100b)1.18 (d, J=7.2 Hz, 6H), 2.9~3.2 (m, 1H), 4.52 (s, 2H) 4.63 (s, 2H), 5.47 (s, 2H), 6.99 (d, J=1.6 Hz, 2H), 7.09 (t, J=2 Hz, 1H), 7.46–7.58 (m, 2H), 7.67–7.68 (m, 2H), 8.11 (d, J=8.2 Hz, 2H), 8.76 (d, J=2.4 Hz, 1H)

In 10 ml of c-HCl was dissolved 730 mg (1.36 mmol)of 2-benzyloxymethyl-5-(3,5-dichlorophenylthio)-4-isopropyl-1-(quinolin-3-ylmethyl)-1H-imidazole (100b); the mixture was refluxed with heating for 1 hour, and worked up. To the reaction mixture, a saturated aqueous sodium hydrogen carbonate solution was added, extracted with methylene chloride, the extract was washed with water and dried, and the solvent was distilled off under reduced pressure. The residue was purified by silica gel column chromatography (ethyl acetate)to give 500 mg of 2-hydroxymethyl-5-(3,5-dichlorophenylthio)-4-isopropyl-1-(quinolin-3-ylmethyl)-1H-imidazole (109)(yield 83%). mp 174–175° C.

$^1$H—NMR (CDCl$_3$)δ ppm: 1.26 (d, J=6.8 Hz, 6H), 3.0~3.2 (m, 1H), 2.6~3.8 (br, 1H), 4.87 (s, 2H), 5.44 (s, 2H), 6.52 (d, J=1.8 Hz, 2H), 6.61 (t, J=2 Hz, 1H), 7.47–7.72 (m, 4H), 8.04 (d, J=9 Hz, 4H), 8.77 (d, J=2 Hz, 1H) Elementary analysis (C$_{23}$H$_{21}$N$_3$Cl$_2$OS) Calc. (%):C, 60.26; H, 4.62; N, 9.17; Cl, 15.47; S, 6.99. Found (%):C, 59.98; H, 4.73; N, 9.08; Cl, 15.11; S, 7.10.

In 5 ml of tetrahydrofuran was dissolved 223 mg (0.50 mmol)of 2-hydroxymethyl-5-(3,5-dichlorophenylthio)-4-isopropyl-1-(quinolin-3-ylmethyl)-1H-imidazole (109), followed by dropwise addition of 72 mg (0.60 mmol)of chloroacetylisocyanate with stirring at 0° C., and the mixture was stirred at room temperature for 30 minutes. After the reaction completion, the mixture was worked up. To the reaction mixture was added a saturated aqueous sodium bicarbonate solution, extracted with methylene chloride, the extract was washed with water and dried. The-solvent was distilled off under reduced pressure, and 2-chloroacetylcarbamoyloxymethyl-5-(3,5-dichlorophenylthio)-4-isopropyl-1-(quinolin-3-ylmethyl)-1H-imidazole (110) suited to the next step of the reaction was obtained. mp 167–170° C. The crystals were dissolved in 20 ml of aqueous methanol, 40 mg of Zn powder was added, and the mixture was stirred at room temperature for 5 hours. After the reaction completion, the mixture was worked up. To the reaction mixture was added a saturated aqueous sodium hydrogen carbonate solution, and the insoluble material was removed by filtration under reduced pressure through Celite. The filtrate was concentrated, extracted with methylene chloride, the extract was washed with water and dried, and the solvent was distilled off. The residual crystals were washed with ethyl acetate and ether to give 195 mg of Compound I-128 (yield 78%). mp 214–216° C.

$^1$H—NMR (CDCl$_3$)δ ppm: (110)1.81 (d, J=6.8 Hz, 6H), 3.1~3.23 (m, 1H), 4.21 (s, 2H), 5.37 (s, 2H), 5.45 (s, 2H), 6.60 (d, J=2 Hz, 2H), 6.73 (t, J=1.6 Hz), 7.26~7.73 (m, 4H), 8.15, (d, J=7.8 Hz, 1H), 8.12 (br, 1H), 8.62 (d, J=2.4 Hz)

Compound I-128 1.30 (d, J=7 Hz, 6H), 3.1~3.2 (m, 1H), 4.6 (br, 2H), 5.33 (s, 2H), 5.43 (s, 2H), 6.52 (d, J=2 Hz, 2H), 6.59 (d, J=1.8 Hz), 7.49~7.69 (m, 4H), 8.00 (d, J=8.8 Hz, 1H), 8.67 (d, J=2.6 Hz) Elementary analysis (C$_{24}$H$_{22}$N$_4$Cl$_2$O$_2$S) Calc. (%):C, 57.74; H, 4.42; N, 11.17; S, 6.39; Cl, 14.14 Found (%):C, 57.30; H, 4.50; N, 11.08; S, 6.59; Cl, 13.92

EXAMPLE 129

Synthesis of 2-carbamoyloxymethyl-5-(3,5-dichlorophenylthio)-4-isopropyl-1-(2-(2-pyridyl)ethyl)-1H-imidazole (Compound I-129).

In 10 ml of methylene chloride was dissolved 2 g of 2-pyridylethanol, the mixture was cooled to −40° C. on a dry-ice bath, and 2.5 ml of thionyl bromide was added. The mixture was allowed to warm up, and after 10 minutes, stirred at 60° C. After 30 minutes, the mixture was cooled and evaporated under reduced pressure. The residue was added to a tetrahydrofuran solution containing 3.6 g of 5-(3,5-dichlorophenylthio)-4-isopropyl-2-(p-methoxybenzyloxymethyl)-imidazole (101b), 650 mg of powdery sodium hydroxide and 262 mg of tetrabutylammonium bromide under ice-cooling. The temperature was raised up to room temperature, and powdery sodium hydroxide was further added to make alkaline. After 5 hours, the mixture was diluted with water, extracted with diethyl ether, the extract was dried over sodium sulfate, and the solvent was distilled off under reduced pressure. The residue was purified by silica gel chromatography (hexane:ethyl acetate= 2:1)to give 1.9 g of 5-(3,5-dichlorophenylthio)-4-isopropyl-2-(p-methoxybenzyloxymethyl)-1-(2-(2-pyridyl)ethyl)-1H-imidazole (yield 43%).

$^1$H—NMR (CDCl$_3$—TMS)δ ppm: 1.25 (d, J=7.0 Hz, 6H), 3.08 (m, 3H), 3.79 (s, 3H), 4.36 (m, 2H), 4.48 (s, 4H), 6.72–6.95 (m, 5H), 7.07–7.16 (m, 2H), 7.17–7.30 (m, 2H), 7.50 (m, 1H), 8.52 (m, 1H)

To 1.43 g of 5-(3,5-dichlorophenylthio)-4-isopropyl-2-(p-methoxybenzyloxymethyl)-1-(2-(2-pyridyl)ethyl)-1H-imidazole was added 20 ml of ethanol and 40 ml of 36% hydrochloric acid, and the mixture was stirred at 90° C. for 2 hours. After completion of the reaction, the solvent was distilled off under reduced pressure, an aqueous sodium hydrogen carbonate solution was added, and extracted with ethyl acetate. The extract was dried over sodium sulfate, and the solvent was distilled off under reduced pressure. The residue was purified by silica gel chromatography (ethyl acetate:methanol=10:1)to give 571 mg of 5-(3,5-dichlorophenylthio)-4-isopropyl-2-hydroxymethyl-1-(2-(2-pyridyl)ethyl)-1H-imidazole (112a)(yield 51%).

$^1$H—NMR (CDCl$_3$—TMS)δ ppm: 1.29 (d, J=6.8 Hz, 6H), 3.15 (m, 3H), 4.52 (m, 2H), 4.76 (s, 2H), 6.87 (d, 2H), 6.80–7.40 (m, 3H), 7.60 (m, 1H), 8.50 (m, 1H) Elementary analysis (C$_{20}$H$_{21}$Cl$_2$N$_3$OS) Calc. (%):C, 56.87; H, 5.01; N, 9.95; Cl, 16.79; S, 7.59 Found (%):C, 56.58; H, 5.13; N, 9.90; Cl, 16.65; S, 7.53

In 20 ml of tetrahydrofuran was dissolved 521 mg of 5-(3,5-dichlorophenylthio)-4-isopropyl-2-hydroxymethyl-1-(2-pyridylethyl)-1H-imidazole (112a,), and the mixture was cooled to −40° C. Under stirring, 221 μl of trichloroacetylisocyanate was added, the mixture was allowed to stand to reach room temperature, and stirred for 30 minutes. Added was 500 μl of triethylamine, 5 ml of water and 5 ml of methanol, and the mixture was stirred at 70° C. for 1 hour. After completion of the reaction, the solvent was distilled off under reduced pressure, an aqueous sodium hydrogen carbonate solution was added, and extracted with ethyl acetate. The extract was dried over sodium sulfate, and the solvent was distilled off under reduced pressure. The residue was purified by silica gel column chromatography (ethyl acetate:methanol=10:1)to give 520 mg of Compound I-129 (yield 91%).

$^1$H—NMR (CDCl$_3$—TMS)δ ppm: 1.25 (d, J=7.0 Hz, 6H), 3.08 (m, 3H), 4.35 (m, 2H), 5.11 (s, 2H), 5.31 (br, 2H), 6.84 (d, 2H), 6.94 (m, 1H), 7.13 (d, 1H), 7.18 (m, 1H), 7.60 (m, 1H), 8.51 (m, 1H)

EXAMPLE 130

Synthesis of 2-carbamoyloxymethyl-5-(3,5-dichlorophenylthio)-4-isopropyl-1-(3-(2-pyridyl)propyl)-1H-imidazole (Compound I-130).

In 20 ml of methylene chloride was dissolved 500 mg of 2-pyridinepropanol, the mixture was cooled to −40° C. on a dry-ice bath, and 564 μl of thionyl bromide was added. The mixture was allowed to warm up, and after 10 minutes, stirred at 60° C. After 30 minutes, the mixture was cooled, the solution was distilled off under reduced pressure. The residue was added to tetrahydrofuran solution containing 891 mg of 2-benzyloxymethyl-5-(3,5-dichlorophenylthio)-4-isopropylimidazole (101a), 365 mg of powdery sodium hydroxide and 118 mg of tetrabutylammonium bromide under ice-cooling. The temperature was raised up to room temperature, and powdery, sodium hydroxide was further added to make alkaline. After 5 hours, the mixture was diluted with water, extracted with diethyl ether, the extract was dried over sodium sulfate, and the solvent was distilled off under reduced pressure. The residue was purified by silica gel chromatography (hexane:ethyl acetate=2:1)to give 300 mg of 2-benzyloxymethyl-5-(3,5-dichlorophenylthio)-4-isopropyl-1-(3-(2-pyridyl)propyl)-1H-imidazole (yield 26%).

$^1$H—NMR (CDCl$_3$—TMS)δ ppm: 1.25 (d, J=7.0 Hz, 6H), 2.05 (m, 2H), 2.73 (m, 2H), 3.09 (sept, 1H), 3.97 (m, 2H), 4.52 (s, 2H), 4.66 (s, 2H), 6.74 (d, 2H), 6.95 (m, 1H), 7.09 (d, 1H), 7.12 (m, 1H), 7.31 (m, 5H), 7.54 (m, 1H), 8.49 (m, 1H)

To 300 mg of 2-benzyloxymethyl-5-(3,5-dichlorophenylthio)-4-isopropyl-1-(3-(2-pyridyl)propyl)imidazole was added 10 ml of ethanol and 20 ml of 36% hydrochloric acid, and the mixture was stirred at 90° C. for 2 hours. After completion of the reaction, the solvent was distilled off under reduced pressure, an aqueous sodium hydrogen carbonate solution was added, and extracted with ethyl acetate. The extract was dried over sodium sulfate, and the solvent was distilled off under reduced pressure. The residue was purified by silica gel chromatography (ethyl acetate:methanol=10:1)to give 127 mg of 5-(3,5-dichlorophenylthio)-4-isopropyl-2-hydroxymethyl-1-(3-(2-pyridyl)propyl)-1H-imidazole (yield 51%).

$^1$H—NMR (CDCl$_3$—TMS)δ ppm: 1.18 (d, J=7.0 Hz, 6H), 2.16 (m, 2H), 2.85 (m, 2H), 3.05 (sept, 1H), 4.02 (m, 2H), 4.76 (s, 2H), 6.75 (d, 2H), 7.05–7.19 (m, 3H), 7.60 (m, 1H), 8.49 (m, 1H) Elementary analysis (C$_{21}$H$_{23}$Cl$_2$N$_3$OS.0.3H$_2$O) Calc. (%):C, 57.09; H, 5.38; N, 9.51; Cl, 16.05; S, 7.25 Found (%):C, 57.34; H, 5.37; N, 9.70; Cl, 15.78; S, 7.07

In 10 ml of tetrahydrofuran was dissolved 110 mg of 5-(3,5-dichlorophenylthio)-4-isopropyl-2-hydroxymethyl-1-(3-(2-pyridyl)propyl)-1H-imidazole, and the mixture was cooled to −40° C. Under stirring, 45.1 μl of trichloroacetylisocyanate was added, the mixture was allowed to warm up to room temperature, and stirred for 30 minutes. Added were 100 μl of triethylamine, 600 μl of water and 600 μl of methanol, and the mixture was stirred at 70° C. for 1 hour. After completion of the reaction, the solution was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (ethyl acetate:methanol=10:1)to give 80 mg of Compound I-130 (yield 83%).

$^1$H—NMR (CDCl$_3$—TMS)δ ppm: 1.24 (d, J=7.0 Hz, 6H), 2.08 (m, 2H), 2.78 (m, 2H), 3.08 (sept, 1H), 3.97 (m, 2H), 5.22 (s, 2H), 6.00 (br, 2H), 6.76 (d, 2H), 7.09 (m, 3H), 7.59 (m, 1H), 8.45 (m, 1H) Elementary analysis (C$_{22}$H$_{24}$Cl$_2$N$_4$O$_2$S.0.3H$_2$O) Calc. (%):C, 54.50; H, 5.11; N, 11.57; Cl, 14.62; S, 6.61 Found (%):C, 54.52; H, 5.21; N, 11.78; Cl, 14.51; S, 6.53

EXAMPLE 131

Synthesis of 2-carbamoyloxymethyl-5-(3,5-dichlorophenylthio)-1-(5,6-dihydro-6-oxopyridin-3-ylmethyl)-4-isopropyl-1H-imidazole (Compound I-131).

In 5 ml of methylene chloride was dissolved 375 mg of 2-methoxy-5-hydroxymethylpyridine, the mixture was cooled to −40° C. on a dry-ice bath, and 209 μl of thionyl bromide was added. The mixture was allowed to warm up, after 10 minutes, stirred at 60° C. After 30 minutes, the mixture was cooled, and the solution was distilled off under reduced pressure. The residue was added to a tetrahydrofuran solution containing 1179 mg of 2-benzyloxymethyl-5-(3,5-dichlorophenylthio)-4-isopropyl-1H-imidazole (101a), 215 mg of powdery sodium hydroxide and 87 mg of tetrabutylammonium bromide under ice-cooling. The temperature was raised up to room temperature, and powdery sodium hydroxide was further added to make alkaline. After 5 hours, the mixture was diluted with water, extracted with diethyl ether, the extract was dried over sodium sulfate, and the solvent was distilled off under reduced pressure. The residue was purified by silica gel chromatography (methylene chloride:ethyl acetate=4:1)to give 290 mg of 2-benzyloxymethyl-5-(3,5-dichlorophenylthio)-4-isopropyl-1-(2-methoxypyridin-5-ylmethyl)-1H-imidazole (114a)(yield 19%).

$^1$H—NMR (CDCl$_3$—TMS)δ ppm: 1.26 (d, 6H), 3.09 (sept, 1H), 3.83 (s, 3H), 4.58 (s, 2H), 4.70 (s, 2H), 5.08 (s, 2H), 6.46 (d, 1H), 6.54 (d, 2H), 6.99 (m, 1), 7.18~7.40 (m, 6H), 7.88 (d, 1H)

To a solution of 83 mg of potassium iodide in acetonitrile was added 64 μl of trimethylsilyl chloride under ice-cooling and stirring. The mixture was allowed to warm up, and after 10 minutes, 150 mg of 2-benzyloxymethyl-5-(3,5-dichlorophenylthio)-1-(2-methoxypyridin-5-ylmethyl)-4-isopropyl-1H-imidazole was added, and the mixture was stirred with heating at 60° C. After 1 hour, the solution was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (ethyl acetate:methanol=10:1)to give 50 mg of 2-benzyloxymethyl-5-(3,5-dichlorophenylthio)-1-(5,6-dihydro-6-oxopyridin-3-ylmethyl)-4-isopropyl-1H-imidazole (115a)(yield 34%).

$^1$H—NMR (CDCl$_3$—TMS)δ ppm: 1.30 (d, J=7.0 Hz, 6H), 3.12 (sept, 1H), 4.65 (s, 2H), 4.76 (s, 2H), 4.95 (s, 2H), 6.35 (d, 1H), 6.66 (d, J=2.0 Hz, 2H), 7.05 (d, J=2.0 Hz, 1H), 7.08 (d, 1H), 7.23~7.46 (m, 6H)

In a mixture of 5 ml of ethanol and 10 ml of 36% hydrochloric acid was dissolved 50 mg of 2-benzyloxymethyl-5-(3,5-dichlorophenylthio)-1-(5,6-dihydro-6-oxopyridin-3-ylmethyl)-4-isopropyl-1H-imidazole, and the mixture was stirred at 90° C. for 2 hours. After completion of the reaction, the solvent was distilled off under reduced pressure. An aqueous sodium hydrogen carbonate solution was added, the mixture was extracted with ethyl acetate, the extract was dried over sodium sulfate, and the solvent was distilled off under reduced pressure. The crystals were washed with diethyl ether, filtered, and 10 mg of 5-(3,5-dichlorophenylthio)-2-hydroxymethyl-1-(5,6-dihydro-6-oxopyridin-3-ylmethyl)-4-isopropyl-1H-imidazole (116a)was obtained (yield 24%). mp 220° C.

$^1$H—NMR (CD$_3$OD—TMS)δ ppm: 1.25 (d, J=7.0 Hz, 6H), 3.13 (sept, 1H), 4.84 (s, 2H), 5.17 (s, 2H), 6.33 (d, J=9.0 Hz, 1H), 6.67 (d, J=1.6 Hz, 2H), 7.16 (d, J=1.6 Hz, 1H), 7.34 (d, J=2.4 Hz, 1H), 7.57 (d, J=9.0 Hz, 1H) Elementary analysis (C$_{19}$H$_{19}$Cl$_2$N$_3$O$_2$S.0.5H$_2$O) Calc. (%):C, 52.66; H, 4.65; N, 9.70; Cl, 16.36; S, 7.40 Found (%):C, 52.41; H, 4.54; N, 9.58; Cl, 16.98; S, 7.24

In 10 ml of tetrahydrofuran was dissolved 51 mg of 5-(3,5-dichlorophenylthio)-2-hydroxymethyl-1-(5,6-dihydro-6-oxopyridin-3-ylmethyl)-4-isopropyl-1H-imidazole (116a), and the mixture was cooled to −40° C. Under stirring, 22 μl of trichloroacetylisocyanate was added, the mixture was allowed to stand to reach room temperature, and stirred for 30 minutes. There were added 500 μl of triethylamine, 1 ml of water and 2 ml of methanol, and the mixture was stirred at 70° C. for 1 hour. After completion of the reaction, the solution was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (ethyl acetate:methanol=10:1)to give 46 mg of Compound I-131 was obtained (yield 82%).

$^1$H—NMR (CD$_3$OD—TMS)δ ppm: 1.22 (d, J=7.0 Hz, 6H), 3.10 (sept, 1H), 5.13 (s, 2H), 5.27 (s, 2H), 6.35 (d, J=9.4 Hz, 1H), 6.67 (d, J=1.6 Hz, 2H), 7.14 (d, J=1.6 Hz, 1H), 7.18 (d, J=1.8 Hz, 1H), 7.36 (d, J=9.4 Hz, 1H)

EXAMPLE 132

Synthesis of 2-carbamoyloxymethyl-5-(3,5-dichlorophenylthio)-1-(1,2-dihydro-2-oxopyridin-3-ylmethyl)-4-isopropyl-1H-imidazole (Compound I-132).

In 15 ml of methylene chloride was dissolved 720 mg of 2-methoxy-3-hydroxymethylpyridine, the mixture was cooled to −40° C. on a dry-ice bath, and 802 μl of thionyl bromide was added. The mixture was allowed to warm up, and after 10 minutes, stirred at 60° C. After 30 minutes, the mixture was cooled, and the solution was distilled off under reduced pressure. The residue was added to a tetrahydrofuran solution containing 1264 mg of 2-benzyloxymethyl-5-(3,5-dichlorophenylthio)-4-isopropyl-1H-imidazole (101a), 517 mg of powdery sodium hydroxide and 167 mg of tetrabutylammonium bromide under ice-cooling. The temperature was raised up to room temperature, and powdery sodium hydroxide was further added to make alkaline. After 5 hours, the mixture was diluted with water, extracted with ethyl acetate, the extract was dried over sodium sulfate, and the solvent was distilled off under reduced pressure. The residue was purified by silica gel chromatography (hexane:ethyl acetate=2:1)to give 1.4 g of 2-benzyloxymethyl-5-(3,5-dichlorophenylthio)-4-isopropyl-1-(2-methoxypyridin-3-ylmethyl)-1H-imidazole. This was dissolved in acetonitrile, followed by addition of 2.2 g of potassium iodide, and with stirring under ice-cooling, 1.7 ml of trimethylsilyl chloride was added. The mixture was allowed to warm up, and after 10 minutes, the mixture was stirred with heating at 60° C. After 1 hour, the solution was distilled off under reduced pressure, an aqueous sodium hydrogen carbonate solution was added, extracted with ethyl acetate, the extract was dried over sodium sulfate, and the solvent was distilled off under reduced pressure. The residue was purified by silica gel chromatography (ethyl acetate)to give 590 mg of 2-benzyloxymethyl-5-(3,5-dichlorophenylthio)-1-(1,2-dihydro-2-oxopyridin-3-ylmethyl)-4-isopropyl-1H-imidazole (115b)(yield 38%).

$^1$H—NMR (CDCl$_3$—TMS)δ ppm: 1.29 (d, J=6.6 Hz, 6H), 3.15 (sept, 1H), 4.53 (s, 2H), 4.73 (s, 2H), 5.09 (s, 2H), 5.97 (m, 1H), 6.68 (m, 1H), 6.71 (d, J=1.6 Hz, 2H), 7.01 (d, J=2.0 Hz, 1H), 7.11 (m, 1H), 7.26 (m, 5H) Elementary analysis (C$_{26}$H$_{25}$Cl$_2$N$_3$O$_2$S.0.6H$_2$O) Calc. (%):C, 59.45; H, 5.03; N, 8.00; Cl, 13.50; S, 6.10 Found (%):C, 59.79; H, 5.13; N, 8.29; Cl, 13.05; S, 6.16

In a mixture of 15 ml of ethanol and 20 ml of 36% hydrochloric acid was dissolved 590 mg of 2-benzyloxymethyl-5-(3,5-dichlorophenylthio)-1-(1,2-dihydro-2-oxopyridin-3-ylmethyl)-4-isopropyl-1H-imidazole (115b), and the mixture was stirred at 90° C. for 4 hours. After completion of the reaction, the solvent was distilled off under reduced pressure. To the residue, an aqueous sodium hydrogen carbonate solution was added, extracted with ethyl acetate, the extract was dried over sodium sulfate, and the solvent was distilled off under reduced pressure. The crystals were washed with diethyl ether, and filtered to give 264 mg of 5-(3,5-dichlorophenylthio)-2-hydroxymethyl-1-(2 (1H)-pyridon-3-ylmethyl)-4-isopropyl-1H-imidazole (116b)(yield 54%). mp 244° C.

$^1$H—NMR (CD$_3$OD—TMS)δ ppm: 1.26 (d,J=7.0 Hz, 6H), 3.11 (sept, 1H), 4.83 (s, 2H), 5.18 (s, 2H), 6.01 (m, 1H), 6.71 (d, 2H), 7.05–7.20 (m, 3H) Elementary analysis (C$_{19}$H$_{19}$Cl$_2$N$_3$O$_2$S.0.2H$_2$O) Calc. (%):C, 53.33; H, 4.57; N, 9.82; Cl, 16.57; S, 7.49 Found (%):C, 53.62; H, 4.62; N, 9.79; Cl, 16.28; S, 7.60

In 20 ml of tetrahydrofuran was dissolved 200 mg of 5-(3,5-dichlorophenylthio)-2-hydroxymethyl-1-(1,2-dihydro-2-oxopyridinylmethyl)-4-isopropyl-1H-imidazole (116b), the mixture was cooled to −40° C. Under stirring, 84 μl of trichloroacetylisocyanate was added, the mixture was allowed to stand to reach room temperature, and stirred for 30 minutes. There were added 500 μl of triethylamine, 5 ml of water and 5 ml of methanol, and the mixture was stirred at 70° C. for 1 hour. After completion of the reaction, the solution was distilled off under reduced pressure, an aqueous sodium hydrogen carbonate solution was added, extracted with ethyl acetate, the extract was dried over sodium sulfate, and the solvent was distilled off under reduced pressure. The crystals were washed with diethyl ether, filtered, and 177 mg of Compound I-132 was obtained (yield 80%) mp 214° C.

$^1$H—NMR (CD$_3$OD—TMS)δ ppm: 1.23 (d, J=7.0 Hz, 6H), 3.13 (sept, 1H), 5.17 (s, 2H), 5.33 (s, 2H), 5.99 (m, 1H), 6.71 (d, J=2.0 Hz, 2H), 7.00 (m, 1H), 7.11 (d, J=2.0 Hz, 1H), 7.14 (m, 1H)

EXAMPLE 133

Synthesis of 2-carbamoyloxymethyl-5-(3,5-dichlorophenylthio)-4-isopropyl-1-(2-methylpyridin-3-ylmethyl)-1H-imidazole (Compound I-133).

In 10 ml of methylene chloride was dissolved 463 mg of 2-methyl-3-hydroxymethylpyridine, and 582 μl of thionyl bromide was added thereto with cooling to −40° C. on a dry-ice bath. The mixture was allowed to warm up, and after 10 minutes, stirred at 60° C. After 30 minutes the mixture was cooled, and evaporated under reduced pressure. The residue was added to a tetrahydrofuran solution containing 918 mg of 2-benzyloxymethyl-5-(3,5-dichlorophenylthio)-4-isopropyl-1H-imidazole (101a), 376 mg of powdery sodium hydroxide and 121 mg of tetrabutylammonium bromide under ice-cooling. The temperature was raised up to room temperature, and powdery sodium hydroxide was further added to make alkaline. After 5 hours, the mixture was diluted with water, extracted with ethyl acetate, the extract was dried over sodium sulfate, and the solvent was distilled off under reduced pressure. The residue was purified by silica gel chromatography (methylene chloride:ethyl acetate=5:1) to give 609 mg of 2-benzyloxymethyl-5-(3,5-dichlorophenylthio)-4-isopropyl-1-(2-methyl-3-pyridin-3-ylmethyl)-1H-imidazole (118a)(yield 53%).

$^1$H—NMR (CDCl$_3$—TMS)δ ppm: 1.32 (d, J=6.8 Hz, 6H), 2.48 (s, 3H), 3.17 (sept, 1H), 4.90 (s, 2H), 4.58 (s, 2H), 5.12 (s, 2H), 6.62 (m, 1H), 6.68 (m, 2H), 6.90 (m, 1H), 7.00 (m, 1H), 7.15 (m, 2H), 7.26 (m, 3H), 8.28 (m, 1H) Elementary analysis (C$_{27}$H$_{27}$Cl$_2$N$_3$OS.0.2H$_2$O) Calc. (%):C, 62.83; H, 5.35; N, 8.14; Cl, 13.74; S, 6.21 Found (%):C, 62.59; H, 5.47; N, 7.89; Cl, 13.27; S, 6.03

In a mixture of 15 ml of ethanol and 20 ml of 36% hydrochloric acid was dissolved 609 mg of 2-benzyloxymethyl-5-(3,5-dichlorophenylthio)-4-isopropyl-1-(2-methylpyridin-3-ylmethyl)-1H-imidazole (118a), and the mixture was stirred at 90° C. for 3 hours. After completion of the reaction, the solvent was distilled off under reduced pressure. An aqueous sodium hydrogen carbonate solution was added, extracted with ethyl acetate, the extract was dried over sodium sulfate, and the solvent was distilled off under reduced pressure. The crystals were washed with diethyl ether, filtered, and 500 mg of 5-(3,5-dichlorophenylthio)-2-hydroxymethyl-4-isopropyl-1-(2-methylpyridin-3-ylmethyl)-1H-imidazole (119a)was obtained (yield 99%). mp 136° C.

$^1$H—NMR (CDCl$_3$—TMS)δ ppm: 1.27 (d, J=6.8 Hz, 6H), 2.57 (s, 3H), 3.17 (sept, 1H), 4.69 (s, 2H), 5.24 (s, 2H), 6.65 (m, 1H), 6.69 (m, 2H), 6.94 (m, 1H), 7.02 (m, 1H), 8.29 (m, 1H) Elementary analysis (C$_{20}$H$_{21}$Cl$_2$N$_3$OS.0.2H$_2$O) Calc. (%):C, 56.39; H, 5.06; N, 9.86; Cl, 16.65; S, 7.53 Found (%):C, 56.34; H, 5.05; N, 9.83; Cl, 16.79; S, 7.56

In 20 ml of tetrahydrofuran was dissolved 405 mg of 5-(3,5-dichlorophenylthio)-2-hydroxymethyl-4-isopropyl-1-(2-methylpyridin-3-ylmethyl)-1H-imidazole (119a), and the mixture was cooled to −40° C. With stirring, 171 μl of trichloroacetylisocyanate was added, the mixture was allowed to stand to reach room temperature, and stirred for 30 minutes. There were added 200 μl of triethylamine, 5 ml of water and 10 ml of methanol, and the mixture was stirred at 70° C. for 2 hours. After completion of the reaction, the solution was distilled off under reduced pressure, an aqueous sodium hydrogen carbonate solution was added, extracted with ethyl acetate, the extract was dried over sodium sulfate, and the solvent was distilled off under reduced pressure. The crystals were washed with diethyl ether, filtered, and 400 mg of Compound I-133 was obtained (yield 90%). mp 127° C.

$^1$H—NMR (CDCl$_3$—TMS)δ ppm: 1.32 (d, J=7.0 Hz, 6H), 2.56 (s, 3H), 3.19 (sept, 1H), 4.48 (br, 2H), 5.18 (s, 2H), 5.20 (s, 2H), 6.52 (m, 1H), 6.72 (m, 2H), 6.95 (m, 1H), 7.05 (m, 1H), 8.31 (m, 1H)

EXAMPLE 134

Synthesis of 1-(2-carbamoyloxyethyl)-2-carbamoyloxymethyl-5-(3,5-dichlorophenylthio)-4-isopropyl-1H-imidazole (Compound I-134).

In 50 ml of dry acetonitrile was dissolved 5.0 g (12.3 mmol)of imidazole compound (101a), followed by addition of 3.4 g (25 mmol)of potassium carbonate and 3.1 g (18.6 mmol) of ethyl bromoacetate, and the mixture was stirred with heating at 60° C. for 8 hours. The mixture was diluted with ice-water, and extracted with ethyl acetate. The extract was washed with water, dried over anhydrous sodium sulfate, filtered, and concentrated under reduced pressure. The residue was purified by silica gel column chromatography (ethyl acetate:n-hexane 1:2)to give 5.6 g of 2-[2-benzyloxymethyl-5-(3,5-dichlorophenylthio)-4-isopropyl-1H-imidazol-1-yl)]ethyl acetate (118b)as oil (yield 92%).

$^1$H—NMR (CDCl$_3$—TMS)δ ppm: 1.10 (t, J=7.2 Hz, 3H), 1.27 (d, J=6.8 Hz, 6H), 3.11 (sept, 1H), 3.95 (q, J=7.2 Hz, 2H), 4.50 (s, 2H), 4.70 (s, 2H), 4.76 (s, 2H), 6.83 (m, 2H), 7.10 (m, 1H), 7.30 (m, 5H)

In 30 ml of dry diethyl ether was dissolved 3.0 g (6.0 mmol)of the ester compound (118b), followed by addition of 230 mg (6.0 mmol)of lithium aluminium hydride under ice-cooling. At room temperature the mixture was stirred for 15 minutes, and water was added. The mixture was extracted with ethyl acetate, the extract was washed with water and dried over anhydrous sodium sulfate, filtered, and concentrated under reduced pressure. The residue was purified by silica gel column chromatography (ethyl acetate), and further recrystallized from n-hexane to obtain 2.17 g of 2-[2-benzyloxymethyl-5-(3,5-dichlorophenylthio)-4-isopropyl-1H-imidazol-1-yl)]ethanol (118c)as crystals (yield 79%). mp 78–80° C.

$^1$H—NMR (CDCl$_3$—TMS)δ ppm: 1.25 (t, J=6.8 Hz, 6H), 2.55 (t, J=5.4 Hz, 1H), 3.10 (sept, 1H), 3.72 (m, 2H), 4.09 (t, J=5.0 Hz, 2H), 4.61 (s, 2H), 4.72 (s, 2H), 6.78 (m, 2H), 7.11 (m, 1H), 7.35 (m, 5H) Elementary analysis (C$_{22}$H$_{24}$Cl$_2$N$_2$O$_2$S) Calc. (%):C, 58.54, H, 5.36, Cl, 15.71, N, 6.21, S, 7.10 Found (%):C, 58.46, H, 5.36, Cl, 15.57, N, 6.23, S, 7.29

Added was 18 ml of concentrated hydrochloric acid to 1.8 g (4.0 mmol)of the alcohol compound (118c), and the mixture was stirred with heating at 110° C. for 7 hours. After cooling, the mixture was neutralized with sodium hydrogen carbonate, and extracted with ethyl acetate. The extract was washed with water, dried over anhydrous sodium sulfate, filtered, and concentrated under reduced pressure. The residue was purified by silica gel column chromatography (ethyl acetate)to give 960 mg of 2-(5-(3,5-dichlorophenylthio)-2-hydroxymethyl-4-isopropyl-1H-imidazol-1-yl)ethanol (119b)as oil (yield 67%).

$^1$H—NMR (CDCl$_3$—TMS)δ ppm: 1.18 (d, J=7.2 Hz, 6H), 3.08 (sept, 1H), 3.76 (t, J=5.0 Hz, 2H), 4.17 (t, J=5.0

Hz, 2H), 4.67 (s, 2H), 4.90 (br, 1H), 6.60 (br, 1H), 6.90 (m, 2H), 7.13 (m, 1H).

In 9 ml of dry tetrahydrofuran was dissolved 910 mg (2.5 mmol)of the diol compound (119b), and the mixture was cooled to −40° C., followed by addition of 1.42 g (7.5 mmol)of trichloroacetylisocyanate. The mixture was warmed gradually to room temperatures and stirred for 1 hour. Added were 4 ml of water and 2 ml of tetraethylamine, and the mixture was stirred at 50° C. for 3 hours The mixture was diluted with water, extracted with ethyl acetate, the extract was washed with water, dried over anhydrous sodium sulfate, filtered and concentrated under reduced pressure. The residue was purified by silica gel column chromatography, and further recrystallized from ethyl acetate-n-hexane to give 900 mg of Compound I-134 as crystals (yield 80%). mp 159–161° C.

$^1$H—NMR (CDCl$_3$—TMS)δ ppm: 1.25 (d, J=7.0 Hz, 6H), 3.10 (sept, 1H), 4.22 (m, 4H), 4.74 (brs, 2H), 4.93 (brs, 2H), 5.27 (s, 2H), 6.80 (m, 2H), 7.12 (m, 1H)

EXAMPLE 135

Synthesis of 2-[5-(3,5-dichlorophenylthio)-4-isopropyl-1-methyl-1H-imidazol-2-yl]acetamide (Compound I-135)

In a mixture of 46 ml of dry methanol and 86 ml of dry ether was dissolved 8.6 g (2.5 mmol)of the cyanomethyl compound (101c), and dry hydrogen chloride was blown into the mixture under ice-cooling to be saturated. The mixture was kept at 4° C. for 15 hours, and ice-water was added little by little under ice-cooling. Then, this reaction mixture was poured into a cooled aqueous sodium hydrogen carbonate solution, and extracted with diethyl ether. The extract was washed with water, dried over anhydrous sodium sulfate, and concentrated under reduced pressure. The residue was subjected to silica gel column chromatography. From the fraction eluted with 3% methanol/methylene chloride, 7.17 g of the ester compound was obtained (yield 76%), while from the fraction eluted with 10% methanol/methylene chloride, 1.85 g of Compound I-135 was obtained as crystals (yield 21%). mp 164–166° C.

$^1$H—NMR (CDCl$_3$—TMS)δ ppm: 1.23 (d, J=6.6 Hz, 6H), 3.12 (sept, 1H), 3.41 (s, 3H), 3.75 (s, 2H), 5.90 (brs, 1H), 6.80 (m, 2H), 7.12 (m, 1H), 7.93 (brs, 1H) IR(Nujol)ν; 3336,3136,3070,1673 cm$^{-1}$ Elementary analysis (C$_{15}$H$_{17}$Cl$_2$N$_3$OS) Calc. (%):C, 50.29, H, 4.78, Cl, 19.79, N, 11.73, S, 8.95 Found (%):C, 50.20, H, 4.82, Cl, 19.65, N, 11.66, S, 9.03

EXAMPLE 136

Synthesis of 2-(2-benzyloxyethyl)-5-(3,5-dichlorophenylthio)-4-isopropyl-1-methyl-1H-imidazole (Compound I-136).

In 20 ml of dry methylene chloride was dissolved 3.0 g (11.9 mmol)of benzyl 2,2,2-trichloroacetoimidate, followed by addition of 3A molecular sieves. At room temperature, 2.7 g (7.8 mmol)of the alcohol compound (101e)was added. After 5 minutes, 5 ml of a dry methylene chloride solution containing 1.7 g of boron trifluoride diethyl ether complex was added. The mixture was allowed to react at room temperature for 40 minutes, and poured into a cooled aqueous solution of sodium hydrogen carbonate. The mixture was extracted with ethyl acetate, the extract was washed with water, dried over anhydrous sodium sulfate, filtered, and concentrated under reduced pressure. The residue was fractionated by silica gel column chromatography (ethyl acetate:n-hexane=1:1), and 2.06 g of Compound I-136 was obtained as crystals (yield 61%). mp 101–103° C.

$^1$H—NMR (CDCl$_3$—TMS)δ ppm: 1.25 (d, J=7.0 Hz, 6H), 3.07 (t, J=6.2 Hz, 2H), 3.10 (sept, 1H), 3.46 (s, 3H), 3.84 (t, J=6.2 Hz, 2H), 4.51 (s, 2H), 6.80 (m, 2H), 7.09 (m, 1H), 7.28 (m, 5H) Elementary analysis (C$_{16}$H$_{20}$Cl$_2$N$_2$OS) Calc. (%):C, 60.69, H, 5.56, Cl, 16.28, N, 6.43, S, 7.36 Found (%):C, 60.67, H, 5.70, Cl, 15.98, N, 6.32, S, 7.16

EXAMPLE 137

Synthesis of 2-(2-carbamoyloxyethyl)-5-(3,5-dichlorophenylthio)-1-ethyl-4-isopropyl-1H-imidazole (Compound I-137).

In 20 ml of dry acetonitrile was dissolved 4.0 (9.5 mmol)of Compound I-136, followed by addition of 1.4 g (19 mmol)of lithium carbonate and 1.8 g (11.7 mmol)of diethyl sulfate, and the mixture was reacted at 70° C. for 9 hours. The mixture was diluted with ice-water, and the mixture was extracted with ethyl acetate. The extract was washed with water, dried over anhydrous sodium sulfate, filtered, and concentrated under reduced pressure. The residue was purified by silica gel column chromatography (ethyl acetate:hexane=1:1)to give 3.9 g of 2-(2-benzyloxyethyl-5-(3,5-dichlorophenylthio)-1-ethyl-4-isopropyl-1H-imidazole (122a)as oil (yield 91%).

$^1$H—NMR (CDCl$_3$—TMS)δ ppm: 1.15 (t, J=7.0 Hz, 3H), 1.24 (d, J=7.0 Hz, 6H), 3.06 (m, 3H), 3.91 (m, 4H), 4.52 (s, 2H), 6.81 (m, 2H), 7.09 (m, 1H) 7.28 (m, 5H)

In 16 ml of concentrated hydrochloric acid was dissolved 3.8 g (8.5 mmol)of the benzyl compound (122a), and the mixture was heated at 100° C. for 2 hours. After cooling, the mixture was neutralized with sodium hydrogen carbonate, extracted with ethyl acetate, the extract was washed with water, dried over anhydrous sodium sulfate, filtered, and concentrated under reduced pressure. The residue was purified by silica gel column chromatography (1% methanol::ethyl acetate), washed with n-hexane, and filtered to give 2.57 g of 2-[5-(3,5-dichlorophenylthio)-1-ethyl-4-isopropyl-1H-imidazol-2-yl]ethanol (123a)as crystals (yield 85%), mp 80–81° C.

$^1$H—NMR (CDCl$_3$—TMS)δ ppm: 1.16 (t, J=7.4 Hz, 3H), 1.22 (d, J=6.6 Hz, 6H), 2.87 (t, J=5.4 Hz, 2H), 3.06 (sept, 1H), 3.87 (q, J=7.4 Hz, 2H), 4.09 (q, J=5.4 Hz, 2H), 4.91 (m, 1H), 6.82 (m, 2H), 7.11 (m, 1H) Elementary analysis (C$_{16}$H$_{20}$Cl$_2$N$_2$OS) Calc. (%):C, 53.48, H, 5.61, Cl, 19.73, N, 7.80, S, 8.92 Found (%):C, 53.48, H, 5.61, Cl, 19.73, N, 7.80, S, 8.92

In 15 ml of dry tetrahydrofuran was dissolved 1.5 g (4.2 mmol)of the alcohol compound (123a), and the mixture was cooled to −30° C., followed by addition of 1.2 g (6.4 mmol)of trichloroacetylisocyanate. After 5 minutes, the mixture was warmed to 0° C., and stirred for 10 minutes. The mixture was diluted with water, and extracted with ethyl acetate. The extract was washed with water, and ethyl acetate was distilled off. To the residue was added 15 ml of methanol, 0.26 g of triethylamine and 0.72 ml of water, and the mixture was heated at 50° C. for 0.5 hours. The mixture was diluted with ice-water, and extracted with ethyl acetate. The extract was washed with water, dried over anhydrous sodium sulfate, filtered, and concentrated under reduced pressure. The residue was purified by silica gel column chromatography (2% methanol:ethyl acetate), and recrystallized from ethyl acetate-n-hexane to give 1.5 g of Compound I-137 as crystals (yield 89%). mp 161–162° C.

¹H—NMR (CDCl₃—TMS)δ ppm: 1.20 (t, J=7.4 Hz, 3H), 1.23 (d, J=7.0 Hz, 6H), 3.07 (sept, 1H), 3.10 (t, J=7.0 Hz, 2H), 3.92 (q, J=7.4 Hz, 2H), 4.47 (t, J=7.0 Hz, 2H), 4.67 (brs, 2H), 6.80 (m, 2H), 7.11 (m, 1H) Elementary analysis (C₁₇H₂₁Cl₂N₃O₂S) Calc. (%):C, 50.75, H, 5.26, Cl, 17.62, N, 10.44, S, 7.97 Found (%):C, 50.79, H, 5.21, Cl, 17.33, N, 10.36, S, 7.78

EXAMPLE 138

Synthesis of 2-(2-carbamoyloxyethyl)-5-(3,5-dichlorophenylthio)-4-isopropyl-1-(pyridin-4-yl)methyl-1H-imidazole (Compound I-138).

In 20 ml of tetrahydrofuran was dissolved 2.0 g (4.7 mmol)of the imidazole compound (Compound I-136), followed by addition of 1.9 ml of 40% aqueous sodium hydroxide solution, 100 mg of n-tetrabutylammonium bromide and 940 mg (5.7 mmol) of 4-chloromethylpyridine hydrochloride, and the mixture was stirred at 50° C. for 6 hours. The mixture was extracted with ethyl acetate, the extract was washed with water, dried over anhydrous sodium sulfate, filtered, and concentrated under reduced pressure. The residue was purified by silica gel column chromatography (2% methanol:ethyl acetate)to give 2.4 g of 4-[2-(2-benzyloxyethyl)-5-(3,5-dichlorophenylthio)-4-isopropyl-1H-imidazol-1-ylmethyl]pyridine (122b)as oil (yield 98%).

¹H—NMR (CDCl₃—TMS)δ ppm: 1.30 (d, J=7.2 Hz, 6H), 2.99 (t, J=6.0 Hz, 2H), 3.16 (sept, 1H), 3.84 (t, J=6.0 Hz, 2H), 4.47 (s, 2H), 5.16 (s, 2H), 6.69 (m, 2H), 6.76 (d, J=6.0 Hz, 2H), 7.01 (m, 1H), 7.22 (m, 5H), 8.37 (d, J=6.0 Hz, 2H)

In 12 ml of concentrated hydrochloric acid was dissolved 2.3 g (4.5 mmol)of the benzyl compound (122b), and the mixture was heated at 100° C. for 4 hours. The mixture was neutralized with sodium hydrogen carbonate, and extracted with ethyl acetate. The extract was washed with water, dried over anhydrous sodium sulfate, filtered, and concentrated under reduced pressure. The residue was purified by silica gel column chromatography (7% methanol/ethyl acetate)to give 1.28 g of 2-[5-(3,5-dichlorophenylthio)-4-isopropyl-1-(pyridin-4-ylmethyl)-1H-imidazol-2-yl]ethanol (123b)as crystals (yield 67%). mp 121–122° C.

¹H—NMR (CDCl₃—TMS)δ ppm: 1.28 (d, J=6.8 Hz, 6H), 2.80 (t, J=5.2 Hz, 2H), 3.15 (sept, 1H), 4.06 (t, J=5.2 Hz, 2H), 4.62 (brs, 1H), 5.09 (s, 2H), 6.71 (m, 2H), 6.77 (d, J=4.6 Hz, 2H), 7.04 (m, 1H), 8.48 (d, J=4.6 Hz, 2H) Elementary analysis (C₂₀H₂₁Cl₂N₃OS) Calc. (%):C, 56.87, H, 5.01, Cl, 16.79, N, 9.95, S, 7.59 Found (%):C, 56.69, H, 5.02, Cl, 16.70, N, 9.89, S, 7.41

In 10 ml of dry tetrahydrofuran was dissolved 1.0 g (2.4 mmol)of the alcohol compound (127b), and the mixture was cooled to −20° C., followed by addition of 540 mg (2.9 mmol)of trichloroacetylisocyanate. After 3 minutes, the mixture was warmed to 0° C. and stirred for 10 minutes. There were added 4 ml of water and 2 ml of triethylamine, and the mixture was warmed at 50° C. for 2 hours. The mixture was diluted with ice-water, extracted with ethyl acetate, the extract was washed with water, dried over anhydrous sodium sulfate, filtered, and concentrated under reduced pressure. The residue was purified by silica gel column chromatography (10% methanol/ethyl acetate), and recrystallized from ethyl acetate to give 930 mg of Compound I-138 as crystals (yield 85%). mp 189–191° C.

¹H—NMR (CDCl₃—TMS)δ ppm: 1.28 (d, J=7.0 Hz, 6H), 3.03 (t, J=6.6 Hz, 2H), 3.14 (sept, 1H), 4.42 (t, J=6.6 Hz, 2H), 4.63 (brs, 2H), 5.13 (s, 2H), 6.71 (m, 2H), 6.81 (d, J=6.0 Hz, 2H), 7.05 (m, 1H), 8.48 (d, J=6.0 Hz, 2H) Elementary analysis (C₂₁H₂₂Cl₂N₄O₂S) Calc. (%):C, 54.20, H, 4.76, Cl, 15.24, N, 12.04, S, 6.89 Found (%):C, 53.91, H, 4.79, Cl, 15.18, N, 11.80, S, 6.79

EXAMPLE 139

Synthesis of 1-(p-aminobenzyl)-5-(3,5-dichlorophenylthio)-2-hydroxyethyl-4-isopropyl-1H-imidazole (Compound I-139).

In 10 ml of tetrahydrofuran was dissolved 1.05 mg (2.5 mmol)of 2-(2-benzyloxyethyl)-5-(3,5-dichlorophenylthio)-4-isopropyl-1H-imidazole (Compound I-136), followed by addition of 220 mg (5.5 mmol)of sodium hydroxide, 48 mg (0.15 mmol) of tetrabutylammonium bromide and 594 mg (2.75 mmol)of nitrobenzylbromide with stirring at room temperature, and the mixture was reacted for 3 hours and worked up. The reaction mixture was distilled off under reduced pressure, and the residue was extracted with ethyl acetate. The extract was washed with water, dried, and the solvent was distilled off. The residue was purified by silica gel column chromatography (ethyl acetate:chloroform=1:9) to give 1.3 g (93%)of 2-(2-benzyloxyethyl)-5-(3,5-dichlorophenylthio)-4-isopropyl-1-p-nitrobenzyl-1H-imidazole (125a)as oil.

¹H—NMR (CDCl₃)δ ppm: 1.32 (d, J=7 Hz, 6H), 3.0–3.2 (m, 1H), 3.03 (t, J=5.8 Hz, 2H), 3.87 (t, J=5.8 Hz, 2H), 4.47 (s, 2H), 5.24 (s, 2H), 6.61 (d, J=2 Hz, 2H), 6.98 (t, J=2 Hz, 1H), 7.0 (d, J=9 Hz, 2H), 7.2~7.3 (m, 5H), 7.93 (d, J=9 Hz, 2H)

To 5 ml of concentrated hydrochloric acid was dissolved 1.3 g (2.34 mmol)of the benzyl compound (125a), the mixture was refluxed with heating for 4 hours and worked up. To the reaction mixture was added a saturated aqueous sodium hydrogen carbonate solution, and extracted with ethyl acetate. The extract was washed with water and dried, distilled off, the residual oil was treated with ether, and crystallized to give 5-(3,5-dichlorophenylthio)-2-(2-hydroxyethyl)-4-isopropyl-1-p-nitrobenzyl-1H-imidazole (126a). m.p. 169–171° C.

¹H—NMR (CDCl₃)δ ppm: 1.27 (d, J=4.4 Hz, 6H), 2.84 (t, 2H), 3.1~3.2 (m, 1H), 4.1 (t, 2H), 4.45 (br, 1H), 5.17 (s, 2H), 6.64 (d, J=1.2 Hz, 2H), 7.00 (t, J=1.2 Hz, 1H), 7.04 (d, J=5.8 Hz, 1H), 8.06 (d, J=5.8 Hz, 1H) Elementary analysis (C₂₁H₂₁N₃Cl₂O₃S) Calc. (%):C, 54.08; H, 4.54; N, 9.01; S, 6.87: Found (%):C, 54.05; H, 4.59; N, 8.84; S, 6.70

In 10 ml of ethyl acetate was dissolved 124 mg (0.26 mmol)of the nitrobenzyl compound (126a), and 120 mg of platinum sulfided carbon was added at room temperature. H₂ gas was introduced for 7 hours under stirring, and the mixture was worked up. The reaction mixture was filtered through Celite under reduced pressure, and the filtrate was distilled off. The residue was purified by silica gel column chromatography (ethyl acetate), the resulting oil was treated with ether for crystallization to give Compound I-139 (yield 33%), mp 142–145° C.

¹H—NMR (CDCl₃)δ ppm: 1.23 (d, J=7 Hz, 6H), 2.85 (t, J=5.4 Hz, 2H), 3.0–3.2 (m, 1H), 4.03 (t, J=5.4 Hz, 2H), 4.94 (s, 2H), 6.47 (d, J=8.2 Hz, 2H), 6.66–6.73 (m, 4H), 7.02 (t, 1H) Elementary analysis (C₂₁H₂₃N₃Cl₂OS.0.5H₂O) Calc. (%):C, 56.63; H, 5.43; N, 9.43; S, 7.19, Cl, 15.92 Found (%):C, 56.72; H, 5.27; N, 9.37; S, 7.09; Cl, 15.81

EXAMPLE 140

Synthesis of 1-(p-aminobenzyl)-2-(2-carbamoyloxyethyl)-5-(3,5-dichlorophenylthio)-4-isopropyl-1H-imidazole (Compound I-140).

In 5 ml of tetrahydrofuran was dissolved 467 mg (1 mmol) of 5-(3,5-dichlorophenylthio)-2-(2-hydroxyethyl)-4- isopropyl-1-p-nitrobenzyl-1H-imidazole (126a), and there was added 0.23 g (1.2 mmol)of trichloroacetylisocyanate under stirring on a cooling bath at −20° C. Then, the bath was taken off, and the mixture was reacted for 2 hours. To the reaction mixture was added a saturated aqueous sodium hydrogen carbonate solution, and extracted with methylene chloride. The extract was washed with water, dried, and the solvent was distilled off, and the trichloroacetylcarbamoyloxy compound which was able to use for the next reaction, was obtained in the residue. The intermediate was dissolved in 10 ml of aqueous methanol (10%), followed by addition of 0.2 ml of triethylamine under stirring at room temperature, and the mixture was stirred with heating at 50° C. for 3 hours and worked up. When the crystals were precipitated, the mixture was filtered directly. When the crystals were not precipitated, a saturated aqueous sodium hydrogen carbonate solution was added to the reaction mixture, and extracted with methylene chloride. The extract was washed with water and dried, the solvent was distilled off, and the residue was purified by silica gel column chromatography (ethyl acetate) to give 2-(2-carbamoyloxyethyl)-5-(3,5-dichlorophenylthio)-4-isopropyl-1-(p-nitrobenzyl)-1H-imidazole (128a)as oil (yield 98%)

$^1$H—NMR (CDCl$_3$)δ ppm: 1.27 (d, J=7 Hz, 6H), 3.08 (t, J=7 Hz, 2H), 3.0~3.2 (m, 1H), 4.43 (t, J=7 Hz, 2H), 5.23 (s, 2H), 6.64 (d, J=2 Hz, 2H), 7.01 (t, J=2 Hz, 1H), 7.05 (d, J=8.6 Hz, 2H), 8.07 (d, J=8.6 Hz, 2H)

In 10 ml of ethyl acetate was dissolved 220 mg (0.43 mmol)of 2-(2-carbamoyloxyethyl)-5-(3,5-dichlorophenylthio)-4-isopropyl-1-(p-nitrobenzyl)-1H-imidazole (128a), and 120 mg of platinum sulfided carbon was added at room temperature. Hydrogen gas was introduced for 7 hours under stirring, and the mixture was worked up. The reaction mixture was filtered through Celite under reduced pressure, and the filtrate was distilled off. The residual oil was treated with ether for crystallization to give Compound I-140 (yield 95%).

$^1$H—NMR (CDCl$_3$)δ ppm: 1.25 (dd, J=7 Hz, 2 Hz, 6H), 3.0~3.2 (m, 3H), 4.3~4.42 (m, 2H), 4.6 (br, 2H), 4.99, 5.05 (s X 2, 2H), 6.45~6.5 (m, 1H), 6.65~6.75 (m, 2H), 7.01 (t, J=2 Hz, 1H)

EXAMPLE 141

Synthesis of 1-(m-aminobenzyl)-5-(3,5-dichlorophenylthio)-2-hydroxyethyl-4-isopropyl-1H-imidazole (Compound I-141).

In 10 ml of tetrahydrofuran was dissolved 1.05 mg (2.5 mmol)of (Compound I-136), followed by addition of 220 mg (5.5 mmol)of sodium hydroxide, 48 mg (0.15 mmol)of tetrabutylammonium bromide and 594 mg (2.75 mmol)of nitrobenzoylchloride under stirring at room temperature, and the mixture was reacted with heating at 60° C. for 3 hours and worked up. The reaction mixture was distilled off under reduced pressure, the residue was extracted with ethyl acetate, the extract was washed with water, dried, and the solvent was distilled off. The residue was purified by silica gel column chromatography (ethyl acetate:chloroform=1:9) to give 1.26 g of 2-(2-benzyloxyethyl)-5-(3,5-dichlorophenylthio)-4-isopropyl-1-m-nitrobenzyl-1H-imidazole (125b)as oil (yield 90%). mp 119–122° C.

$^1$H—NMR (CDCl$_3$)δ ppm: 1.29 (d, J=7 Hz, 6H), 3.0~3.2 (m, 1H), 3.07 (t, J=5.6 Hz, 2H), 3.88 (t, J=5.6 Hz, 2H), 4.48 (s, 2H), 5.25 (s, 2H), 6.59 (d, J=1.8 Hz, 2H), 6.95 (t, J=1.8 Hz, 1H), 7.81 (s, 1H), 7.97 (d, J=6 Hz, 1H)

5-(3,5-Dichlorophenylthio)-2-(2-hydroxyethyl)-4-isopropyl-1-m-nitrobenzyl-1H-imidazole (126b)was obtained from (125b)by the same synthetic process as that for (126a) in Example 139. mp 85–88° C.

$^1$H—NMR (CDCl$_3$)δ ppm: 1.28 (d, J=6.8 Hz, 6H), 2.87 (t, J=4.8 Hz, 2H), 3.1~3.2 (m, 1H), 4.09 (t, J=4.8 Hz, 2H), 5.17 (s, 2H), 6.20 (d, J=1.6 Hz, 2H), 6.72 (t, J=1.6 Hz, 1H), 6.98~6.99 (m, 1H), 7.1~7.15 (m, 1H), 7.36~7.42 (m, 2H), 7.83 (br, s, 1H), 7.98~8.1 (m, 1H) Elementary analysis (C$_{21}$H$_{21}$N$_3$Cl$_2$O$_3$S) Calc. (%):C, 54.08; H, 4.54; N, 9.01; S, 6.87; Cl, 15.20 Found (%):C, 54.32; H, 4.65; N, 8.81; S, 6.72; Cl, 15.39

Compound I-141 was obtained from (126b)by the same synthetic process as that for Compound I-139 in Example 139. mp 114–118° C.

$^1$H—NMR (CDCl$_3$)δ ppm: 1.25 (d, J=7 Hz, 2H), 2.82 (t, J=5.6 Hz, 2H), 3.0~3.2 (m, 1H), 4.02 (t, J=5.6 Hz, 2H), 4.96 (s, 2H), 6.13 (s, 1H), 6.3 (d, 1H), 6.5 (dd, 1H), 6.72 (d, J=1.8 Hz, 2H), 7.0 (d, 1H), 7.04 (t, J=1.8 Hz, 1H)

EXAMPLE 142

Synthesis of 1-(m-aminobenzyl)-2-(2-carbamoyloxyethyl)-5-(3,5-dichlorophenylthio)-4-isopropyl-1H-imidazole (Compound I-142).

2-(2-Carbamoyloxyethyl)-5-(3,5-dichlorophenylthio)-4-isopropyl-1-(m-nitrobenzyl)-1H-imidazole (128b)was obtained from (126b)by the same synthetic process as that for (128a) in Example 140 (yield 83%). mp 167–169° C.

$^1$H—NMR (CDCl$_3$)δ ppm: 1.28 (d, J=7 Hz, 6H), 3.12 (t, J=5.8 Hz, 2H), 3.0–3.2 (m, 1H), 4.47 (t, J=5.8 Hz, 2H), 4.63 (br, 2H), 5.23 (s, 2H), 6.61 (d, J=2 Hz, 2H), 6.97 (t, J=2 Hz, 1H), 7.40 (t, J=8.2 Hz, 1H), 7.81 (br, 1H), 8.02 (d, d, 1H) Elementary analysis (C$_{22}$H$_{22}$N$_4$Cl$_2$O$_4$S.0.2H$_2$O) Calc. (%):C, 51.50; H, 4.40, N, 10.92; S, 6.25; Cl, 13.92 Found (%):C, 51.28; H, 4.40; N, 10.88; S, 6.27; Cl, 13.72

Compound I-142 was obtained from (128b)by the same synthetic process as that for Compound I-140 in Example 140. mp 172–176° C.

$^1$H—NMR (CDCl$_3$)δ ppm: 1.27 (d, J=7 Hz, 6H), 3.0–3.2 (m, 3H), 3.6 (br, 2H), 4.35–4.45 (m, 2H), 4.6 (br, 2H), 5.03 (s, 2H), 6.15 (t, br, 1H), 6.35 (dd, 1H), 6.4–6.6 (m, 1H), 6.72 (d, J=1.6 Hz, 2H), 7.04 (t, J=1.6 Hz, 1H) Elementary analysis (C$_{22}$H$_{24}$N$_4$Cl$_2$O$_2$S.0.8H$_2$O) Calc. (%):C, 53.51; H, 5.23; N, 11.35; S, 6.49 Found (%):C, 53.80; H, 4.86; N, 11.35: S, 6.48

EXAMPLE 143

Synthesis of 1-(o-aminobenzyl)-5-(3,5-dichlorophenylthio)-2-(2-hydroxyethyl)-4-isopropyl-1H-imidazole (Compound I-143).

2-(Benzyloxyethyl)-5-(3,5-dichlorophenylthio)-4-isopropyl-1-(o-nitrobenzyl)-1H-imidazole (125c)was obtained from Compound I-136 by the same synthetic process as that for (125a)in Example 139 as oil (yield 49%).

$^1$H—NMR (CDCl$_3$)δ ppm: 1.32 (d, J=6.6 Hz, 6H), 2.99 (t, J=6.2 Hz, 2H), 3.1–3.22 (m, 1H), 3.84 (t, J=6.2 Hz, 2H), 4.45 (s, 2H), 5.58 (s, 2H), 6.4–6.45 (m, 1H), 6.69 (d, J=2 Hz, 2H), 7.21 (t, J=2 Hz, 1H), 7.95–8.05 (m, 1H)

5-(3,5-Dichlorophenylthio)-2-(2-hydroxyethyl)-4-isopropyl-1-o-nitrobenzyl-1H-imidazole (126c)was obtained from (125c)by the same synthetic process as that for (126a) in Example 139. mp 104–107° C.

$^1$H—NMR (CDCl$_3$)δ ppm: 1.30 (d, J=6.6 Hz, 6H), 2.78 (t, J=5.4 Hz, 2H), 3.1–3.2 (m, 1H), 4.05 (t, J=5.4 Hz, 2H), 5.49

(s, 2H), 6.37 (d, J=8 Hz, 1H), 6.72 (d, J=1.8 Hz, 2H), 6.99 (t, J=1.8 Hz, 1H), 7.36–7.46 (m, 2H), 8.05–8.1 (m, 1H) Elementary analysis ($C_{21}H_{21}N_3Cl_2O_3S$) Calc. (%):C, 54.08; H, 4.54; N, 9.01; S, 6.87; Cl, 15.20 Found (%):C, 54.01; H, 4.62; N, 8.92; S, 6.80; Cl, 15.04

Compound I-143 was obtained from (126c)by the same synthetic process as that for Compound I-139 in Example 139 (yield 62%). mp 137–139° C.

$^1$H—NMR (CDCl$_3$)δ ppm: 1.27 (d, J=6.8 Hz, 6H), 2.77 (t, J=5.6 Hz, 2H), 3.0–3.2 (m, 1H), 3.55 (br, 2H), 4.00 (t, J=5.6 Hz, 2H), 4.91 (s, 2H), 6.3 (d, 1H), 6.6–6.65 (m, 4H), 7.01–7.03 (m, 2H) Elementary analysis ($C_{21}H_{23}N_3Cl_2OS$) Calc. (%):C, 57.92; H, 5.33; N, 9.66; S, 7.35; Cl, 16.07 Found (%):C, 57.54; H, 5.40; N, 9.44; S, 7.20; Cl, 16.49

EXAMPLE 144

Synthesis of 1-(o-aminobenzyl)-2-(2-carbamoyloxyethyl)-5-(3,5-dichlorophenylthio)-4-isopropyl-1H-imidazole (Compound I-144).

2-(2-Carbamoyloxyethyl)-5-(3,5-dichlorophenylthio)-4-isopropyl-1-(o-nitrobenzyl)-1H-imidazole (128c)was obtained from (126c)by the same synthetic process as that for (128a) in Example 140 (yield 87%)mp 163–165° C.

$^1$H—NMR (CDCl$_3$)δ ppm: 1.31 (d, J=6.8 Hz, 6H), 3.01 (t, J=6.2 Hz, 2H), 3.1–3.22 (m, 1H), 4.6 (br, 2H), 5.56 (s, 2H), 6.4 (dd, 1H), 6.72 (d, J=1.4 Hz, 2H), 7.01 (t, J=1.4 Hz, 1H), 7.3–7.5 (m, 2H), 8.07 (dd, 1H) Elementary analysis ($C_{22}H_{22}N_4Cl_2O_4S.0.2H_2O$) Calc. (%):C, 51.50; H, 4.40; N, 10.92; S, 6.25; Cl, 13.82 Found (%):C, 51.29; H, 4.52; N, 10.76; S, 6.01; Cl, 13.51

Compound I-144 was obtained from (128c)by the same synthetic process as that for Compound I-140 in Example 140 (yield 77%). mp 170–174° C.

$^1$H—NMR (CDCl$_3$)δ ppm: 1.28 (d, J=7 Hz, 6H), 3.02 (t, J=6.6 Hz, 2H), 3.05–3.23 (m, 1H), 3.6 (br, 2H), 4.37 (t, J=6.6 Hz, 2H), 4.58 (br, 2H), 4.97 (s, 2H), 6.28 (d, J=7.2 Hz, 1H), 6.6–6.65 (m, 2H), 6.7 (d, J=1.8 Hz, 2H), 7.03 (t, J=1.8 Hz, 1H) Elementary analysis ($C_{22}H_{24}N_4Cl_2O_2S$) Calc. (%):C. 55.12; H, 5.05; N, 11.69; S, 6.09; Cl, 14.79 Found (%):C, 54.89; H, 5.11; N, 11.40: S, 6.56; Cl, 14.56

EXAMPLE 145

Synthesis of 2-(5-(3,5-dichlorophenylthio)-4-isopropyl-1-n-propyl-1H-imidazol-2-yl)ethanol (Compound I-145).

In dry dimethylformamide was dissolved 4.0 g (9.5 mmol) of imidazole compound (Compound I-136), followed by addition of 570 mg (14 mmol)of 60% sodium hydride under ice-cooling. After 5 minutes, 1.75 g (14.2 mmol)of n-propylbromide was added, and the mixture was stirred with heating at 50° C. for 3 hours. The mixture was diluted with ice-water, extracted with ethyl acetate, the extract was washed with water and dried over anhydrous sodium sulfate, filtered, and concentrated under reduced pressure. The residue was purified by silica gel column chromatography (ethyl acetate:n-hexane=1:1)to give 3.19 g of 2-(2-benzyloxyethyl-5-(3,5-dichlorophenylthio)-4-isopropyl-1-n-propyl-1H-imidazole (130a)as oil (yield 73%).

$^1$H—NMR (CDCl$_3$—TMS)δ ppm: 0.83 (t, J=7.4 Hz, 3H), 1.29 (d, J=7.0 Hz, 6H), 1.55 (m, 2H), 3.06 (m, 3H), 3.85 (m, 4H), 4.53 (s, 2H), 6.79 (m, 2H), 7.09 (m, 1H), 7.29 (m, 5H)

In 31 ml concentrated hydrochloric acid was dissolved 3.1 g of the benzyloxy compound (130a), and the mixture was stirred with heating at 110° C. for 2.5 hours. After cooling, the mixture was neutralized with sodium hydrogen carbonate, and extracted with ethyl acetate. The extract was washed with water, dried over anhydrous sodium sulfate, filtered, and concentrated under reduced pressure. The residue was purified by silica gel column chromatography (ethyl acetate), further, and recrystallized from ethyl acetate-n-hexane to give 2.03 g of Compound I-145 as crystals (yield 82%). mp 88–89° C.

$^1$H—NMR (CDCl$_3$—TMS)δ ppm: 0.86 (t, J=7.6 Hz, 3H), 1.21 (d, J=7.0 Hz, 6H), 1.57 (m, 2H), 2.87 (t, J=5.4 Hz, 3.05 (sept, 1H), 3.75 (t, J=7.6 Hz, 2H), 4.10 (m, 2H), 4.98 (brs, 1H), 6.80 (m, 2H), 7.10 (m, 1H) Elementary analysis ($C_{17}H_{22}N_2Cl_2OS$) Calc. (%):C, 54.69; H, 5.94; N, 7.50; S, 8.59; Cl, 18.79 Found (%):C, 54.70: H, 5.99; N, 7.70: S, 8.48; Cl, 18.82

EXAMPLE 146

Synthesis of 2-(1-n-butyl-5-(3,5-dichlorophenylthio)-4-isopropyl-1H-imidazol-2-yl) ethanol (Compound I-146).

In 40 ml of dry dimethylformamide was dissolved 4.0 g (9.5 mmol)of imidazole compound (Compound I-136), and 670 mg (16.8 mmol) of 60% sodium hydride was added under ice-cooling. After 5 minutes, 1.95 g (14.2 mmol)of n-butyl bromide was added, and the mixture was stirred with heating at 50° C. for 30 minutes. After cooling, the reaction mixture was diluted with ice-water, and extracted with ethyl acetate. The extract was washed with water, dried over anhydrous sodium sulfate, filtered, and concentrated under reduced pressure. The residue was purified by silica gel column chromatography (ethyl acetate)to give 4.1 g of 2-(2-benzyloxyethyl-1-butyl-5-(3,5-dichlorophenylthio)-4-isopropyl-1H-imidazole (130b)as oil (yield 90%).

$^1$H—NMR (CDCl$_3$—TMS)δ ppm: 0.82 (t, J=7.2 Hz, 3H), 1.23 (d, J=7.0 Hz, 6H), 1.30 (m, 2H), 1.50 (m, 2H), 3.05 (t, J=6.8 Hz, 2H), 3.08 (sept, 1H), 3.88 (m, 4H), 4.52 (s, 2H), 6.80 (m, 2H), 7.09 (m, 1H), 7.29 (m, 5H)

In 41 ml of concentrated hydrochloric acid was dissolved 4.1 g of the benzyloxy compound (130b), and the mixture was stirred with heating at 110° C. for 2.5 hours. After cooling, the mixture was neutralized with sodium hydrogen carbonate and extracted with ethyl acetate. The extract was washed with water, dried over anhydrous sodium sulfate, filtered, and concentrated under reduced pressure. The residue was purified by silica gel column chromatography (ethyl acetate)to give 3.0 g of Compound I-146 as oil (yield 90%).

$^1$H—NMR (CDCl$_3$—TMS)δ ppm: 0.86 (t, J=7.2 Hz, 3H), 1.21 (d, J=7.0 Hz, 6H), 1.25 (m, 2H), 1.50 (m, 2H), 2.87 (t, J=5.8 Hz, 2H), 3.06 (sept, 1H), 3.79 (t, J=7.4 Hz, 2H), 4.11 (m, 2H), 5.00 (brs, 1H), 6.81 (m, 2H), 7.10 (m, 1H)

EXAMPLE 147

Synthesis of 1,2-di-(2-carbamoyloxyethyl)-5-(3,5-dichlorophenylthio)-4-isopropyl-1H-imidazole (Compound I-147).

In 59 ml of dry acetonitrile was dissolved 5.00 g (11.9 mmol)of imidazole compound (Compound I-136), followed by addition of 3.3 g (23.9 mmol)of potassium carbonate and 3.0 g (18 mmol)of ethyl bromoacetate, and the mixture was heated at 60° C. for 11 hours. After cooling, the reaction mixture was diluted with water, extracted with ethyl acetate, the extract was washed with water, dried over anhydrous sodium sulfate, filtered, and concentrated under reduced pressure. The residue was purified by silica gel column chromatography (ethyl acetate:n-hexane 1:2)to give 5.4 g of (2-(2-benzyloxyethyl)-5-(3,5-dichlorophenylthio)-4-isopropyl-1H-imidazol-1-yl)ethyl acetate (130c)as oil (yield 90%).

$^1$H—NMR (CDCl$_3$—TMS)δ ppm: 1.15 (t, J=7.2 Hz, 3H), 1.26 (d, J=6.8 Hz, 6H), 3.02 (t, J=6.2 Hz, 2H), 3.11 (sept, 1H), 3.83 (t, J=6.2 Hz, 2H), 4.01 (q, J=7.2 Hz, 2H), 4.49 (s, 2H), 4.74 (s, 2H), 6.83 (m, 2H), 7.08 (m, 1H), 7.29 (m, 5H)

In 30 ml of dry diethyl ether was dissolved 3.0 g (5.9 mmol)of the ester compound (130c), followed by addition of 230 mg (6 mmol)of lithium aluminium hydride under ice-cooling, and the mixture was stirred at room temperature for 15 minutes. The mixture was diluted with water, extracted with ethyl acetate, the extract was washed with water, dried over anhydrous sodium sulfate, filtered, and concentrated under reduced pressure. The residue was purified by silica gel column chromatography (ethyl acetate), and further recrystallized from ethyl acetate-n-hexane to give 2.5 g of 2-(2-(2-benzyloxyethyl)-5-(3,5-dichlorophenylthio)-4-isopropyl-1H-imidazol-1-yl)ethanol (130d)as crystals (yield 91%). mp 129–130° C.

$^1$H—NMR (CDCl$_3$—TMS)δ ppm: 1.25 (d, J=7.0 Hz, 6H), 3.11 (m, 4H), 3.63 (m, 2H), 3.92 (t, J=6.2 Hz, 2H), 4.07 (t, J=4.8 Hz, 2H), 4.50 (s, 2H), 6.79 (m, 2H), 7.10 (m, 1H), 7.20–7.31 (m, 5H) Elementary analysis (C$_{23}$H$_{26}$Cl$_2$N$_2$O$_2$S) Calc. (%):C, 59.35, H, 5.63, Cl, 15.23, N, 6.02, S, 6.89 Found (%):C, 59.32, H, 5.65, Cl, 15.00, N, 6.00, S, 6.88

In 15 ml of concentrated hydrochloric acid was dissolved 1.5 g (3.2 mmol)of the alcohol compound (130d), and the mixture was heated at 110° C. for 7 hours. After cooling, the mixture was neutralized with sodium hydrogen carbonate, extracted with ethyl acetate, the extract was washed with water, dried over anhydrous sodium sulfate, filtered, and concentrated under reduced pressure. The residue was purified by silica gel column chromatography (3% methanol/ethyl acetate), and 1.14 g of 2-(5-(3,5-dichlorophenylthio)-2-(2-hydroxyethyl)-4-isopropyl-1H-imidazol-1-yl)ethanol (131c)was obtained as oil (yield 94%).

$^1$H—NMR (CDCl$_3$—TMS)δ ppm: 1.22 (d, J=7.2 Hz, 6H), 2.80 (br., 1H), 2.99 (t, J=5.4 Hz, 2H), 3.08 (sept, 1H), 3.73 (t, J=5.0 Hz, 2H), 4.05 (m, 4H), 4.80 (br, 1H), 6.79 (m, 2H), 7.13 (m, 1H)

In 10 ml of dry tetrahydrofuran was dissolved 1.01 g (2.7 mmol)of the diol (131c). The solution was cooled to −40° C. and 1.52 g (8 mmol)of trichloroacetyl isocyanate was added dropwise. After 5 minutes, the temperature was allowed to increase gradually to room temperature and the mixture was stirred for 1 hour. Then, 2 ml of triethylamine and 4 ml of water were added and the mixture was heated at 50° C. for 3 hours. The reaction mixture was diluted with water and extracted with ethyl acetate. The extract was washed with water, dried over anhydrous sodium sulfate, filtered, and concentrated under reduced pressure. The residue was purified by silica gel column chromatography (5% methanol-ethyl acetate)and recrystallized from ethyl acetate-n-hexane to provide 1.0 g (yield 81%)of Compound I-147 as crystals. mp 152–153° C.

$^1$H—NMR (CDCl$_3$—TMS)δ ppm: 1.23 (d, J=6.8 Hz, 6H), 3.07 (sept, 1H), 3.15 (t, J=7.4 Hz, 2H), 4.13 (m, 4H), 4.52 (t, J=7.2 Hz, 2H), 4.82 (brs., 4H), 6.78 (m, 2H), 7.11 (m, 1H) Elementary analysis (C$_{18}$H$_{22}$Cl$_2$N$_4$O$_4$S) Calc. (%):C, 46.86, H, 4.81, Cl, 15.37, N, 12.14, S, 6.95 Found (%):C, 46.90, H, 4.79, Cl, 15.11, N, 12.04, S, 6.80

EXAMPLE 148

Synthesis of 2-(3-carbamoyloxypropyl)-5-(3,5-dichlorophenylthio)-4-isopropyl-1-methyl-1H-imidazole (Compound I-148)

To 300 ml of dry n-hexane was added 16.4 g (410 mmol)of 60% sodium hydride under ice-cooling and the mixture was stirred. The mixture was then allowed to stand for a while and the hexane layer was discarded. To the residue was added 100 ml of dry N,N-dimethylformamide. Then, 70 g (410 mmol) of benzyl bromide was added dropwise below 40° C. and the mixture was stirred at the same temperature for 30 minutes, then poured in ice-water, and extracted with diethyl ether. The extract was washed with water, dried over sodium sulfate, filtered, and concentrated under reduced pressure. The residue was further purified by fractional distillation under reduced pressure to provide 51.1 g (yield 69%)of 4-benzyloxybutan-1-ol (133a) as oil showing the boiling point of 114° C. /0.5 mmHg.

$^1$H—NMR (CDCl$_3$—TMS)δ ppm: 1.71 (m, 4H), 2.27 (m, 1H), 3.50–3.69 (m, 4H), 4.53 (s, 2H), 7.35 (m, 5H)

A four-necked flask of 2-liter capacity was charged with 406 ml of dry ethyl acetate and 42.3 g (333 mmol)of oxalyl chloride and the mixture was cooled to −70° C. Then, a solution of dry dimethyl sulfoxide (53 g, 666 mmol)in dry ethyl acetate (203 ml)was added dropwise below −70° C. After 15 minutes, a solution of the alcohol (133b)(50 g, 278 mmol) in dry ethyl acetate (203 ml)was added dropwise and the mixture was stirred for 45 minutes. Then, 168 ml of triethylamine was added at −70° C. The mixture was stirred at the same temperature for 0.5 hour and, then, at room temperature for 1 hour. The reaction mixture was diluted with ice-water and extracted with ethyl acetate and the extract was washed with water, dried over sodium sulfate, filtered, and concentrated under reduced pressure. The residue was dissolved in 193 ml of acetonitrile and 51.6 g (333 mmol)of 2,2-dichloro-3-methylbutylaldehyde was added. To this mixture was added 336 ml of 28% aqueous ammonia under ice-cooling and the mixture was then stirred at 40° C. for 7 hours. The reaction mixture was diluted with ice-water and extracted with chloroform. The extract was washed with water, dried over sodium sulfate, filtered, and concentrated under reduced pressure. The resulting product 2-(3-benzyloxypropyl)-4-isopropyl-1H-imidazole (135a)was not purified but subjected to the next iodination reaction.

A four-necked flask of one-liter capacity was charged with 25 g of 40% sodium hydroxide/H$_2$O and 125 ml of water, followed by addition of a solution of the imidazole (135a) obtained above in dioxane (125 ml). Then, 70.5 g (278 mmol) of solid iodine was added under ice-cooling and the mixture was stirred. After 1 hour, an aqueous solution of sodium thiosulfate and, then, dry-ice were added and the mixture was extracted with ethyl acetate. The extract was washed with water, dried over sodium sulfate, and concentrated under reduced pressure. The residue was dissolved in diethyl ether and 39 g of oxalic acid was added to the solution. The precipitated crystals was collected by filtration, neutralized with sodium carbonate, and extracted with chloroform. The extract was washed with water, dried over sodium sulfate, filtered, and concentrated under reduced pressure to provide 86.7 g (yield 82%)of 2-(3-benzyloxypropyl)-5-iodo-4-isopropyl-1H-imidazole (135b) as oil.

$^1$H—NMR (CDCl$_3$—TMS)δ ppm: 1.01 (d, J=7.0 Hz, 6H), 1.98 (quintet, 2H), 2.86 (t, J=5.4 Hz, 2H), 3.63 (t, J=5.4 Hz, 2H), 4.53 (s, 2H), 7.35 (m, 5H), 9.40 (br, 1H)

In 440 ml of dry dimethyl sulfoxide was dissolved 87.6 g (228 mmol)of the above iodide (135b)as well as 48.7 g (137 mmol)of 3,5-dichlorophenyl disulfide. Then, 2.72 g (342 mmol)of lithium hydride was added at room temperature. The temperature was elevated to 40° C. and further to 60° C. After 4 hours, the mixture was poured in ice-water and extracted with ethyl acetate. The extract was washed with water, dried over sodium sulfate, filtered, and concentrated under reduced pressure. The residue was purified by silica gel column chromatography (ethyl acetate)and recrystallized from ethyl acetate-n-hexane to provide 70 g (yield 58%)of 2-(3-benzyloxypropyl)-5-(3,5-dichlorophenylthio)-4-isopropyl-1H-imidazole (101e)as crystals. mp 118–119° C.

$^1$H—NMR (CDCl$_3$—TMS)δ ppm: 0.95 (d, J=6.2 Hz, 6H), 2.04 (m, 2H), 2.93 (m, 2H), 3.02 (sept, 1H), 3.67 (m, 2H), 4.58 (s, 2H), 6.89 (m, 2H), 7.02 (m, 1H), 7.38 (m, 5H), 10.06 (brs, 1H)

In 25 ml of dry acetonitrile was dissolved 5.0 g (11.5 mmol)of imidazole (101e), followed by addition of 1.7 g (23 ml)of lithium carbonate and 2.2 g (17.4 mmol)of dimethyl sulfate. The mixture was stirred under heating at 70° C. for 2 hours. The reaction mixture was diluted with ice-water and extracted with diethyl ether. The extract was washed with water, dried over sodium sulfate, filtered, and concentrated under reduced pressure. The residue was purified by silica gel column chromatography (ethyl acetate)to provide 3.1 g (yield 60%)of 2-(3-benzyloxypropyl)-5-(3,5-dichlorophenylthio)-4-isopropyl-1-methyl-1H-imidazole (136a)as oil.

$^1$H—NMR (CDCl$_3$—TMS)δ ppm: 1.24 (d, J=6.8 Hz, 6H), 2.07 (m, 2H), 2.88 (t, J=7.6 Hz, 2H), 3.09 (sept, 1H), 3.42 (s, 3H), 3.53 (t, J=6.0 Hz, 2H), 4.50 (s, 2H), 6.77 (m, 2H), 7.10 (m, 1H), 7.32 (m, 5H)

To 3.1 g (6.9 mmol)of the above oil (136a)was added 13 ml of concentrated hydrochloric acid and the mixture was heated at 110° C. for 2 hours. After cooling, the mixture was neutralized with sodium hydrogen carbonate and extracted with ethyl acetate. The extract was washed with water, dried over sodium sulfate, filtered, and concentrated under reduced pressure. The residue was purified by silica gel column chromatography (3% methanol-ethyl acetate)and recrystallized from ethyl acetate-n-hexane to provide 1.6 g (yield 39%)of 3-(5-(3,5-dichlorophenylthio)-4-isopropyl-1-methyl-1H-imidazol-2-yl)-propan-1-ol (137a)as crystals. mp 124–125° C.

$^1$H—NMR (CDCl$_3$—TMS)δ ppm: 1.23 (d, J=7.0 Hz, 6H), 2.08 (m, 2H), 2.92 (t, J=6.0 Hz, 2H), 3.08 (sept, 1H), 3.45 (s, 3H), 3.80 (t, J=5.2 Hz 2H), 5.60 (brs., 1H), 6.80 (m, 2H), 7.12 (m, 1H) Elementary analysis (C$_{16}$H$_{20}$Cl$_2$N$_2$OS) Calc, (%):C, 53.48, H, 5.61, Cl, 19.73, N, 7.80, S, 8.92 Found (%):C, 53.30, H, 5.59, Cl, 19.45, N, 7.77, S, 8.77

In 7 ml of dry tetrahydrofuran was dissolved 700 mg (1.9 mmol)of the above alcohol (137a), and after the solution was cooled to −40° C., 550 mg (2.9 mmol)of trichloroacetyl isocyanate was added. After 5 minutes, the temperature was elevated gradually to room temperature and the mixture was stirred for 30 minutes. Then, 2 ml of water and 1 ml of triethylamine were added and the mixture was stirred at room temperature for 3 days. The reaction mixture was diluted with water and extracted with ethyl acetate and the extract was washed with water, dried over sodium sulfate, filtered, and concentrated under reduced pressure. The residue was purified by silica gel column chromatography (3% methanol-ethyl acetate)and recrystallized from ethyl acetate-n-hexane to provide 690 mg (yield 88%)of Compound I-148 as crystals. mp 135–137° C.

$^1$H—NMR (CDCl$_3$—TMS)δ ppm: 1.23 (d, J=7.0 Hz, 6H), 2.11 (m, 2H), 2.84 (t, J=7.8 Hz, 2H), 3.10 (sept, 1H), 3.44 (s, 3H), 4.17 (t, J=6.2 Hz, 2H), 4.71 (brs., 2H), 6.78 (m, 2H), 7.11 (m, 1H) Elementary analysis (C$_{17}$H$_{21}$Cl$_2$N$_3$O$_2$S) Calc. (%):C, 50.75, H, 5.26, Cl, 17.62, N, 10.44, S, 7.97 Found (%):C, 50.60, H, 5.25, Cl, 17.40, N, 10.37, S, 7.85

EXAMPLE 149

Synthesis of 2-(3-carbamoyloxypropyl)-5-(3,5-dichlorophenylthio)-1-ethyl-4-isopropyl-1H-imidazole (Compound I-149)

In 25 ml of dry acetonitrile was dissolved 5.0 g (11.5 mmol)of imidazole (101e), followed by addition of 1.7 g (23 mmol)of lithium carbonate and 2.7 g (17.5 mmol)of diethyl sulfate. The mixture was stirred under heating at 70° C. for 23 hours. After cooling, the reaction mixture was diluted with water and extracted with ethyl acetate. The extract was washed with water, dried over sodium sulfate, filtered, and concentrated under reduced pressure. The residue was purified by silica gel column chromatography (ethyl acetate)to provide 5.3 g (yield 98%)of 2-(3-benzyloxypropyl)-5-(3,5-dichlorophenylthio)-4-isopropyl-1-ethyl-1H-imidazole (136b)as oil.

$^1$H—NMR (CDCl$_3$—TMS)δ ppm: 1.15 (t, J=7.4 Hz, 3H), 1.23 (d, J=6.6 Hz, 6H), 2.10 (m, 2H), 2.85 (t, J=7.4 Hz, 2H), 3.07 (sept, 1H), 3.54 (t, J=5.4 Hz, 2H), 3.85 (q, J=7.4 Hz, 2H), 4.50 (s, 2H), 6.78 (m, 2H), 7.08 (m, 1H), 7.31 (m, 5H)

To 5.3 g (11.4 mmol)of the above oil (136b)was added 24 ml of concentrated hydrochloric acid and the mixture was heated at 110° C. for 2 hours. After cooling, the mixture was neutralized with sodium hydrogen carbonate and extracted with ethyl acetate. The extract was washed with water, dried over sodium sulfate, and concentrated under reduced pressure. The residue was purified by silica gel column chromatography (3% methanol-ethyl acetate)and recrystallized from n-hexane to provide 3.2 g (yield 75%)of 3-(5-(3,5-dichlorophenylthio)-1-ethyl-4-isopropyl-1H-imidazol-2-yl)-propan-1-ol (137b)as crystals. mp 73° C.

$^1$H—NMR (CDCl$_3$—TMS)δ ppm: 1.17 (t, J=7.2 Hz, 3H), 1.22 (t, J=6.8 Hz, 6H), 2.90 (m, 2H), 2.73 (t, J=6.02 Hz, 2H), 3.06 (sept, 1H), 3.80 (d, J=5.2 Hz, 2H), 3.90 (q, J=7.2 Hz, 2H), 5.94 (brs, 2H), 6.82 (m, 2H), 7.11 (m, 1H) Elementary analysis (C$_{17}$H$_{22}$Cl$_2$N$_2$OS) Calc. (%):C, 54.69, H, 5.94, Cl, 18.99, N, 7.50, S, 8.59 Found (%):C, 54.54, H, 5.88, Cl, 18.76, N, 7.49, S, 8.63

In 7 ml of dry tetrahydrofuran was dissolved 700 mg (1.9 mmol)of the alcohol (137b), and after the solution was cooled to −40° C., 530 mg (2.8 mmol)of trichloroacetyl isocyanate was added, the temperature was elevated to room temperature. After 30 minutes, 2 ml of water and 1 ml of triethylamine were added and the mixture was stirred at room temperature for 3 days. The reaction mixture was diluted with water and extracted with ethyl acetate and the extract was washed with water, dried over sodium sulfate, filtered, and concentrated under reduced pressure. The residue was purified by silica gel column chromatography (3%. methanol-ethyl acetate)and recrystallized from ethyl acetate-n-hexane to provide 705 mg (yield 90%)of Compound I-149 as crystals. mp 128–129° C.

$^1$H—NMR (CDCl$_3$—TMS)δ ppm: 1.18 (t, J=7.2 Hz, 3H), 1.23 (d, J=6.8 Hz, 6H), 2.15 (m, 2H), 2.82 (t, J=7.6 Hz, 2H), 3.08 (sept, 1H), 3.87 (q, J=7.2 Hz, 2H), 4.18 (t, J=6.2 Hz, 2H), 4.70 (brs, 2H), 6.80 (m, 2H), 7.10 (m, 1H) Elementary analysis (C$_{18}$H$_{23}$Cl$_2$N$_3$O$_2$S) Calc. (%):C, 51.92, H, 5.57, Cl, 17.03, N, 10.09, S, 7.70 Found (%):C, 52.09, H, 5.59, Cl, 16.69, N, 10.01, S, 7.53

EXAMPLE 150

Synthesis of 2-(3-carbamoyloxypropyl)-5-(3,5-dichlorophenylthio)-4-isopropyl-1-(pyridin-4-yl) methyl-1H-imidazole (Compound I-150)

In 50 ml of tetrahydrofuran was dissolved 5.0 g (11.5 mmol)of imidazole (101e), followed by addition of 5 ml of water and 1.84 g (46 mmol)of sodium hydroxide, and then, 250 mg (0.8 mmol)of n-tetrabutylammonium bromide and 2.3 g (14 mmol)of 4-chloromethylpyridine hydrochloride were further added. The mixture was stirred under heating at 50° C. for 8 hours. After cooling, the reaction mixture was diluted with water and extracted with ethyl acetate. The extract was washed with water, dried over sodium sulfate, filtered, and concentrated under reduced pressure. The residue was purified by silica gel column chromatography (5% methanol-ethyl acetate)to provide 2-(3-benzyloxypropyl)-5-(3,5-dichlorophenylthio)-4-isopropyl-1-(pyridin-4-yl) methyl-1H-imidazole (136c)as oil. To thus-obtained oil (136c)was added 27 ml of concentrated hydrochloric acid and the fixture was heated at 110° C. for 2 hours. After cooling, the mixture was neutralized with sodium hydrogen carbonate and extracted with ethyl acetate. The extract was washed with water, dried over sodium sulfate, filtered, and concentrated under reduced pressure. The residue was purified by silica gel column chromatography (5% methanol-ethyl acetate)and recrystallized from ethyl acetate-n-hexane to provide 3.8 g (yield 76%)of 3-(5-(3,5-dichlorophenylthio)-4-isopropyl-1-(pyridin-4-ylmethyl)-1H-imidazol-2-yl)-propan-1-ol (137c)as crystals. mp 106–107° C.

$^1$H—NMR (CDCl$_3$—TMS)δ ppm: 1.28 (d, J=7.0 Hz, 6H), 2.01 (m, 2H), 2.83 (t, J=6.2 Hz, 2H), 3.14 (sept, 1H), 3.78 (t, J=5.6 Hz, 2H), 5.10 (s, 2H), 5.34 (brs., 1H), 6.71 (m, 2H), 6.78 (d, J=6.0 Hz, 2H), 7.04 (m, 1H), 8.48 (d, J=6.0 Hz, 2H) Elementary analysis (C$_{21}$H$_{23}$Cl$_2$N$_3$OS) Calc. (%):C, 57.80, H, 5.31, Cl, 16.25, N, 9.63, S, 7.35 Found (%):C, 57.45, H, 5.40, Cl, 16.02, N, 9.50, S, 7.28

In 7 ml of dry tetrahydrofuran was dissolved 700 mg (1.6 mmol)of the alcohol (137c), and after the solution was cooled to −40° C., 450 mg (2.4 mmol)of trichloroacetyl isocyanate was added and the temperature was elevated gradually to room temperature. After stirring for 30 minutes, 2 ml of water and 1 ml of triethylamine were added and the mixture was stirred at room temperature for 3 days. The reaction mixture was diluted with water and extracted with ethyl acetate. The extract was washed with water, dried over sodium sulfate, filtered, and concentrated under reduced pressure. The residue was purified by silica gel column chromatography (5% methanol-ethyl acetate)and recrystallized from ethyl acetate-n-hexane to provide 610 mg (yield 79%)of Compound I-150 as crystals. mp 114–115° C.

$^1$H—NMR (CDCl$_3$—TMS)δ ppm: 1.29 (d, J=6.8 Hz, 6H), 2.10 (m, 2H), 2.73 (t, J=7.4 Hz, 2H), 3.15 (sept, 1H), 4.12 (t, J=6.0 Hz, 2H), 4.56 (brs., 2H), 5.08 (s, 2H), 6.70 (m, 2H), 6.80 (d, J=5.4 Hz, 2H), 7.04 (m, 1H), 8.47 (d, J=5.4 Hz, 2H) Elementary analysis (C$_{18}$H$_{23}$Cl$_2$N$_3$O$_2$S) Calc. (%):C, 51.92, H, 5.57, Cl, 17.03, N, 10.09, S, 7.70 Found (%):C, 52.09, H, 5.59, Cl, 16.69, N, 10.01, S, 7.53

EXAMPLE 151

Synthesis of 1-(2-carbamoyloxyethyl)-2-(3-carbamoyloxypropyl)-5-(3,5-dichlorophenylthio)-4-isopropyl-1H-imidazole (Compound I-151)

In 50 ml of dry acetonitrile was dissolved 5.0 g (11.5 mmol)of the imidazole (101e), followed by addition of 3.2 g (23.2 mmol)of potassium carbonate and 2.9 g (17.4 mmol)of ethyl bromoacetate, and the mixture was heated at 60° C. for 11 hours. The reaction mixture was diluted with ice-water and extracted with ethyl acetate. The extract was washed with water, dried over sodium sulfate, filtered, and concentrated under reduced pressure. The residue was purified by silica gel column chromatography (ethyl acetate:n-hexane=1:2)to provide 5.75 g (yield 96%)of (2-(3-benzyloxypropyl)-5-(3,5-dichlorophenylthio)-4-isopropyl-1H-imidazol-1-yl)-ethyl acetate (136d)as oil.

$^1$H—NMR (CDCl$_3$—TMS)δ ppm: 1.15 (t, J=7.2 Hz, 3H), 1.24 (d, J=7.0 Hz, 6H), 2.08 (m, 2H), 2.80 (t, J=7.2 Hz, 2H), 3.09 (sept, 1H), 3.52 (t, J=5.8 Hz, 2H), 4.03 (q, J=7.2 Hz, 2H), 4.48 (s, 2H), 4.60 (s, 2H), 6.82 (m, 2H), 7.08 (m, 1H), 7.31 (m, 5H)

In 30 ml of dry diethyl ether was dissolved 3.0 g (5.8 mmol)of the ester (130d), to the mixture was added 220 mg (5.8 mmol)of lithium aluminium hydride under ice-cooling. The mixture was stirred at room temperature for 15 minutes. The reaction mixture was diluted with water and extracted with ethyl acetate. The extract was washed with water, dried over anhydrous sodium sulfate, filtered, and concentrated under reduced pressure. The residue was purified by silica gel column chromatography (ethyl acetate), and further recrystallized from n-hexane to provide 2.4 g (yield 87%)of 2-(2-(3-benzyloxypropyl)-5-(3,5-dichlorophenylthio)-4-isopropyl-1H-imidazol-1-yl)-ethanol (136e)as crystals. mp 104–106° C.

$^1$H—NMR (CDCl$_3$—TMS)δ ppm: 1.23 (d, J=7.0 Hz, 6H), 2.12 (quintet, 2H), 2.42 (brs., 1H), 2.93 (t, J=7.2 Hz, 2H), 3.08 (sept, 1H), 3.55 (t, J=6.0 Hz, 2H), 3.64 (m, 2H), 3.96 (t, J=5.8 Hz, 2H), 4.45 (s, 2H), 6.77 (m, 2H), 7.10 (m, 1H), 7.30 (m, 5H) Elementary analysis (C$_{24}$H$_{28}$Cl$_2$N$_2$O$_2$S) Calc. (%);C, 60.12, H, 5.89, Cl, 14.79, N, 5.84, S, 6.69 Found (%):C, 60.06, H, 5.91, Cl, 14.54, N, 5.78, S, 6.64

To 14 ml of concentrated hydrochloric acid, 1.4 g (2.9 mmol)of the alcohol (136e)was added and the mixture was heated at 110° C. for 7 hours. After cooling, the mixture was neutralized with sodium hydrogen carbonate and extracted with ethyl acetate. The extract was washed with water, dried over sodium sulfate, filtered, and concentrated under reduced pressure. The residue was purified by silica gel column chromatography (5% methanol-ethyl acetate)to provide 300 mg (yield 26%)of 3-(5-(3,5-dichlorophenylthio)-1-(2-hydroxyethyl)-4-isopropyl-1H-imidazol-2-yl)-propan-1-ol (137d)as oil.

$^1$H—NMR (CDCl$_3$—TMS)δ ppm: 1.22 (d, J=6.8 Hz, 6H), 2.06 (m, 2H), 2.60 (br, 1H), 3.00 (t, J=6.2 Hz, 2H), 3.07 (sept, 1H), 3.76 (m, 2H), 4.01 (t, J=5.4 Hz, 2H), 4.60 (br, 1H), 6.80 (m, 2H), 7.13 (m, 1H), In 5 ml of dry acetonitrile was dissolved 240 mg (0.6 mmol)of the diol (137d), and after the solution was cooled to −40° C., 400 mg (2.11 mmol)of trichloroacetyl isocyanate was added dropwise. After 5 minutes, the temperature was elevated gradually to room temperature and the mixture was stirred for 1 hour. To the mixture was added 3 ml of water and 1.5 ml of triethylamine and the mixture was heated at 50° C. for 3 hours. The reaction mixture was diluted with ice-water and extracted with ethyl acetate. The extract was washed with water, dried over sodium sulfate, filtered, and concentrated under reduced pressure. The residue was purified by silica gel column chromatography (ethyl acetate)and recrystallized from ethyl acetate-n-hexane to provide 127 mg (yield 43%)of Compound I-151 as crystals. mp 155–163° C.

$^1$H—NMR (CDCl$_3$—TMS)δ ppm: 1.26 (d, J=7.0 Hz, 6H), 2.16 (m, 2H), 2.86 (m, 2H), 3.07 (sept, 1H), 4.14 (m, 6H), 4.88 (brs, 4H), 6.78 (m, 2H), 7.11 (m, 1H) Elementary analysis (C$_{19}$H$_{24}$Cl$_2$N$_4$O$_4$S) Calc. (%):C, 48.00, H, 5.09, Cl, 14.92, N, 11.79, S, 6.74 Found (%):C, 47.96, H, 5.19, Cl, 14.64, N, 11.52, S, 6.71

EXAMPLE 152

Synthesis of 2-carbamoyloxymethyl-1-(2-carbamoyloxypropyl)-5-(3,5-dichlorophenylthio)-4-isopropyl-1H-imidazole (Compound I-152)

In 20 ml of acetone was dissolved 5.0 g of the imidazole (101a)and 1.36 g (14.7 mmol)of monochloroacetone, followed by addition of 2.46 g (12.27 mmol)of potassium iodide, and the mixture was stirred at room temperature for 30 minutes. Then, to the mixture was added 2.04 g (14.8 mmol)of potassium carbonate, and the mixture was stirred with heating at 50° C. for 4 hours and worked up. The reaction mixture was distilled off under reduced pressure, and the residue was extracted with methylene chloride. The extract was washed with water, dried and the solvent was distilled off. The residue was purified by silica gel column chromatography (methylene chloride:ethyl acetate=9:1)to provide 3.1 g (yield 54%)of 2-benzyloxymethyl-5-(3,5-dichlorophenylthio)-4-isopropyl-1-acetylmethyl-1H-imidazole (139)as solid.

$^1$H—NMR (CDCl$_3$)δ ppm: 1.26 (d, J=7.2 Hz, 6H), 3.0–3.2 (m, 1H), 4.45 (s, 2H), 4.63 (s, 2H), 4.75 (s, 2H), 6.80 (d, J=2 Hz, 2H), 7.26–7.32 (m, 5H)

In 50 ml of methanol was dissolved 3.6 g of the ketone (139), followed by addition of 352 mg (10 mmol)of NaBH$_4$ under ice-cooling and stirring, the mixture was stirred at room temperature for 3 hours and worked up. The reaction mixture was distilled off under reduced pressure, the residue was extracted with methylene chloride, washed with water, dried and the solvent was distilled off. The residue was purified by silica gel column chromatography (methylene chloride:ethyl acetate=9:1)to provide almost quantitatively, 2-benzyloxymethyl-5-(3,5-dichlorophenylthio)-1-(2-hydroxypropyl)-4-isopropyl-1H-imidazole (140a)as oil.

$^1$H—NMR (CDCl$_3$)δ ppm: 1.40 (d, J=3.6 Hz, 3H), 1.22–1.3 (m, 6H), 2.67 (m, 1H), 3.0–3.2 (m, 1H), 4.61 (d, J=1.4 Hz, 2H), 4.64, 4.78 (ABq, J=12.2 Hz, 29.4 Hz, 2H), 6.28)d, J=1.2 Hz, 2H), 7.11 (t, J=1.6 Hz), 7.33–7.36 (5H)

In 55 ml of concentrated hydrochloric acid was dissolved 13.4 g (28.7 mmol)of the alcohol (140a), and after the mixture was stirred with heating at 110° C. for 2 hours, a saturated aqueous sodium hydrogen carbonate solution was added to the reaction mixture. The mixture was distilled off under reduced pressure and the residue was extracted with ethyl acetate. The extract was washed with water, dried and the solvent was distilled off. The residue was purified by silica gel column chromatography (methylene chloride-ethyl acetate=9:1), the oil was treated with ether and crystallized to provide 9.1 g (yield 84%)of 5-(3,5-dichlorophenylthio)-2-hydroxymethyl-1-(2-hydroxypropyl)-4-isopropyl-1H-imidazole (141a). mp 159–161° C.

$^1$H—NMR (CDCl$_3$)δ ppm: 1.18–1.24 (m, 9H), 3.0–3.2 (m, 1H), 3.88–4.00 (m, 3H), 4.68, 4.78 (ABq, J=13.2 Hz, 21.4 Hz, 2H), 6.79 (d, J=1.6 Hz, 2H), 7.13 (t, J=2 Hz, 1H)

In 20 ml of tetrahydrofuran was dissolved 1.13 g (3 mmol) of the diol (141a), followed by addition of 0.43 g (3.6 mmol) of chloroacetyl isocyanate under ice-cooling and the mixture was stirred at room temperature for 1.5 hours. After the reaction, to the reaction mixture was added a saturated aqueous sodium hydrogen carbonate solution, distilled off under reduced pressure and the residue was extracted with methylene chloride. The extract was washed with water, dried and the solvent was distilled off. The residue was purified by silica gel column chromatography (methylene chloride:ethyl acetate=1:2). From the first eluted fraction, 290 mg (yield 20%)of 2-(N-chloroacetyl)carbamoyloxymethyl-1-(2-(N-chloroacetyl)carbamoyloxypropyl)-5-(3,5-dichlorophenylthio)-4-isopropyl-1H-imidazole (142b)was obtained as powder. As the second eluted fraction, 1.08 g (yield 59%)of 2-(N-chloroacetyl)carbamoyloxymethyl-5-(3,5-dichlorophenylthio)-1-(2-hydroxypropyl)-4-isopropyl-1H-imidazole (142a)was obtained as oil.

$^1$H—NMR (CDCl$_3$)δ ppm: (142a)1.20–1.26 (m, 9H), 3.0–3.20 (m, 1H), 3.8–4.1 (m, 3H), 4.44 (s, 2H), 5.30, 5.47 (ABq, J=13.2 Hz, 34.8 Hz, 2H), 6.76 (d, J=2 Hz, 2H), 7.14 (t, J=3.4 Hz, 1H), 8.43 (br, 1H)

(142b), 1.21–1.63 (m, 9H), 3.0–3.2 (m, 1H), 4.1–4.23 (m, 2H), 4.37–4.45 (m, 3H), 5.37 (s, 2H), 6.77 (d, J=2 Hz, 2H), 7.18–7.19 (m, 1H), 8.15–8.45 (m, 1H), 8.45–8.47 (m, 1H)

In 15 ml of water-methanol (1:15)was dissolved 1.08 g (2.18 mmol)of the mono(N-chloroacetyl)compound (142a), followed by addition of 50 mg of zinc powder and the mixture was stirred at room temperature for 6 hours. To the reaction mixture was added a saturated aqueous sodium hydrogen carbonate solution, the mixture was filtered through Celite under reduced pressure, and the filtrate was distilled off under reduced pressure. The residue was extracted with methylene chloride. The extract was washed with water, dried and the solvent was distilled off. The residue was purified by silica gel column chromatography (ethyl acetate)to provide 820 mg (yield 90%)of 2-carbamoyloxymethyl-5-(3,5-dichlorophenylthio)-1-(2-hydroxypropyl)-4-isopropyl-1H-imidazole (143a)as powder.

$^1$H—NMR (CDCl$_3$)δ ppm: 1.94–1.27 (m, 9H), 3.0–3.2 (m, 1H), 3.96 (s, 2H), 3.9–3.98 (m, 1H), 4.86 (br, 2H), 5.2, 5.36 (ABq, J=13 hZ, 32 Hz, 2H), 6.78 (d, J=2 Hz, 2H), 7.12 (t, J=2 Hz, 1H) Elementary analysis (C$_{17}$H$_{21}$N$_3$Cl$_2$O$_3$S) Calc. (%):C, 48.81; H, 5.16; N, 10.04; Cl, 16.05; S, 7.66 Found (%).C, 48.75; H, 5.27; N, 9.90; Cl, 16.22; S, 7.46

In 5 ml of water-methanol (1:15)was dissolved 290 mg (0.47 mmol)of the di(N-chloroacetyl)compound (142b), followed by addition of 30 mg of zinc powder and the mixture was stirred at room temperature for 6 hours. To the reaction mixture was added a saturated aqueous sodium hydrogen carbonate solution, the mixture was filtered through Celite under reduced pressure, the filtrate was distilled off under reduced pressure. The residue was extracted with methylene chloride. The extract was washed with water, dried and the solvent was distilled off. The residue was purified by silica gel column chromatography (ethyl acetate:methylene chloride=2:1)to provide 130 mg (yield 60%)of Compound I-152. mp 82° C.

$^1$H—NMR (CDCl$_3$)δ ppm: 1.17–1.26 (m, 9H), 3.0–3.2 (m, 1H), 3.99–4.2 (m, 2H), 4.68–4.93 (br, m, 2H), 5.28 (d, J=3.8 Hz, 2H), 3.78 (d, J=1.6 Hz, 2H), 7.13 (t, J=1.6 Hz, 1H) Elementary analysis (C$_{18}$H$_{22}$N$_4$Cl$_2$O$_4$S.0.15H$_2$O) Calc. (%):C; 46.59; H, 4.84; N, 12.07; S, 6.91 Found (%):C, 46.98; H, 5.05; N, 11.57; S, 6.57

EXAMPLE 153

Synthesis of 5-(3,5-dichlorophenylthio)-2-hydroxymethyl-1-(2-hydroxy-2-methylpropyl)-4-isopropyl-1H-imidazole (Compound I-153)

In 5 ml of tetrahydrofuran was dissolved 464 mg (1 mmol) of the ketone (139), followed by addition dropwise of 134 mg (1.1 mmol)of methylmagnesium bromide (tetrahydrofuran; 2 ml) under ice-cooling and stirring, and the mixture was stirred at room temperature for 30 minutes. To the reaction mixture was added an aqueous solution of ammonium chloride, the mixture was distilled off under reduced pressure, and the residue was extracted with ethyl acetate. The extract was washed with water, dried and the solvent was distilled off. The residue was purified by silica gel column chromatography (ethyl acetate:methylene chloride=1:1)to provide 350 mg (yield 73%)of 2-benzyloxymethyl-5-(3,5-dichlorophenylthio)-1-(2-hydroxy-2-methylpropyl)-4-isopropyl-1H-imidazole (140b) as oil.

$^1$H—NMR (CDCl$_3$)δ ppm: 1.12 (s, 3H), 1.24 (d, J=6.6 Hz, 3H), 3.0–3.2 (m, 1H), 4.02 (s, 1H), 4.02 (s, 2H), 4.60 (s, 2H), 4.78 (s, 2H), 6.70 (d, J=2 Hz, 2H), 7.11 (t, J=2 Hz, 1H)

In 2 ml of concentrated hydrochloric acid was dissolved 350 mg (0.73 mmol)of the benzyl compound (140b)and the solution was stirred under heating at 110° C. for 3 hours. To this reaction mixture was added a saturated aqueous solution of NaHCO$_3$ and the solvent was distilled off under reduced pressure. The residue was extracted with ethyl acetate and the extract was washed with water and dried. The solvent was then distilled off and the residue was purified by silica gel column chromatography (ethyl acetate)to provide 150 mg (yield 53%)of Compound I-153 as crystals. mp 181–182° C.

$^1$H—NMR (CDCl$_3$)δ ppm: 1.18~1.24 (m, 12H), 3.0~3.2 (m, 1H), 4.04 (s, 2H), 4.8 (s, 2H), 6.71 (d, J=1.6 Hz, 2H), 7.12 (t, J=1.6 Hz, 1H) Elementary analysis (C$_{27}$H$_{22}$N$_2$Cl$_2$OS) Calc. (%):C, 52.44; H, 5.70; N, 7.20; S, 8.23; Cl, 18.21 Found (%):C, 52.30; H, 5.74; N, 7.19; S, 8.30; Cl, 18.04

The following formulation examples are illustrative of the medicinal composition of the present invention. In these examples, the term "active ingredient" means a pharmaceutically acceptable compound according to the present invention.

FORMULATION EXAMPLE 1

Preparation of tablets

The following compositions A, B and C were prepared by wet-granulating the ingredients with a solution of hydroxypropylcellulose, adding magnesium stearate, and compressing the respective mixtures.

Composition A

|  | mg/tablet | mg/tablet |
|---|---|---|
| (a) Active ingredient | 200 | 50 |
| (b) Lactose | 260 | 5.2 |
| (c) Hydroxypropylcellulose | 15 | 1.8 |
| (d) Sodium starch glycolate | 20 | 2.4 |
| (e) Magnesium stearate | 5 | 0.6 |
| Total | 500 | 60 |

Composition B

|  | mg/tablet |
|---|---|
| (a) Active ingredient | 200 |
| (b) Lactose | 200 |
| (c) Crystalline cellulose | 60 |
| (d) Hydroxypropylcellulose | 15 |
| (e) Sodium starch glycolate | 20 |
| (f) Magnesium stearate | 5 |
| Total | 500 |

Composition C

|  | mg/tablet |
|---|---|
| (a) Active ingredient | 200 |
| (b) Lactose | 35 |
| (c) Starch | 50 |
| (d) Hydroxypropylcellulose | 12 |
| (e) Magnesium stearate | 3 |
| Total | 300 |

Composition D was prepared by compressing directly the mixed ingredients.

Composition D

|  | mg/capsule |
|---|---|
| (a) Active ingredient | 200 |
| (b) Lactose | 150 |
| (c) Crystalline cellulose | 100 |
| Total | 450 |

Controlled release composition E

The composition was prepared by mixing the following ingredients to be a solution of hydroxypropylcellulose, wet-granulating, adding magnesium stearate, and compressing the respective mixtures.

Composition E

|  | mg/tablet |
|---|---|
| (a) Active ingredient | 400 |
| (b) Hydroxypropylcellulose H | 110 |
| (c) Crystalline cellulose | 60 |
| (d) Hydroxypropylcellulose SL | 24 |
| (f) Magnesium stearate | 6 |
| Total | 600 |

FORMULATION EXAMPLE 2

Preparation of capsules

Composition A

This capsule was manufactured by mixing above ingredients, and filling the mixture in hard gelatin capsule shells.

|  | mg/capsule |
|---|---|
| (a) Active ingredient | 200 |
| (b) Lactose | 173 |
| (c) Sodium starch glycolate | 25 |
| (d) Magnesium stearate | 2 |
| Total | 400 |

Composition B

This capsule was manufactured by melting macrogol 4000, dispersing the active ingredient in the melt, and filling the mixture in hard gelatin capsule shells.

|  | mg/capsule |
|---|---|
| (a) Active ingredient | 200 |
| (b) Macrogol 4000 | 300 |
| Total | 500 |

Composition C

This capsule was manufactured by dispersing the active ingredient in lecithin and sesame oil and filling the mixture in hard gelatin capsule shells.

|  | mg/capsule |
|---|---|
| (a) Active ingredient | 200 |
| (b) Lecithin | 100 |

157
-continued

|  | mg/capsule |
|---|---|
| (c) Sesame oil | 100 |
| Total | 400 |

Composition D (controlled release capsules)

This controlled release capsule was manufactured by extruding the ingredients (a~c)with a suitable extruder, molding the extrudate into pellets, and drying them. This dry pelletized product was coated with a release-control film and filled in hard gelatin capsule shells.

|  | mg/capsule |
|---|---|
| (a) Active ingredient | 200 |
| (b) Microcrystalline cellulose | 125 |
| (c) Lactose | 120 |
| (d) Wax | 10 |
| Total | 455 |

FORMULATION EXAMPLE 3
Preparation of a syrup

The active ingredient was dissolved in most part of the purified water together with sodium carboxymethylcellulose, followed by addition of sodium benzoate solution, D-sorbitol solution, and perfume. Then, purified water was added to make 5 ml and the whole mixture was blended thoroughly, sieved, and homogenized.

| (a) Active ingredient | 0.20 g |
|---|---|
| (b) Sucrose | 0.50 g |
| (c) D-sorbitol (70% aq. sol.) | 1.00 g |
| (d) Sodium carboxymethylcellulose | 0.02 g |
| (e) Polysorbate 80 | 0.005 g |
| (f) Sodium benzoate | 0.005 g |
| (g) Perfume | 0.01 g |
| (h) Purified water | To make a total of 5.00 ml |

FORMULATION EXAMPLE 4
Preparation of suppositories

Fats and oil base material was melt at 45° C. The active ingredient was added to this fats and oil base material with mixing to yield a suspension. Filled was 2.0 g of this mixture in a 2 ml-plastic mold and the mold was cooled to room temperature to provide suppositories.

|  | mg/suppository |
|---|---|
| (a) Active ingredient | 200 |
| (b) Fats and oil base material | 1800 |
| Total | 2000 |

158
FORMULATION EXAMPLE 5
Preparation of granules

The ingredients were added to hydroxypropylcellulose, the mixture was kneaded, granulated by an extruder-type granulator and dried to provide granules.

|  | mg/1 g of granules |
|---|---|
| (a) Active ingredient | 200 |
| (b) Corn starch | 325 |
| (c) Calucium carboxymethylcellulose | 50 |
| (d) Lactose | 350 |
| (e) Hydroxypropylcellulose | 25 |
| (f) CARPLEX | 50 |
| Total | 1000 |

TEST EXAMPLE 1

The anti-HIV activity of each of the compounds produced in Examples was assayed by the following procedures. (1)Human T cell line MOLT-4 clone 8 persistently infected by HIV (HTLV-IIIB strain)was cultured in an RPMI-1640 medium supplemented with 10% fetal calf serum, the culture supernatant was filtered, and the titer of virus was determined; the culture supernatant was stored at −80° C. On the other hand, the test compound was diluted with the above culture medium to predetermined concentrations and distributed in 50 µl aliquots into a 96-well microtiter plate. Then, a suspension of MT-4 cells was added in 100 µl aliquots (3.5×10$^4$ cells per well)and then the above HIV-containing supernatant diluted with the above culture medium was added, 50 µl (60 pfu (plaque forming units))per well. (2)The plate was incubated in a $CO_2$ incubator at 37° C. for 5 days. Then, 30 µl/well of 3-(4,5-dimethyl thiazol-2-yl)-2,5-diphenyltetrazolium bromide (MTT)(5 mg/ml PBS)was added and the incubation was further continued for 1 hour. The surviving cells reducing MTT yield precipitation of formazan. Thereafter, 150 µl portions of the culture supernatant were removed front all wells and, instead, 150 µl of a solution (10% Triton X-100 and 0.4% (v/v)HCl-added isopropyl alcohol) was added. The plate was shaken on a plate mixer to dissolve the formazan. The OD of formazan was measured with a microreader at 560 nm and 690 nm (reference wavelength)and the result was compared with that of control. The concentration at which the compound inhibited the cytotoxic effect of the virus by 50% was expressed as $EC_{50}$. The results are shown in Tables 1 and 2.

TABLE 1

| Compound number | EC$_{50}$ ($\mu$g/ml) | Compound number | EC$_{50}$ ($\mu$g/ml) | Compound number | EC$_{50}$ ($\mu$g/ml) | Compound number | EC$_{50}$ ($\mu$g/ml) | Compound number | EC$_{50}$ ($\mu$g/ml) |
|---|---|---|---|---|---|---|---|---|---|
| I-1 | 0.008 | I-25 | 0.004 | I-48 | 0.016 | I-72 | 0.03~0.06 | I-93' | 0.00006~0.00013 |
| I-2 | 0.008 | I-26 | 0.004~0.008 | I-49 | 0.004~0.008 | I-73 | 0.016 | I-94 | 0.03 |
| I-3 | 0.03 | I-27 | 0.03 | I-50 | 0.008 | I-74 | 0.25 | I-95 | 0.03~0.06 |
| I-4 | 0.016 | I-28 | 0.002~0.004 | I-51 | 0.003~0.005 | I-75 | 0.01 | I-95' | 0.005 |
| I-5 | 0.06 | I-29 | 0.016~0.03 | I-52 | 0.003 | I-76 | 0.016 | I-96 | 0.03 |
| I-6 | 0.03~0.06 | I-30 | 0.005~0.01 | I-53 | 0.004~0.008 | I-77 | 0.03~0.006 | I-97 | 0.06~0.13 |
| I-7 | 0.13 | I-31 | 0.06 | I-54 | 0.004 | I-78 | 1 | I-98 | 1 |
| I-8 | 0.016 | I-32 | 0.06 | I-55 | 0.008 | I-79 | 0.25 | I-99 | 6.3 |
| I-9 | 0.008 | I-32' | 0.002~0.004 | I-56 | 0.008 | I-80 | 0.5~1 | I-100 | 1 |
| I-10 | 1 | I-33 | 0.016 | I-57 | 0.005~0.001 | I-80a | 0.002~0.004 | I-101 | 1 |
| I-11 | 0.25 | I-34 | 0.006 | I-58 | 0.002 | I-81 | 0.13 | I-102 | 0.5~1 |
| I-12 | 50 | I-35 | 0.004~0.008 | I-59 | 12.5 | I-81a | 0.001 | I-103 | 0.5 |
| I-13 | 0.06 | I-36 | 0.002 | I-60 | 0.5~ | I-82 | 0.25 | I-104 | 1~10 |
| I-14 | 0.03 | I-37 | 0.0005 | I-61 | 0.5 | I-83 | 1.6 | I-105 | 0.5 |
| I-15 | 0.005~0.01 | I-38 | 6.3 | I-62 | 0.03~0.06 | I-84 | 1 | I-106 | 1~10 |
| I-16 | 0.008~0.016 | I-39 | 1~10 | I-63 | 0.25 | I-85 | 0.13 | I-107 | 0.78 |
| I-17 | 0.005~0.01 | I-40 | 0.016 | I-64 | >CC$_{50}$ | I-86 | 1 | I-108 | 1 |
| I-18 | >CC$_{50}$ | I-41 | 0.016 | I-65 | >CC$_{50}$ | I-87 | 0.5~1 | I-109 | 0.5 |
| I-19 | 0.004~0.008 | I-42 | 0.07 | I-66 | 0.016 | I-88 | >CC$_{50}$ | I-110 | 10 |
| I-20 | 0.008 | I-43 | 0.25 | I-67 | 0.13~0.25 | I-89 | 1 | I-111 | >CC$_{50}$ |
| I-21 | 0.008 | I-44 | 1 | I-68 | 0.016 | I-90 | 0.13 | I-112 | >100 |
| I-22 | 0.002 | I-45 | 0.004~0.008 | I-69 | 0.25 | I-91 | 0.06 | I-113 | 100 |
| I-23 | 0.004 | I-46 | 0.08~0.016 | I-70 | 0.03 | I-92 | 0.001 | I-114 | 10 |
| I-24 | 0.008 | I-47 | 0.002 | I-71 | 0.008 | I-93 | 0.0005~0.001 | I-115 | >CC$_{50}$ |

TABLE 2

| Compound number | EC$_{50}$ ($\mu$g/ml) | Compound number | EC$_{50}$ ($\mu$g/ml) |
|---|---|---|---|
| I-116 | 1.6 | 122b | 0.5–1 |
| 103a | <0.008 | 123b | 0.003 |
| 104a | <0.008 | I-138 | 0.008 |
| I-117 | 0.05–0.01 | 126a | 0.008 |
| 103b | 0.008 | I-139 | <0.008 |
| I-118 | 0.05–0.01 | 128a | 3.1–6.3 |
| 103c | 0.06–0.13 | I-140 | 0.03–0.06 |
| I-119 | 0.13–0.25 | 126b | 0.008–0.016 |
| I-120 | 0.13 | I-141 | <0.008 |
| I-121 | 0.06 | 128b | 0.13 |
| I-122 | 0.008 | I-142 | 0.016–0.03 |
| I-123 | 0.06 | 126c | 0.13 |
| I-124 | 0.25 | I-143 | 0.008 |
| I-125 | 0.5–1 | 128c | 0.25 |
| I-126 | 0.03 | I-144 | 0.78 |
| I-127 | 0.016 | 130a | — |
| 109 | 0.008 | I-145 | — |
| I-128 | <0.008 | 130b | — |
| 112a | 0.008 | I-146 | — |
| I-129 | 0.06 | 130c | 0.5 |
| 112b | <0.008 | 130d | 0.5–1 |
| I-130 | <0.008 | 131c | <0.008 |
| 116a | 0.004 | I-147 | 0.005 |
| I-131 | 0.003 | 137a | 0.008 |
| 116b | 0.016 | I-148 | 0.005–0.01 |
| I-132 | 0.78 | 137b | 0.005–0.01 |
| 119a | <0.008 | I-149 | 0.01 |

TABLE 2-continued

| Compound number | EC$_{50}$ ($\mu$g/ml) | Compound number | EC$_{50}$ ($\mu$g/ml) |
|---|---|---|---|
| I-133 | 0.008 | 137c | 0.003–0.005 |
| 118b | 0.25 | I-150 | 0.008 |
| 118c | 1 | 136d | 0.5 |
| 119b | <0.008 | 136e | 0.5–1 |
| I-134 | 0.0013 | 137d | <0.008 |
| I-135 | 0.016–0.03 | I-151 | 0.0006 |
| I-136 | 0.008–0.016 | 141a | 0.002–0.004 |
| 122a | 0.13 | I-152 | <0.008 |
| 123a | 0.0006 | I-153 | 0.016 |
| I-137 | 0.004–0.008 | | |

TEST EXAMPLE 2

The cytotoxicity of each of the compounds produced in Examples was assayed. In place of the HIV-containing supernatant (the virus suspension) in (1) in Test Example 1, 50$\mu$l of the culture medium was added to each well, and the cytotoxicity was determined in the same manner as that for (2) in Test Example 1. The concentration at which the compound shows the cytotoxicity by 50% was expressed as CC$_{50}$. The results are shown in Table 3 and 4.

TABLE 3

| Compound number | CC$_{50}$ (μg/ml) | Compound number | CC$_{50}$ (μg/ml) | Compound number | CC$_{50}$ (μg/ml) | Compound number | CC$_{50}$ (μg/ml) | Compound number | CC$_{50}$ (μg/ml) |
|---|---|---|---|---|---|---|---|---|---|
| I-1 | 6.3~12.5 | I-25 | 10~100 | I-48 | 25~50 | I-72 | 1~10 | I-93' | 10~100 |
| I-2 | 25 | I-26 | 10~100 | I-49 | 25 | I-73 | 6.3 | I-94 | 12.5~25 |
| I-3 | 12.5 | I-27 | 10~100 | I-50 | >100 | I-74 | 12.5~25 | I-95 | 6.3 |
| I-4 | 12.5 | I-28 | 12.5 | I-51 | 6.3~12.5 | I-75 | 16.5 | I-95' | 6.3~12.5 |
| I-5 | 1~10 | I-29 | 12.5 | I-52 | 10 | I-76 | 6.3~12.5 | I-96 | 10~100 |
| I-6 | 10 | I-30 | 10~100 | I-53 | 10~100 | I-77 | 10 | I-97 | 10~100 |
| I-7 | 10~100 | I-31 | 100 | I-54 | 12.5 | I-78 | 1~10 | I-98 | 10~100 |
| I-8 | 12.5 | I-32 | 10~100 | I-55 | 10~100 | I-79 | 1~10 | I-99 | >100 |
| I-9 | 10 | I-32' | 12.5~25 | I-56 | 10~100 | I-80 | 10~100 | I-100 | 12.5 |
| I-10 | >100 | I-33 | 10~100 | I-57 | 25~50 | I-80a | 100 | I-101 | 10~100 |
| I-11 | 1~10 | I-34 | 13.5 | I-58 | 10~100 | I-81 | 10~100 | I-102 | 1~10 |
| I-12 | 50~100 | I-35 | 12.5~25 | I-59 | 12.5~25 | I-81a | 12.5 | I-103 | 10~100 |
| I-13 | 25 | I-36 | 10~100 | I-60 | 12.5~25 | I-82 | 1.5~3.2 | I-104 | 10~100 |
| I-14 | 12.5~25 | I-37 | 25 | I-61 | 6.3~12.5 | I-83 | 6.3~12.5 | I-105 | 50~100 |
| I-15 | 6.3~12.5 | I-38 | 12.5~25 | I-62 | 12.5~25 | I-84 | 1~10 | I-106 | 100 |
| I-16 | 12.5~25 | I-39 | 10~100 | I-63 | 12.5 | I-85 | 1~10 | I-107 | >100 |
| I-17 | 6.3~12.5 | I-40 | 12.5~25 | I-64 | 12.5~25 | I-86 | 1 | I-108 | 10~100 |
| I-18 | 10~100 | I-41 | 8.5 | I-65 | 12.5~25 | I-87 | 10~100 | I-109 | >100 |
| I-19 | 10~100 | I-42 | 8 | I-66 | 6.3~12.5 | I-88 | 1~10 | I-110 | 10~100 |
| I-20 | 6.3~12.5 | I-43 | 1~10 | I-67 | 12.5~25 | I-89 | 1~10 | I-111 | 1~10 |
| I-21 | 6.3~12.5 | I-44 | 1~10 | I-68 | 1~10 | I-90 | 10~100 | I-112 | >100 |
| I-22 | 25 | I-45 | 12.5 | I-69 | 6.3 | I-91 | 6.3~12.5 | I-113 | 100 |
| I-23 | 25 | I-46 | 12.5~25 | I-70 | 6.3~12.5 | I-92 | 12.5~24 | I-114 | 10~100 |
| I-24 | 25 | I-47 | 6.3~12.5 | I-71 | 1~10 | I-93 | 12.5 | I-115 | 10~100 |

TABLE 4

| Compound number | CC$_{50}$ (μg/ml) | Compound number | CC$_{50}$ (μg/ml) |
|---|---|---|---|
| I-116 | 25 | 122b | 6.3 |
| 103a | 6.3–12.5 | 123b | 12.5–25 |
| 104a | 12.5–25 | I-138 | 12.5 |
| I-117 | 50 | 126a | 6.3 |
| 103b | 50 | I-139 | 6.3 |
| I-118 | 12.5–25 | 128a | 6.3 |
| 103c | 6.3–12.5 | I-140 | 6.3–12.5 |
| I-119 | 3.1 | 126b | 3.1–6.3 |
| I-120 | 100 | I-141 | 25–50 |
| I-121 | 12.5 | 128b | 6.3–12.5 |
| I-122 | 6.3–12.5 | I-142 | 6.3–12.5 |
| I-123 | 12.5 | 126c | 6.3 |
| I-124 | 12.5 | I-143 | 12.5 |
| I-125 | 12.5 | 128c | 6.3–12.5 |
| I-126 | 12.5–25 | I-144 | 6.3–12.5 |
| I-127 | 12.5–25 | 130a | — |
| 109 | 100 | I-145 | — |
| I-128 | >100 | 130b | — |
| 112a | 6.3 | I-146 | — |
| I-129 | 12.5–25 | 130c | 12.5 |
| I-112b | 6.3–12.5 | 130d | 6.3 |
| I-130 | 6.3–12.5 | 131c | 6.3–12.5 |
| 116a | 30.7 | I-147 | 50–100 |
| I-131 | 38.8 | 137a | 6.3–12.5 |
| 116b | 50 | I-148 | 6.3–12.5 |
| I-132 | 12.5–25 | 137b | 6.3–12.5 |
| 119a | 12.5 | I-149 | 6.3 |
| I-133 | 12.5 | 137c | 6.3–12.5 |
| 118b | 12.5–25 | I-150 | 6.3–12.5 |
| 118c | 6.3–12.5 | 136d | 12.5 |
| 119b | 12.5–25 | 136e | 6.3–12.5 |
| I-134 | 12.5–25 | 137d | 6.3–12.5 |
| I-135 | 25–50 | I-151 | 50–100 |
| I-136 | 12.5 | 141a | 12.5–25 |
| 122a | 6.3 | I-152 | 12.5–25 |
| 123a | 6.3–12.5 | I-153 | 12.5 |
| I-137 | 50 | | |

TEST EXAMPLE 3

The reverse transcriptase activity of each of the compounds synthesized in Examples was assayed by the following procedures.

Using the purified recombinant HIV-1 reverse transcriptase (RT, E.C. 2.7.7.49)obtained by expression in *Escherichia coli*, a 96-well plate assay system was established for assaying a large number of samples. The RT inhibitory activity was determined as follows. To 11 μl of a solution of the test inhibitor in water or DMSO was added 100 μl of a reaction mixture (0.1 unit/100 μl RT, 50 mM Tris-HCl pH 8.3, 150 mM KCl, 10 mM MgCl$_2$, 3 mM dithiothreitol, 0.1% Nonidet P-40, 10 μg/ml poly(rA)and 10 μg/ml (dT)12–18 as template and primer, and 4 μM dTTP, 1 μCi/100 μl [$^3$H]dTTP as substrate) and the mixture was incubated at 37° C. for 1 hour and, then, immediately cooled on ice. Using a cell harvester, the reaction mixture was transferred to a DEAE-filter mat (LKB-Pharmacia). Then, using the wash line of the cell harvester, the cells were washed twice with 5% Na$_2$HPO$_4$/H$_2$O and once with water and dried at 95° C. for 15 minutes. Then, 10 ml of a scintillator and the filter mat were put in a special bag and the uptake of [$^3$H]dTMP was measured with a scintillation counter (LKB 1205 Betaplate). The inhibitory activity was expressed in percent inhibition relative to the uptake on water or DMSO control.

The concentration at which the compound inhibited the reverse transcriptase by 50% was expressed as the IC$_{50}$ of the compound. The results are presented in Tables 5 and 6.

TABLE 5

| Compound number | RT IC$_{50}$ (μg/ml) | Compound number | RT IC$_{50}$ (μg/ml) | Compound number | RT IC$_{50}$ (μg/ml) | Compound number | RT IC$_{50}$ (μg/ml) | Compound number | RT IC$_{50}$ (μg/ml) |
|---|---|---|---|---|---|---|---|---|---|
| I-1 | 1.2 | I-25 | 0.48 | I-48 | 0.45 | I-72 | 0.8 | I-93' | 0.16 |
| I-2 | 2.1 | I-26 | 0.91 | I-49 | — | I-73 | 0.25 | I-94 | 1.9 |
| I-3 | 1.0 | I-27 | 1.2 | I-50 | — | I-74 | 5.7 | I-95 | 0.71 |
| I-4 | 1.7 | I-28 | 0.20 | I-51 | 0.38 | I-75 | 0.22 | I-95' | 0.48 |
| I-5 | 2.3 | I-29 | 0.60 | I-52 | 0.18 | I-76 | 3.5 | I-96 | 4.6 |
| I-6 | 36.6 | I-30 | 0.91 | I-53 | 0.21 | I-77 | 1.3 | I-97 | 7.4 |
| I-7 | 43.2 | I-31 | | I-54 | 0.46 | I-78 | 46.2 | I-98 | 36.8 |
| I-8 | 1.0 | I-32 | 2.7 | I-55 | 2.5 | I-79 | 12.9 | I-99 | >100 |
| I-9 | 2.4 | I-32' | 0.57 | I-56 | 0.93 | I-80 | 1.1 | I-100 | 12.5 |
| I-10 | >100 | I-33 | 3.9 | I-57 | 0.04 | I-80a | 0.11 | I-101 | 25.2 |
| I-11 | 16.5 | I-34 | 1.4 | I-58 | 0.15 | I-81 | 3.0 | I-102 | 24.1 |
| I-12 | >100 | I-35 | 0.69 | I-59 | >100 | I-81a | 0.14 | I-103 | 6.8 |
| I-13 | 0.8 | I-36 | 0.18 | I-60 | >100 | I-82 | 0.44 | I-104 | >100 |
| I-14 | 1.3 | I-37 | 0.06 | I-61 | 77.3 | I-83 | 81.2 | I-105 | 52.5 |
| I-15 | 0.75 | I-38 | 81.1 | I-62 | 6.8 | I-84 | >100 | I-106 | >100 |
| I-16 | 1.5 | I-39 | 65.7 | I-63 | 4.7 | I-85 | 2.6 | I-107 | 62.7 |
| I-17 | <0.8 | I-40 | 10.7 | I-64 | >100 | I-86 | 12.5 | I-108 | — |
| I-18 | >100 | I-41 | 0.5 | I-65 | >100 | I-87 | >100 | I-109 | — |
| I-19 | 0.72 | I-42 | 1.7 | I-66 | 0.69 | I-88 | >100 | I-110 | — |
| I-20 | 2.1 | I-43 | 5.3 | I-67 | 5.4 | I-89 | >100 | I-111 | — |
| I-21 | 2.9 | I-44 | 43.2 | I-68 | 0.61 | I-90 | 2.5 | I-112 | — |
| I-22 | 0.56 | I-45 | 0.65 | I-69 | 2.3 | I-91 | 0.34 | I-113 | — |
| I-23 | 0.32 | I-46 | 0.8 | I-70 | 1.8 | I-92 | 0.35 | I-114 | — |
| I-24 | 1.0 | I-47 | 0.98 | I-71 | 0.34 | I-93 | 0.49 | I-115 | — |

TABLE 6

| Compound number | RT IC$_{50}$ (μg/ml) | Compound number | RT IC$_{50}$ (μg/ml) |
|---|---|---|---|
| I-116 | >100 | 122b | 36.6 |
| 103a | 13.0 | 123b | 0.15 |
| 104a | 1.3 | I-138 | 1.5 |
| I-117 | 3.8 | 126a | 1.21 |
| 103b | 11.3 | I-139 | 1.6 |
| I-118 | 0.9 | 128a | 53.1 |
| 103c | 26.2 | I-140 | 14.3 |
| I-119 | 3.3 | 126b | 4.0 |
| I-120 | 49.2 | I-141 | 1.8 |
| I-121 | 35.9 | 128b | >100 |
| I-122 | 3.1 | I-142 | 12.0 |
| I-123 | 34.8 | 126c | 28.4 |
| I-124 | >100 | I-143 | 33.6 |
| I-125 | >100 | 128c | >100 |
| I-126 | 13.9 | I-144 | >100 |
| I-127 | 6.1 | 130a | — |
| 109 | 2.0 | I-145 | — |
| I-128 | 2.7 | 130b | — |
| 112a | 0.96 | I-146 | — |
| I-129 | 35.8 | 130c | >100 |
| 112b | 2.6 | 130d | >100 |
| I-130 | 1.9 | 131c | 0.97 |
| 116a | 1.3 | I-147 | 2.0 |
| I-131 | 1.3 | 137a | 2.0 |
| 116b | 3.2 | I-148 | 0.36 |
| I-132 | 0.65 | 137b | 0.37 |
| 119a | 6.2 | I-149 | 0.32 |
| I-133 | 33.6 | 137c | 0.31 |
| 118b | >100 | I-150 | 0.9 |
| 118c | >100 | 136d | >100 |
| 119b | 0.62 | 136e | >100 |
| I-134 | 0.69 | 137d | 2.6 |
| I-135 | 3.8 | I-151 | 2.9 |
| I-136 | 2.0 | 141a | 0.57 |
| 122a | 19.0 | I-152 | 1.5 |
| 123a | 0.15 | I-153 | 10.0 |
| I-137 | 3.3 | | |

We claim:

1. A compound selected from the group consisting of an imidazole compound of the formula (I) or a pharmaceutically acceptable salt thereof:

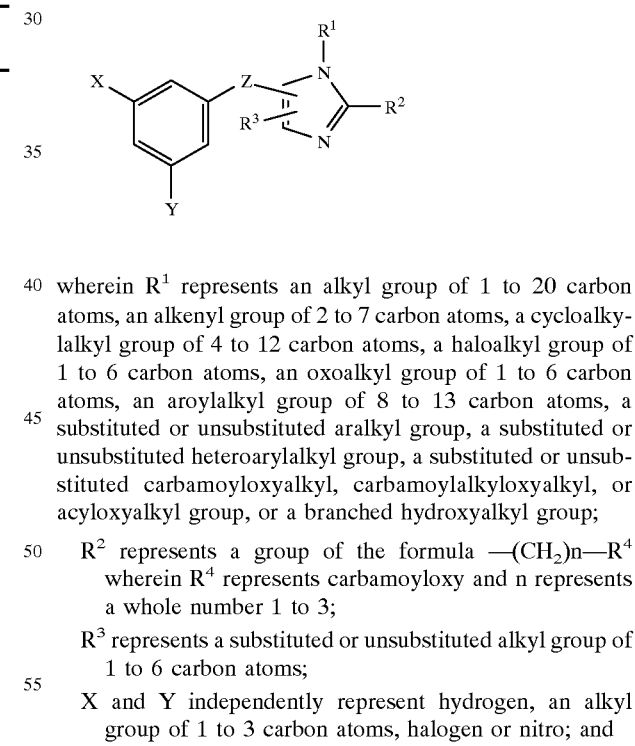

(I)

wherein R$^1$ represents an alkyl group of 1 to 20 carbon atoms, an alkenyl group of 2 to 7 carbon atoms, a cycloalkylalkyl group of 4 to 12 carbon atoms, a haloalkyl group of 1 to 6 carbon atoms, an oxoalkyl group of 1 to 6 carbon atoms, an aroylalkyl group of 8 to 13 carbon atoms, a substituted or unsubstituted aralkyl group, a substituted or unsubstituted heteroarylalkyl group, a substituted or unsubstituted carbamoyloxyalkyl, carbamoylalkyloxyalkyl, or acyloxyalkyl group, or a branched hydroxyalkyl group;

R$^2$ represents a group of the formula —(CH$_2$)n—R$^4$ wherein R$^4$ represents carbamoyloxy and n represents a whole number 1 to 3;

R$^3$ represents a substituted or unsubstituted alkyl group of 1 to 6 carbon atoms;

X and Y independently represent hydrogen, an alkyl group of 1 to 3 carbon atoms, halogen or nitro; and Z represents S, SO, SO$_2$ or CH$_2$.

2. A compound according to claim 1 wherein said imidazole compound is 2-carbamoyloxymethyl-5-(3,5-dichlorophenylthio)-1-ethyl-4-isopropyl-1H-imidazole, 2-carbamoyloxymethyl-5-(3,5-dichlorophenylthio)-4-isopropyl-1-(pyridin-4-yl)methyl-1H-imidazole, 2-[2-(carbamoyloxy)ethyl]-5-(3,5-dichlorophenylthio-1-ethyl-4-isopropyl-1H-imidazole, or 2-carbamoyloxymethyl-5-(3,5-dichlorophenylthio)-1-(5,6-dihydro-6-oxopyridin-3-yl)methyl-4-isopropyl-1H-imidazole.

3. A medicinal composition comprising a pharmaceutically effective amount of a compound or salt thereof according to claim 1 as an active ingredient and a pharmaceutically acceptable carrier therefor.

4. An anti-HIV composition comprising an anti-HIV effective amount of a compound or salt thereof according to claim 1 as an active ingredient and a pharmaceutically acceptable carrier therefor.

* * * * *